US009724418B2

(12) United States Patent
Linders et al.

(10) Patent No.: US 9,724,418 B2
(45) Date of Patent: *Aug. 8, 2017

(54) DRUG COMBINATIONS COMPRISING A DGAT INHIBITOR AND A PPAR-AGONIST

(71) Applicant: Janssen Pharmaceutica NV, Beerse (BE)

(72) Inventors: Joannes Theodorus Maria Linders, Eindhoven (NL); Peter Walter Maria Roevens, Malle (BE); Brian Joel Hrupka, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/793,896

(22) Filed: Jul. 8, 2015

(65) Prior Publication Data
US 2015/0320741 A1 Nov. 12, 2015

Related U.S. Application Data

(63) Continuation of application No. 12/993,491, filed as application No. PCT/EP2009/056800 on Jun. 3, 2009, now Pat. No. 9,107,946.

(30) Foreign Application Priority Data

| Jun. 5, 2008 | (WO) | PCT/EP2008/056983 |
| Jun. 5, 2008 | (WO) | PCT/EP2008/057008 |
| Jun. 5, 2008 | (WO) | PCT/EP2008/057011 |
| Jun. 6, 2008 | (WO) | PCT/EP2008/057060 |
| Dec. 5, 2008 | (EP) | 08170780 |

(51) Int. Cl.
*C07D 295/192* (2006.01)
*A61K 31/216* (2006.01)
*A61K 31/496* (2006.01)
*A61K 45/06* (2006.01)

(52) U.S. Cl.
CPC ........... *A61K 45/06* (2013.01); *A61K 31/216* (2013.01); *A61K 31/496* (2013.01); *C07D 295/192* (2013.01)

(58) Field of Classification Search
CPC .... A61K 45/06; A61K 31/216; A61K 31/496; A61K 2300/00; C07D 295/192
See application file for complete search history.

(56) References Cited

U.S. PATENT DOCUMENTS

| 4,698,352 | A | 10/1987 | Narita et al. |
| 5,429,770 | A | 7/1995 | Closs et al. |
| 5,574,055 | A | 11/1996 | Borgulya et al. |
| 5,789,412 | A | 8/1998 | Halazy et al. |
| 6,492,368 | B1 | 12/2002 | Dorsch et al. |
| 6,884,868 | B1 | 4/2005 | Tojo et al. |
| 7,186,683 | B2 | 3/2007 | Henriksen et al. |
| 2003/0055055 | A1 | 3/2003 | Teuber et al. |
| 2003/0060472 | A1 | 3/2003 | Learmonth et al. |
| 2004/0038858 | A1 | 2/2004 | Dorsch et al. |
| 2004/0162282 | A1 | 8/2004 | Pennell et al. |
| 2004/0220191 | A1 | 11/2004 | Schwink et al. |
| 2005/0059650 | A1 | 3/2005 | Jones et al. |
| 2005/0209241 | A1 | 9/2005 | Jolidon |
| 2006/0030612 | A1 | 2/2006 | Steffan |
| 2007/0021339 | A1 | 1/2007 | Alloza Miravete et al. |
| 2007/0027093 | A1 | 2/2007 | Ogawa et al. |
| 2007/0207999 | A1 | 9/2007 | Stadtmueller et al. |
| 2007/0249620 | A1 | 10/2007 | Kurata et al. |
| 2009/0069304 | A1 | 3/2009 | Hayahsi et al. |

FOREIGN PATENT DOCUMENTS

| CN | 1749256 A | 3/2006 |
| EP | 030371 A | 6/1981 |
| EP | 0321131 A | 6/1989 |
| EP | 0378207 A | 7/1990 |
| EP | 0630954 A | 12/1994 |
| EP | 0657440 A | 6/1995 |
| EP | 1764360 A | 3/2007 |
| GB | 1383906 A | 2/1974 |
| JP | 11139969 | 5/1999 |
| JP | 2005-206492 A | 8/2005 |
| JP | 2005-330266 A | 12/2005 |
| JP | 2007-131584 A | 5/2007 |
| WO | WO 96/01820 A | 1/1996 |
| WO | WO 96/10822 A | 1/1996 |

(Continued)

OTHER PUBLICATIONS

Aarmadaka et al., "Synthesis and Evaluation of Urea and Thiourea Derivatives of Oxazolidinones as Antibacterial Agents.", Chem. Pharm. Bull., Feb. 1, 2007, pp. 236-240, vol. 55.
Abstract RN854989-58-5, Jul. 13, 2005.
Abstract RN859099-41-5, Aug. 9, 2005.
Abstract RN859135-44-7, Aug. 9, 2005.
Abstract RN859646-88-1, Aug. 11, 2005.
Abstract RN860081-71-6, Aug. 12, 2005.
Abstract RN860458-98-6, Aug. 15, 2005.
Abstract RN861994-10-7, Aug. 29, 2005.
Abstract RN884476-57-7, May 16, 2006.
Abstract RN892188-37-3, Jul. 12, 2006.
Abstract RN892208-87-6, Jul. 12, 2006.
Abstract RN892693-34-4, Jul. 16, 2006.

(Continued)

*Primary Examiner* — Sarah Pihonak
*Assistant Examiner* — Jason A Deck

(57) ABSTRACT

The present invention relates to combinations of a DGAT inhibitor and a peroxisome proliferator-activator receptor (PPAR) agonist or a prodrug thereof. The invention further relates to methods for preparing such combinations, pharmaceutical compositions comprising said combinations as well as the use as a medicament of said combinations.
The present invention also relates to novel DGAT inhibitors. The invention further relates to methods for preparing such compounds, pharmaceutical compositions comprising said compounds as well as the use as a medicament of said compounds.

2 Claims, 10 Drawing Sheets

(56) References Cited

FOREIGN PATENT DOCUMENTS

| | | |
|---|---|---|
| WO | WO 96/02525 A1 | 2/1996 |
| WO | WO 96/21648 A1 | 7/1996 |
| WO | WO 97/05877 A | 2/1997 |
| WO | WO 97/05878 A | 2/1997 |
| WO | WO 97/30995 A1 | 3/1997 |
| WO | WO 98/24766 A | 6/1998 |
| WO | WO 99/16751 A | 8/1999 |
| WO | WO 00/05225 A1 | 2/2000 |
| WO | WO 00/32582 | 6/2000 |
| WO | WO 00/71107 | 11/2000 |
| WO | WO 01/58885 A | 8/2001 |
| WO | WO 01/95856 A2 | 12/2001 |
| WO | WO 01/97810 | 12/2001 |
| WO | WO 01/98251 A1 | 12/2001 |
| WO | WO 02/20501 | 3/2002 |
| WO | WO 02/48117 A1 | 6/2002 |
| WO | WO 02/055012 A1 | 7/2002 |
| WO | WO 02/081460 | 10/2002 |
| WO | WO 03/064386 A | 8/2003 |
| WO | WO 03/076421 A1 | 9/2003 |
| WO | WO 03/076422 A1 | 9/2003 |
| WO | WO 03/082864 A | 10/2003 |
| WO | WO 03/087057 A1 | 10/2003 |
| WO | WO 2004/018439 A1 | 3/2004 |
| WO | WO 2004/047755 A2 | 6/2004 |
| WO | WO 2004/069792 A2 | 8/2004 |
| WO | WO 2004/072025 A | 8/2004 |
| WO | WO 2004/100881 A2 | 11/2004 |
| WO | WO 2004/110375 A | 12/2004 |
| WO | WO 2005/072740 A3 | 8/2005 |
| WO | WO 2006/004200 A1 | 1/2006 |
| WO | WO 2006/034441 A1 | 3/2006 |
| WO | WO 2006/038039 A | 4/2006 |
| WO | WO 2006/044775 A | 4/2006 |
| WO | WO 2006/047277 A1 | 5/2006 |
| WO | WO 2006/064189 A1 | 6/2006 |
| WO | WO 2006/067071 A1 | 6/2006 |
| WO | WO 2006/086445 A3 | 8/2006 |
| WO | WO 2006/094842 A | 9/2006 |
| WO | WO 2006/105127 A2 | 10/2006 |
| WO | WO 2006/106326 A | 10/2006 |
| WO | WO 2006/113919 A2 | 10/2006 |
| WO | WO 2006/113919 A3 | 10/2006 |
| WO | WO 2006/134317 A | 12/2006 |
| WO | WO 2007/071023 A1 | 6/2007 |
| WO | WO 2007/071966 A1 | 6/2007 |
| WO | WO 2007/096351 A1 | 8/2007 |
| WO | WO 2007/100990 A | 9/2007 |
| WO | WO 2007/102392 A1 | 9/2007 |
| WO | WO 2008/003766 A2 | 1/2008 |
| WO | WO 2008/052638 A1 | 5/2008 |
| WO | WO 2008/087057 A1 | 7/2008 |
| WO | WO 2008/122787 A1 | 10/2008 |
| WO | WO 2008/141976 A1 | 11/2008 |
| WO | WO 2008/148840 A1 | 12/2008 |
| WO | WO 2008/148849 A2 | 12/2008 |
| WO | WO 2008/148851 A1 | 12/2008 |
| WO | WO 2008/148868 A1 | 12/2008 |
| WO | WO 2009/147170 A2 | 12/2009 |

OTHER PUBLICATIONS

Abstract RN897172-00-8, Jul. 28, 2006.
Abstract RN897548-47-9, Jul. 31, 2006.
Abstract RN898117-91-4, Aug. 2, 2006.
Abstract RN898111-33-6, Aug. 2, 2006.
Birch et al., "DGAT1 inhibitors as anti-obesity and anti-diabetic agents", Current Opinion in Drug Discovery & Development, 2010, pp. 489-496, vol. 13(4).
Bose et al., "Glucagon-like Peptide 1 Can Directly Protect the Heart Against Ischemia/Reperfusion Injury.", Diabetes, Jan. 2005, vol. 54, pp. 146-151.
Buhman et al., "DGAT1 Is Not Essential for Intestinal Triacylglycerol Absorption or Chylomicron Synthesis.", J. Biol. Chem. Jul. 12, 2002, vol. 277(28), pp. 25474-25479.
Cao et al., "Targeting Acyl-CoA:Diacylglycerol Acyltransferase 1 (DGAT1) With Small Molecule Inhibitors for the Treatment of Metabolic Diseases.", J. Biol. Chem., 2011, pp. 41838-41851, vol. 286.
Cases et al., "Cloning of DGAT2, a Second Mammalian Diacylglycerol Acyltransferase, and Related Family Members.", J. Biol. Chem., Oct. 19, 2001, vol. 276(42), pp. 38870-38876.
Cases et al., "Identification of a gene encoding an acyl CoA:diacylglycerol acyltransferase, a key enzyme in triacylglycerol synthesis.", Proc. Natl. Acad. Sci., Oct. 1998, vol. 95, pp. 13018-13023.
Chen et al., "DGAT and Triglyceride Synthesis: A New Target for Obesity Treatment?", Trends Cardiovasc. Med., 2000, vol. 10(5), pp. 188-192.
Chen et al., "Enhancing energy and gluconse metabolism by disruption triglyceride synthesis; Lessons from mice lacking DGAT1.", Nutrition & Metabolism, Jan. 31, 2006; pp. 1-4, vol. 3(10).
Chen et al., "Increased insulin and leptin sensitivity in mice lacking acyl CoA:diacylglycerol acyltransferase 1.", J. Clin. Invest., 2002, vol. 109(8), pp. 1049-1055.
Chen et al., "Inhibition of Triglyceride Synthesis as a Treatment Strategy for Obesity. Lessons from DGAT1-Deficient Mice.", Arterioscler. Thromb. Vasc. Biol., 2005, pp. 482-486, vol. 25.
Database Registry, Apr. 17, 2007, XP002458843.
Database Registry, Aug. 3, 2005, XP002501332.
Database Registry, Aug. 5, 2005, XP002501333.
Database Registry, Aug. 8, 2005, XP002501334.
Database Registry, Aug. 8, 2005, XP002501335.
Database Registry, Mar. 22, 2004, XP002459101.
Database Registry, Mar. 22, 2004, XP002459102.
Database Registry, Mar. 22, 2004, XP002459103.
Database Registry, Nov. 3, 2004, XP002459099.
Farese et al., "Lipopenia and Skin Barrier Abnormalities in DGAT2-deficient Mice*.", J. Biol. Chem., Mar. 19, 2004, pp. 11767-1176, vol. 279(12).
Farese et al., "Triglyceride synthesis: insights from the cloning of diacylglycerol acytransferase.", Curr. Opin. Lipidol. 2000, vol. 11, pp. 229-234.
Glass et al., "4-(4-Guanidinobenzoyl)-2-Imidazolones and Related Compounds: Phosphodiesterase Inhibitors and Novel Cardiotonics With Combined Histamine H2 Receptor Agonist and PDE III Inhibirot Activity.", Archiv. Der Pharmazie, 1995, vol. 328 (10), pp. 709-719, XP009002222.
Griffett et al., "Effects of 6-[p(4-phenylacetylpiperazine-1-yl)phenyl1]-4, 5-dihydro-3(2 H)pyridazinone (CCI 17810) and aspirin on platelet aggregation and adhesiveness.", Database Medline, British J. of Pharmacology, Apr. 1981, vol. 72(4), pp. 697-705, XP002459094.
Guanming et al., "Synthesis and Platelet Aggregation Inhibitory Activity of Pyridazines.", Chinese J. Med. Chem., 1994, pp. 162-170, vol. 4.
Khalaj et al., "Synthesis and antibacterial activity of 2-(4-substituted phenyl)-3(2H)-isothiazolones.", European Journal of Med. Chem., Aug. 2004, vol. 39(8), pp. 699-705, Paris, France, XP004523234.
Kuwabara et al., "A Nove Novel Selective Peroxisome Proliferator-Activated Receptor Agonist, 2-Methyl-c-5-[4-[5-methyl-2-(4-methylphenyl)-4-oxazolyl]butyl]-1,3-dioxane-r-2-carboxylic acid (NS-220),Potently Decreases Plasma Triglyceride and Glucose Levels and Modifies Lipoprotein Profiles in KK-Ay Mice.", J. Pharmacol. Exp. Ther., 2004, pp. 970-977, vol. 309(3).
Lee et al., "Inhibition of Diaclyglycerol Acyltransferase by Alkamides Isolated from the Fruits of Piper longum and Piper nigrum.", J. Agric. Food Chem., 2006, pp. 9759-9763, vol. 54.
Lewis et al., "Disordered fat storage and mobilization in the pathogenesis of insulin resistance and type 2 diabetes.", Endocrine Reviews, 2002, vol. 23(1), pp. 201-229.
Malloy and Kane, Pathogenesis and treatment in cardiomyopathy. , Adv. Intern. Med., 2001, vol. 47, pp. 111-136.
Matsuda and Tomoda, "DGAT inhibitors for obesity", Current Opinion in Investigational Drugs, 2007, pp. 836-841, vol. 8(10).

(56) References Cited

OTHER PUBLICATIONS

Nikolaidis et al., "Glucagon-Like Peptide-1 Limits Myocardial Stunning following Brief Coronary Occlusion and Reperfusion in Conccious Canines.", Journal of Pharm. and Experimental Therapeutics, 2005, vol. 312(1), pp. 303-308.
Oelkers et al., "Characterizations of Two Human Genes Encoding Acyl Coenzyme A: Cholesterol Acyltransferase-related Enzymes.", J. Biol. Chem., Oct. 8, 1998, vol. 273(41), pp. 26765-26771, U.S.A.
Okawa et al., "Role of MGAT2 and DGAT1 in the release of gut peptides after triglyceride ingestion", Biochemical and Biophysical Research Communications, 2009, pp. 377-381, vol. 390.
Pearson et al., "Preparation of Functionalized P-Phenylenediamine Derivatives using Arene-Iron Chemistry.", J. of Org. Chem., 1996, vol. 61(4), pp. 1297-1305, Easton, US, XP002938137.
Perry et al., "Evidence of GLP-1-mediated neuroprotection in an animal model of pyridoxine-induced peripheral sensory neuropathy.", Experimental Neurology, 2007, vol. 203(2), pp. 293-301.
Phillips et al., "Structure-antibacterial activity of arylcarbonyl- and arylsulfonyl-piperazine 5-Triazolylmethyl oxazolidinones.", Eur.J. Med. Chem., Nov. 29, 2006, pp. 214-225, vol. 42.
Shandala et al., "Reactions of Acetylenic Esters with Cyclic Ketones and Substituted Acetophenones.", Journal f. prakt. Chemic. Band, 1979, pp. 899-904, vol. 321(6).
Smith et al., "Obesity resistance and multiple mechanisms of triglyceride synthesis in mice lacking Dgat.", Nature Genetics May, 2000, vol. 25(1), pp. 87-90.
Stone et al., "Lipopenia and Skin Barrier Abnormalities in DGAT2-deficient Mice.", J. Biol. Chem., Mar. 19, 2004, vol. 279(12), pp. 11767-11776.
Vippangunta et al., "Crystalline Solids.", Advanced Drug Delivery Reviews, 2001, pp. 3-26, vol. 48.
Watt, M.J., "Storing Up Trouble: Does Accumulation of Intramyocellular Triglyceride Protect Skeletal Muscle from Insulin Resistance?", Clinical and Experimental Pharmacolgy and Physiology, 2009, pp. 5-11, vol. 36.
International Search Report relating to International Patent Application No. PCT/EP2009/056800. Date of Mailing of International Search Report, Mar. 29, 2010.
Written Opinion of the International Searching Authority relating to International Patent Application No. PCT/EP2009/056800. Date of Mailing of Written Opinion, Mar. 29, 2010.
Jiang et al., "Synthesis and platelet aggregation inhibitory activity of 6-(4-substituted phenyl)-4,5-dihydro-3(2H)-pyridazinones.", Acta Pharmaceutica Sinica, 1990 vol. 25(8), pp. 598-603; Database CA, Chemical Abstracts Service, XP002459098, Abstract.
Wu, et al., "Synthesis and platelet aggregation inhibitory activities of 6-[4(4-substituted-piperazine-1-yl)phenyl]-5-methyl-4,5-dihydro-3(2H)-pyridazinone derivatives.", Zhongguo Yaowu Huaxue Zazhi, 2000, 10(4), pp. 254-257, Database CA, Chemical Abstracts Service, XP002459096, Abstract.
Zhang et al., "Synthesis and platelet aggregation inhibitory activity of pyridazinones.", Zhongguo Yaowu Huaxua Zazhi, 1994, 4(3), pp. 162-70, Database CA, Chemical Abstracts Service, XP002459097, Abstract.
Zhao et al., "Synthesis of 6-[4(4-substituted piperazyl)phenyl]-4,5-dihydro-3(2H)-pyridazinone derivatives by phase-transfer - catalysis.", Qufu Shifan Daxue XUebao, Ziran Kexueban, 2002, 28(4), pp. 94-96, Database CA, Chemical Abstracts Service, XP002459095, Abstract.

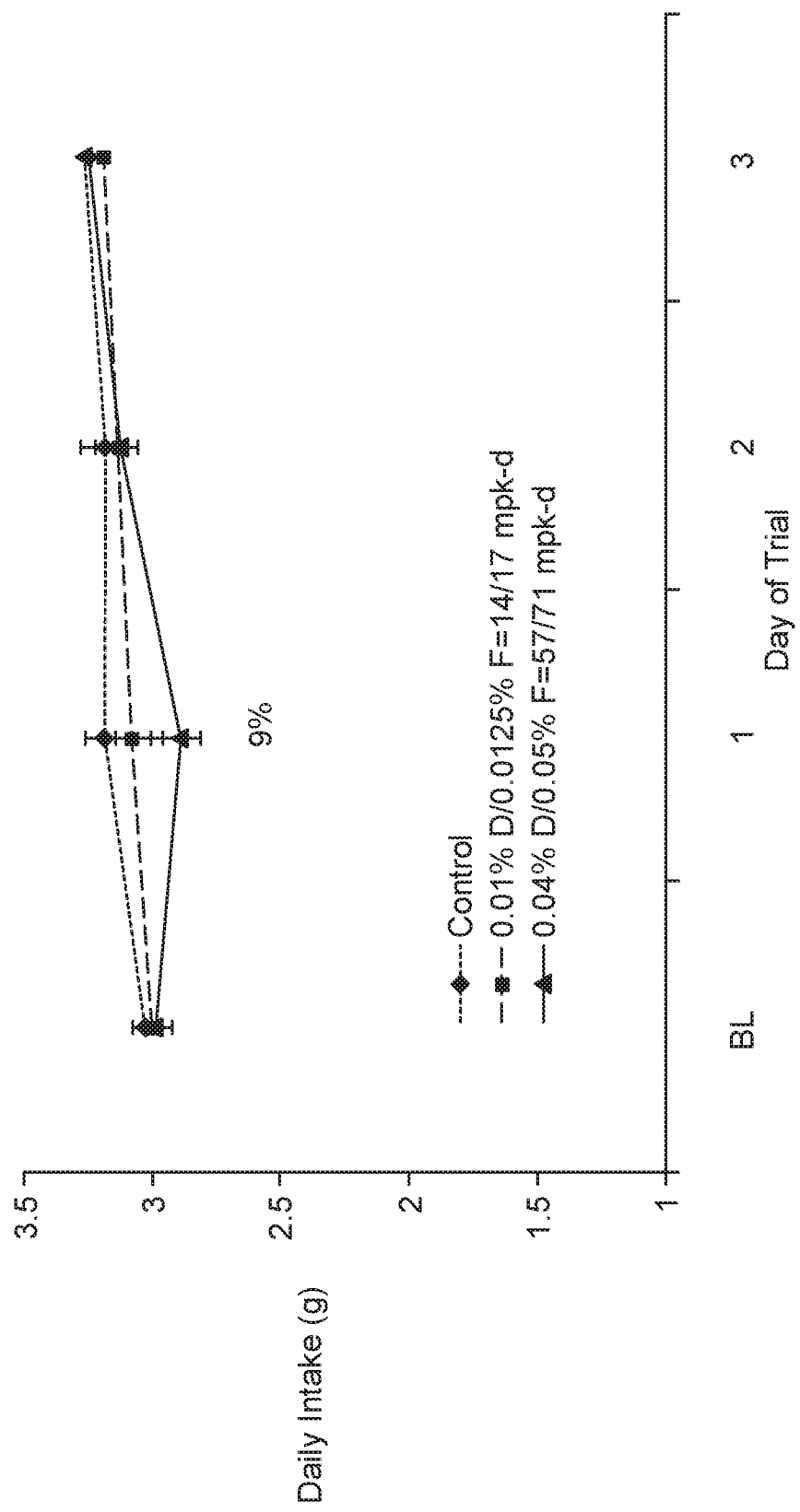

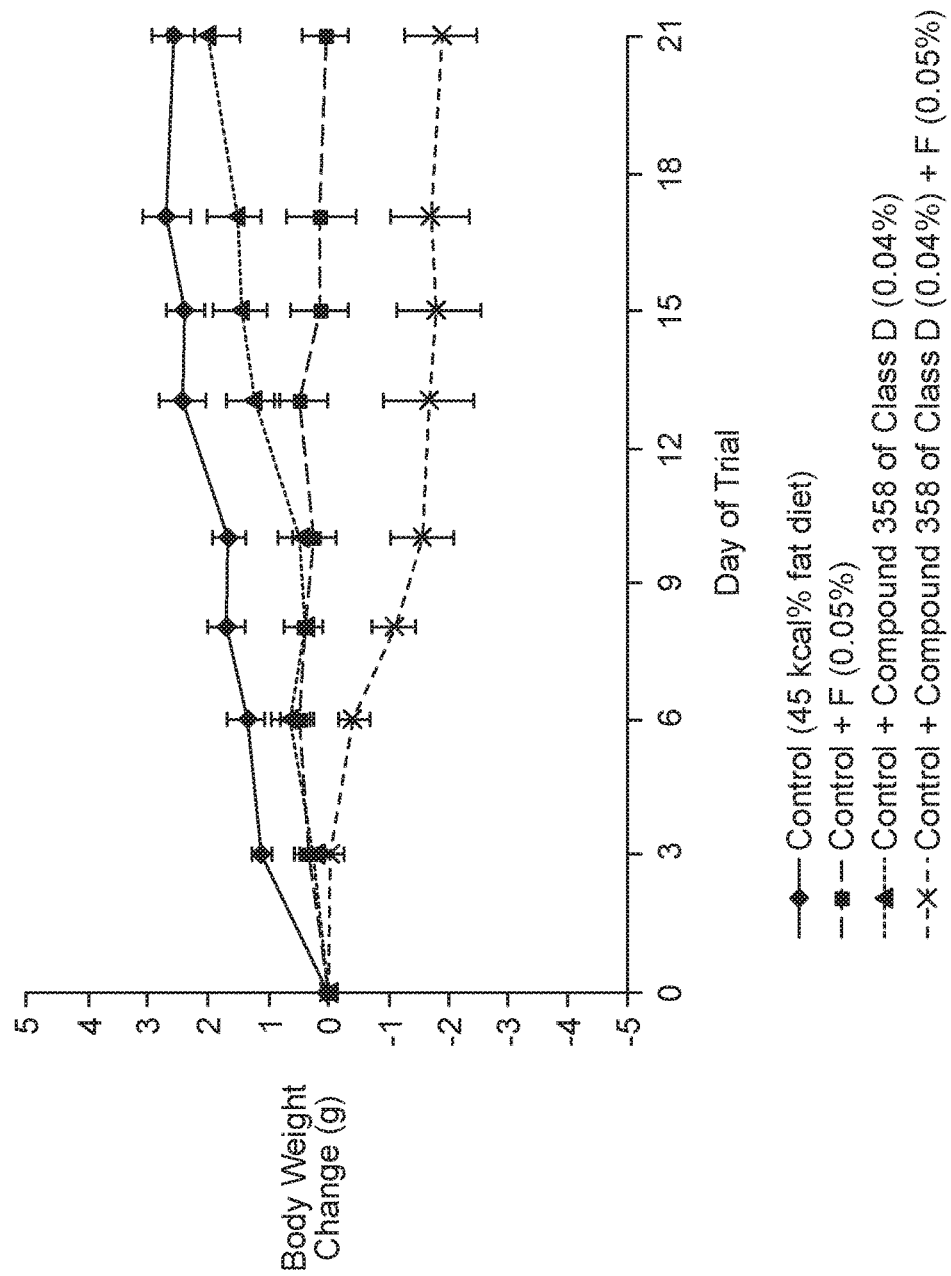

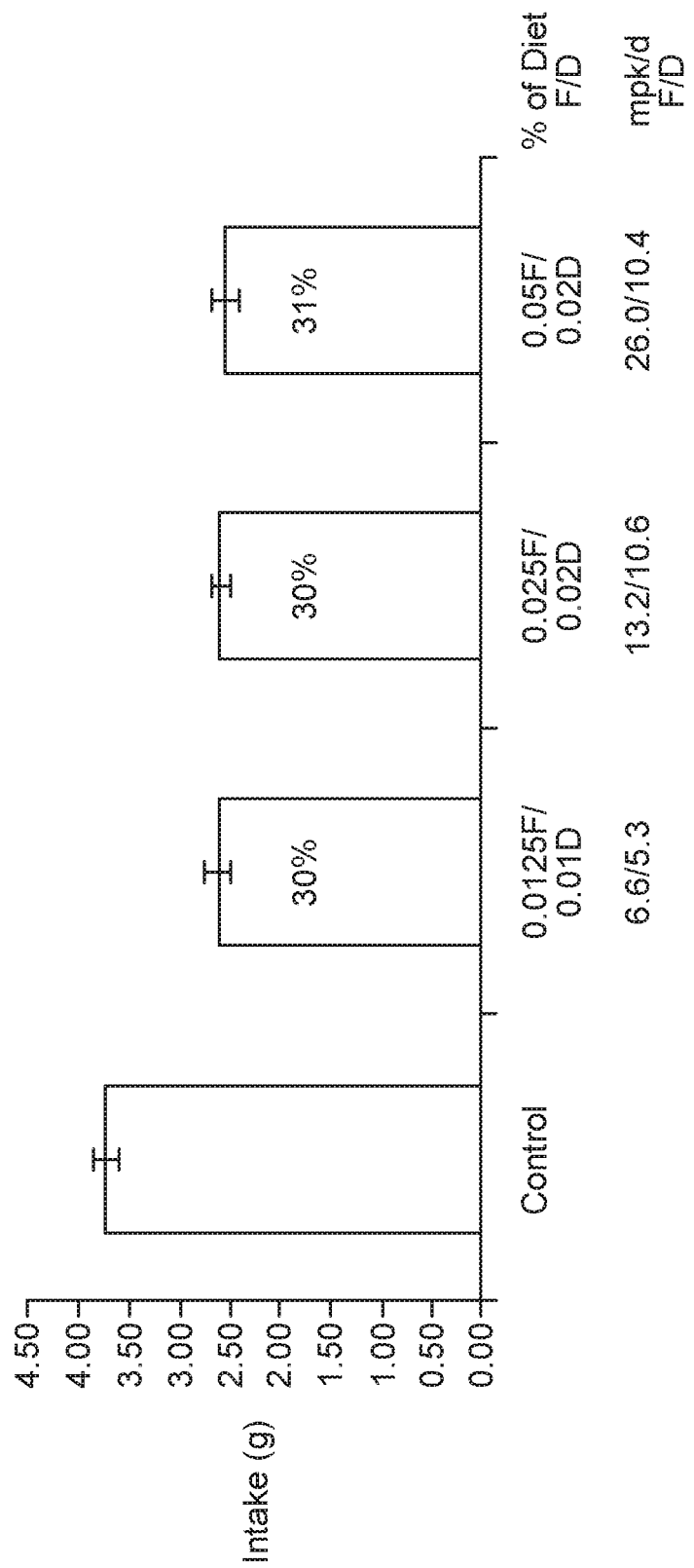

DRUG COMBINATIONS COMPRISING A DGAT INHIBITOR AND A PPAR-AGONIST

CROSS REFERENCE TO RELATED APPLICATIONS

This application a continuation application of U.S. patent application Ser. No. 12/993,491, filed Nov. 19, 2010, currently pending, the disclosure of which is hereby incorporated by reference, which is the U.S. national stage of Application No. PCT/EP2009/056800, filed Jun. 3, 2009, which application claims priority from PCT/EP2008/057060, filed Jun. 6, 2008; PCT/EP2008/057008, filed Jun. 5, 2008;PCT/EP/056983, filed Jun. 5, 2008; PCT/EP2008/057011, filed Jun. 5, 2008 and EP 08170780.4, filed Dec. 5, 2008.

FIELD OF THE INVENTION

This invention concerns novel drug combinations comprising an acyl CoA:diacylglycerol acyltransferase (DGAT) inhibitor, in particular a DGAT1 inhibitor, and a peroxisome proliferator-activated receptor (PPAR) agonist, in particular a PPAR-α agonist, pharmaceutical compositions comprising said novel drug combinations as active ingredients, as well as the use of said combinations as a medicament and for the manufacture of a medicament.

The present invention also concerns new piperidine/piperazine derivatives having DGAT inhibitory activity, in particular DGAT1 inhibitory activity. The invention further relates to methods for their preparation and pharmaceutical compositions comprising them. The invention also relates to the use of said compounds for the manufacture of a medicament for the prevention or the treatment of a disease mediated by DGAT, in particular DGAT 1.

BACKGROUND OF THE INVENTION

Triglycerides represent the major form of energy stored in eukaryotes. Disorders or imbalances in triglyceride metabolism are implicated in the pathogenesis of and increased risk for obesity, insulin resistance syndrome and type II diabetes, nonalcoholic fatty liver disease and coronary heart disease (see, Lewis, et al, *Endocrine Reviews* (2002) 23:201 and Malloy and Kane, *Adv. Intern. Med.* (2001) 47:11 1). Additionally, hypertriglyceridemia is often an adverse consequence of cancer therapy (see, Bast, et al. *Cancer Medicament,* 5th Ed., (2000) B.C. Decker, Hamilton, Ontario, Calif.).

A key enzyme in the synthesis of triglycerides is acyl CoA:diacylglycerol acyltransferase, or DGAT. DGAT is a microsomal enzyme that is widely expressed in mammalian tissues and that catalyzes the joining of 1,2-diacylglycerol (DAG) and fatty acyl CoA to form triglycerides (TG) at the endoplasmic reticulum (reviewed in Chen and Farese, *Trends Cardiovasc. Med.* (2000) 10: 188 and Farese, et al, *Curr. Opin. Lipidol.* (2000) 11:229). It was originally thought that DGAT uniquely controlled the catalysis of the final step of acylation of diacylglycerol to triglyceride in the two major pathways for triglyceride synthesis, the glycerol phosphate and monoacylglycerol pathways. Because triglycerides are considered essential for survival, and their synthesis was thought to occur through a single mechanism, inhibition of triglyceride synthesis through inhibiting the activity of DGAT has been largely unexplored.

Genes encoding mouse DGAT1 and the related human homologs ARGP1 (human DGAT1) and ARGP2 (human ACAT2) now have been cloned and characterized (Cases, et al, *Pro.c Nat.l Acad. Sci.* (1998) 95:13018; Oelkers, et al, *J. Biol. Chem.* (1998) 273:26765). The gene for mouse DGAT1 has been used to create DGAT knock-out mice to better elucidate the function of the DGAT gene.

Unexpectedly, mice unable to express a functional DGAT1 enzyme (Dgat1−/− mice) are viable and still able to synthesize triglycerides, indicating that multiple catalytic mechanisms contribute to triglyceride synthesis (Smith, et al, *Nature Genetics* (2000) 25:87). Other enzymes that catalyze triglyceride synthesis, for example, DGAT2 and diacylglycerol transacylase, also have been identified (Cases, et al, *J. Biol. Chem.* (2001) 276:38870). Gene knockout studies in mice have revealed that DGAT2 plays a fundamental role in mammalian triglyceride synthesis and is required for survival. DGAT2 deficient mice are lipopenic and die soon after birth, apparently from profound reductions in substrates for energy metabolism and from impaired permeability barrier function in the skin. (Farese, et al., *J. Biol. Chem.* (2004) 279: 11767).

Significantly, Dgat1−/− mice are resistant to diet-induced obesity and remain lean. Even when fed a high fat diet (21% fat) Dgat1−/− mice maintain weights comparable to mice fed a regular diet (4% fat) and have lower total body triglyceride levels. The obesity resistance in Dgat1−/− mice is not due to decreased caloric intake, but the result of increased energy expenditure and decreased resistance to insulin and leptin (Smith, et al, *Nature Genetics* (2000) 25:87; Chen and Farese, *Trends Cardiovasc. Med.* (2000) 10: 188; and Chen, et al, *J. Clin. Invest.* (2002) 109:1049). Additionally, Dgat1−/− mice have reduced rates of triglyceride absorption (Buhman, et al, *J. Biol. Chem.* (2002) 277:25474). In addition to improved triglyceride metabolism, Dgat1−/− mice also have improved glucose metabolism, with lower glucose and insulin levels following a glucose load, in comparison to wild-type mice (Chen and Farese, *Trends Cardiovasc. Med.* (2000) 10: 188).

The finding that multiple enzymes contribute to catalyzing the synthesis of triglyceride from diacylglycerol is significant, because it presents the opportunity to modulate one catalytic mechanism of this biochemical reaction to achieve therapeutic results in an individual with minimal adverse side effects. Compounds that inhibit the conversion of diacylglycerol to triglyceride, for instance by specifically inhibiting the activity of DGAT1, will find use in lowering corporeal concentrations and absorption of triglycerides to therapeutically counteract the pathogenic effects caused by abnormal metabolism of triglycerides in obesity, insulin resistance syndrome and overt type II diabetes, congestive heart failure and atherosclerosis, and as a consequence of cancer therapy.

Because of the ever increasing prevalence of obesity, type II diabetes, heart disease and cancer in societies throughout the world, there is a pressing need in developing new therapies to effectively treat and prevent these diseases. Therefore there is an interest in developing compounds that can potently and specifically inhibit the catalytic activity of DGAT, in particular DGAT1.

We have now unexpectedly found that novel compounds exhibiting DGAT inhibitory activity, in particular DGAT1 inhibitory activity, and these compounds can therefore be used to prevent or treat a disease associated with or mediated by DGAT, such as for example obesity, type II diabetes, heart disease and cancer. The compounds of the invention differ from the prior art compounds in structure, in their pharmacological activity, pharmacological potency, and/or pharmacological profile.

We have also unexpectedly found that DGAT inhibitors, including the DGAT inhibitors of the present invention, can be used to elevate the levels of one or more satiety hormones, in particular glucagon-like-peptide-1 (GLP-1) and therefore DGAT inhibitors, in particular DGAT1 inhibitors, can also be used to prevent or treat a disease which can benefit from elevated levels of a satiety hormone, in particular GLP-1. Glucagon-like peptide 1 (GLP-1) is an intestinal hormone which generally stimulates insulin secretion during hyperglycemia, suppresses glucagon secretion, stimulates (pro) insulin biosynthesis and decelerates gastric emptying and acid secretion. GLP-1 is secreted from L cells in the small and large bowel following the ingestion of fat and proteins. GLP-1 has been suggested, among other indications, as a possible therapeutic agent for the management of type II non-insulin-dependent diabetes mellitus as well as related metabolic disorders, such as obesity.

The present novel compounds make it possible to treat a disease which can benefit from elevated levels of GLP-1 with small molecules (compared to large molecules such as proteins or protein-like compounds, e.g. GLP-1 analogues).

The peroxisome proliferator-activated receptors (PPAR) belong to the steroid hormone nuclear receptor superfamily of ligand-activated transcription factors that mediate the specific effects of small lipophilic compounds, such as steroids, retinoids and fatty acids, on DNA transcription. They play an important role in the regulation of lipid metabolism, in the regulation of energy homeostasis, inflammation, artherosclerosis and glucose control. Three subtypes are identified so far, namely PPAR-α, PPAR-β/δ and PPAR-γ. The three isoforms exhibit different tissue distribution as well as different ligand specificities.

PPAR-α plays a crucial role in the intracellular lipid metabolism. The PPAR-α subtype is mainly expressed in tissues with elevated mitochondrial and peroxisomal fatty acid β-oxidation rates, that efficiently harvest energy from lipids, including liver, skeletal muscle, heart muscle, proximal tubular epithelial cells of the kidney, and brown fat (brown adipose tissue). PPAR-α is also present in cells of the arterial wall, in monocytes/macrophages, smooth muscle cells, endothelial cells, in hepatocytes, and in cardiac myocytes.

Saturated and unsaturated fatty acids are found to be the primary natural PPAR-α ligands. In general, PPAR-α can be activated by a heterogeneous group of compounds, which include natural and synthetic agonists, such as eicosanoids, leukotriene β$_4$, carbaprostacyclin, nonsteroidal anti-inflammatory drugs, pirinixic acid (WY-14643; PPAR-α/γ agonist), phthalate ester plasticizers, pterostilbene, fibrates or active metabolites thereof, α-substituted phenyl-propanoic acid derivatives and isoxazolyl-serine-based compounds. Finally, PPAR-α is induced by glucocorticoids in response to stress and follows a diurnal rhythm.

Fibrates or active metabolites thereof such as fibric acid derivatives, are PPAR-α agonists, and have been used to treat dyslipidemia for several decades because of their triglyceride lowering and high-density lipoprotein (HDL) cholesterol elevating effects. Fibric acid derivatives lower the levels of triglyceride-rich lipoproteins, such as very low-density lipoproteins (VLDL), raise HDL levels, and have variable effect on low-density lipoproteins (LDL) levels. The effects on VLDL levels appear to result primarily from an increase in lipoprotein lipase activity, especially in muscle. This leads to enhanced hydrolysis of VLDL triglyceride content and an enhanced VLDL catabolism. Fibric acid agents also may alter the composition of the VLDL, for example, by decreasing hepatic production of apoC-III, an inhibitor of lipoprotein lipase activity. These compounds are also reported to decrease hepatic VLDL triglyceride synthesis, possibly by inhibiting fatty acid synthesis and by promoting fatty acid oxidation. In addition, they have been documented to be beneficial in the prevention of ischemic heart disease in individuals with dyslipidemia and they can also modestly decrease elevated fibrinogen and PAI-1 levels. Well-known examples of fibrates are fenofibrate (fenofibric acid as active metabolite), ABT-335 (which is the choline salt of fenofibric acid), bezafibrate, clofibrate, ciprofibrate, etofibrate, pirifibrate, beclofibrate and gemfibrozil (PPAR-α modulator).

Because of the ever increasing prevalence of obesity, type II diabetes, heart disease and cancer in societies throughout the world, there is a pressing need in developing new therapies to effectively treat and prevent these diseases.

We have now unexpectedly found that the combination of a compound showing DGAT inhibitory activity, in particular DGAT1 inhibitory activity, with a PPAR agonist, in particular a PPAR-α agonist, may exhibit an increased and/or accelerated effect on weight loss, compared to the effect of the DGAT inhibitor or the PPAR agonist each separately, and additional can decrease food intake. The combinations of the present invention may show synergy compared to administration of the composing ingredients alone.

BACKGROUND PRIOR ART

WO 2006/034441 discloses heterocyclic derivatives and their use as stearoyl CoA desaturase inhibitors (SCD-1 inhibitors).

WO 2006/086445 relates to a combination therapy of a SCD-1 inhibitor and another drug to treat adverse weight gain.

WO 2006/004200 and JP2007131584 relate to urea and amino derivatives having DGAT inhibitory activity.

WO 2004/047755 relates to fused bicyclic nitrogen-containing heterocycles having DGAT inhibitory activity.

WO2005/072740 relates to an anorectic action of a compound having DGAT inhibitory activity.

WO 2007/071966 discloses a conjoint treatment of pyrimido-[4,5-B]-oxazines showing DGAT inhibitory activity together with anti-dyslipidaemia agents such as PPAR-α agonists.

WO2008/148851, WO2008/148840, WO2008/148849 and WO2008/148868 concern piperidine/piperazine derivatives having DGAT inhibitory activity.

DESCRIPTION OF THE DRAWINGS

FIG. 1D shows food intake of lean C57BL/6 mice fed a low-fat diet containing compound 223 of Class D (D) and fenofibrate (F).

FIG. 2C shows the change in body weight (g) of DIO C57BL/6 mice fed with a high-fat diet containing DGAT inhibitor (compound 358 of Class D), fenofibrate or both.

FIG. 3A shows food intake on day 1 of DIO C57BL/6 mice fed with a high-fat diet containing compound 223 of Class D and fenofibrate (D+F).

DESCRIPTION OF THE INVENTION

Figure 1A:
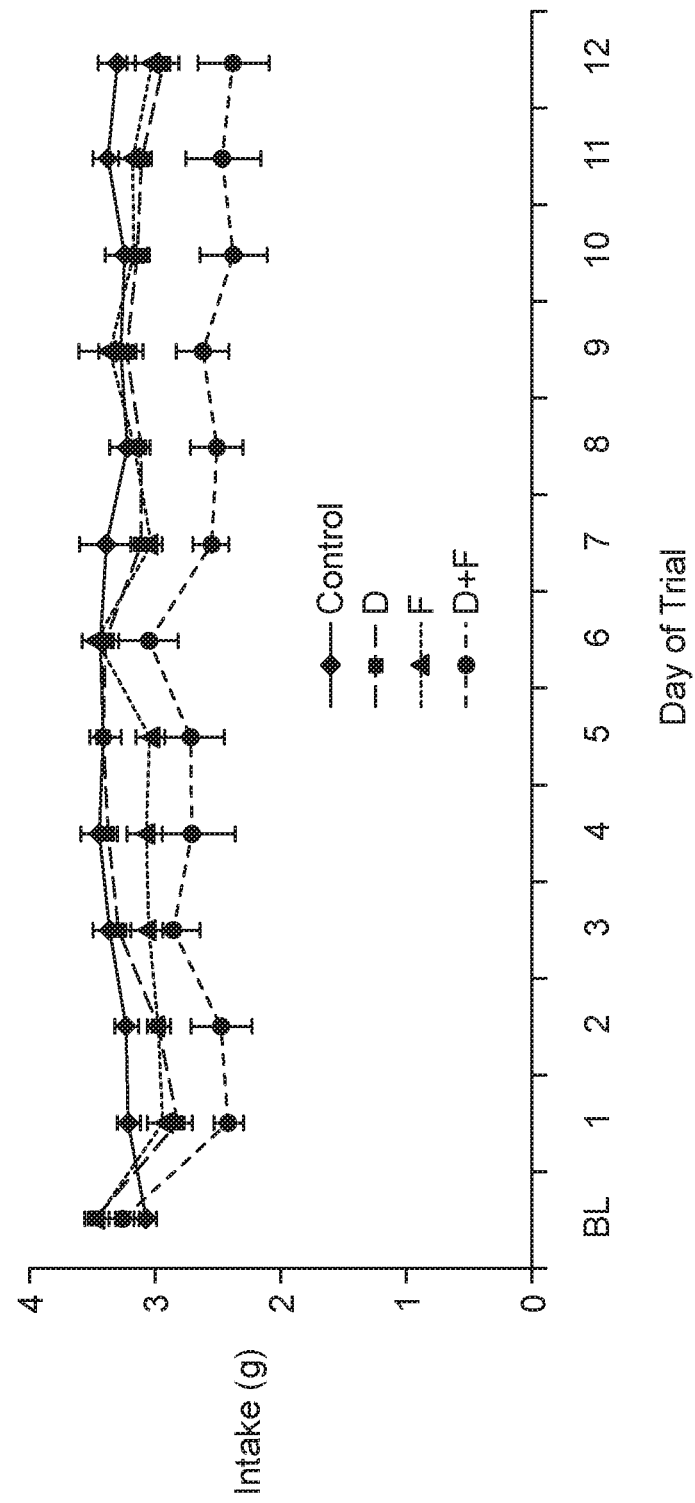
FIG. 1A shows the food intake of mice treated with a DGAT inhibitor (compound 223 of Class D—called D in FIG. 1A), fenofibrate (F) or both, compared to the control group. 'BL' means baseline food intake.
Figure 1B:
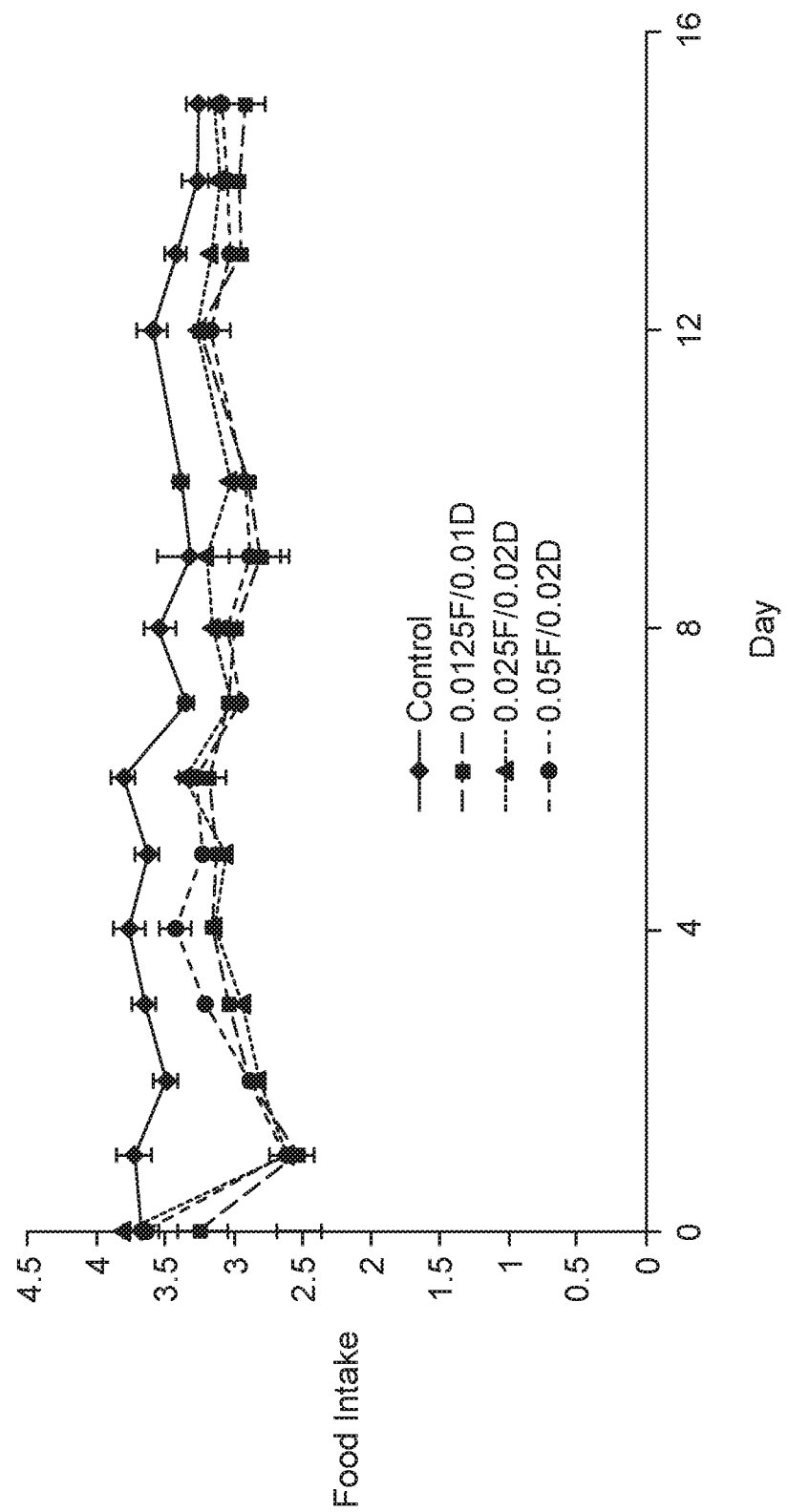
FIG. 1B shows the food intake of DIO C57BL/6 mice fed with a high-fat diet containing fenofibrate (F) and compound 223 of Class D (D).
Figure 1C:
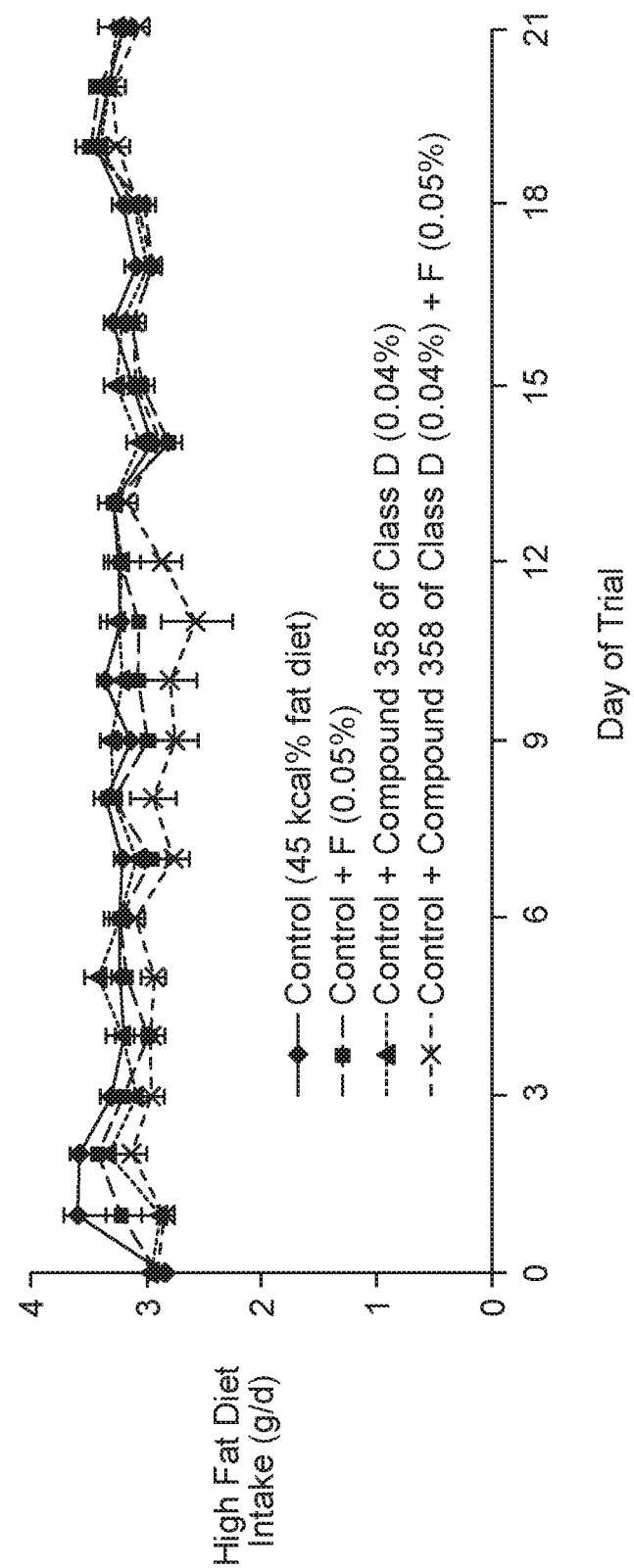
FIG. 1C shows the high fat diet intake (g) of DIO C57BL/6 mice treated with a DGAT inhibitor (compound 358 of Class D), fenofibrate (F) or both, compared to the control group.
Figure 2A:
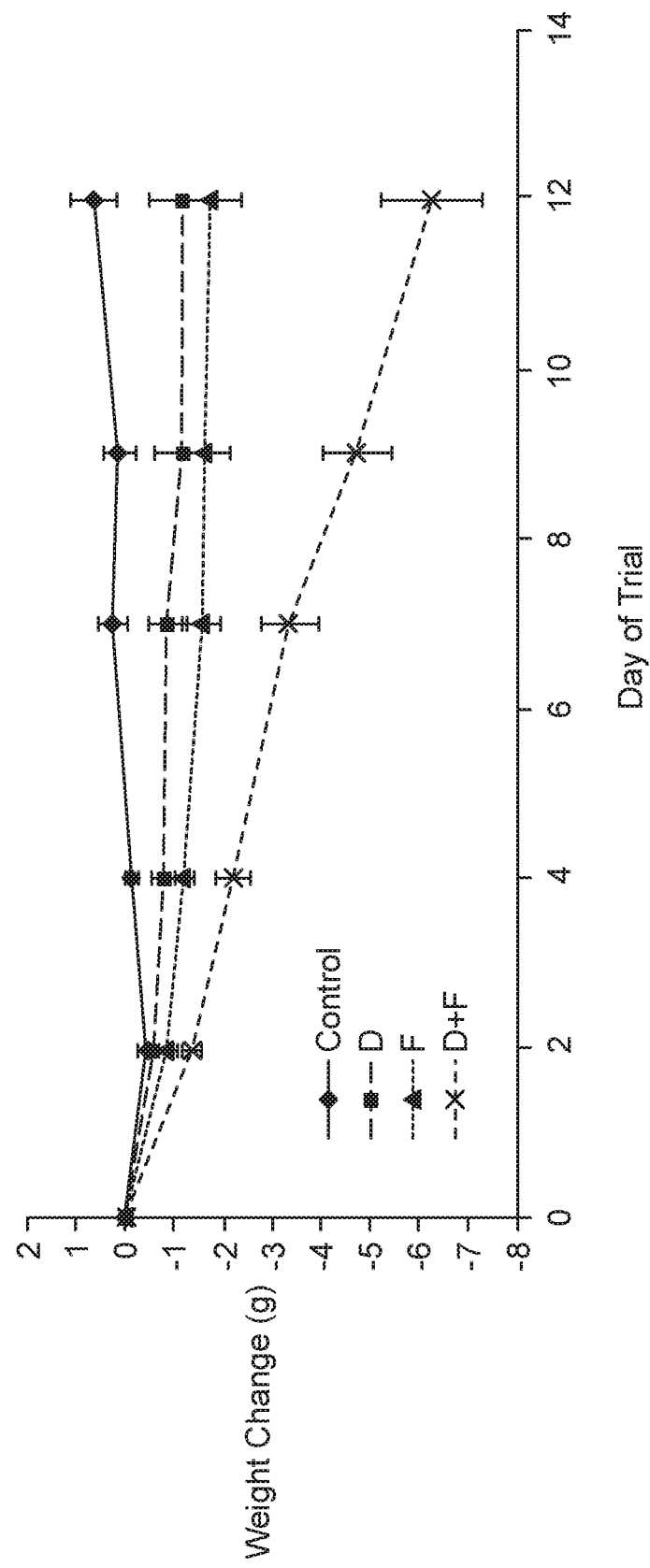
FIG. 2A shows the change in body weight (g) of DIO C57BL/6 mice treated with a DGAT inhibitor (compound 223 of Class D—25 mpk/d), fenofibrate (31 mpk/d) or both.
Figure 2B:
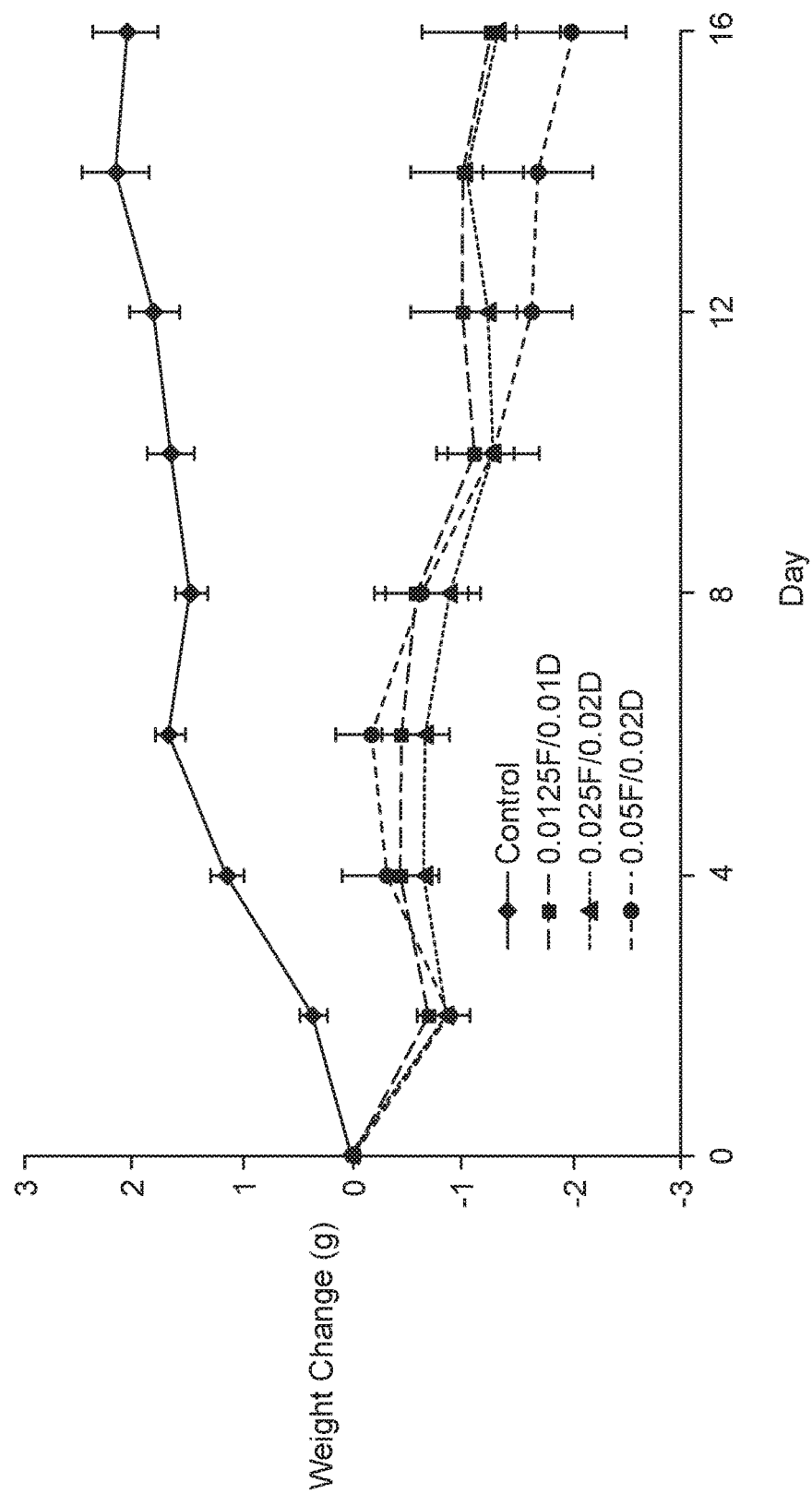
FIG. 2B shows the body weight change of DIO C57BL/6 mice fed with a high-fat diet containing fenofibrate (F) and compound 223 of Class D (D).
Figure 2D:
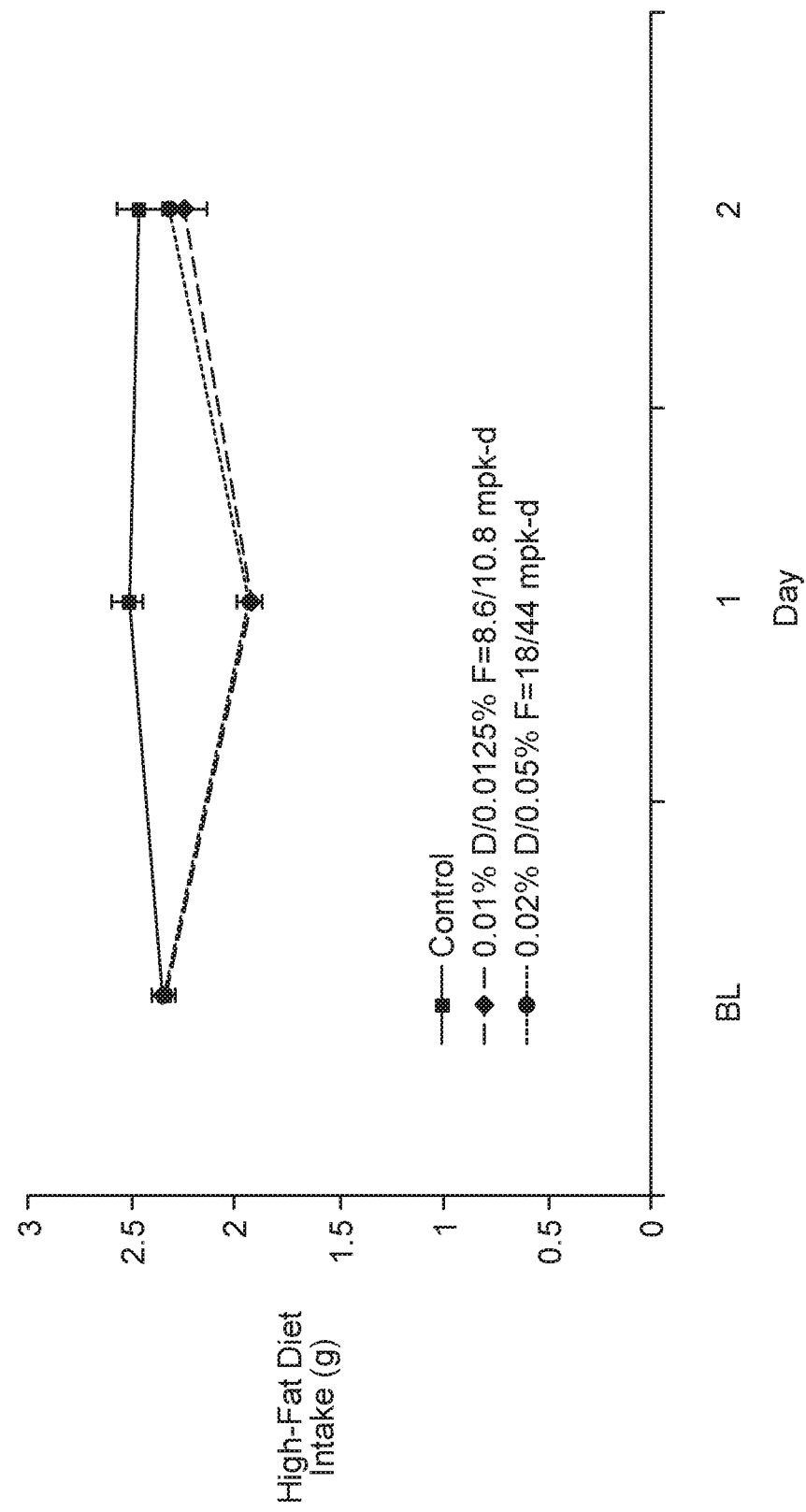
FIG. 2D shows food intake of lean C57BL/6 mice fed a high-fat diet containing compound 223 of Class D (D) and fenofibrate (F).
Figure 3B:
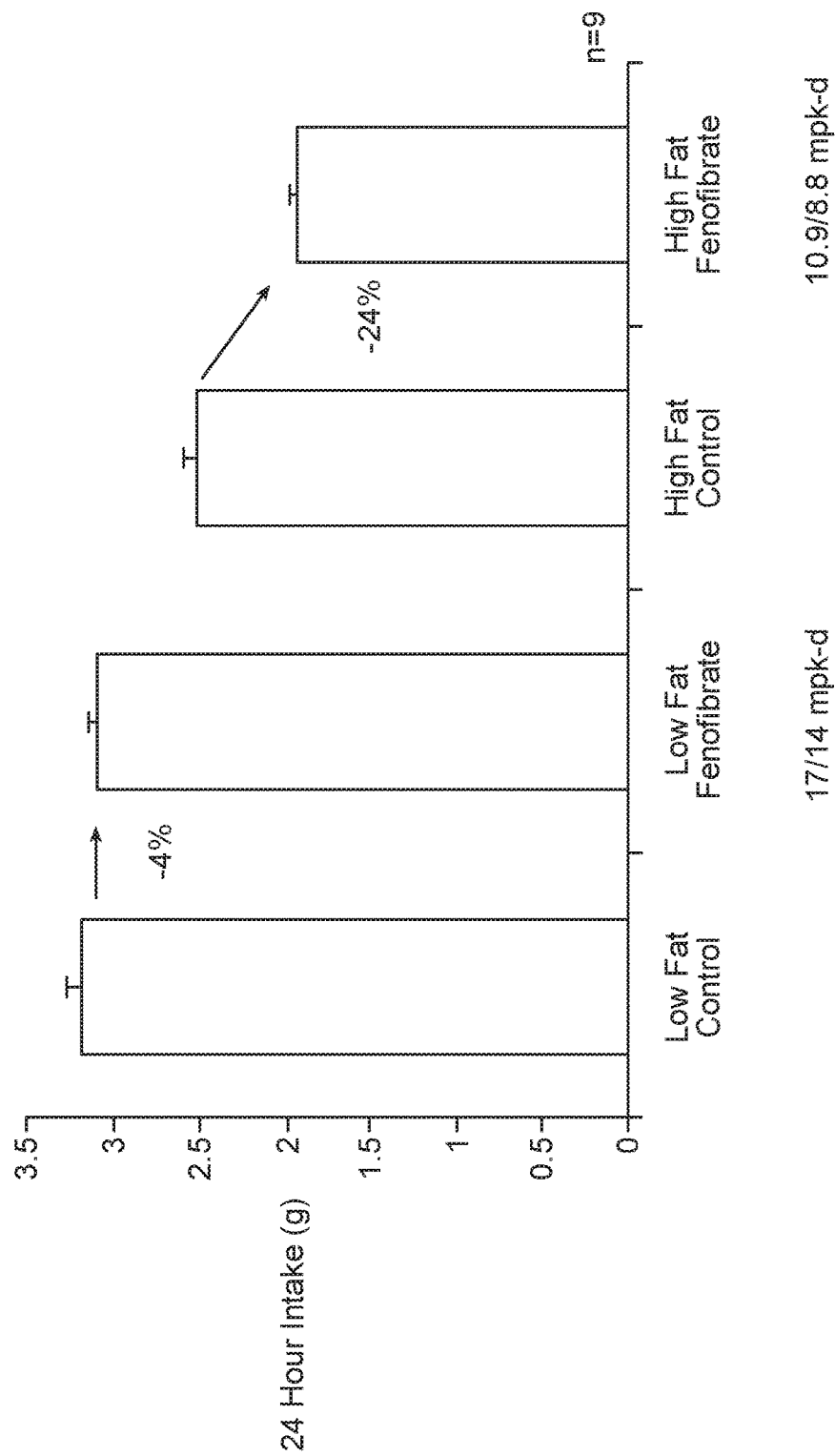
FIG. 3B shows day-1 food intake of mice fed a low and high-fat diet containing 0.01/0.0125% w/w compound 223 of Class D/fenofibrate (D/F). DIO C57BL/6 mice were acclimated to cages designed for measuring food intake. After adaptation to either a low-fat (10 kcal % fat) or high-fat (45 kcal % fat) diet, mice were switched to a diet with the same fat content (10 kcal % and 45 kcal % fat respectively), but supplemented with 0.01/0.0125% w/w D/F.

The present invention relates to combinations of a DGAT inhibitor and a peroxisome proliferator-activator receptor (PPAR) agonist or a prodrug thereof.

In an embodiment, the present invention relates to combinations of a DGAT inhibitor and a PPAR-α agonist or a prodrug thereof.

In an embodiment, the present invention relates to combinations of a DGAT1 inhibitor and a PPAR agonist or a prodrug thereof.

In an embodiment, the present invention relates to combinations of a DGAT1 inhibitor and a PPAR-α agonist or a prodrug thereof.

In an embodiment, the present invention relates to combinations of a DGAT inhibitor, in particular a DGAT1 inhibitor, and a PPAR-α agonist or a prodrug thereof selected from the group of fibrates.

In an embodiment, the present invention relates to combinations of a DGAT inhibitor, in particular a DGAT1 inhibitor, and fenofibrate.

In an embodiment, the present invention relates to combinations of a PPAR agonist or a prodrug thereof and a DGAT inhibitor wherein the DGAT inhibitor is selected from a) a compound having the formula

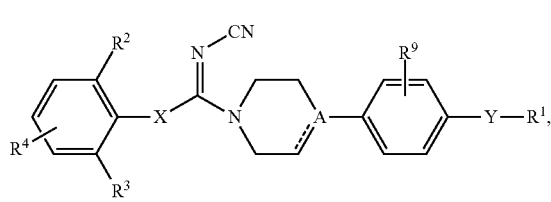

(I)

including any stereochemically isomeric form thereof, wherein

A represents CH or N;

X represents O or $NR^x$;

the dotted line represents an optional bond in case A represents a carbon atom;

Y represents a direct bond; $—NR^x—C(=O)—$; $—C(=O)—NR^x—$; $—NR^x—C(=O)—Z—$; $—NR^x—C(=O)—Z—NR^y—$; $—NR^x—C(=O)—Z—NR^y—C(=O)—$; $—NR^x—C(=O)—Z—NR^y—C(=O)—O—$; $—NR^x—C(=O)—Z—O—$; $—NR^x—C(=O)—Z—O—C(=O)—$; $—NR^x—C(=O)—Z—C(=O)—$; $—NR^x—C(=O)—Z—C(=O)—O—$; $—NR^x—C(=O)—O—Z—C(=O)—$; $—NR^x—C(=O)—O—Z—C(=O)—O—$; $—NR^x—C(=O)—O—Z—O—C(=O)—$; $—NR^x—C(=O)—Z—C(=O)—NR^y—$; $—NR^x—C(=O)—Z—NR^y—C(=O)—NR^y—$; $—C(=O)—Z—$; $—C(=O)—Z—O—$; $—C(=O)—NR^x—Z—$; $—C(=O)—NR^x—Z—O—$; $—C(=O)—NR^x—Z—C(=O)—O—$; $—C(=O)—NR^x—Z—O—C(=O)—$; $—C(=O)—NR^x—O—Z—$; $—C(=O)—NR^x—Z—NR^y—$; $—C(=O)—NR^x—Z—NR^y—C(=O)—$; $—C(=O)—NR^x—Z—NR^y—C(=O)—O—$;

Z represents a bivalent radical selected from $C_{1-6}$alkanediyl, $C_{2-6}$alkenediyl or $C_{2-6}$ alkynediyl; wherein each of said $C_{1-6}$alkanediyl, $C_{2-6}$alkenediyl or $C_{2-6}$alkynediyl may optionally be substituted with $C_{1-4}$alkyloxy, $C_{1-4}$alkylthio, hydroxyl, cyano or aryl; and wherein two hydrogen atoms attached to the same carbon atom in the definition of Z may optionally be replaced by $C_{1-6}$alkanediyl;

$R^x$ represents hydrogen or $C_{1-4}$alkyl;

$R^y$ represents hydrogen; $C_{1-4}$alkyl optionally substituted with $C_{3-6}$cycloalkyl or aryl or Het; $C_{2-4}$alkenyl; or $—S(=O)_p$-aryl;

$R^1$ represents $C_{1-12}$alkyl optionally substituted with cyano, $C_{1-4}$alkyloxy, $C_{1-4}$alkyl-oxy$C_{1-4}$alkyloxy, $C_{3-6}$cycloalkyl or aryl; $C_{2-6}$alkenyl; $C_{2-6}$alkynyl; $C_{3-6}$cycloalkyl; $aryl^1$; $aryl^1C_{1-6}$alkyl; $Het^1$; or $Het^1C_{1-6}$alkyl; provided that when Y represents $—NR^x—C(=O)—Z—$; $—NR^x—C(=O)—Z—NR^y$; $—NR^x—C(=O)—Z—C(=O)—NR^y—$; $—C(=O)—Z—$; $—NR^x—C(=O)—Z—NR^y—C(=O)—NR^y—$; $—C(=O)—NR^x—Z—$; $—C(=O)—NR^x—O—Z—$; or $—C(=O)—NR^x—Z—NR^y—$; then $R^1$ may also represent hydrogen;

$R^2$ and $R^3$ each independently represent hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono-or di($C_{1-4}$alkyl)aminocarbonyl; $C_{1-6}$alkylcarbonyl; nitro; amino; mono-or di($C_{1-4}$alkyl)amino; $—S(=O)_p—C_{1-4}$alkyl;

$R^4$ represents hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono-or di($C_{1-4}$alkyl)amino; $C_{1-4}$alkylcarbonylamino; $—S(=O)_p—C_{1-4}$alkyl; $R^6R^5N—C(=O)—$; $R^6R^5N—C_{1-4}$alkyl; $C_{3-6}$cycloalkyl; aryl; aryloxy; aryl$C_{1-4}$alkyl; aryl-C(=O)—$C_{1-4}$alkyl; aryl-C(=O)—$; Het; Het$C_{1-4}$alkyl; Het-C(=O)—$C_{1-4}$alkyl; Het-C(=O)—$; Het-O—$;

$R^5$ represents hydrogen; $C_{1-4}$alkyl optionally substituted with hydroxyl or $C_{1-4}$alkyloxy; $R^8R^7N—C_{1-4}$alkyl; $C_{1-4}$alkyloxy; Het; aryl; $R^8R^7N—C(=O)—C_{1-4}$alkyl;

$R^6$ represents hydrogen or $C_{1-4}$alkyl;

$R^7$ represents hydrogen; $C_{1-4}$alkyl; $C_{1-4}$alkylcarbonyl;

$R^8$ represents hydrogen or $C_{1-4}$alkyl; or $R^7$ and $R^8$ may be taken together with the nitrogen to which they are attached to form a saturated monocyclic 5, 6 or 7-membered heterocycle which may further contain one or more heteroatoms each independently selected from O, S, $S(=O)_p$ or N; and which heterocycle may optionally be substituted with $C_{1-4}$alkyl;

$R^9$ represents hydrogen, halo, $C_{1-4}$alkyl, $C_{1-4}$alkyl substituted with hydroxyl;

aryl represents phenyl or phenyl substituted with at least one substituent, in particular one, two, three, four or five substituents, each substituent independently being selected from hydroxyl; carboxyl; halo; $C_{1-6}$alkyl optionally substituted with $C_{1-4}$alkyloxy, amino or mono-or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono-or di($C_{1-4}$alkyl)aminocarbonyl; $C_{1-6}$alkylcarbonyl; nitro; amino; mono-or di($C_{1-4}$alkyl)amino; $-S(=O)_p-C_{1-4}$alkyl;

aryl$^1$ represents phenyl, naphthalenyl or fluorenyl; each of said phenyl, naphthalenyl or fluorenyl optionally substituted with at least one substituent, in particular one, two, three, four or five substituents, each substituent independently being selected from hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)aminocarbonyl; $C_{1-6}$alkylcarbonyl; amino; mono-or di($C_{1-4}$alkyl)amino; $R^6R^5N-C_{1-6}$alkyl; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; Het$C_{1-4}$alkyl-NR$^x$—; $-S(=O)_p-C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; aryl-C(=O)—$C_{1-4}$alkyl; Het; Het$C_{1-4}$alkyl; Het-C(=O)—; Het-C(=O)—$C_{1-4}$alkyl; Het-O—;

Het represents a monocyclic non-aromatic or aromatic heterocycle containing at least one heteroatom each independently selected from O, S, $S(=O)_p$ or N; or a bicyclic or tricyclic non-aromatic or aromatic heterocycle containing at least one heteroatom each independently selected from O, S, $S(=O)_p$ or N; said monocyclic heterocycle or said bi-or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with $C_{1-4}$alkyloxy, amino or mono-or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono-or di($C_{1-4}$alkyl)aminocarbonyl; $C_{1-6}$alkylcarbonyl; nitro; amino; mono-or di($C_{1-4}$alkyl)amino; $-S(=O)_p-C_{1-4}$alkyl;

Het$^1$ represents a monocyclic non-aromatic or aromatic heterocycle containing at least one heteroatom each independently selected from O, S, $S(=O)_p$ or N; or a bicyclic or tricyclic non-aromatic or aromatic heterocycle containing at least one heteroatom each independently selected from O, S, $S(=O)_p$ or N; said monocyclic heterocycle or said bi-or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)aminocarbonyl; $C_{1-6}$alkylcarbonyl; amino; mono-or di($C_{1-6}$alkyl)amino; $R^6R^5N-C_{1-6}$alkyl; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; Het$C_{1-4}$alkyl-NR$^x$—; $-S(=O)_p-C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; aryl-C(=O)—$C_{1-4}$alkyl; Het; Het$C_{1-4}$alkyl; Het-C(=O)—; Het-C(=O)—$C_{1-4}$alkyl; Het-O—;

p represents 1 or 2;

a N-oxide thereof, a pharmaceutically acceptable salt thereof or a solvate thereof;

b) a compound having the formula

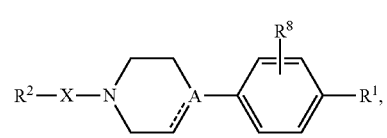

(I)

including any stereochemically isomeric form thereof, wherein

A represents CH or N;

the dotted line represents an optional bond in case A represents a carbon atom;

X represents —NR$^x$—C(=O)—; —Z—C(=O)—; —Z—NR$^x$—C(=O)—; —S(=O)p-; C(=S)—; —NR$^x$—C(=S)—; —Z—C(=S)—; —Z—NR$^x$—C(=S)—; —O—C(=O)—; —C(=O)—C(=O)—;

Z represents a bivalent radical selected from $C_{1-6}$alkanediyl, $C_{2-6}$alkenediyl or $C_{2-6}$alkynediyl; wherein each of said $C_{1-6}$alkanediyl, $C_{2-6}$alkenediyl or $C_{2-6}$alkynediyl may optionally be substituted with hydroxyl or amino; and wherein two hydrogen atoms attached to the same carbon atom in $C_{1-6}$alkanediyl may optionally be replaced by $C_{1-6}$alkanediyl;

R$^x$ represents hydrogen or $C_{1-4}$alkyl;

R$^1$ represents a 5-membered monocyclic heterocycle containing at least 2 heteroatoms; a 6-membered aromatic monocyclic heterocycle; or a 5-membered heterocycle containing at least 2 heteroatoms fused with phenyl, cyclohexyl or a 5-or 6-membered heterocycle; wherein each of said heterocycles may optionally be substituted with at least one substituent, in particular one, two, three, four or five substituents, each substituent independently being selected from hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)-aminocarbonyl; $C_{1-6}$alkylcarbonyl; amino; mono-or di($C_{1-4}$alkyl)amino; $R^5R^4N-C_{1-6}$alkyl; $C_{3-6}$cycloalkyl-NR$^x$—; aryl-NR$^x$—; Het-NR$^x$—; $C_{3-6}$cycloalkyl-$C_{1-4}$alkyl-NR$^x$—; aryl$C_{1-4}$alkyl-NR$^x$—; Het$C_{1-4}$alkyl-NR$^x$—; $-S(=O)_p-C_{1-4}$alkyl; $C_{3-6}$cycloalkyl; $C_{3-6}$cycloalkyl$C_{1-4}$alkyl; $C_{3-6}$cycloalkyl-C (=O)—; aryl; aryloxy; arylC$_{1-4}$alkyl; aryl-C(=O)—; aryl-C(=O)—C$_{1-4}$alkyl; Het; HetC$_{1-4}$alkyl; Het-C(=O)—; Het-C(=O)—C$_{1-4}$alkyl; Het-O—;

R$^2$ represents R$^3$;

R$^3$ represents C$_{3-6}$cycloalkyl, phenyl, naphtalenyl, 2,3-dihydro-1,4-benzodioxinyl, 1,3-benzodioxolyl, 2,3-dihydrobenzofuranyl or a 6-membered aromatic heterocycle containing 1 or 2 N atoms, wherein said C$_{3-6}$cycloalkyl, phenyl, naphtalenyl, 2,3-dihydro-1,4-benzodioxinyl, 1,3-benzodioxolyl, 2,3-dihydrobenzofuranyl or 6-membered aromatic heterocycle may optionally be substituted with at least one substituent, in particular one, two, three, four or five substituents, each substituent independently selected from hydroxyl; carboxyl; halo; C$_{1-6}$alkyl optionally substituted with hydroxy; polyhaloC$_{1-6}$alkyl; C$_{1-6}$alkyloxy optionally substituted with C$_{1-4}$alkyloxy; C$_{1-6}$alkylthio; polyhalo-C$_{1-6}$alkyloxy; C$_{1-6}$alkyloxycarbonyl wherein C$_{1-6}$alkyl may optionally be substituted with aryl; cyano; C$_{1-6}$alkylcarbonyl; nitro; amino; mono- or di(C$_{1-4}$alkyl)amino; C$_{1-4}$alkylcarbonylamino; —S(=O)$_p$—C$_{1-4}$alkyl; R$^5$R$^4$N—C(=O)—; R$^5$R$^4$N—C$_{1-6}$alkyl; C$_{3-6}$cycloalkyl; C$_{3-6}$cycloalkylC$_{1-4}$alkyl; C$_{3-6}$cycloalkyl-C(=O)—; aryl; aryloxy; arylC$_{1-4}$alkyl; aryl-C(=O)—C$_{1-4}$alkyl; aryl-C(=O)—; Het; HetC$_{1-4}$alkyl; Het-C(=O)—C$_{1-4}$alkyl; Het-C(=O)—; Het-O—;

R$^4$ represents hydrogen; C$_{1-4}$alkyl optionally substituted with hydroxyl or C$_{1-4}$alkyloxy; R$^7$R$^6$N—C$_{1-4}$alkyl; C$_{1-4}$alkyloxy; Het; aryl; R$^7$R$^6$N—C(=O)—C$_{1-4}$alkyl;

R$^5$ represents hydrogen or C$_{1-4}$alkyl;

R$^6$ represents hydrogen; C$_{1-4}$alkyl; C$_{1-4}$alkylcarbonyl;

R$^7$ represents hydrogen or C$_{1-4}$alkyl; or

R$^6$ and R$^7$ may be taken together with the nitrogen to which they are attached to form a saturated monocyclic 5, 6 or 7-membered heterocycle which may further contain one or more heteroatoms selected from O, S, S(=O)$_p$ or N; and which heterocycle may optionally be substituted with C$_{1-4}$alkyl;

R$^8$ represents hydrogen, halo, C$_{1-4}$alkyl, C$_{1-4}$alkyl substituted with hydroxyl;

aryl represents phenyl or phenyl substituted with at least one substituent, in particular one, two, three, four or five substituents, each substituent independently being selected from hydroxyl; carboxyl; halo; C$_{1-6}$alkyl optionally substituted with C$_{1-4}$alkyloxy, amino or mono- or di(C$_{1-4}$alkyl)amino; polyhaloC$_{1-6}$alkyl; C$_{1-6}$alkyloxy optionally substituted with C$_{1-4}$alkyloxy; C$_{1-6}$alkylthio; polyhaloC$_{1-6}$alkyloxy; C$_{1-6}$alkyloxycarbonyl; cyano; C$_{1-6}$alkylaminocarbonyl; mono- or di(C$_{1-4}$alkyl)aminocarbonyl; C$_{1-6}$alkylcarbonyl; nitro; amino; mono- or di(C$_{1-4}$alkyl)amino; —S(=O)$_p$—C$_{1-4}$alkyl;

Het represents a monocyclic non-aromatic or aromatic heterocycle containing at least one heteroatom selected from O, S, S(=O)$_p$ or N; or a bicyclic or tricyclic non-aromatic or aromatic heterocycle containing at least one heteroatom selected from O, S, S(=O)$_p$ or N; said monocyclic heterocycle or said bi-or tricyclic heterocycle optionally being substituted with at least one substituent, in particular one, two, three, four or five substituents, each substituent independently being selected from hydroxyl; oxo; carboxyl; halo; C$_{1-6}$alkyl optionally substituted with C$_{1-4}$alkyloxy, amino or mono- or di(C$_{1-4}$alkyl)amino; polyhaloC$_{1-6}$alkyl; C$_{1-6}$alkyloxy optionally substituted with C$_{1-4}$alkyloxy; C$_{1-6}$alkylthio; polyhaloC$_{1-6}$alkyloxy; C$_{1-6}$alkyl-oxycarbonyl; cyano; aminocarbonyl; mono-or di(C$_{1-4}$alkyl)aminocarbonyl; C$_{1-6}$alkylcarbonyl; nitro; amino; mono-or di(C$_{1-4}$alkyl)amino; —S(=O)$_p$—C$_{1-4}$alkyl p represents 1 or 2;

a N-oxide thereof, a pharmaceutically acceptable salt thereof or a solvate thereof;

c) a compound having the formula

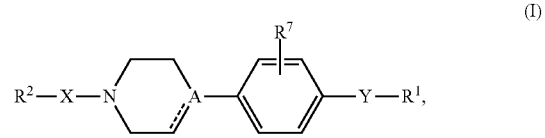

including any stereochemically isomeric form thereof, wherein

A represents CH or N;

the dotted line represents an optional bond in case A represents a carbon atom;

X represents —O—C(=O)—; —C(=O)—C(=O)—; —NR$^x$—C(=O)—; —Z—C(=O)—; —Z—NR$^x$—C(=O)—; —C(=O)—Z—; —NR$^x$—C(=O)—Z—; C(=S)—; —S(=O)p-; —NR$^x$—C(=S)—; —Z—C(=S)—; —Z—NR$^x$—C(=S)—; —C(=S)—Z—; —NR$^x$—C(=S)—Z—;

Z represents a bivalent radical selected from C$_{1-6}$alkanediyl, C$_{2-6}$alkenediyl or C$_{2-6}$alkynediyl; wherein each of said C$_{1-6}$alkanediyl, C$_{2-6}$alkenediyl or C$_{2-6}$alkynediyl may optionally be substituted with hydroxyl or amino; and wherein two hydrogen atoms attached to the same carbon atom in C$_{1-6}$alkanediyl may optionally be replaced by C$_{1-6}$alkanediyl;

R$^x$ represents hydrogen or C$_{1-4}$alkyl;

Y represents —C(=O)—NR$^x$— or NR$^x$—C(=O)—;

R$^1$ represents adamantanyl, C$_{3-6}$cycloalkyl; aryl$^1$ or Het$^1$;

R$^2$ represents hydrogen, C$_{1-6}$alkyl, C$_{2-6}$alkenyl, C$_{3-6}$cycloalkyl, phenyl, naphtalenyl, 2,3-dihydro-1,4-benzodioxinyl, 1,3-benzodioxolyl, 2,3-dihydrobenzofuranyl or a 6-membered aromatic heterocycle containing 1 or 2 N atoms, wherein said C$_{3-6}$cycloalkyl, phenyl, naphtalenyl, 2,3-dihydro-1,4-benzodioxinyl, 1,3-benzodioxolyl or 6-membered aromatic heterocycle containing 1 or 2 N atoms may optionally be substituted with at least one substituent, in particular one, two, three, four or five substituents, each substituent independently selected from hydroxyl; carboxyl; halo; C$_{1-6}$alkyl optionally substituted with hydroxy; polyhaloC$_{1-6}$alkyl; C$_{1-6}$alkyloxy optionally substituted with C$_{1-4}$alkyloxy; C$_{1-6}$alkylthio; polyhalo-C$_{1-6}$alkyloxy; C$_{1-6}$alkyloxycarbonyl wherein C$_{1-6}$alkyl may optionally be substituted with aryl; cyano; C$_{1-6}$alkylcarbonyl; nitro; amino; mono-or di(C$_{1-4}$alkyl)amino; C$_{1-4}$alkylcarbonylamino; —S(=O)$_p$—C$_{1-4}$alkyl; R$^4$R$^3$N—C(=O)—; R$^4$R$^3$N—C$_{1-6}$alkyl; C$_{3-6}$cycloalkyl; C$_{3-6}$cycloalkylC$_{1-4}$alkyl; C$_{3-6}$cycloalkyl-C(=O)—; aryl; aryloxy; arylC$_{1-4}$alkyl; aryl-C(=O)—C$_{1-4}$alkyl; aryl-C(=O)—; Het; HetC$_{1-4}$alkyl; Het-C(=O)—C$_{1-4}$alkyl; Het-C(=O)—; Het-O—;

R$^3$ represents hydrogen; C$_{1-4}$alkyl optionally substituted with hydroxyl or C$_{1-4}$alkyloxy; R$^6$R$^5$N—C$_{1-4}$alkyl; C$_{1-4}$alkyloxy; Het; Het-C$_{1-4}$alkyl; aryl; R$^6$R$^5$N—C(=O)—C$_{1-4}$alkyl;

R$^4$ represents hydrogen or C$_{1-4}$alkyl;

R$^5$ represents hydrogen; C$_{1-4}$alkyl; C$_{1-4}$alkylcarbonyl;

R$^6$ represents hydrogen or C$_{1-4}$alkyl; or

R$^5$ and R$^6$ may be taken together with the nitrogen to which they are attached to form a saturated monocyclic 5, 6 or 7-membered heterocycle which may further contain one or more heteroatoms each independently selected from O, S, S(=O)$_p$ or N; and which heterocycle may optionally be substituted with C$_{1-4}$alkyl;

R$^7$ represents hydrogen, halo, C$_{1-4}$alkyl, C$_{1-4}$alkyl substituted with hydroxyl;

aryl represents phenyl or phenyl substituted with at least one substituent, in particular one, two, three, four or five substituents, each substituent independently being selected from hydroxyl; carboxyl; halo; C$_{1-6}$alkyl optionally substituted with C$_{1-4}$alkyloxy, amino or mono-or di(C$_{1-4}$alkyl)amino; polyhaloC$_{1-6}$alkyl; C$_{1-6}$alkyloxy optionally substituted with C$_{1-4}$alkyloxy; C$_{1-6}$alkylthio; polyhaloC$_{1-6}$alkyloxy; C$_{1-6}$alkyloxycarbonyl; cyano; aminocarbonyl; mono-or di(C$_{1-4}$alkyl)aminocarbonyl; C$_{1-6}$alkylcarbonyl; nitro; amino; mono-or di(C$_{1-4}$alkyl)amino; —S(=O)$_p$—C$_{1-4}$alkyl;

aryl$^1$ represents phenyl, naphthalenyl or fluorenyl; each of said phenyl, naphthalenyl or fluorenyl optionally substituted with at least one substituent, in particular one, two, three, four or five substituents, each substituent independently being selected from hydroxyl; oxo; carboxyl; halo; C$_{1-6}$alkyl optionally substituted with carboxyl, C$_{1-4}$alkyloxycarbonyl or aryl-C(=O)—; hydroxyC$_{1-6}$alkyl optionally substituted with aryl or aryl-C(=O)—; polyhaloC$_{1-6}$alkyl; C$_{1-6}$alkyloxy optionally substituted with C$_{1-4}$alkyloxy; C$_{1-6}$alkylthio; polyhaloC$_{1-6}$alkyloxy; C$_{1-6}$alkyloxy-carbonyl wherein C$_{1-6}$alkyl may optionally be substituted with aryl; cyano; aminocarbonyl; mono-or di(C$_{1-4}$alkyl)aminocarbonyl; C$_{1-6}$alkylcarbonyl; nitro; amino; mono-or di(C$_{1-6}$alkyl)amino; R$^4$R$^3$N—C$_{1-6}$alkyl; C$_{3-6}$cycloalkyl-NR$^x$—; aryl-NR$^x$—; Het-NR$^x$—; C$_{3-6}$cycloalkylC$_{1-4}$alkyl-NR$^x$—; arylC$_{1-4}$alkyl-NR$^x$—; HetC$_{1-4}$alkyl-NR$^x$—; —S(=O)$_p$—C$_{1-4}$alkyl; C$_{3-6}$cycloalkyl; C$_{3-6}$cycloalkylC$_{1-4}$alkyl; C$_{3-6}$cycloalkyl-C(=O)—; aryl; aryloxy; arylC$_{1-4}$alkyl; aryl-C(=O)—C$_{1-4}$alkyl; aryl-C(=O)—; Het; HetC$_{1-4}$alkyl; Het-C(=O)—C$_{1-4}$alkyl; Het-C(=O)—; Het-O—;

Het represents a monocyclic non-aromatic or aromatic heterocycle containing at least one heteroatom each independently selected from O, S, S(=O)$_p$ or N; or a bicyclic or tricyclic non-aromatic or aromatic heterocycle containing at least one heteroatom each independently selected from O, S, S(=O)$_p$ or N; said monocyclic heterocycle or said bi-or tricyclic heterocycle optionally being substituted with at least one substituent, in particular one, two, three, four or five substituents, each substituent independently being selected from hydroxyl; oxo; carboxyl; halo; C$_{1-6}$alkyl optionally substituted with C$_{1-4}$alkyloxy, amino or mono-or di(C$_{1-4}$alkyl)amino; polyhaloC$_{1-6}$alkyl; C$_{1-6}$alkyloxy optionally substituted with C$_{1-4}$alkyloxy; C$_{1-6}$alkylthio; polyhaloC$_{1-6}$alkyloxy; C$_{1-6}$alkyloxycarbonyl; cyano; aminocarbonyl; mono-or di(C$_{1-4}$alkyl)aminocarbonyl; C$_{1-6}$alkylcarbonyl; nitro; amino; mono-or di(C$_{1-4}$alkyl)amino; —S(=O)$_p$—C$_{1-4}$alkyl;

Het$^1$ represents a monocyclic non-aromatic or aromatic heterocycle containing at least one heteroatom each independently selected from O, S, S(=O)$_p$ or N; or a bicyclic or tricyclic non-aromatic or aromatic heterocycle containing at least one heteroatom each independently selected from O, S, S(=O)$_p$ or N; said monocyclic heterocycle or said bi-or tricyclic heterocycle optionally being substituted with at least one substituent, in particular one, two, three, four or five substituents, each substituent independently being selected from hydroxyl; oxo; carboxyl; halo; C$_{1-6}$alkyl optionally substituted with aryl-C(=O)—; hydroxyC$_{1-6}$alkyl optionally substituted with aryl or aryl-C(=O)—; polyhaloC$_{1-6}$alkyl; C$_{1-6}$alkyloxy optionally substituted with C$_{1-4}$alkyloxy; C$_{1-6}$alkylthio; polyhaloC$_{1-6}$alkyloxy; C$_{1-6}$alkyloxy-carbonyl wherein C$_{1-6}$alkyl may optionally be substituted with aryl; cyano; aminocarbonyl; mono-or di(C$_{1-4}$alkyl)aminocarbonyl; C$_{1-6}$alkylcarbonyl; nitro; amino; mono-or di(C$_{1-6}$alkyl)amino; R$^4$R$^3$N—C$_{1-6}$alkyl; C$_{3-6}$cycloalkyl-NR$^x$—; aryl-NR$^x$—; Het-NR$^x$—; C$_{3-6}$cycloalkylC$_{1-4}$alkyl-NR$^x$—; arylC$_{1-4}$alkyl-NR$^x$—; HetC$_{1-4}$alkyl-NR$^x$—; —S(=O)$_p$—C$_{1-4}$alkyl; C$_{3-6}$cycloalkyl; C$_{3-6}$cycloalkylC$_{1-4}$alkyl; C$_{3-6}$cycloalkyl-C(=O)—; aryl; aryloxy; arylC$_{1-4}$alkyl; aryl-C(=O)—C$_{1-4}$alkyl; aryl-C(=O)—; Het; HetC$_{1-4}$alkyl; Het-C(=O)—C$_{1-4}$alkyl; Het-C(=O)—; Het-O—;

p represents 1 or 2;

a N-oxide thereof, a pharmaceutically acceptable salt thereof or a solvate thereof;

or d) a compound having the formula

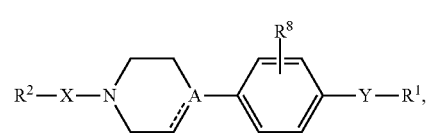

(I)

including any stereochemically isomeric form thereof, wherein

A represents CH or N;

the dotted line represents an optional bond in case A represents a carbon atom;

X represents —C(=O)—; —O—C(=O)—; —C(=O)—C(=O)—; —NR$^x$—C(=O)—; —Z$^1$—C(=O)—; —Z$^1$—NR$^x$—C(=O)—; —C(=O)—Z$^1$—; —NR$^x$—C(=O)—Z$^1$—; —S(=O)p-; C(=S)—; —NR$^x$—C(=S)—; —Z$^1$—C(=S)—; —Z$^1$—NR$^x$—C(=S)—; —C(=S)—Z$^1$—; —NR$^x$—C(=S)—Z$^1$—;

Z$^1$ represents a bivalent radical selected from C$_{1-6}$alkanediyl, C$_{2-6}$alkenediyl or C$_{2-6}$alkynediyl; wherein each of said C$_{1-6}$alkanediyl, C$_{2-6}$alkenediyl or C$_{2-6}$alkynediyl may optionally be substituted with hydroxyl or amino; and wherein two hydrogen atoms attached to the same carbon atom in C$_{1-6}$alkanediyl may optionally be replaced by C$_{1-6}$alkanediyl;

Y represents NR$^x$—C(=O)—Z$^2$—; —NR$^x$—C(=O)—Z$^2$—NR$^y$—; —NR$^x$—C(=O)—Z$^2$—NR$^y$—C(=O)—; —NR$^x$—C(=O)—Z$^2$—NR$^y$—C(=O)—O—; —NR$^x$—C(=O)—Z$^2$—O—; —NR$^x$—C(=O)—Z$^2$—O—C(=O)—; —NR$^x$—C(=O)—Z$^2$—C(=O)—; —NR$^x$—C(=O)—Z$^2$—C(=O)—O—; —NR$^x$—C(=O)—O—Z$^2$—C(=O)—; —NR$^x$—C(=O)—O—Z$^2$—C(=O)—O—; —NR$^x$—C(=O)—O—Z$^2$—O—C(=O)—; —NR$^x$—C(=O)—Z$^2$—C(=O)—NR$^y$—; —NR$^x$—C(=O)—Z$^2$—NR$^y$—C(=O)—NR$^y$—; —C(=O)—Z$^2$—; —C(=O)—Z$^2$—O—; —C(=O)—NR$^x$—Z$^2$—; —C(=O)—NR$^x$—Z$^2$—O—; —C(=O)—NR$^x$—Z$^2$—C(=O)—O—; —C(=O)—NR$^x$—Z$^2$—O—C(=O)—; —C(=O)—NR$^x$—O—Z$^2$—; —C(=O)—NR$^x$—Z$^2$—NR$^y$—; —C(=O)—NR$^x$—Z$^2$—NR$^y$—C(=O)—; —C(=O)—NR$^x$—Z$^2$—NR$^y$—C(=O)—O—;

Z$^2$ represents a bivalent radical selected from C$_{1-6}$alkanediyl, C$_{2-6}$alkenediyl or C$_{2-6}$alkynediyl; wherein each of said C$_{1-6}$alkanediyl, C$_{2-6}$alkenediyl or C$_{2-6}$alkynediyl may optionally be substituted with C$_{1-4}$alkyloxy, C$_{1-4}$alkylthio, hydroxyl, cyano or aryl; and wherein two hydrogen atoms attached to the same carbon atom in the definition of $Z^2$ may optionally be replaced by $C_{1-6}$alkanediyl;

$R^x$ represents hydrogen or $C_{1-4}$alkyl;

$R^y$ represents hydrogen; $C_{1-4}$alkyl optionally substituted with $C_{3-6}$cycloalkyl or aryl or Het; $C_{2-4}$ alkenyl; or —S(=O)$_p$-aryl;

$R^1$ represents $C_{1-12}$alkyl optionally substituted with cyano, $C_{1-4}$alkyloxy, $C_{1-4}$alkyl-oxy$C_{1-4}$alkyloxy, $C_{3-6}$cycloalkyl or aryl; $C_{2-6}$alkenyl; $C_{2-6}$alkynyl; $C_{3-6}$cycloalkyl; adamantanyl; aryl$^1$; aryl$^1$C$_{1-6}$alkyl; Het$^1$; or Het$^1$C$_{1-6}$alkyl; provided that when Y represents —NR$^x$—C(=O)—Z$^2$—; —NR$^x$—C(=O)—Z$^2$—NR$^y$—; —NR$^x$—C(=O)—Z$^2$—C(=O)—NR$^y$—; —C(=O)—Z$^2$—; —NR$^x$—C(=O)—Z$^2$—NR$^y$—C(=O)—NR$^y$—; —C(=O)—NR$^x$—Z$^2$—; —C(=O)—NR$^x$—O—Z$^2$—; or —C(=O)—NR$^x$—Z$^2$—NR$^y$—; then $R^1$ may also represent hydrogen;

$R^2$ represents hydrogen, $C_{1-12}$alkyl, $C_{2-6}$alkenyl or $R^3$;

$R^3$ represents $C_{3-6}$cycloalkyl, phenyl, naphtalenyl, 2,3-dihydro-1,4-benzodioxinyl, 1,3-benzodioxolyl, 2,3-dihydrobenzofuranyl or a 6-membered aromatic heterocycle containing 1 or 2 N atoms, wherein said $C_{3-6}$cycloalkyl, phenyl, naphtalenyl, 2,3-dihydro-1,4-benzodioxinyl, 1,3-benzodioxolyl or 6-membered aromatic heterocycle containing 1 or 2 N atoms may optionally be substituted with at least one substituent, in particular one, two, three, four or five substituents, each substituent independently selected from hydroxyl; carboxyl; halo; $C_{1-6}$alkyl optionally substituted with hydroxy; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono- or di($C_{1-4}$alkyl)amino; $C_{1-4}$alkylcarbonylamino; —S(=O)$_p$—C$_{1-4}$alkyl; R$^5$R$^4$N—C(=O)—; R$^5$R$^4$N—C$_{1-6}$alkyl; $C_{3-6}$cycloalkyl; $C_{3-6}$cycloalkylC$_{1-4}$alkyl; $C_{3-6}$cycloalkyl-C(=O)—; aryl; aryloxy; arylC$_{1-4}$alkyl; aryl-C(=O)—C$_{1-4}$alkyl; aryl-C(=O)—; Het; HetC$_{1-4}$alkyl; Het-C(=O)—C$_{1-4}$alkyl; Het-C(=O)—; Het-O—;

$R^4$ represents hydrogen; $C_{1-4}$alkyl optionally substituted with hydroxyl or $C_{1-4}$alkyloxy; R$^7$R$^6$N—C$_{1-4}$alkyl; $C_{1-4}$alkyloxy; Het; Het-C$_{1-4}$alkyl; aryl; R$^7$R$^6$N—C(=O)—C$_{1-4}$alkyl;

$R^5$ represents hydrogen or $C_{1-4}$alkyl;

$R^6$ represents hydrogen; $C_{1-4}$alkyl; $C_{1-4}$alkylcarbonyl;

$R^7$ represents hydrogen or $C_{1-4}$alkyl; or $R^6$ and $R^7$ may be taken together with the nitrogen to which they are attached to form a saturated monocyclic 5, 6 or 7-membered heterocycle which may further contain one or more heteroatoms each independently selected from O, S, S(=O)$_p$ or N; and which heterocycle may optionally be substituted with $C_{1-4}$alkyl;

$R^8$ represents hydrogen, halo, $C_{1-4}$alkyl, $C_{1-4}$alkyl substituted with hydroxyl;

aryl represents phenyl or phenyl substituted with at least one substituent, in particular one, two, three, four or five substituents, each substituent independently being selected from hydroxyl; carboxyl; halo; $C_{1-6}$alkyl optionally substituted with $C_{1-4}$alkyloxy, amino or mono-or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono-or di($C_{1-4}$alkyl)aminocarbonyl; $C_{1-6}$alkylcarbonyl; nitro; amino; mono-or di($C_{1-4}$alkyl)amino; —S(=O)$_p$—C$_{1-4}$alkyl;

aryl$^1$ represents phenyl, naphthalenyl or fluorenyl; each of said phenyl, naphthalenyl or fluorenyl optionally substituted with at least one substituent, in particular one, two, three, four or five substituents, each substituent independently being selected from hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)aminocarbonyl; $C_{1-6}$alkylcarbonyl; nitro; amino; mono-or di($C_{1-6}$alkyl)amino; R$^5$R$^4$N—C$_{1-6}$alkyl; $C_{3-6}$cycloalkyl-NR$^x$—; aryl-NR$^x$—; Het-NR$^x$—; $C_{3-6}$cycloalkylC$_{1-4}$alkyl-NR$^x$—; arylC$_{1-4}$alkyl-NR$^x$—; HetC$_{1-4}$alkyl-NR$^x$—; —S(=O)$_p$—C$_{1-4}$alkyl; $C_{3-6}$cycloalkyl; $C_{3-6}$cycloalkylC$_{1-4}$alkyl; $C_{3-6}$cycloalkyl-C(=O)—; aryl; aryloxy; arylC$_{1-4}$alkyl; aryl-C(=O)—C$_{1-4}$alkyl; aryl-C(=O)—; Het; HetC$_{1-4}$alkyl; Het-C(=O)—C$_{1-4}$alkyl; Het-C(=O)—; Het-O—;

Het represents a monocyclic non-aromatic or aromatic heterocycle containing at least one heteroatom each independently selected from O, S, S(=O)$_p$ or N; or a bicyclic or tricyclic non-aromatic or aromatic heterocycle containing at least one heteroatom each independently selected from O, S, S(=O)$_p$ or N; said monocyclic heterocycle or said bi-or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with $C_{1-4}$alkyloxy, amino or mono-or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono-or di($C_{1-4}$alkyl)aminocarbonyl; $C_{1-6}$alkylcarbonyl; nitro; amino; mono-or di($C_{1-4}$alkyl)amino; —S(=O)$_p$—C$_{1-4}$alkyl;

Het$^1$ represents a monocyclic non-aromatic or aromatic heterocycle containing at least one heteroatom each independently selected from O, S, S(=O)$_p$ or N; or a bicyclic or tricyclic non-aromatic or aromatic heterocycle containing at least one heteroatom each independently selected from O, S, S(=O)$_p$ or N; said monocyclic heterocycle or said bi-or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)aminocarbonyl; $C_{1-6}$alkylcarbonyl; nitro; amino; mono-or di($C_{1-6}$alkyl)amino; R$^5$R$^4$N—C$_{1-6}$alkyl; $C_{3-6}$cycloalkyl-NR$^x$—; aryl-NR$^x$—; Het-NR$^x$—; $C_{3-6}$cycloalkylC$_{1-4}$alkyl-NR$^x$—; arylC$_{1-4}$alkyl-NR$^x$—; HetC$_{1-4}$alkyl-NR$^x$—; —S(=O)$_p$—C$_{1-4}$alkyl; $C_{3-6}$cycloalkyl; $C_{3-6}$cycloalkylC$_{1-4}$alkyl; $C_{3-6}$cycloalkyl-C(=O)—; aryl; aryloxy; arylC$_{1-4}$alkyl; aryl-C(=O)—C$_{1-4}$alkyl; aryl-C(=O)—; Het; HetC$_{1-4}$alkyl; Het-C(=O)—C$_{1-4}$alkyl; Het-C(=O)—; Het-O—;

p represents 1 or 2;

provided that if X represents —O—C(=O)—, then $R^2$ represents $R^3$;

a N-oxide thereof, a pharmaceutically acceptable salt thereof or a solvate thereof.

Hereinafter, the compounds of formula (I) as defined under a) are indicated as class A compounds, the compounds as defined under b) are indicated as class B compounds, the compounds as defined under c) are indicated as class C compounds, and the compounds as defined under d) are indicated as class D compounds.

In an embodiment, the present invention relates to combinations of a DGAT inhibitor wherein the DGAT inhibitor is selected from
a) a compound of class A, class B, class C, or class D; and
b) a PPAR-α agonist or a prodrug thereof.

In an embodiment, the present invention relates to combinations of a DGAT inhibitor wherein the DGAT inhibitor is selected from
a) a compound of class A, class B, class C, or class D; and
b) a fibrate.

In an embodiment, the present invention relates to combinations of a DGAT inhibitor wherein the DGAT inhibitor is selected from
a) a compound of class A, class B, class C, or class D; and
b) fenofibrate.

In an embodiment, the present invention relates to any of the preceding embodiments wherein the DGAT inhibitor is selected from a compound of Class A.

In an embodiment, the present invention relates to any of the preceding embodiments wherein the DGAT inhibitor is selected from a compound of Class B.

In an embodiment, the present invention relates to any of the preceding embodiments wherein the DGAT inhibitor is selected from a compound of Class C.

In an embodiment, the present invention relates to any of the preceding embodiments wherein the DGAT inhibitor is selected from a compound of Class D.

In an embodiment, the present invention relates to any of the preceding or the following embodiments wherein the PPAR agonist or a prodrug thereof, is a PPAR-α agonist or a prodrug thereof, more in particular a fibrate, even more in particular a fenofibrate.

In an embodiment, the present invention relates to any of the preceding or following embodiments wherein the DGAT inhibitor is a DGAT1 inhibitor.

The present invention also concerns methods for the preparation of compounds of class A, class B, class C or class D, and combinations or pharmaceutical compositions comprising them.

The combinations according to the present invention are suitable for use as a medicament.

The combinations according to the present invention are suitable for reducing food intake, for reducing weight, for suppressing appetite, for inducing satiety; or for the treatment or prevention, in particular treatment, of metabolic disorders, such as obesity and/or obesity related disorders (including, but not limited to, peripheral vascular disease, cardiac failure, myocardial ischaemia, cerebral ischaemia, cardiac myopathies), diabetes, in particular type II diabetes mellitus, and/or complications arising therefrom (such as retinopathy, neuropathy, nephropathy), syndrome X, insulin resistance, impaired glucose tolerance, conditions of impaired fasting glucose, hypoglycemia, hyperglycemia, hyperuricemia, hyperinsulinemia, pancreatitis, hypercholesterolemia, hyperlipidemia, dyslipidemia, mixed dyslipidemia, hypertriglyceridemia, nonalcoholic fatty liver disease, fatty liver, increased mesenteric fat, non-alcoholic steatohepatitis, liver fibrosis, metabolic acidosis, ketosis, dysmetabolic syndrome; dermatological conditions such as acne, psoriasis; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis or vascular stenosis; alzheimer's disease; neoplastic diseases, such as solid tumors, skin cancer, melanoma, lymphoma or endothelial cancers, e.g., breast cancer, lung cancer, colorectal cancer, stomach cancer, other cancers of the gastrointestinal tract (e.g., esophageal cancer or pancreatic cancer), prostate cancer, kidney cancer, liver cancer, bladder cancer, cervical cancer, uterine cancer, testicular cancer or ovarian cancer.

The combinations according to the present invention are particularly suitable for the treatment of prevention, in particular treatment, of obesity, type II diabetes mellitus; for suppressing appetite, for inducing satiety and/or for reducing food intake.

The present invention also relates to the use of the combinations according to the present invention for the manufacture of a medicament for the treatment or prevention, in particular treatment, of the above mentioned diseases or conditions.

The present invention also relates to the use of a combination of a DGAT inhibitor, in particular a DGAT1 inhibitor, and a PPAR agonist or a prodrug thereof, in particular a PPAR-α agonist or a prodrug thereof, more in particular a fibrate, even more in particular fenofibrate, for the manufacture of a medicament for the prevention or the treatment, in particular for the treatment, of a disease which can benefit from elevated levels of one or more satiety hormones, in particular GLP-1.

The present invention also relates to a product containing a) a DGAT inhibitor, in particular a DGAT1 inhibitor, more in particular a compound of Class A, Class B, Class C or Class D, and (b) an agonist of peroxisome proliferators-activator receptor such as for example fenofibrate, as a combined preparation for simultaneous, separate or sequential use in the treatment of a disease which can benefit from an elevated level of GLP-1 or DGAT inhibition, such as for example diabetes, in particular type II diabetes mellitus, obesity, for suppressing appetite, inducing satiety or for reducing food intake.

In an embodiment, the present invention also relates to pharmaceutical compositions comprising a pharmaceutically acceptable carrier, and as active ingredient a therapeutically effective amount of the combinations mentioned hereinbefore or hereinafter.

The present invention further relates to novel compounds, wherein the compound is selected from:
N-[4-[4-[[2-chloro-4-(1-pyrrolidinylmethyl)phenyl]acetyl]-1-piperazinyl]phenyl]-4-methoxy-benzeneacetamide (compound 355 Class D);
4-[4-[[2-chloro-4-(1-pyrrolidinylmethyl)phenyl]acetyl]-1-piperazinyl]-N-[3-(1-pyrrolidinyl)phenyl]-benzamide (compound 151 Class C);
4-[4-[[2-chloro-4-(1-pyrrolidinylmethyl)phenyl]acetyl]-1-piperazinyl]-N-[[3-(1-pyrrolidinyl)phenyl]methyl]-benzamide (compound 354 Class D);
4-[4-[[2-chloro-4-(1-pyrrolidinylmethyl)phenyl]hydroxyacetyl]-1-piperazinyl]-N-[[3-(1-pyrrolidinyl)phenyl]methyl]-benzamide (compound 356 Class D);
4-[4-[[2-chloro-4-(1-pyrrolidinylmethyl)phenyl]hydroxyacetyl]-1-piperazinyl]-N-[3-(1-pyrrolidinyl)phenyl]-benzamide (compound 152 Class C);

4-[4-[[2,6-dichloro-4-(1-pyrrolidinylmethyl)phenyl]acetyl]-1-piperazinyl]-N-[(3,5-dimethoxyphenyl)methyl]-benzamide (compound 358 Class D);
4-[4-[[2-chloro-4-(1-pyrrolidinylmethyl)phenyl]acetyl]-1-piperazinyl]-N-[(3,5-dimethoxyphenyl)methyl]-benzamide (compound 353 Class D);
4-[4-[[2-chloro-4-(1-pyrrolidinylmethyl)phenyl]hydroxyacetyl]-1-piperazinyl]-N-[(3,5-dimethoxyphenyl)methyl]-benzamide (compound 357 Class D);
4-[4-[[2,6-dichloro-4-(1-pyrrolidinylmethyl)phenyl]acetyl]-1-piperazinyl]-N-[3-(1-pyrrolidinyl)phenyl]-benzamide (compound 147 Class C);
4-[4-[[2,6-dichloro-4-[(4-ethyl-1-piperazinyl)methyl]phenyl]acetyl]-1-piperazinyl]-N-[(3,5-dimethoxyphenyl)methyl]-benzamide (compound 360 Class D);
4-[4-[[2,6-dichloro-4-[(4-ethyl-1-piperazinyl)methyl]phenyl]acetyl]-1-piperazinyl]-N-[[3-(1-pyrrolidinyl)phenyl]methyl]-benzamide (compound 359 Class D);
4-[4-[[2,6-dichloro-4-[[4-(methylsulfonyl)-1-piperazinyl]methyl]phenyl]acetyl]-1-piperazinyl]-N-[(3,5-dimethoxyphenyl)methyl]-benzamide (compound 364 Class D);
4-[4-[[4-[(4-acetyl-1-piperazinyl)methyl]-2,6-dichlorophenyl]acetyl]-1-piperazinyl]-N-[[3-(1-pyrrolidinyl)phenyl]methyl]-benzamide (compound 361 Class D);
4-[4-[[2,6-dichloro-4-[[4-(methylsulfonyl)-1-piperazinyl]methyl]phenyl]acetyl]-1-piperazinyl]-N-[[3-(1-pyrrolidinyl)phenyl]methyl]-benzamide (compound 363 Class D);
4-[4-[[4-[(4-acetyl-1-piperazinyl)methyl]-2,6-dichlorophenyl]acetyl]-1-piperazinyl]-N-[(3,5-dimethoxyphenyl)methyl]-benzamide (compound 362 Class D);
4-[4-[[2,6-dichloro-4-[[4-(methylsulfonyl)-1-piperazinyl]methyl]phenyl]acetyl]-1-piperazinyl]-N-[3-(1-pyrrolidinyl)phenyl]-benzamide (compound 150 Class C);
4-[4-[[4-[(4-acetyl-1-piperazinyl)methyl]-2,6-dichlorophenyl]acetyl]-1-piperazinyl]-N-[3-(1-pyrrolidinyl)phenyl]-benzamide (compound 149 Class C);
4-[4-[[2,6-dichloro-4-[(4-ethyl-1-piperazinyl)methyl]phenyl]acetyl]-1-piperazinyl]-N-[3-(1-pyrrolidinyl)phenyl]-benzamide (compound 148 Class C);
including any stereochemically isomeric forms thereof; N-oxides thereof, pharmaceutically acceptable salts thereof or solvates thereof.

Hereinafter, the novel compounds as defined in the list hereinabove (compounds 147 till 152 from Class C, and compounds 353 till 364 from Class D; including any stereochemically isomeric forms thereof; N-oxides thereof, pharmaceutically acceptable salts thereof or solvates thereof), are indicated as compounds of group Q.

The present invention further relates to the novel compound 4-[4-[[2,6-dichloro-4-(1-pyrrolidinylmethyl)phenyl]acetyl]-1-piperazinyl]-N-[(3,5-dimethoxyphenyl)methyl]-benzamide (compound 358 Class D); including any stereochemically isomeric forms thereof; N-oxides thereof, pharmaceutically acceptable salts thereof or solvates thereof.

The present invention also relates to a compound of group Q for use as a medicament.

The present invention also relates to a compound of group Q for the prevention or the treatment of a disease mediated by DGAT, in particular the present invention relates to a compound of group Q for the prevention or the treatment of a disease which can benefit from inhibition of DGAT, in particular for the treatment of a disease which can benefit from inhibition of DGAT, in particular DGAT1.

The present invention also relates to a compound of group Q for the prevention or the treatment, in particular for the treatment, of a disease which can benefit from elevated levels of one or more satiety hormones, in particular GLP-1.

The present invention also relates to the use of a compound of group Q for the manufacture of a medicament for the treatment or prevention, in particular treatment, of the above mentioned diseases or conditions.

In an embodiment, the present invention also relates to pharmaceutical compositions comprising a pharmaceutically acceptable carrier, and as active ingredient a therapeutically effective amount of a compound of group Q.

The present invention will now be further described. In the following passages, different aspects of the invention are defined in more detail.

DETAILED DESCRIPTION

All terms used are to be construed in accordance with the following definitions, unless the context indicates otherwise. In general, the terms are valid for the compounds of class A, class B, class C and class D, unless it is indicated that a certain definition for a term is only valid for a certain class or subset of classes.

As used hereinbefore or hereinafter $C_{0-3}$alkyl as a group or part of a group defines straight or branched chain saturated hydrocarbon radicals having from 0 (then it represents a direct bond) to 3 carbon atoms such as methyl, ethyl, propyl, 1-methylethyl; $C_{1-2}$alkyl as a group or part of a group defines straight or branched chain saturated hydrocarbon radicals having 1 or 2 carbon atoms such as methyl, ethyl; $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-5}$alkyl as a group or part of a group defines straight or branched chain saturated hydrocarbon radicals having from 1 to 5 carbon atoms such as the group defined for $C_{1-4}$alkyl and pentyl, 2-methylbutyl and the like; $C_{1-6}$alkyl as a group or part of a group defines straight or branched chain saturated hydrocarbon radicals having from 1 to 6 carbon atoms such as the group defined for $C_{1-4}$alkyl and for $C_{1-5}$alkyl and hexyl, 2-methylpentyl and the like; $C_{1-12}$alkyl as a group or part of a group defines straight or branched chain saturated hydrocarbon radicals having from 1 to 12 carbon atoms such as the group defined for $C_{1-6}$alkyl and heptyl, 2-methylheptyl and the like; $C_{1-6}$alkanediyl defines straight or branched chain saturated bivalent hydrocarbon radicals having from 1 to 6 carbon atoms such as methylene, 1,2-ethanediyl or 1,2-ethylidene, 1,3-propanediyl or 1,3-propylidene, 1,4-butanediyl or 1,4-butylidene, 1,5-pentanediyl and the like; $C_{2-4}$alkenyl as a group or part of a group defines straight or branched chain hydrocarbon radicals having from 2 to 4 carbon atoms and having a double bond such as ethenyl, propenyl, butenyl and the like; $C_{2-6}$alkenyl as a group or part of a group defines straight or branched chain hydrocarbon radicals having from 2 to 6 carbon atoms and having a double bond such as the group defined for $C_{2-4}$alkenyl and pentenyl, hexenyl, 3-methylbutenyl and the like; $C_{2-6}$alkenediyl defines straight or branched chain bivalent hydrocarbon radicals having from 2 to 6 carbon atoms and having a double bond such as 1,2-ethenediyl, 1,3-propenediyl, 1,4-butenediyl, 1,5-pentenediyl and the like; $C_{2-6}$alkynyl defines straight and branched chain hydrocarbon radicals having from 2 to 6 carbon atoms and having a triple bond such as ethynyl, propynyl, butynyl, pentynyl, hexynyl and the like; $C_{2-6}$alkynediyl as a group or part of a group defines straight or branched chain bivalent hydrocarbon radicals having from 2 to 6 carbon atoms and having a triple bond such as 1,2-ethynediyl, 1,3-propynediyl, 1,4-butynediyl, 1,5-pentynediyl and the like; $C_{3-6}$cycloalkyl is generic to cyclopropyl, cyclobutyl, cyclopentyl and cyclohexyl.

The term halo is generic to fluoro, chloro, bromo and iodo. As used hereinbefore or hereinafter, polyhalo$C_{1-6}$alkyl as a group or part of a group is defined as $C_{1-6}$alkyl substituted with one or more, such as for example 2, 3, 4 or 5 halo atoms, for example methyl substituted with one or more fluoro atoms, for example, difluoromethyl or trifluoromethyl, 1,1-difluoro-ethyl, 1,1-difluoro-2,2,2-trifluoroethyl and the like. In case more than one halogen atoms are attached to a $C_{1-6}$alkyl group within the definition of polyhalo$C_{1-6}$alkyl, they may be the same or different.

As used herein before, the term (=O) forms a carbonyl moiety when attached to a carbon atom, a sulfoxide moiety when attached to a sulfur atom and a sulfonyl moiety when two of said terms are attached to a sulfur atom. Oxo means =O.

The radical $R^1$, as defined hereinabove for the compounds of class B, may be an optionally substituted 5-membered monocyclic heterocycle containing at least 2 heteroatoms, an optionally substituted 6-membered aromatic monocyclic heterocycle or an optionally substituted 5-membered heterocycle containing at least 2 heteroatoms fused with a phenyl, cyclohexyl or a 5-or 6-membered heterocycle.

A 5-membered monocyclic heterocycle as defined hereinabove or hereinafter may be a 5-membered monocyclic non-aromatic (fully saturated or partially saturated) or aromatic heterocycle containing at least 2 heteroatom, in particular 2 or 3 heteroatoms, each independently selected from O, S, $S(=O)_p$ or N. Examples of such unsubstituted monocyclic 5-membered heterocycles comprise, but are not limited to, non-aromatic (fully saturated or partially saturated) or aromatic 5-membered monocyclic heterocycles such as for example 1,3-dioxolanyl, imidazolidinyl, thiazolidinyl, dihydrooxazolyl, isothiazolidinyl, isoxazolidinyl, oxadiazolidinyl, triazolidinyl, thiadiazolidinyl, pyrazolidinyl, imidazolinyl, pyrazolinyl, imidazolyl, oxazolyl, isoxazolyl, thiazolyl, isothiazolyl, pyrazolyl, triazolyl, thiadiazolyl, oxadiazolyl, tetrazolyl and the like. Optional substituents of the above heterocycles are hydroxyl; oxo; carboxyl; halo; $C_{1-6}$alkyl optionally substituted with carboxyl, $C_{1-4}$alkyloxy-carbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)-aminocarbonyl; $C_{1-6}$alkylcarbonyl; amino; mono-or di($C_{1-6}$alkyl)amino; $R^5R^4N$—$C_{1-6}$alkyl; $C_{3-6}$cycloalkyl-$NR^x$—; aryl-$NR^x$—; Het-$NR^x$—; $C_{3-6}$cycloalkyl$C_{1-4}$alkyl-$NR^x$—; aryl$C_{1-4}$alkyl-$NR^x$—; Het$C_{1-4}$alkyl-$NR^x$—; —$S(=O)_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; aryl-C(=O)—$C_{1-4}$alkyl; Het; Het$C_{1-4}$alkyl; Het-C(=O)—; Het-C(=O)—$C_{1-4}$alkyl; Het-O—.

A 6-membered aromatic monocyclic heterocycle as defined hereinabove or hereinafter contains at least one heteroatom, in particular 1, 2 or 3 heteroatoms, each independently selected from O, S, $S(=O)_p$ or N. Examples of such unsubstituted monocyclic 6-membered aromatic heterocycles comprise, but are not limited to, pyridyl, pyrimidinyl, pyrazinyl, pyridazinyl, triazinyl, pyranyl and the like. Optional substituents of the above heterocycles are hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)aminocarbonyl; $C_{1-6}$alkylcarbonyl; amino; mono-or di($C_{1-6}$alkyl)amino; $R^5R^4N$—$C_{1-6}$alkyl; $C_{3-6}$cycloalkyl-$NR^x$—; aryl-$NR^x$—; Het-$NR^x$—; $C_{3-6}$cycloalkyl$C_{1-4}$alkyl-$NR^x$—; aryl$C_{1-4}$alkyl-$NR^x$—; Het$C_{1-4}$alkyl-$NR^x$—; —$S(=O)_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; aryl-C(=O)—$C_{1-4}$alkyl; Het; Het$C_{1-4}$alkyl; Het-C(=O)—; Het-C(=O)—$C_{1-4}$alkyl; Het-O—.

A 5-membered heterocycle containing at least 2 heteroatoms fused with phenyl, cyclohexyl or a 5-or 6-membered heterocycle as defined hereinabove or hereinafter may be a non-aromatic (fully saturated or partially saturated) or aromatic 5-membered heterocycle containing at least 2 heteroatoms, in particular 2 or 3 heteroatoms, each independently selected from O, S, $S(=O)_p$ or N, in particular O, S or N, more in particular O or N, fused with phenyl, cyclohexyl or a 5-or 6-membered non-aromatic (fully saturated or partially saturated) or aromatic heterocycle containing at least one heteroatom, in particular 1, 2 or 3 heteroatoms, each independently selected from O, S, $S(=O)_p$ or N. Examples of such unsubstituted bicyclic heterocycles comprise, but are not limited to, non-aromatic (fully saturated or partially saturated) or aromatic 8-or 9-membered bicyclic heterocycles such as for example 1,3-benzodioxolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, imidazopyrazolyl, isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl and the like. Optional substituents of the above heterocycles are hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)aminocarbonyl; $C_{1-6}$alkylcarbonyl; amino; mono-or di($C_{1-6}$alkyl)amino; $R^5R^4N$—$C_{1-6}$alkyl; $C_{3-6}$cycloalkyl-$NR^x$—; aryl-$NR^x$—; Het-$NR^x$—; $C_{3-6}$cycloalkyl$C_{1-4}$alkyl-$NR^x$—; aryl$C_{1-4}$alkyl-$NR^x$—; Het$C_{1-4}$alkyl-$NR^x$—; —$S(=O)_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; aryl-C(=O)—$C_{1-4}$alkyl; Het; Het$C_{1-4}$alkyl; Het-C(=O)—; Het-C(=O)—$C_{1-4}$alkyl; Het-O—.

The radical Het or Het$^1$ as defined hereinabove may be an optionally substituted monocyclic non-aromatic or aromatic heterocycle containing at least one heteroatom, in particular 1, 2 or 3 heteroatoms, each independently selected from O, S, S(=O)$_p$ or N; or an optionally substituted bi-or tricyclic non-aromatic or aromatic heterocycle containing at least one heteroatom, in particular 1, 2, 3, 4 or 5 heteroatoms, each independently selected from O, S, S(=O)$_p$ or N. Examples of such unsubstituted monocyclic heterocycles comprise, but are not limited to, non-aromatic (fully saturated or partially saturated) or aromatic 4-, 5-, 6-or 7-membered monocyclic heterocycles such as for example azetidinyl, tetrahydrofuranyl, pyrrolidinyl, dioxolanyl, imidazolidinyl, thiazolidinyl, tetrahydrothienyl, dihydrooxazolyl, isothiazolidinyl, isoxazolidinyl, oxadiazolidinyl, triazolidinyl, thiadiazolidinyl, pyrazolidinyl, piperidinyl, hexahydropyrimidinyl, hexahydropyrazinyl, dioxanyl, morpholinyl, dithianyl, thiomorpholinyl, piperazinyl, trithianyl, hexahydrodiazepinyl, pyrrolinyl, imidazolinyl, pyrazolinyl, pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl and the like. Examples of such unsubstituted bicyclic or tricyclic heterocycles comprise, but are not limited to, non-aromatic (fully saturated or partially saturated) or aromatic 8- to 17-membered bicyclic or tricyclic heterocycles such as for example decahydroquinolinyl, octahydroindolyl, 2,3-dihydrobenzofuranyl, 1,3-benzodioxolyl, 2,3-dihydro-1,4-benzodioxinyl, indolinyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, imidazopyrazolyl; isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, phenoxazinyl and the like. Optional substituents for Het heterocycles are hydroxyl; oxo; carboxyl; halo; $C_{1-6}$alkyl optionally substituted with $C_{1-4}$alkyloxy, amino or mono-or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono-or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl. Optional substituents for Het$^1$ substituents are hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)aminocarbonyl; $C_{1-6}$alkylcarbonyl; amino; mono-or di($C_{1-6}$alkyl)amino; $R^6R^5N$—$C_{1-6}$alkyl; $C_{3-6}$cycloalkyl-$NR^x$—; aryl-$NR^x$—; Het-$NR^x$—; $C_{3-6}$cycloalkyl$C_{1-4}$alkyl-$NR^x$—; aryl$C_{1-4}$alkyl-$NR^x$—; Het$C_{1-4}$alkyl-$NR^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; aryl-C(=O)—$C_{1-4}$alkyl; Het; Het$C_{1-4}$alkyl; Het-C(=O)—; Het-C(=O)—$C_{1-4}$alkyl; Het-O—.

Examples of a 6-membered aromatic heterocycle containing 1 or 2 N atoms in the definition of $R^3$ (class B and class D) and $R^2$ (class C) are pyridyl, pyrimidinyl, pyridazinyl, pyrazinyl.

When any variable occurs more than one time in any constituent (e.g. aryl, Het), each definition is independent.

The term Het or Het$^1$ is meant to include all the possible isomeric forms of the heterocycles, for instance, pyrrolyl comprises 1H-pyrrolyl and 2H-pyrrolyl.

The term $R^1$ (in class B) is meant to include all the possible isomeric forms of the heterocycles, for instance, pyrrolyl comprises 1H-pyrrolyl and 2H-pyrrolyl.

The carbocycles or heterocycles covered by the terms aryl, Het, aryl$^1$, Het$^1$, $R^1$ (in class B) or $R^3$ (in class B, class C or class D) may be attached to the remainder of the molecule of formula (I) of class A, class B, class C or class D through any ring carbon or heteroatom as appropriate, if not otherwise specified. Thus, for example, when the heterocycle is imidazolyl, it may be 1-imidazolyl, 2-imidazolyl, 4-imidazolyl and the like, or when the carbocycle is naphthalenyl, it may be 1-naphthalenyl, 2-naphthalenyl and the like.

Lines drawn from substituents into ring systems indicate that the bond may be attached to any of the suitable ring atoms.

When X is defined as for instance —$NR^x$—C(=O)—, this means that the nitrogen of $NR^x$ is linked to the $R^2$ substituent (not applicable for class A) and the carbon atom of C(=O) is linked to the nitrogen of the ring

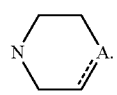

Thus the left part of the bivalent radical in the definition of X is linked to the $R^2$ substituent and the right part of the bivalent radical in the definition of X is linked to the ring moiety

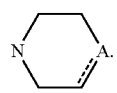

When Y is defined for instance as —$NR^x$—C(=O)— in class A or class C, this means that the nitrogen of $NR^x$ is linked to the phenyl moiety and the carbon atom of C(=O) is linked to the R¹ substituent. Thus the left part of the bivalent radical in the definition of Y is linked to the phenyl moiety and the right part of the bivalent radical in the definition of Y is linked to the R¹ substituent.

When Y is defined as for instance —NR$^x$—C(=O)—Z²— in class D, this means that the nitrogen of NR$^x$ is linked to the phenyl ring and the Z² is linked to the R¹ substituent. Thus the left part of the bivalent radical in the definition of Y is linked to the phenyl ring and the right part of the bivalent radical in the definition of Y is linked to R¹ substituent.

Some of the compounds of class A, class B, class C or class D may also exist in their tautomeric form. Such forms although not explicitly indicated in the above formula are intended to be included within the scope of the present invention.

Whenever used hereinbefore or hereinafter that substituents can be selected each independently out of a list of numerous definitions, such as for example for R² and R³ in class A, R⁴ and R⁵ in class B and class D, and R³ and R⁴ in class C, all possible combinations are intended which are chemically possible.

For therapeutic use, salts of the compounds of class A, class B, class C or class D are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable salts as mentioned hereinbefore or hereinafter are meant to comprise the therapeutically active non-toxic acid addition salt forms which the compounds of class A, class B, class C or class D are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfonic, 2-hydroxybenzoic, 4-amino-2-hydroxybenzoic and the like acids. Conversely the salt form can be converted by treatment with alkali into the free base form.

The compounds of class A, class B, class C or class D containing acidic protons may be converted into their therapeutically active non-toxic metal or amine addition salt forms by treatment with appropriate organic and inorganic bases. The pharmaceutically acceptable salts as mentioned hereinbefore or hereinafter are meant to also comprise the therapeutically active non-toxic metal or amine addition salt forms (base addition salt forms) which the compounds of class A, class B, class C or class D are able to form. Appropriate base addition salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like.

Conversely the salt form can be converted by treatment with acid into the free acid form.

The term salt also comprises the quaternary ammonium salts (quaternary amines) which the compounds of class A, class B, class C or class D are able to form by reaction between a basic nitrogen of a compound of class A, class B, class C or class D and an appropriate quaternizing agent, such as, for example, an optionally substituted C$_{1-6}$alkylhalide, arylhalide, C$_{1-6}$alkyl-carbonylhalide, arylcarbonylhalide, or arylC$_{1-6}$alkylhalide, e.g. methyliodide or benzyliodide. Other reactants with good leaving groups may also be used, such as for example C$_{1-6}$alkyl trifluoromethanesulfonates, C$_{1-6}$alkyl methanesulfonates, and C$_{1-6}$alkyl p-toluenesulfonates. A quaternary amine has a positively charged nitrogen. Pharmaceutically acceptable counterions include chloro, bromo, iodo, trifluoroacetate, acetate, triflate, sulfate, sulfonate. The counterion of choice can be introduced using ion exchange resins.

The term solvate comprises the hydrates and solvent addition forms which the compounds of class A, class B, class C or class D are able to form, as well as salts thereof. Examples of such forms are e.g. hydrates, alcoholates and the like.

The N-oxide forms of the present compounds are meant to comprise the compounds of class A, class B, class C or class D wherein one or several tertiary nitrogen atoms are oxidized to the so-called N-oxide.

It will be appreciated that some of the compounds of class A, class B, class C or class D may contain one or more centers of chirality and exist as stereochemically isomeric forms.

The term "stereochemically isomeric forms" as used hereinbefore or hereinafter defines all the possible stereoisomeric forms which the compounds of class A, class B, class C or class D may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of the basis molecular structure and their N-oxides, salts or solvates, substantially free, i.e. associated with less than 10%, preferably less than 5%, in particular less than 2% and most preferably less than 1% of the other isomers. Thus, when a compound of class A, class B, class C or class D is for instance specified as (E), this means that the compound is substantially free of the (Z) isomer.

In particular, stereogenic centers may have the R-or S-configuration; substituents on bivalent cyclic (partially) saturated radicals may have either the cis-or trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the compounds of class A, class B, class C or class D are obviously intended to be embraced within the scope of this invention.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where the first R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S-[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

The compounds of (I) may be synthesized in the form of racemic mixtures of enantiomers which can be separated from one another following art-known resolution procedures. The racemic compounds of class A, class B, class C or class D may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of class A, class B, class C or class D involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

Whenever used hereinbefore or hereinafter, the term "compounds of class A", "compounds of class B", "compounds of class C" or "compounds of class D" or any subgroup thereof, is meant to also include their N-oxide forms, their salts, their stereochemically isomeric forms and their solvates. Of special interest are those compounds of class A, class B, class C or class D which are stereochemically pure.

Whenever used hereinbefore or hereinafter, the term "compounds of group Q", is meant to also include their N-oxide forms, their salts, their stereochemically isomeric forms and their solvates. Of special interest are those compounds group Q which are stereochemically pure.

By PPAR agonist, in particular PPAR-α agonist, is meant a compound or a prodrug thereof, or a composition containing said compound or prodrug thereof; which directly or indirectly stimulates or increases an in vivo or in vitro reaction typical for the PPAR receptor, in particular the PPAR-α receptor, e.g. transcriptional regulation activity, as measured by an assay known to one skilled in the art such as, for example, described in Kuwabara K, Murakami K, Todo M, Aoki T, Asaki T, Mura M, and Yano J (2004) A novel selective peroxisome proliferator-activated receptor a agonist, 2-methyl-c-5-[4-[5-methyl-2-(4-methylphenyl)-4-oxazolyl]butyl]-1,3-dioxane-r-2-carboxylic acid (NS-220), potently decreases plasma triglyceride and glucose levels and modifies lipoprotein profiles in KK-A$^y$ mice. *J Pharmacol Exp Ther* Vol. 309, No. 3: 970-977.

Non-limiting examples of PPAR-α agonists or prodrugs thereof include natural and synthetic agonists, such as eicosanoids, leukotriene $\beta_4$, carbaprostacyclin, nonsteroidal anti-inflammatory drugs, pirinixic acid (WY-14643; PPAR-α/γ agonist), phthalate ester plasticizers, pterostilbene, fibrates or active metabolites thereof, α-substituted phenylpropanoic acid derivatives, isoxazolyl-serine-based compounds.

A preferred PPAR-α agonist or a prodrug thereof is a fibrate compound including, but not limited to fenofibrate (fenofibric acid as active metabolite), bezafibrate, clofibrate, ciprofibrate, etofibrate, ABT-335 (which is the choline salt of fenofibric acid), pirifibrate, beclofibrate or gemfibrozil (a PPAR-α modulator) and analogues, derivatives and pharmaceutically acceptable salts thereof.

Whenever the term 'prodrug' is used within the context of this invention, this refers to a pharmacological substance (drug) that is administered in an inactive or significantly less active form. Once administered, the prodrug is metabolised in vivo into an active metabolite. For example, the prodrug fenofibrate (ester) is metabolised to fenofibric acid which is the active metabolite (PPAR-α agonist).

A preferred fibrate is fenofibrate.

In the present invention, fibrates include fibric acid derivatives and pharmaceutically acceptable salts of such fibric acid derivatives.

The next embodiments of the present invention are those combinations of a DGAT inhibitor, more in particular a DGAT1 inhibitor and a PPAR agonist, in particular a PPAR-α agonist, more in particular a fibrate, even more in particular fenofibrate; wherein the DGAT inhibitor is selected from compounds of Class A. Preferred embodiments of compounds of class A are:

A-1) compounds of class A having the following formula (I)

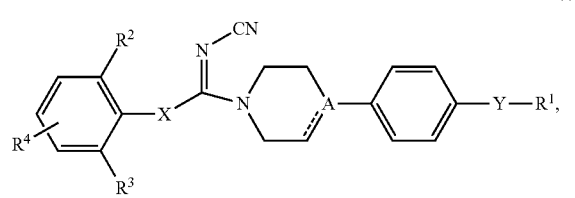

(I)

including any stereochemically isomeric form thereof, wherein

A represents CH or N;

X represents O or NR$^x$;

the dotted line represents an optional bond in case A represents a carbon atom;

Y represents a direct bond; —NR$^x$—C(=O)—; —C(=O)—NR$^x$—; —NR$^x$—C(=O)—Z—; —NR$^x$—C(=O)—Z—NR$^y$—; —NR$^x$—C(=O)—Z—NR$^y$—C(=O)—; —NR$^x$—C(=O)—Z—NR$^y$—C(=O)—O—; —NR$^x$—C(=O)—Z—O—; —NR$^x$—C(=O)—Z—O—C(=O)—; —NR$^x$—C(=O)—Z—C(=O)—; —NR$^x$—C(=O)—Z—C(=O)—O—; —NR$^x$—C(=O)—O—Z—C(=O)—; —NR$^x$—C(=O)—O—Z—C(=O)—O—; —NR$^x$—C(=O)—O—Z—O—C(=O)—; —NR$^x$—C(=O)—Z—NR$^y$—; —NR$^x$—C(=O)—Z—NR$^y$—C(=O)—NR$^y$—; —C(=O)—Z—; —C(=O)—Z—O—; —C(=O)—NR$^x$—Z—; —C(=O)—NR$^x$—Z—O—; —C(=O)—NR$^x$—Z—C(=O)—O—; —C(=O)—NR$^x$—Z—O—C(=O)—; —C(=O)—NR$^x$—O—Z—; —C(=O)—NR$^x$—Z—NR$^y$—; —C(=O)—NR$^x$—Z—NR$^y$—C(=O)—; —C(=O)—NR$^x$—Z—NR$^y$—C(=O)—O—;

Z represents a bivalent radical selected from $C_{1-6}$alkanediyl, $C_{2-6}$alkenediyl or $C_{2-6}$alkynediyl; wherein each of said $C_{1-6}$alkanediyl, $C_{2-6}$alkenediyl or $C_{2-6}$alkynediyl may optionally be substituted with $C_{1-4}$alkyloxy, $C_{1-4}$alkylthio, hydroxyl, cyano or aryl; and wherein two hydrogen atoms attached to the same carbon atom in the definition of Z may optionally be replaced by $C_{1-6}$alkanediyl;

$R^x$ represents hydrogen or $C_{1-4}$alkyl;

$R^y$ represents hydrogen; $C_{1-4}$alkyl optionally substituted with $C_{3-6}$cycloalkyl or aryl or Het; $C_{2-4}$ alkenyl; or —S(=O)$_p$-aryl;

$R^1$ represents $C_{1-12}$alkyl optionally substituted with cyano, $C_{1-4}$alkyloxy, $C_{1-4}$alkyl-oxy$C_{1-4}$alkyloxy, $C_{3-6}$cycloalkyl or aryl; $C_{2-6}$alkenyl; $C_{2-6}$alkynyl; $C_{3-6}$cycloalkyl; aryl$^1$; aryl$^1C_{1-6}$alkyl; Het$^1$; or Het$^1C_{1-6}$alkyl; provided that when Y represents —NR$^x$—C(=O)—Z—; —NR$^x$—C(=O)—Z—NR$^y$; —NR$^x$—C(=O)—Z—C(=O)—NR$^y$—; —C(=O)—Z—; —NR$^x$—C(=O)—Z—NR$^y$—C(=O)—NR$^y$—; —C(=O)—NR$^x$—Z—; —C(=O)—NR$^x$—O—Z—; or —C(=O)—NR$^x$—Z—NR$^y$—; then $R^1$ may also represent hydrogen;

$R^2$ and $R^3$ each independently represent hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$ alkylthio; polyhalo$C_{1-6}$alkyloxy; $C_{1-6}$alkyloxycarbonyl; cyano; aminocarbonyl; mono-or di($C_{1-4}$alkyl)aminocarbonyl; $C_{1-6}$alkylcarbonyl; nitro; amino; mono-or di($C_{1-4}$alkyl)amino; —S(=O)$_p$—$C_{1-4}$alkyl;

$R^4$ represents hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono-or di($C_{1-4}$alkyl)amino; —S(=O)$_p$—$C_{1-4}$alkyl; $R^6R^5$N—C(=O)—; $R^6R^5$N—$C_{1-4}$alkyl; $C_{3-6}$cycloalkyl; aryl; aryloxy; aryl$C_{1-4}$alkyl; aryl-C(=O)—; Het; Het$C_{1-4}$alkyl; Het-C(=O)—; Het-O—;

$R^5$ represents hydrogen; $C_{1-4}$alkyl optionally substituted with hydroxyl or $C_{1-4}$alkyloxy; $R^8R^7$N—$C_{1-4}$alkyl; $C_{1-4}$alkyloxy; Het; aryl; $R^8R^7$N—C(=O)—$C_{1-4}$alkyl;

$R^6$ represents hydrogen or $C_{1-4}$alkyl;

$R^7$ represents hydrogen; $C_{1-4}$alkyl; $C_{1-4}$alkylcarbonyl;

$R^8$ represents hydrogen or $C_{1-4}$alkyl; or $R^7$ and $R^8$ may be taken together with the nitrogen to which they are attached to form a saturated monocyclic 5, 6 or 7-membered heterocycle which may further contain one or more heteroatoms selected from O, S, S(=O)$_p$ or N; and which heterocycle may optionally be substituted with $C_{1-4}$alkyl;

aryl represents phenyl or phenyl substituted with at least one substituent, in particular one, two, three, four or five substituents, each substituent independently being selected from hydroxyl; carboxyl; halo; $C_{1-6}$alkyl optionally substituted with $C_{1-4}$alkyloxy, amino or mono-or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono-or di($C_{1-4}$alkyl)aminocarbonyl; $C_{1-6}$alkylcarbonyl; nitro; amino; mono-or di($C_{1-4}$alkyl) amino; —S(=O)$_p$—$C_{1-4}$alkyl;

aryl$^1$ represents phenyl, naphthalenyl or fluorenyl; each of said phenyl, naphthalenyl or fluorenyl optionally substituted with at least one substituent, in particular one, two, three, four or five substituents, each substituent independently being selected from hydroxyl; oxo; carboxyl; halo; $C_{1-6}$alkyl optionally substituted with aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)aminocarbonyl; $C_{1-6}$alkylcarbonyl; nitro; amino; mono-or di($C_{1-4}$alkyl)amino; $C_{3-6}$cycloalkyl-NR$^x$—; aryl-NR$^x$—; Het-NR$^x$—; $C_{3-6}$cycloalkyl$C_{1-4}$alkyl-NR$^8$—; aryl$C_{1-4}$alkyl-NR$^x$—; Het$C_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; Het$C_{1-4}$alkyl; Het-C(=O)—; Het-O—;

Het represents a monocyclic non-aromatic or aromatic heterocycle containing at least one heteroatom selected from O, S, S(=O)$_p$ or N; or a bicyclic or tricyclic non-aromatic or aromatic heterocycle containing at least one heteroatom selected from O, S, S(=O)$_p$ or N; said monocyclic heterocycle or said bi-or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with $C_{1-4}$alkyloxy, amino or mono-or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono-or di($C_{1-4}$alkyl)aminocarbonyl; $C_{1-6}$alkylcarbonyl; nitro; amino; mono-or di($C_{1-4}$alkyl)amino; —S(=O)$_p$—$C_{1-4}$alkyl;

Het$^1$ represents a monocyclic non-aromatic or aromatic heterocycle containing at least one heteroatom selected from O, S, S(=O)$_p$ or N; or a bicyclic or tricyclic non-aromatic or aromatic heterocycle containing at least one heteroatom selected from O, S, S(=O)$_p$ or N; said monocyclic heterocycle or said bi-or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)aminocarbonyl; $C_{1-6}$alkylcarbonyl; nitro; amino; mono-or di($C_{1-4}$alkyl)amino; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; Het$C_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; Het$C_{1-4}$alkyl; Het-C(=O)—; Het-O—;

p represents 1 or 2;

a N-oxide thereof, a pharmaceutically acceptable salt thereof or a solvate thereof;

or

A-2) compounds of class A or any subgroup thereof as mentioned hereinbefore as embodiment, wherein X represents NR$^x$, in particular NH;

or

A-3) compounds of class A or, whenever possible, any subgroup thereof as mentioned hereinbefore as embodiment, wherein X represents O;

or

A-4) compounds of class A or, whenever possible, any subgroup thereof as mentioned hereinbefore as embodiment wherein A represents N;

or

A-5) compounds of class A or, whenever possible, any subgroup thereof as mentioned hereinbefore as embodiment wherein A represents CH, in particular wherein A represents CH and the dotted line does not represent a bond;

or

A-6) compounds of class A or any subgroup thereof as mentioned hereinbefore as embodiment wherein Y represents —$NR^x$—C(=O)—; —$NR^x$—C(=O)—Z—, —$NR^x$—C(=O)—Z—$NR^y$—; —$NR^x$—C(=O)—Z—O—C(=O)—; in particular wherein Y represents —$NR^x$—C(=O)— or —$NR^x$—C(=O)—Z— with Z representing $C_{1-6}$alkanediyl;

or

A-7) compounds of class A or, whenever possible, any subgroup thereof as mentioned hereinbefore as embodiment wherein Y represents a direct bond, in particular wherein Y represents a direct bond and $R^1$ represents $Het^1$;

or

A-8) compounds of class A or, whenever possible, any subgroup thereof as mentioned hereinbefore as embodiment wherein Y represents —$NR^x$—C(=O)—, in particular wherein Y represents —$NR^x$—C(=O)— and $R^1$ represents $Aryl^1$ or $Het^1$;

or

A-9) compounds of class A or, whenever possible, any subgroup thereof as mentioned hereinbefore as embodiment wherein Y represents —$NR^x$—C(=O)—Z—$NR^y$—, in particular wherein Y represents —$NR^x$—C(=O)—Z—$NR^y$— and $R^1$ represents $Aryl^1$ or $Het^1$;

or

A-10) compounds of class A or, whenever possible, any subgroup thereof as mentioned hereinbefore as embodiment wherein Y represents —$NR^x$—C(=O)—Z—C(=O)—O— or —$NR^x$—C(=O)—Z—O—C(=O)—, in particular —$NR^x$—C(=O)—Z—O—C(=O)—;

or

A-11) compounds of class A or, whenever possible, any subgroup thereof as mentioned hereinbefore as embodiment wherein $R^2$ or $R^3$ each independently represent hydrogen, halo or $C_{1-6}$alkyl, in particular both $R^2$ and $R^3$ represent halo, more in particular both $R^2$ and $R^3$ represent chloro or fluoro;

or

A-12) compounds of class A or, whenever possible, any subgroup thereof as mentioned hereinbefore as embodiment wherein $R^4$ is placed in para position;

or

A-13) compounds of class A or, whenever possible, any subgroup thereof as mentioned hereinbefore as embodiment wherein $R^4$ represents hydrogen; carboxyl; $C_{1-6}$alkyloxycarbonyl; amino; mono-or di($C_{1-4}$alkyl)amino; $R^6R^5$N—C(=O)—; $R^6R^5$N—$C_{1-6}$alkyl; Het-C(=O)— or Het$C_{1-4}$alkyl, in particular Het-C(=O)— or Het$C_{1-4}$alkyl;

or

A-14) compounds of class A or, whenever possible, any subgroup thereof as mentioned hereinbefore as embodiment wherein $R^4$ is placed in para position and represents hydrogen; carboxyl; $C_{1-6}$alkyloxy-carbonyl; amino; mono-or di($C_{1-4}$alkyl)amino; $R^6R^5$N—C(=O)—; $R^6R^5$N—$C_{1-6}$alkyl; Het-C(=O)— or Het$C_{1-4}$alkyl, in particular Het-C(=O)— or Het$C_{1-4}$alkyl;

or

A-15) compounds of class A or, whenever possible, any subgroup thereof as mentioned hereinbefore as embodiment wherein p represents 2;

or

A-16) compounds of class A or, whenever possible, any subgroup thereof as mentioned hereinbefore as embodiment wherein $R^1$ represents hydrogen; $C_{1-12}$alkyl; $aryl^1$ or $Het^1$; in particular $Aryl^1$ or $Het^1$; more in particular $Aryl^1$; more in particular optionally substituted phenyl wherein the optional substituent is preferably selected from aryl, Het or $C_{1-6}$alkyloxy; even more in particular phenyl;

or

A-17) compounds of class A or, whenever possible, any subgroup thereof as mentioned hereinbefore as embodiment wherein Z represents $C_{1-6}$alkanediyl;

or

A-18) compounds of class A or, whenever possible, any subgroup thereof as mentioned hereinbefore as embodiment wherein $R^x$ represents hydrogen;

or

A-19) compounds of class A or, whenever possible, any subgroup thereof as mentioned hereinbefore as embodiment wherein $R^y$ represents hydrogen;

or

A-20) compounds of class A or, whenever possible, any subgroup thereof as mentioned hereinbefore as embodiment wherein $R^9$ represents hydrogen;

or

A-21) compounds of class A or, whenever possible, any subgroup thereof as mentioned hereinbefore as embodiment wherein $R^9$ represents halo, $C_{1-4}$alkyl, $C_{1-4}$alkyl substituted with hydroxyl;

or

A-22) compounds of class A or any subgroup thereof as mentioned hereinbefore as embodiment wherein one or more, preferably all, of the following restrictions apply:
a) X represents NH;
b) $R^2$ represents hydrogen, halo or $C_{1-6}$alkyl; in particular halo; more in particular chloro;
c) $R^3$ represents hydrogen, halo or $C_{1-6}$alkyl; in particular halo; more in particular chloro;
d) $R^4$ represents hydrogen;
e) A represents N;
f) the dotted line does not represent an additional bond;
g) Y represents —$NR^x$—C(=O)—Z—;
h) Z represents $C_{1-6}$alkanediyl;
i) $R^1$ represents $aryl^1$; in particular optionally substituted phenyl; more in particular phenyl.
j) $R^x$ represents hydrogen;

or

A-23) compounds of class A or any subgroup thereof as mentioned hereinbefore as embodiment wherein one or more, preferably all, of the following restrictions apply:
a) X represents NH or O;
b) $R^2$ represents hydrogen, halo or $C_{1-6}$alkyl; in particular halo; more in particular chloro or fluoro;
c) $R^3$ represents hydrogen, halo or $C_{1-6}$alkyl; in particular halo; more in particular chloro or fluoro;
d) $R^4$ represents hydrogen; carboxyl; $C_{1-6}$alkyloxycarbonyl; Het-C(=O)— or Het$C_{1-4}$alkyl, in particular Het-C(=O)— or Het$C_{1-4}$alkyl;
e) A represents N;
f) the dotted line does not represent a bond;
g) Y represents —$NR^x$—C(=O)—; —$NR^x$—C(=O)—Z—, —$NR^x$—C(=O)—Z—$NR^y$—; —$NR^x$—C(=O)—Z—O—C(=O)—;
h) Z represents $C_{1-6}$alkanediyl;

i) R¹ represents hydrogen; C₁₋₁₂alkyl; aryl¹ or Het¹; in particular aryl¹; more in particular optionally substituted phenyl wherein the optional substituent is preferably selected from aryl, Het or C₁₋₆alkyloxy; more in particular phenyl;
j) R$^x$ represents hydrogen;
k) R$^y$ represents hydrogen;
l) R$^9$ represents hydrogen;
m) R⁴ is placed in para position;
or
A-24) compounds of class A selected from

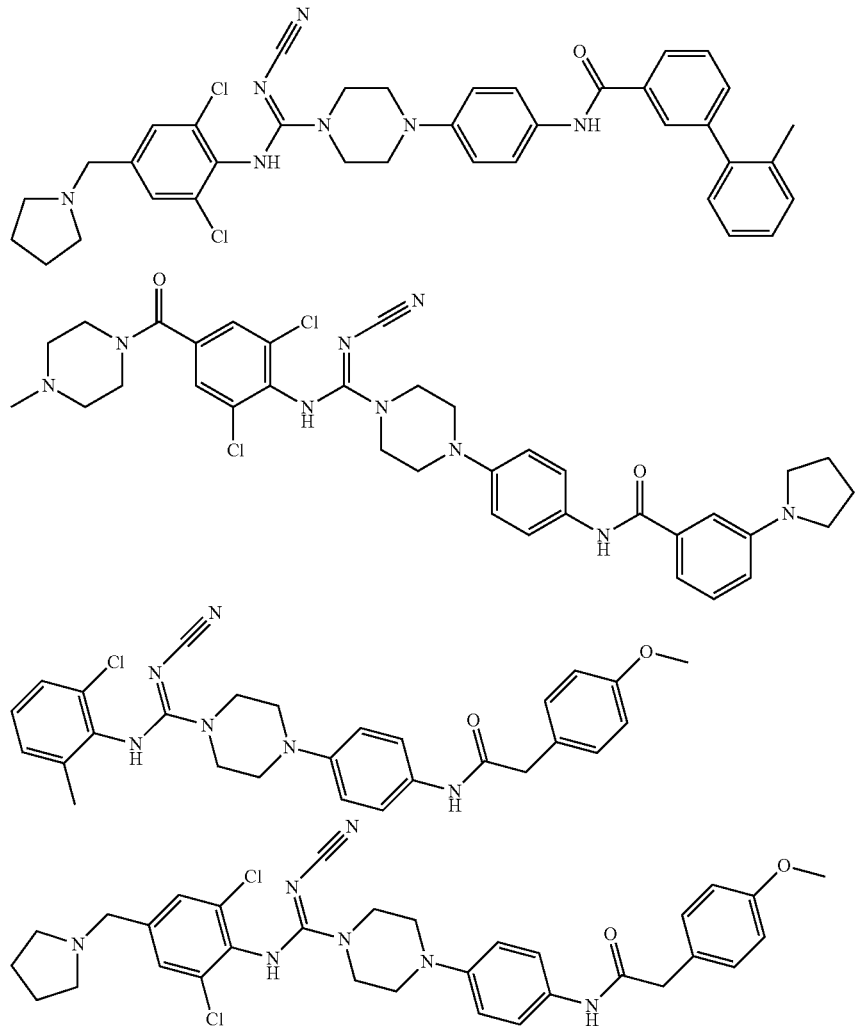

including any stereochemically isomeric form thereof;

a N-oxide thereof, a pharmaceutically acceptable salt thereof or a solvate thereof.

The next embodiments of the present invention are those combinations of a DGAT inhibitor, more in particular a DGAT1 inhibitor and a PPAR agonist, in particular a PPAR-α agonist, more in particular a fibrate, even more in particular fenofibrate; wherein the DGAT inhibitor is selected from compounds of Class B. Preferred embodiments of compounds of class B are:

B-1) compounds of class B having the following formula (I)

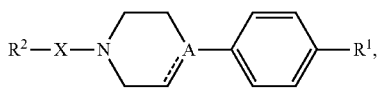

(I)

including any stereochemically isomeric form thereof, wherein
A represents CH or N;
the dotted line represents an optional bond in case A represents a carbon atom;

X represents —NR$^x$—C(=O)—; —Z—C(=O)—; —Z—NR$^x$—C(=O)—; —S(=O)p-; C(=S)—; —NR$^x$—C(=S)—; —Z—C(=S)—; —Z—NR$^x$—C(=S)—;

Z represents a bivalent radical selected from C₁₋₆alkanediyl, C₂₋₆alkenediyl or C₂₋₆alkynediyl; wherein each of said C₁₋₆alkanediyl, C₂₋₆alkenediyl or C₂₋₆alkynediyl may optionally be substituted with hydroxyl;

R$^x$ represents hydrogen or C₁₋₄alkyl;

R¹ represents a 5-membered monocyclic heterocycle containing at least 2 heteroatoms; a 6-membered aromatic monocyclic heterocycle; or a 5-membered heterocycle containing at least 2 heteroatoms fused with phenyl, cyclohexyl or a 5-or 6-membered heterocycle; wherein each of said heterocycles may optionally be substituted with at least one substituent, in particular one, two, three, four or five substituents, each substituent independently being selected from hydroxyl; oxo; carboxyl; halo; $C_{1-6}$alkyl optionally substituted with aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)aminocarbonyl; $C_{1-6}$alkylcarbonyl; nitro; amino; mono-or di($C_{1-6}$alkyl)amino; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; Het$C_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; Het$C_{1-4}$alkyl; Het-C(=O)—; Het-O—;

$R^2$ represents $R^3$;

$R^3$ represents $C_{3-6}$cycloalkyl, phenyl, naphtalenyl, 2,3-dihydro-1,4-benzodioxinyl, 1,3-benzodioxolyl, wherein said $C_{3-6}$cycloalkyl, phenyl, naphtalenyl, 2,3-dihydro-1,4-benzodioxinyl, 1,3-benzodioxolyl may optionally be substituted with at least one substituent, in particular one, two, three, four or five substituents, each substituent independently selected from hydroxyl; carboxyl; halo; $C_{1-6}$alkyl optionally substituted with hydroxy; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxy-carbonyl wherein $C_{1-6}$alkyl may optionally be substituted with aryl; cyano; $C_{1-6}$alkylcarbonyl; nitro; amino; mono-or di($C_{1-4}$alkyl)amino; —S(=O)$_p$—$C_{1-4}$alkyl; $R^5R^4N$—C(=O)—; $R^5R^4N$—$C_{1-6}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; Het$C_{1-4}$alkyl; Het-C(=O)—; Het-O—;

$R^4$ represents hydrogen; $C_{1-4}$alkyl optionally substituted with hydroxyl or $C_{1-4}$alkyloxy; $R^7R^6N$—$C_{1-4}$alkyl; $C_{1-4}$alkyloxy; Het; aryl; $R^7R^6N$—C(=O)—$C_{1-4}$alkyl;

$R^5$ represents hydrogen or $C_{1-4}$alkyl;

$R^6$ represents hydrogen; $C_{1-4}$alkyl; $C_{1-4}$alkylcarbonyl;

$R^7$ represents hydrogen or $C_{1-4}$alkyl; or $R^6$ and $R^7$ may be taken together with the nitrogen to which they are attached to form a saturated monocyclic 5, 6 or 7-membered heterocycle which may further contain one or more heteroatoms selected from O, S, S(=O)$_p$ or N; and which heterocycle may optionally be substituted with $C_{1-4}$alkyl;

aryl represents phenyl or phenyl substituted with at least one substituent, in particular one, two, three, four or five substituents, each substituent independently being selected from hydroxyl; carboxyl; halo; $C_{1-6}$alkyl optionally substituted with $C_{1-4}$alkyloxy, amino or mono-or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono-or di($C_{1-4}$alkyl)aminocarbonyl; $C_{1-6}$alkylcarbonyl; nitro; amino; mono-or di($C_{1-4}$alkyl) amino; —S(=O)$_p$—$C_{1-4}$alkyl;

Het represents a monocyclic non-aromatic or aromatic heterocycle containing at least one heteroatom selected from O, S, S(=O)$_p$ or N; or a bicyclic or tricyclic non-aromatic or aromatic heterocycle containing at least one heteroatom selected from O, S, S(=O)$_p$ or N; said monocyclic heterocycle or said bi-or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with $C_{1-4}$alkyloxy, amino or mono-or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono-or di($C_{1-4}$alkyl)aminocarbonyl; $C_{1-6}$alkylcarbonyl; nitro; amino; mono-or di($C_{1-4}$alkyl)amino; —S(=O)$_p$—$C_{1-4}$alkyl;

p represents 1 or 2;

a N-oxide thereof, a pharmaceutically acceptable salt thereof or a solvate thereof;

or

B-2) compounds of class B or, whenever possible, any subgroup thereof as mentioned hereinbefore as embodiment wherein X represents —NR$^x$—C(=O)—; —Z—C(=O)—; —Z—NR$^x$—C(=O)—; —S(=O)p-; —NR$^x$—C(=S)— or —O—C(=O)—; in particular X represents —NR$^x$—C(=O)—; —Z—C(=O)—; —Z—NR$^x$—C(=O)—; more in particular X represents —NR$^x$—C(=O)— or —Z—C(=O)—;

or

B-3) compounds of class B or, whenever possible, any subgroup thereof as mentioned hereinbefore as embodiment wherein A represents N;

or

B-4) compounds of class B or, whenever possible, any subgroup thereof as mentioned hereinbefore as embodiment wherein A represents CH, in particular wherein A represents CH and the dotted line does not represent a bond;

or

B-5) compounds of class B or, whenever possible, any subgroup thereof as mentioned hereinbefore as embodiment wherein $R^1$ represents a 5-membered monocyclic heterocycle containing at least 2 heteroatoms, in particular pyrazolyl, triazolyl or oxadiazolyl; a 6-membered monocyclic aromatic heterocycle, in particular pyrimidinyl; or a 5-membered aromatic heterocycle containing at least 2 heteroatoms fused with a 5-membered heterocycle, in particular imidazopyrazolyl or imidazothiazolyl; wherein each of said heterocycles may optionally be substituted, preferably with one or two substituents. Particular substituents of said heterocycles include oxo, $C_{1-6}$alkyl optionally substituted with aryl-C(=O)— or $C_{1-4}$alkyloxycarbonyl; hydroxy$C_{1-6}$alkyl optionally substituted with aryl or aryl-C(=O)—; amino; mono-or di($C_{1-6}$alkyl)amino; $R^5R^4N$—$C_{1-6}$alkyl; $C_{3-6}$cycloalkyl-NR$^x$—; aryl-NR$^x$—; Het-NR$^x$—; $C_{3-6}$cycloalkyl-$C_{1-4}$alkyl-NR$^x$—; aryl$C_{1-4}$alkyl-NR$^x$—; Het$C_{1-4}$alkyl-NR$^x$—; $C_{3-6}$cycloalkyl; $C_{3-6}$cycloalkyl$C_{1-4}$alkyl; aryl; aryloxy; aryl$C_{1-4}$alkyl; aryl-C(=O)—; aryl-C(=O)—$C_{1-4}$alkyl; Het; Het$C_{1-4}$alkyl; Het-C(=O)—; Het-C(=O)—$C_{1-4}$alkyl; Het-O—; more in particular $C_{1-6}$alkyl optionally substituted with aryl-C(=O)— or $C_{1-4}$alkyloxycarbonyl; hydroxy$C_{1-6}$alkyl optionally substituted with aryl; mono-or di($C_{1-6}$alkyl)amino; $R^5R^4N$—$C_{1-6}$alkyl; $C_{3-6}$cycloalkyl-NR$^x$—; Het-NR$^x$—; aryl$C_{1-4}$alkyl-NR$^x$—; $C_{3-6}$cycloalkyl; $C_{3-6}$cycloalkyl-$C_{1-4}$alkyl; aryl; aryl$C_{1-4}$alkyl; aryl-C(=O)—$C_{1-4}$alkyl or Het;

or

B-6) compounds of class B or, whenever possible, any subgroup thereof as mentioned hereinbefore as embodiment wherein the compound of class B is a compound of formula (I')

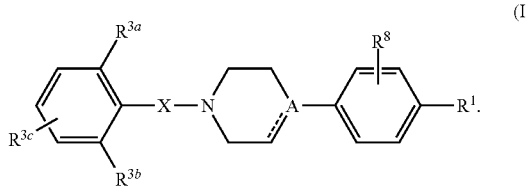

wherein $R^{3a}$ and $R^{3b}$ each independently represent hydrogen; hydroxyl; carboxyl; halo; $C_{1-6}$alkyl optionally substituted with hydroxyl; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono-or di($C_{1-4}$alkyl)aminocarbonyl; $C_{1-6}$alkylcarbonyl; nitro; amino; mono-or di($C_{1-4}$alkyl) amino; $C_{1-4}$alkylcarbonylamino; —S(=O)$_p$—$C_{1-4}$alkyl; and wherein $R^{3c}$ represents hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono-or di($C_{1-4}$alkyl) amino; —S(=O)$_p$—$C_{1-4}$alkyl; $R^5R^4N$—C(=O)—; $R^5R^4N$—$C_{1-6}$alkyl; $C_{3-6}$cyclo-alkyl; aryl; aryloxy; aryl$C_{1-4}$alkyl; aryl-C(=O)—; Het; HetC$_{1-4}$alkyl; Het-C(=O)—; Het-O—.
or
B-7) compounds of class B or, whenever possible, any subgroup thereof as mentioned hereinbefore as embodiment wherein the compound of class B is a compound of formula (I")

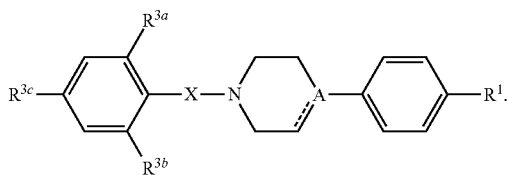

wherein $R^{3a}$ and $R^{3b}$ each independently represent hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono-or di($C_{1-4}$alkyl)aminocarbonyl; $C_{1-6}$alkylcarbonyl; nitro; amino; mono-or di($C_{1-4}$alkyl)amino; —S(=O)$_p$—$C_{1-4}$alkyl; and wherein $R^{3c}$ represents hydrogen; hydroxyl; carboxyl; halo; $C_{1-6}$alkyl optionally substituted with hydroxyl; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono-or di($C_{1-4}$alkyl) amino; $C_{1-4}$alkylcarbonylamino; —S(=O)$_p$—$C_{1-4}$alkyl; $R^5R^4N$—C(=O)—; $R^5R^4N$—$C_{1-6}$alkyl; $C_{3-6}$cycloalkyl; aryl; aryloxy; aryl$C_{1-4}$alkyl; aryl-C(=O)—; Het; HetC$_{1-4}$alkyl; Het-C(=O)—; Het-O—;
or
B-8) compounds of class B or, whenever possible, any subgroup thereof as mentioned hereinbefore as embodiment wherein the compound of formula (I) is a compound of formula (I') or (I") and wherein $R^{3a}$ and $R^{3b}$ each independently represent halo, polyhalo$C_{1-6}$alkyl, $C_{1-6}$alkyl or $C_{1-6}$alkyloxy, in particular both $R^{3a}$ and $R^{3b}$ represent halo, more in particular both $R^{3a}$ and $R^{3b}$ represent chloro;
or
B-9) compounds of class B or, whenever possible, any subgroup thereof as mentioned hereinbefore as embodiment wherein the compound of class B is a compound of formula (I') or (I") and wherein $R^{3c}$ represents hydrogen, hydroxyl, carboxyl; halo; amino; mono- or di-($C_{1-4}$alkyl) amino; $C_{1-6}$alkyl; $C_{1-6}$alkyloxy; $C_{1-6}$alkyloxycarbonyl; $C_{1-6}$alkylthio; $C_{1-4}$alkylcarbonylamino; $R^5R^4N$—C(=O)—; $R^5R^4N$—$C_{1-6}$alkyl; Het-C(=O)— or HetC$_{1-4}$alkyl; or $R^{3c}$ represents hydrogen;
or
B-10) compounds of class B or, whenever possible, any subgroup thereof as mentioned hereinbefore as embodiment wherein p represents 2;
or
B-11) compounds of class B or, whenever possible, any subgroup thereof as mentioned hereinbefore as embodiment wherein Z represents $C_{1-6}$alkanediyl, in particular $CH_2$ or $CH_2$—$CH_2$;
or
B-12) compounds of class B or, whenever possible, any subgroup thereof as mentioned hereinbefore as embodiment wherein $R^8$ represents hydrogen;
or
B-13) compounds of class B or, whenever possible, any subgroup thereof as mentioned hereinbefore as embodiment wherein $R^8$ represents hydrogen;
or
B-14) compounds of class B or, whenever possible, any subgroup thereof as mentioned hereinbefore as embodiment wherein $R^8$ represents halo, $C_{1-4}$alkyl or $C_{1-4}$alkyl substituted with hydroxyl; in particular $R^8$ represents halo or $C_{1-4}$alkyl;
or
B-15) compounds of class B or, whenever possible, any subgroup thereof as mentioned hereinbefore as embodiment wherein $R^3$ represents $C_{3-6}$cycloalkyl, phenyl, naphtalenyl, 1,3-benzodioxolyl or a 6-membered aromatic heterocycle containing 1 or 2 N atoms, wherein said $C_{3-6}$cyclo-alkyl, phenyl, naphtalenyl, 1,3-benzodioxolyl or 6-membered aromatic heterocycle may optionally be substituted with at least one substituent, in particular one or two substituents, preferably each substituent independently selected from hydroxyl; carboxyl; halo; $C_{1-6}$alkyl optionally substituted with hydroxy; polyhalo$C_{1-6}$alkyl; $C_{1-6}$alkyloxy; $C_{1-6}$alkylthio; $C_{1-6}$alkyloxycarbonyl; amino; mono-or di($C_{1-4}$alkyl)amino; $C_{1-4}$alkylcarbonylamino; Het; HetC$_{1-4}$alkyl;
or
B-16) compounds of class B or any subgroup thereof as mentioned hereinbefore as embodiment wherein one or more, preferably all, of the following restrictions apply:
a) X represents —NR$^x$—C(=O)—; or —Z—C(=O)—;
b) the compound of class B is a compound of formula (I"), in particular a compound of formula (I") wherein $R^{3a}$ and $R^{3b}$ represent halo; more in particular chloro; and wherein R³ᶜ represents hydrogen;
c) A represents N;
d) A represents CH;
e) the dotted line does not represent a bond;
f) Z represents C₁₋₆alkanediyl;
g) R¹ represents a 5-membered monocyclic aromatic heterocycle containing at least 2 heteroatoms, in particular pyrazolyl or triazolyl; a 6-membered monocyclic aromatic heterocycle; or a 5-membered aromatic heterocycle containing at least 2 heteroatoms fused with a 5-membered heterocycle; each of said heterocycles optionally being substituted, in particular substituted with oxo, $C_{1-6}$alkyl optionally substituted with aryl-C(=O)—; hydroxyC₁₋₆alkyl optionally substituted with aryl; C₃₋₆cycloalkyl-NRˣ—; Het-NRˣ—; arylC₁₋₄alkyl-NRˣ—; aryl; arylC₁₋₄alkyl.
h) Rˣ represents hydrogen;
or
B-17) compounds of class B or any subgroup thereof as mentioned hereinbefore as embodiment wherein one or more, preferably all, of the following restrictions apply:
a) A represents CH or N;
b) the dotted line does not represents a bond in case A represents a carbon atom;
c) X represents —NRˣ—C(=O)—; —Z—C(=O)—; —Z—NRˣ—C(=O)—;
d) Z represents a bivalent radical selected from C₁₋₆alkanediyl;
e) Rˣ represents hydrogen;
f) R¹ represents a 5-membered monocyclic heterocycle containing at least 2 heteroatoms; a 6-membered aromatic monocyclic heterocycle; or a 5-membered heterocycle containing at least 2 heteroatoms fused with a 5-membered heterocycle; wherein each of said heterocycles such as for example pyrazolyl, triazolyl, oxadiazolyl, pyrimidinyl, imidazopyrazolyl or imidazothienyl, may optionally be substituted with at least one substituent, in particular one or two substituents, each substituent independently being selected from oxo; C₁₋₆alkyl optionally substituted with C₁₋₄alkyloxycarbonyl; hydroxy-C₁₋₆alkyl optionally substituted with aryl; mono-or di(C₁₋₆alkyl)amino; R⁵R⁴N—C₁₋₆alkyl; Het-NRˣ—; arylC₁₋₄alkyl-NRˣ—; C₃₋₆cycloalkyl; C₃₋₆cycloalkyl-C₁₋₄alkyl; aryl; arylC₁₋₄alkyl; aryl-C(=O)—C₁₋₄alkyl; Het;
g) R³ represents C₃₋₆cycloalkyl, phenyl, naphtalenyl, 1,3-benzodioxolyl, or a 6-membered aromatic heterocycle containing 1 or 2 N atoms, wherein said C₃₋₆cyclo-alkyl, phenyl, naphtalenyl, 1,3-benzodioxolyl or 6-membered aromatic heterocycle may optionally be substituted with at least one substituent, in particular one or two substituents, each substituent independently selected from hydroxyl; carboxyl; halo; C₁₋₆alkyl optionally substituted with hydroxy; polyhaloC₁₋₆alkyl; C₁₋₆alkyloxy; C₁₋₆alkylthio; C₁₋₆alkyloxycarbonyl; mono-or di(C₁₋₄alkyl) amino; C₁₋₄alkylcarbonylamino; Het; HetC₁₋₄alkyl;
h) R⁴ represents hydrogen or C₁₋₄alkyl;
i) R⁵ represents hydrogen or C₁₋₄alkyl;
j) R⁸ represents hydrogen;
k) aryl represents phenyl or phenyl substituted with at least one substituent, in particular one substituent, said substituent being selected from halo; C₁₋₆alkyl; C₁₋₆alkyloxy;
l) Het represents a monocyclic non-aromatic or aromatic heterocycle containing at least one heteroatom selected from O, S, S(=O)ₚ or N; said monocyclic heterocycle optionally being substituted with C₁₋₆alkyloxycarbonyl;
or
B-181 compounds of class B selected from

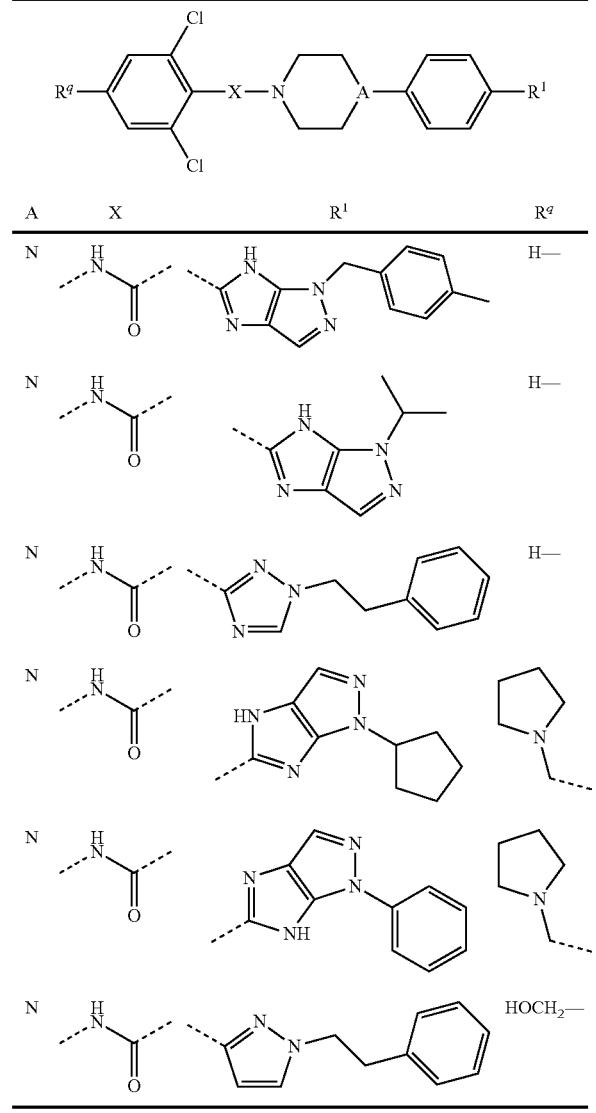

including any stereochemically isomeric form thereof;
a N-oxide thereof, a pharmaceutically acceptable salt thereof or a solvate thereof.

The next embodiments of the present invention are those combinations of a DGAT inhibitor, more in particular a DGAT1 inhibitor and a PPAR agonist, in particular a PPAR-α agonist, more in particular a fibrate, even more in particular fenofibrate; wherein the DGAT inhibitor is selected from compounds of Class C. Preferred embodiments of compounds of class C are:
C-1) compounds of class C having the following formula (D

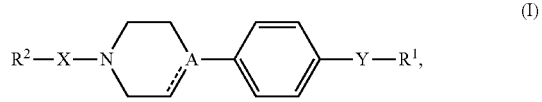

including any stereochemically isomeric form thereof, wherein

A represents CH or N;

the dotted line represents an optional bond in case A represents a carbon atom;

X represents —NR$^x$—C(=O)—; —Z—C(=O)—; —Z—NR$^x$—C(=O)—; —C(=O)—Z—; —NR$^x$—C(=O)—Z—; —C(=S)—; —NR$^x$—C(=S)—; —Z—C(=S)—; —Z—NR$^x$—C(=S)—; —C(=S)—Z—; —NR$^x$—C(=S)—Z—;

Z represents a bivalent radical selected from $C_{1-6}$alkanediyl, $C_{2-6}$alkenediyl or $C_{2-6}$alkynediyl; wherein each of said $C_{1-6}$alkanediyl, $C_{2-6}$alkenediyl or $C_{2-6}$alkynediyl may optionally be substituted with hydroxyl;

R$^x$ represents hydrogen or $C_{1-4}$alkyl;

Y represents —C(=O)—NR$^x$— or NR$^x$—C(=O)—;

R$^1$ represents $C_{3-6}$cycloalkyl; aryl$^1$ or Het$^1$;

R$^2$ represents $C_{3-6}$cycloalkyl, phenyl, naphtalenyl, 2,3-dihydro-1,4-benzodioxinyl, 1,3-benzodioxolyl, wherein said $C_{3-6}$cycloalkyl, phenyl, naphtalenyl, 2,3-dihydro-1,4-benzodioxinyl, 1,3-benzodioxolyl may optionally be substituted with at least one substituent, in particular one, two, three, four or five substituents, each substituent independently selected from hydroxyl; carboxyl; halo; $C_{1-6}$alkyl optionally substituted with hydroxy; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono-or di($C_{1-4}$alkyl)amino; —S(=O)$_p$—$C_{1-4}$alkyl; R$^4$R$^3$N—C(=O)—; R$^4$R$^3$N—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; Het$C_{1-4}$alkyl; Het-C(=O)—; Het-O—;

R$^3$ represents hydrogen; $C_{1-4}$alkyl optionally substituted with hydroxyl or $C_{1-4}$alkyloxy; R$^6$R$^5$N—$C_{1-4}$alkyl; $C_{1-4}$alkyloxy; Het; aryl; R$^6$R$^5$N—C(=O)—$C_{1-4}$alkyl;

R$^4$ represents hydrogen or $C_{1-4}$alkyl;

R$^5$ represents hydrogen; $C_{1-4}$alkyl; $C_{1-4}$alkylcarbonyl;

R$^6$ represents hydrogen or $C_{1-4}$alkyl; or

R$^5$ and R$^6$ may be taken together with the nitrogen to which they are attached to form a saturated monocyclic 5, 6 or 7-membered heterocycle which may further contain one or more heteroatoms selected from O, S, S(=O)$_p$ or N; and which heterocycle may optionally be substituted with $C_{1-4}$alkyl;

aryl represents phenyl or phenyl substituted with at least one substituent, in particular one, two, three, four or five substituents, each substituent independently being selected from hydroxyl; carboxyl; halo; $C_{1-6}$alkyl optionally substituted with $C_{1-4}$alkyloxy, amino or mono-or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono-or di($C_{1-4}$alkyl)aminocarbonyl; $C_{1-6}$alkylcarbonyl; nitro; amino; mono-or di($C_{1-4}$alkyl)amino; —S(=O)$_p$—$C_{1-4}$alkyl;

aryl$^1$ represents phenyl, naphthalenyl or fluorenyl; each of said phenyl, naphthalenyl or fluorenyl optionally substituted with at least one substituent, in particular one, two, three, four or five substituents, each substituent independently being selected from hydroxyl; oxo; carboxyl; halo; $C_{1-6}$alkyl optionally substituted with aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)aminocarbonyl; $C_{1-6}$alkylcarbonyl; nitro; amino; mono-or di($C_{1-6}$alkyl)amino; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; Het$C_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; Het$C_{1-4}$alkyl; Het-C(=O)—; Het-O—;

Het represents a monocyclic non-aromatic or aromatic heterocycle containing at least one heteroatom selected from O, S, S(=O)$_p$ or N; or a bicyclic or tricyclic non-aromatic or aromatic heterocycle containing at least one heteroatom selected from O, S, S(=O)$_p$ or N; said monocyclic heterocycle or said bi-or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with $C_{1-4}$alkyloxy, amino or mono-or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono-or di($C_{1-4}$alkyl)aminocarbonyl; $C_{1-6}$alkylcarbonyl; nitro; amino; mono-or di($C_{1-4}$alkyl)amino; —S(=O)$_p$—$C_{1-4}$alkyl;

Het$^1$ represents a monocyclic non-aromatic or aromatic heterocycle containing at least one heteroatom selected from O, S, S(=O)$_p$ or N; or a bicyclic or tricyclic non-aromatic or aromatic heterocycle containing at least one heteroatom selected from O, S, S(=O)$_p$ or N; said monocyclic heterocycle or said bi-or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)aminocarbonyl; $C_{1-6}$alkylcarbonyl; nitro; amino; mono-or di($C_{1-6}$alkyl)amino; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; Het$C_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; Het$C_{1-4}$alkyl; Het-C(=O)—; Het-O—;

p represents 1 or 2;

a N-oxide thereof, a pharmaceutically acceptable salt thereof or a solvate thereof;

or

C-2) compounds of class C or, whenever possible, any subgroup thereof as mentioned hereinbefore as embodiment wherein X represents —O—C(=O)—; —NR$^x$—C(=O)—; —Z—C(=O)—; —Z—NR$^x$—C(=O)—; —C(=O)—Z—; —NR$^x$—C(=O)—Z—; —NR$^x$—C(=S)—; in particular wherein X represents —NR$^x$—C(=O)—; —Z—C(=O)—; —Z—NR$^x$—C(=O)—; —C(=O)—Z—; —NR$^x$—C(=O)—Z—; —NR$^x$—C(=S)—; more in particular wherein X represents —NR$^x$—C(=O)—; —Z—C(=O)—; —Z—NR$^x$—C(=O)—; even further in particular X represents —NR$^x$—C(=O)— or —Z—NR$^x$—C(=O)—; or X represents —NR$^x$—C(=O)— or —Z—C(=O)—. Or X represents —O—C(=O)—; —C(=O)—C(=O)—; —NR$^x$—C (=O)—; —Z—C(=O)—; —Z—NR$^x$—C(=O)—; C(=S)—; —NR$^x$—C(=S)—; —Z—C(=S)—; —Z—NR$^x$—C(=S)—;

or

C-3) compounds of class C or, whenever possible, any subgroup thereof as mentioned hereinbefore as embodiment wherein A represents N;

or

C-4) compounds of class C or, whenever possible, any subgroup thereof as mentioned hereinbefore as embodiment wherein A represents CH, in particular wherein A represents CH and the dotted line does not represent a bond;

or

C-5) compounds of class C or, whenever possible, any subgroup thereof as mentioned hereinbefore as embodiment wherein R$^1$ represents aryl$^1$ or Het$^1$; in particular optionally substituted phenyl, optionally substituted fluorenyl or an optionally substituted monocyclic non-aromatic or aromatic heterocycle containing at least one heteroatom each independently selected from O, S, S(=O)$_p$ or N, in particular S or N; more in particular phenyl or fluorenyl, said phenyl or fluorenyl optionally substituted with one or two substituents, said substituents independently selected from oxo, carboxyl, halo, C$_{1-6}$alkyl optionally substituted with carboxyl or C$_{1-4}$alkyloxycarbonyl, C$_{1-6}$alkyloxy, C$_{1-6}$alkyloxycarbonyl, amino, aryl, Het or polyhaloC$_{1-6}$alkyl; or a 4-, 5-or 6-membered non-aromatic or aromatic heterocycle, such as for example azetidinyl, thiazolidinyl, thiazolyl, pyrrolidinyl, piperidinyl, said 5-or 6-membered heterocycle optionally substituted with one or two substituents, said substituents independently selected from hydroxyl, oxo, C$_{1-6}$alkyl, C$_{1-6}$alkyloxycarbonyl, aryl or Het;

or

C-6) compounds of class C or, whenever possible, any subgroup thereof as mentioned hereinbefore as embodiment wherein R$^2$ represents C$_{3-6}$cycloalkyl, phenyl, 2,3-dihydro-1,4-benzodioxinyl or a 6-membered aromatic heterocycle containing 1 or 2 N atoms such as for example pyridyl, wherein said phenyl or heterocycle are optionally substituted with one to four substituents, preferably each substituent independently selected from halo, C$_{1-6}$alkyl, C$_{1-6}$alkyloxy, C$_{1-6}$alkylthio, C$_{1-6}$alkyloxycarbonyl, nitro, amino, mono-or di(C$_{1-4}$alkyl)amino, aryloxy, R$^4$R$^3$N—C$_{1-6}$alkyl, Het-C(=O)—C$_{1-4}$alkyl;

or

C-7) compounds of class C or, whenever possible, any subgroup thereof as mentioned hereinbefore as embodiment wherein the compound of class C is a compound of formula (I')

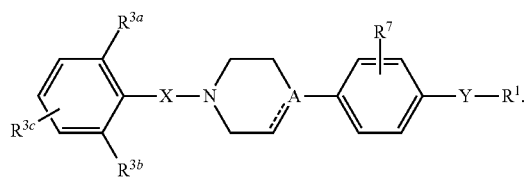

(I')

wherein R$^{3a}$ and R$^{3b}$ each independently represent hydrogen; hydroxyl; carboxyl; halo; C$_{1-6}$alkyl; polyhalo-C$_{1-6}$alkyl; C$_{1-6}$alkyloxy optionally substituted with C$_{1-4}$alkyloxy; C$_{1-6}$alkylthio; polyhaloC$_{1-6}$alkyloxy; C$_{1-6}$alkyloxycarbonyl; cyano; aminocarbonyl; mono-or di(C$_{1-4}$alkyl)aminocarbonyl; C$_{1-6}$alkylcarbonyl; nitro; amino; mono-or di(C$_{1-4}$alkyl)amino; —S(=O)$_p$—C$_{1-4}$alkyl; and wherein R$^{3c}$ represents hydrogen; hydroxyl; carboxyl; halo; C$_{1-6}$alkyl; polyhaloC$_{1-6}$alkyl; C$_{1-6}$alkyloxy optionally substituted with C$_{1-4}$alkyloxy; C$_{1-6}$alkylthio; polyhalo-C$_{1-6}$alkyloxy; C$_{1-6}$alkyloxycarbonyl wherein C$_{1-6}$alkyl may optionally be substituted with aryl; cyano; C$_{1-6}$alkylcarbonyl; nitro; amino; mono-or di(C$_{1-4}$alkyl)amino; —S(=O)$_p$—C$_{1-4}$alkyl; R$^4$R$^3$N—C(=O)—; R$^4$R$^3$N—C$_{1-6}$alkyl; C$_{3-6}$cycloalkyl; aryl; aryloxy; arylC$_{1-4}$alkyl; aryl-C(=O)—C$_{1-4}$alkyl; aryl-C(=O)—; Het; HetC$_{1-4}$alkyl; Het-C(=O)—C$_{1-4}$alkyl; Het-C(=O)—; Het-O—;

or

C-8) compounds of class C or, whenever possible, any subgroup thereof as mentioned hereinbefore as embodiment wherein the compound of class C is a compound of formula (I")

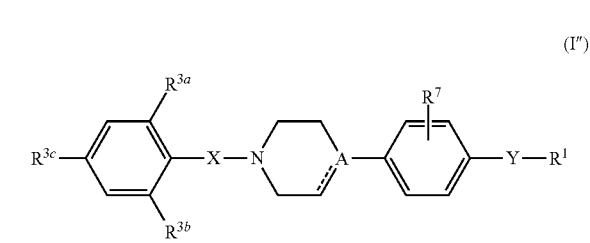

(I")

wherein R$^{3a}$ and R$^{3b}$ each independently represent hydrogen; hydroxyl; carboxyl; halo; C$_{1-6}$alkyl; polyhalo-C$_{1-6}$alkyl; C$_{1-6}$alkyloxy optionally substituted with C$_{1-4}$alkyloxy; C$_{1-6}$alkylthio; polyhaloC$_{1-6}$alkyloxy; C$_{1-6}$alkyloxycarbonyl; cyano; aminocarbonyl; mono-or di(C$_{1-4}$alkyl)aminocarbonyl; C$_{1-6}$alkylcarbonyl; nitro; amino; mono-or di(C$_{1-4}$alkyl)amino; —S(=O)$_p$—C$_{1-4}$alkyl; and wherein R$^{3c}$ represents hydrogen; hydroxyl; carboxyl; halo; C$_{1-6}$alkyl; polyhaloC$_{1-6}$alkyl; C$_{1-6}$alkyloxy optionally substituted with C$_{1-4}$alkyloxy; C$_{1-6}$alkylthio; polyhalo-C$_{1-6}$alkyloxy; C$_{1-6}$alkyloxycarbonyl wherein C$_{1-6}$alkyl may optionally be substituted with aryl; cyano; C$_{1-6}$alkylcarbonyl; nitro; amino; mono-or di(C$_{1-4}$alkyl)amino; —S(=O)$_p$—C$_{1-4}$alkyl; R$^4$R$^3$N—C(=O)—; R$^4$R$^3$N—C$_{1-6}$alkyl; C$_{3-6}$cycloalkyl; aryl; aryloxy; arylC$_{1-4}$alkyl; aryl-C(=O)—C$_{1-4}$alkyl; aryl-C(=O)—; Het; HetC$_{1-4}$alkyl; Het-C(=O)—C$_{1-4}$alkyl; Het-C(=O)—; Het-O—;

or

C-9) compounds of class C or any subgroup thereof as mentioned hereinbefore as embodiment wherein the compound of formula (I) is a compound of formula (I') or (I") and wherein R$^{3a}$ and R$^{3b}$ each independently represent halo, C$_{1-6}$alkyl or C$_{1-6}$alkyloxy; in particular halo or C$_{1-6}$alkyl; more in particular both R$^{3a}$ and R$^{3b}$ represent halo, more in particular both R$^{3a}$ and R$^{3b}$ represent chloro;

or

C-10) compounds of class C or, whenever possible, any subgroup thereof as mentioned hereinbefore as embodiment wherein the compound of formula (I) is a compound of formula (I') or (I") and wherein R$^{3c}$ represents amino; mono-or di(C$_{1-4}$alkyl)amino; R$^4$R$^3$N—C(=O)—; R$^4$R$^3$N—C$_{1-4}$alkyl; Het-C(=O)— or HetC$_{1-4}$alkyl; or R$^{3c}$ represents hydrogen;

or

C-11) compounds of class C or, whenever possible, any subgroup thereof as mentioned hereinbefore as embodiment wherein p represents 2;

or

C-12) compounds of class C or, whenever possible, any subgroup thereof as mentioned hereinbefore as embodiment wherein Z represents $C_{1-6}$alkanediyl or $C_{2-6}$alkenediyl, in particular $C_{1-6}$alkanediyl, more in particular —$CH_2$—;

or

C-13) compounds of class C or, whenever possible, any subgroup thereof as mentioned hereinbefore as embodiment wherein $R^x$ represents hydrogen;

or

C-14) compounds of class C or, whenever possible, any subgroup thereof as mentioned hereinbefore as embodiment wherein Y represents —$NR^x$—$C(=O)$—;

or

C-15) compounds of class C or, whenever possible, any subgroup thereof as mentioned hereinbefore as embodiment wherein Y represents —$C(=O)$—$NR^x$—;

or

C-16) compounds of class C or, whenever possible, any subgroup thereof as mentioned hereinbefore as embodiment wherein $R^7$ represents hydrogen;

or

C-17) compounds of class C or, whenever possible, any subgroup thereof as mentioned hereinbefore as embodiment wherein $R^7$ represents halo, $C_{1-4}$alkyl or $C_{1-4}$alkyl substituted with hydroxyl; in particular halo;

or

C-18) compounds of class C or, whenever possible, any subgroup thereof as mentioned hereinbefore as embodiment wherein aryl represents phenyl or phenyl substituted with halo, $C_{1-6}$alkyl, polyhalo$C_{1-6}$alkyl or $C_{1-6}$alkyloxycarbonyl;

or

C-19) compounds of class C or, whenever possible, any subgroup thereof as mentioned hereinbefore as embodiment wherein Het represents a monocyclic non-aromatic or aromatic heterocycle containing at least one heteroatom each independently selected from O, S, $S(=O)_p$ or N; or a bicyclic non-aromatic or aromatic heterocycle containing at least one heteroatom each independently selected from O, S, $S(=O)_p$ or N, in particular N; said monocyclic heterocycle or said bicyclic heterocycle optionally being substituted with one or two substituents, each substituent independently being selected from oxo; or $C_{1-6}$alkyl;

or

C-20) compounds of class C or, whenever possible, any subgroup thereof as mentioned hereinbefore as embodiment wherein one or more, preferably all, of the following restrictions apply:
a) X represents —$NR^x$—$C(=O)$—; —Z—$NR^x$—$C(=O)$—; or —$NR^x$—$C(=S)$—;
b) $R^1$ represents aryl$^1$ or Het$^1$;
c) $R^2$ represents $C_{3-6}$cycloalkyl, phenyl or 2,3-dihydro-1,4-benzodioxinyl, wherein said phenyl is optionally substituted with one to four substituents, each substituent independently selected from halo, $C_{1-6}$alkyl, $C_{1-6}$alkyloxy, $C_{1-6}$alkylthio, $C_{1-6}$alkyloxycarbonyl, nitro, amino, mono- or di($C_{1-4}$alkyl)amino, aryloxy;
d) A represents N;
e) A represents CH;
f) Z represents $C_{1-6}$alkanediyl or $C_{2-6}$alkenediyl;
g) $R^x$ represents hydrogen.
h) aryl$^1$ represents phenyl or fluorenyl, said phenyl or fluorenyl optionally substituted with halo, $C_{1-6}$alkyl or polyhalo$C_{1-6}$alkyl;
i) Het$^1$ represents a 4-, 5-or 6-membered non-aromatic or aromatic heterocycle, such as for example azetidinyl, thiazolidinyl, thiazolyl, pyrrolidinyl, piperidinyl, said 5-or 6-membered heterocycle optionally substituted with hydroxyl, oxo, $C_{1-6}$alkyl, $C_{1-6}$alkyloxycarbonyl, aryl or Het;
j) Y represents —$NR^x$—$C(=O)$—;
k) $R^7$ represents hydrogen;

or

C-21) compounds of class C or, whenever possible, any subgroup thereof as mentioned hereinbefore as embodiment wherein one or more, preferably all, of the following restrictions apply:
a) A represents CH;
b) A represents N;
c) the dotted line represents a bond in case A represents a carbon atom;
d) the dotted line doesn't represents a bond in case A represents a carbon atom;
e) X represents —O—$C(=O)$—; —$NR^x$—$C(=O)$—; —Z—$C(=O)$—; —Z—$NR^x$—$C(=O)$—; —$NR^x$—$C(=S)$—;
f) Z represents $C_{1-6}$alkanediyl;
g) $R^x$ represents hydrogen;
h) Y represents —$C(=O)$—$NR^x$— or $NR^x$—$C(=O)$—;
i) $R^1$ represents aryl$^1$ or Het$^1$;
j) $R^2$ represents $C_{3-6}$cycloalkyl, phenyl, 2,3-dihydro-1,4-benzodioxinyl, or a 6-membered aromatic heterocycle containing 1 or 2 N atoms, wherein said $C_{3-6}$cycloalkyl, phenyl, 2,3-dihydro-1,4-benzodioxinyl, or 6-membered aromatic heterocycle containing 1 or 2 N atoms may optionally be substituted with at least one substituent, in particular one to four substituents, each substituent independently selected from halo; $C_{1-6}$alkyl; $C_{1-6}$alkyloxy; $C_{1-6}$alkylthio; $C_{1-6}$alkyloxycarbonyl; nitro; mono-or di($C_{1-4}$alkyl)amino; $R^4R^3N$—$C_{1-6}$alkyl; aryloxy; Het-C$(=O)$—$C_{1-4}$alkyl;
k) $R^3$ represents $C_{1-4}$alkyl;
l) $R^4$ represents $C_{1-4}$alkyl;
m) $R^7$ represents hydrogen or halo;
n) aryl represents phenyl or phenyl substituted with halo; $C_{1-6}$alkyl; polyhalo$C_{1-6}$alkyl; $C_{1-6}$alkyloxycarbonyl;
o) aryl$^1$ represents phenyl or fluorenyl; each of said phenyl or fluorenyl optionally substituted with one or two substituents, each substituent independently being selected from oxo; carboxyl; halo; $C_{1-6}$alkyl optionally substituted with carboxyl or $C_{1-4}$alkyloxycarbonyl; $C_{1-6}$alkyloxy; $C_{1-6}$alkyloxy-carbonyl; amino; aryl; Het;
p) Het represents a monocyclic non-aromatic or aromatic heterocycle containing at least one heteroatom each independently selected from O, S, $S(=O)_p$ or N; or a bicyclic non-aromatic or aromatic heterocycle containing at least one heteroatom each independently selected from N; said monocyclic heterocycle or said bicyclic heterocycle optionally being substituted with one or two substituents, each substituent independently being selected from oxo or $C_{1-6}$alkyl;
q) Het$^1$ represents a monocyclic non-aromatic or aromatic heterocycle containing at least one heteroatom each independently selected from S or N; said monocyclic heterocycle optionally being substituted with at least one substituent, in particular one or two substituents, each substituent independently being selected from hydroxyl; oxo; $C_{1-6}$alkyl; $C_{1-6}$alkyloxy-carbonyl; aryl; Het;
r) p represents 2;

or

C-22) compounds of class C selected from
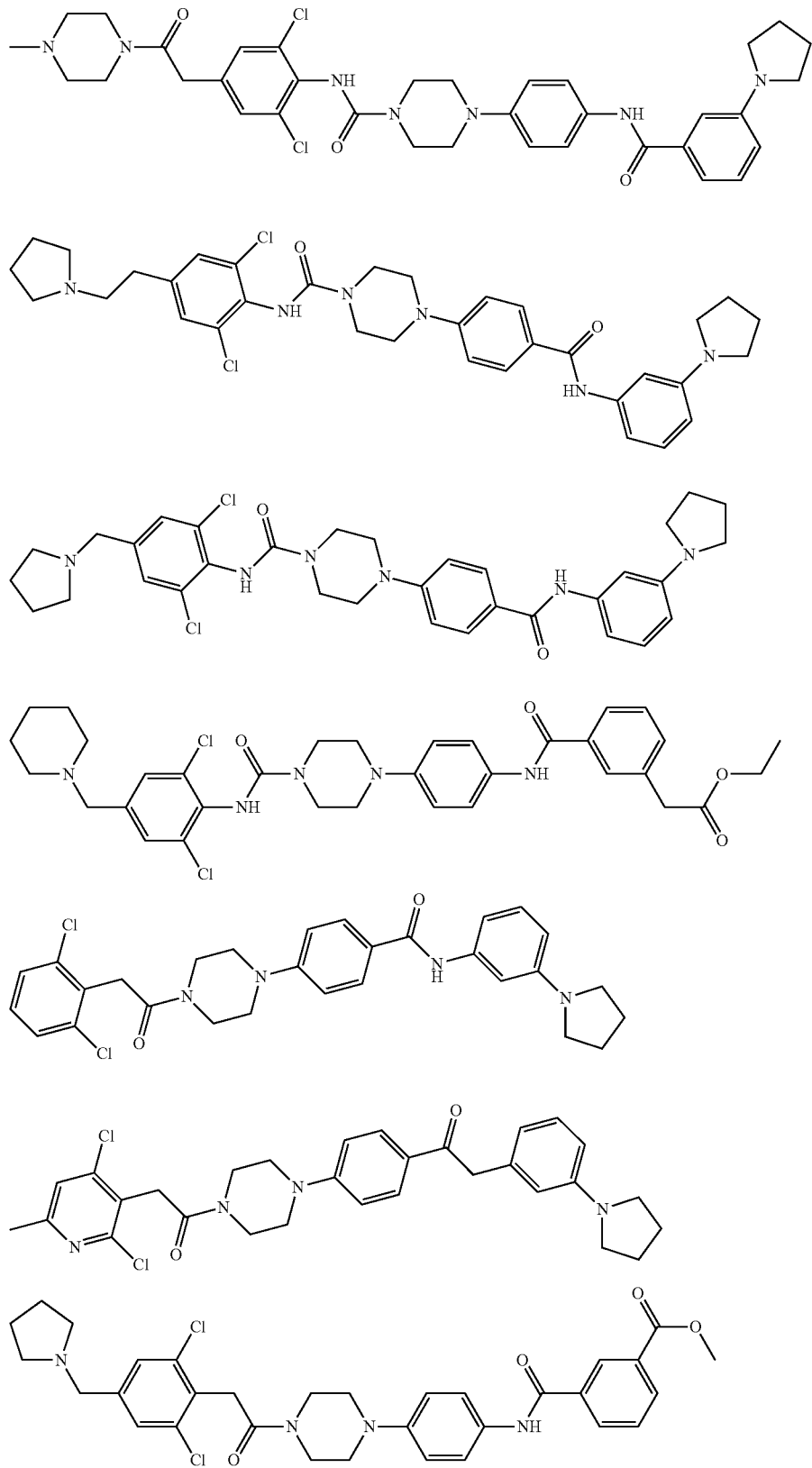
including any stereochemically isomeric form thereof;

a N-oxide thereof, a pharmaceutically acceptable salt thereof or a solvate thereof;
or
C-23) compounds of formula (I), wherein the compound is selected from 4-[4-[[2-chloro-4-(1-pyrrolidinylmethyl)phenyl]acetyl]-1-piperazinyl]-N-[3-(1-pyrrolidinyl)phenyl]-benzamide (compound 151 Class C);

4-[4-[[2-chloro-4-(1-pyrrolidinylmethyl)phenyl]hydroxyacetyl]-1-piperazinyl]-N-[3-(1-pyrrolidinyl)phenyl]-benzamide (compound 152 Class C);

4-[4-[[2,6-dichloro-4-(1-pyrrolidinylmethyl)phenyl]acetyl]-1-piperazinyl]-N-[3-(1-pyrrolidinyl)phenyl]-benzamide (compound 147 Class C);

4-[4-[[2,6-dichloro-4-[[4-(methylsulfonyl)-1-piperazinyl]methyl]phenyl]acetyl]-1-piperazinyl]-N-[3-(1-pyrrolidinyl)phenyl]-benzamide (compound 150 Class C);

4-[4-[[4-[(4-acetyl-1-piperazinyl)methyl]-2,6-dichlorophenyl]acetyl]-1-piperazinyl]-N-[3-(1-pyrrolidinyl)phenyl]-benzamide (compound 149 Class C);

4-[4-[[2,6-dichloro-4-[(4-ethyl-1-piperazinyl)methyl]phenyl]acetyl]-1-piperazinyl]-N-[3-(1-pyrrolidinyl)phenyl]-benzamide (compound 148 Class C);

including any stereochemically isomeric form thereof;
a N-oxide thereof, a pharmaceutically acceptable salt thereof or a solvate thereof;
or
C-24) compounds of class C or, whenever possible, any subgroup thereof as mentioned hereinbefore as embodiment wherein $R^2$ represents hydrogen, $C_{1-6}$alkyl or $C_{2-6}$alkenyl.

The next embodiments of the present invention are those combinations of a DGAT inhibitor, more in particular a DGAT1 inhibitor and a PPAR agonist, in particular a PPAR-α agonist, more in particular a fibrate, even more in particular fenofibrate; wherein the DGAT inhibitor is selected from compounds of Class D. Preferred embodiments of compounds of class D are:

D-1) compounds of class D having the following formula (I)

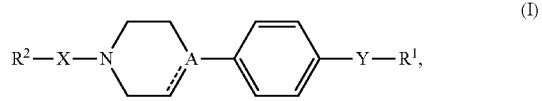

including any stereochemically isomeric form thereof, wherein
A represents CH or N;
the dotted line represents an optional bond in case A represents a carbon atom;
X represents —C(=O)—; —NR$^x$—C(=O)—; —Z$^1$—C(=O)—; —Z$^1$—NR$^x$—C(=O)—; —C(=O)—Z$^1$—; —NR$^x$—C(=O)—Z$^1$—; —S(=O)p-; C(=S)—; —NR$^x$—C(=S)—; —Z$^1$—C(=S)—; —Z$^1$—NR$^x$—C(=S)—; —C(=S)—Z$^1$—; —NR$^x$—C(=S)—Z$^1$—;

$Z^1$ represents a bivalent radical selected from $C_{1-6}$alkanediyl, $C_{2-6}$alkenediyl or $C_{2-6}$alkynediyl; wherein each of said $C_{1-6}$alkanediyl, $C_{2-6}$alkenediyl or $C_{2-6}$alkynediyl may optionally be substituted with hydroxyl;

Y represents —NR$^x$—C(=O)—Z$^2$—; —NR$^x$—C(=O)—Z$^2$—NR$^y$—; —NR$^x$—C(=O)—Z$^2$—NR$^y$—C(=O)—; —NR$^x$—C(=O)—Z$^2$—NR$^y$—C(=O)—O—; —NR$^x$—C(=O)—Z$^2$—O—; —NR$^x$—C(=O)—Z$^2$—O—C(=O)—; —NR$^x$—C(=O)—Z$^2$—C(=O)—O—; —NR$^x$—C(=O)—O—Z$^2$—C(=O)—O—; —NR$^x$—C(=O)—O—Z$^2$—O—C(=O)—; —NR$^x$—C(=O)—Z$^2$—C(=O)—NR$^y$—; —NR$^x$—C(=O)—Z$^2$—NR$^y$—C(=O)—NR$^y$—; —C(=O)—Z$^2$—; —C(=O)—Z$^2$—O—; —C(=O)—NR$^x$—Z$^2$—; —C(=O)—NR$^x$—Z$^2$—O—; —C(=O)—NR$^x$—Z$^2$—C(=O)—O—; —C(=O)—NR$^x$—Z$^2$—O—C(=O)—; —C(=O)—NR$^x$—O—Z$^2$—; —C(=O)—NR$^x$—Z$^2$—NR$^y$—; —C(=O)—NR$^x$—Z$^2$—NR$^y$—C(=O)—; —C(=O)—NR$^x$—Z$^2$—NR$^y$—C(=O)—O—;

$Z^2$ represents a bivalent radical selected from $C_{1-6}$alkanediyl, $C_{2-6}$alkenediyl or $C_{2-6}$alkynediyl; wherein each of said $C_{1-6}$alkanediyl, $C_{2-6}$alkenediyl or $C_{2-6}$alkynediyl may optionally be substituted with $C_{1-4}$alkyloxy, $C_{1-4}$alkylthio, hydroxyl, cyano or aryl; and wherein two hydrogen atoms attached to the same carbon atom in the definition of $Z^2$ may optionally be replaced by $C_{1-6}$alkanediyl;

$R^x$ represents hydrogen or $C_{1-4}$alkyl;
$R^y$ represents hydrogen; $C_{1-4}$alkyl optionally substituted with $C_{3-6}$cycloalkyl or aryl or Het; $C_{2-4}$alkenyl; or —S(=O)$_p$-aryl;

$R^1$ represents $C_{1-12}$alkyl optionally substituted with cyano, $C_{1-4}$alkyloxy, $C_{1-4}$alkyl-oxyC$_{1-4}$alkyloxy, $C_{3-6}$cycloalkyl or aryl; $C_{2-6}$alkenyl; $C_{2-6}$alkynyl; $C_{3-6}$cycloalkyl; aryl$^1$; aryl$^1$C$_{1-6}$alkyl; Het$^1$; or Het$^1$C$_{1-6}$alkyl; provided that when Y represents —NR$^x$—C(=O)—Z$^2$—; —NR$^x$—C(=O)—Z$^2$—NR$^y$; —NR$^x$—C(=O)—Z$^2$—C(=O)—NR$^y$—; —C(=O)—Z$^2$—; —NR$^x$—C(=O)—Z$^2$—NR$^y$—C(=O)—NR$^y$—; —C(=O)—NR$^x$—Z$^2$—; —C(=O)—NR$^x$—O—Z$^2$—; or —C(=O)—NR$^x$—Z$^2$—NR$^y$—; then $R^1$ may also represent hydrogen;

$R^2$ represents hydrogen, $C_{1-6}$alkyl, $C_{2-6}$alkenyl or $R^3$;

$R^3$ represents $C_{3-6}$cycloalkyl, phenyl, naphtalenyl, 2,3-dihydro-1,4-benzodioxinyl, 1,3-benzodioxolyl, wherein said $C_{3-6}$cycloalkyl, phenyl, naphtalenyl, 2,3-dihydro-1,4-benzodioxinyl, 1,3-benzodioxolyl may optionally be substituted with at least one substituent, in particular one, two, three, four or five substituents, each substituent independently selected from hydroxyl; carboxyl; halo; $C_{1-6}$alkyl optionally substituted with hydroxy; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono-or di($C_{1-4}$alkyl)amino; —S(=O)$_p$—$C_{1-4}$alkyl; $R^5R^4$N—C(=O)—; $R^5R^4$N—$C_{1-6}$alkyl; $C_{3-6}$cycloalkyl; $C_{3-6}$cycloalkylC$_{1-4}$alkyl; $C_{3-6}$cycloalkyl-C(=O)—; aryl; aryloxy; arylC$_{1-4}$alkyl; aryl-C(=O)—; Het; HetC$_{1-4}$alkyl; Het-C(=O)—; Het-O—;

$R^4$ represents hydrogen; $C_{1-4}$alkyl optionally substituted with hydroxyl or $C_{1-4}$alkyloxy; $R^7R^6$N—$C_{1-4}$alkyl; $C_{1-4}$alkyloxy; Het; aryl; $R^7R^6$N—C(=O)—$C_{1-4}$alkyl;

$R^5$ represents hydrogen or $C_{1-4}$alkyl;
$R^6$ represents hydrogen; $C_{1-4}$alkyl; $C_{1-4}$alkylcarbonyl;
$R^7$ represents hydrogen or $C_{1-4}$alkyl; or
$R^6$ and $R^7$ may be taken together with the nitrogen to which they are attached to form a saturated monocyclic 5, 6 or 7-membered heterocycle which may further contain one or more heteroatoms selected from O, S, S(=O)$_p$ or N; and which heterocycle may optionally be substituted with $C_{1-4}$alkyl;

aryl represents phenyl or phenyl substituted with at least one substituent, in particular one, two, three, four or five substituents, each substituent independently being selected from hydroxyl; carboxyl; halo; $C_{1-6}$alkyl optionally substituted with $C_{1-4}$alkyloxy, amino or mono-or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono-or di($C_{1-4}$alkyl)aminocarbonyl; $C_{1-6}$alkylcarbonyl; nitro; amino; mono-or di($C_{1-4}$alkyl)amino; —S(=O)$_p$—$C_{1-4}$alkyl;

aryl$^1$ represents phenyl, naphthalenyl or fluorenyl; each of said phenyl, naphthalenyl or fluorenyl optionally substituted with at least one substituent, in particular one, two, three, four or five substituents, each substituent independently being selected from hydroxyl; oxo; carboxyl; halo; $C_{1-6}$alkyl optionally substituted with aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)aminocarbonyl; $C_{1-6}$alkylcarbonyl; nitro; amino; mono-or di($C_{1-6}$alkyl)amino; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; HetC$_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; HetC$_{1-4}$alkyl; Het-O—;

Het represents a monocyclic non-aromatic or aromatic heterocycle containing at least one heteroatom selected from O, S, S(=O)$_p$ or N; or a bicyclic or tricyclic non-aromatic or aromatic heterocycle containing at least one heteroatom selected from O, S, S(=O)$_p$ or N; said monocyclic heterocycle or said bi-or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with $C_{1-4}$alkyloxy, amino or mono-or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono-or di($C_{1-4}$alkyl)aminocarbonyl; $C_{1-6}$alkylcarbonyl; nitro; amino; mono-or di($C_{1-4}$alkyl)amino; —S(=O)$_p$—$C_{1-4}$alkyl;

Het$^1$ represents a monocyclic non-aromatic or aromatic heterocycle containing at least one heteroatom selected from O, S, S(=O)$_p$ or N; or a bicyclic or tricyclic non-aromatic or aromatic heterocycle containing at least one heteroatom selected from O, S, S(=O)$_p$ or N; said monocyclic heterocycle or said bi-or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono-or di($C_{1-4}$alkyl)aminocarbonyl; $C_{1-6}$alkylcarbonyl; nitro; amino; mono-or di($C_{1-6}$alkyl)amino; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; HetC$_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; HetC$_{1-4}$alkyl; Het-C(=O)—; Het-O—;

p represents 1 or 2;
a N-oxide thereof, a pharmaceutically acceptable salt thereof or a solvate thereof;

or

D-2) compounds of class D or any subgroup thereof as mentioned hereinbefore as embodiment wherein X represents —C(=O)—C(=O)—; —O—C(=O)—; —NR$^x$—C(=O)—; —Z$^1$—C(=O)—; —Z$^1$—NR$^x$—C(=O)—; —C(=O)—Z$^1$—; —NR$^x$—C(=O)—Z$^1$—; —S(=O)p-; —NR$^x$—C(=S)—; in particular X represents —NR$^x$—C(=O)—; —Z$^1$—C(=O)—; —Z$^1$—NR$^x$—C(=O)—; —C(=O)—Z$^1$—; —NR$^x$—C(=O)—Z$^1$—; —S(=O)p-; —NR$^x$—C(=S)—; more in particular X represents —NR$^x$—C(=O)—; —Z$^1$—C(=O)—; —C(=O)—Z$^1$—; —Z$^1$—NR$^x$—C(=O)—; —NR$^x$—C(=S)— or —S(=O)p-; even more in particular X represents —NR$^x$—C(=O)— or —Z$^1$—NR$^x$—C(=O)—; even more in particular —NR$^x$—C(=O)—;

or

D-3) compounds of class D or any subgroup thereof as mentioned hereinbefore as embodiment wherein A represents N;

or

D-4) compounds of class D or any subgroup thereof as mentioned hereinbefore as embodiment wherein A represents CH, in particular wherein A represents CH and the dotted line does not represent a bond;

or

D-5) compounds of class D or any subgroup thereof as mentioned hereinbefore as embodiment wherein R$^1$ represents $C_{3-6}$cycloalkyl; adamantanyl; aryl$^1$; aryl$^1C_{1-6}$alkyl; Het$^1$; or Het$^1C_{1-6}$alkyl; aryl$^1$; in particular aryl$^1C_{1-6}$alkyl; Het$^1$; or Het$^1C_{1-6}$alkyl; more in particular aryl$^1$; aryl$^1C_{1-6}$alkyl; Het$^1$; or Het$^1C_{1-6}$alkyl, wherein said aryl$^1$ or Het$^1$ represent phenyl, naphthalenyl, morpholinyl, piperidinyl, piperazinyl, pyrrolidinyl, furanyl, imidazolyl, thienyl, pyridyl; each of said cycles representing aryl$^1$ or Het$^1$ being optionally substituted with one or two substituents; in particular with aryl, $C_{1-6}$alkyl, aryl$C_{1-4}$alkyl, hydroxyl, halo, polyhalo$C_{1-6}$alkyl, $C_{1-6}$alkyloxy, nitro, $C_{1-6}$alkyloxycarbonyl, —S(=O)$_2$—$C_{1-4}$alkyl; more in particular with aryl, $C_{1-6}$alkyl, aryl$C_{1-4}$alkyl, halo, $C_{1-6}$alkyloxy, $C_{1-6}$alkyloxycarbonyl, —S(=O)$_2$—$C_{1-4}$alkyl. More in particular R$^1$ represents aryl$^1$ wherein aryl$^1$ represents preferably optionally substituted phenyl. Even more in particular R$^1$ represents phenyl substituted with $C_{1-6}$alkyloxy, e.g. methoxy;

or

D-6) compounds of class D or any subgroup thereof as mentioned hereinbefore as embodiment wherein R$^1$ represents $C_{1-12}$alkyl optionally substituted with cyano, $C_{1-4}$alkyloxy, $C_{1-4}$alkyl-oxy$C_{1-4}$alkyloxy, $C_{3-6}$cycloalkyl or aryl; $C_{2-6}$alkenyl; $C_{2-6}$alkynyl; provided that when Y represents —NR$^x$—C(=O)—Z$^2$—; —NR$^x$—C(=O)—Z$^2$—NR$^y$—; —NR$^x$—C(=O)—Z$^2$—C(=O)—NR$^y$—; —C(=O)—Z$^2$—; —NR$^x$—C(=O)—Z$^2$—NR$^y$—C(=O)—NR$^y$—; —C(=O)—NR$^x$—Z$^2$—; —C(=O)—NR$^x$—O—Z$^2$—; or —C(=O)—NR$^x$—Z$^2$—NR$^y$—; then R$^1$ may also represent hydrogen;

or

D-7) compounds of class D or any subgroup thereof as mentioned hereinbefore as embodiment wherein R$^2$ represents $C_{1-12}$alkyl; in particular $C_{1-6}$alkyl;

or

D-8) compounds of class D or any subgroup thereof as mentioned hereinbefore as embodiment wherein R$^2$ represents $C_{1-6}$alkyl or R$^3$; in particular wherein R$^2$ represents R$^3$ and said R$^3$ represents phenyl, naphthalenyl, 2,3-dihydrobenzofuranyl or 6-membered aromatic heterocycle containing 1 or 2 N atoms, each of said cycles, in particular phenyl, being optionally substituted with one to five substituents, said substituents being in particular halo, $C_{1-6}$alkyl optionally substituted with hydroxy, polyhalo$C_{1-6}$alkyl, $C_{1-6}$alkylthio, polyhalo$C_{1-6}$alkyloxy, carboxyl, hydroxyl, $C_{1-6}$alkylcarbonyl, $C_{1-6}$alkyloxy, $C_{1-6}$alkyloxycarbonyl, nitro, $R^5R^4N$—C(=O)—, $R^5R^4N$—$C_{1-6}$alkyl, Het$C_{1-4}$alkyl, Het-C(=O)—$C_{1-4}$alkyl, Het-C(=O)—; said substituents being more in particular halo, $C_{1-6}$alkyl optionally substituted with hydroxy, polyhalo$C_{1-6}$alkyl, polyhalo$C_{1-6}$alkyloxy, carboxyl, hydroxyl, $C_{1-6}$alkylcarbonyl, $C_{1-6}$alkyloxy, $C_{1-6}$alkylthio, $C_{1-6}$alkyloxycarbonyl, nitro, $R^5R^4N$—$C_{1-6}$alkyl, Het$C_{1-4}$alkyl; more in particular wherein $R^2$ represents phenyl substituted with one, two or three substituents, preferably three substituents, each substituent being selected from halo, e.g. chloro, or Het$C_{1-4}$alkyl, e.g. pyrrolidinylmethyl;

or

D-9) compounds of class D or any subgroup thereof as mentioned hereinbefore as embodiment wherein the compound of class D is a compound of formula (I')

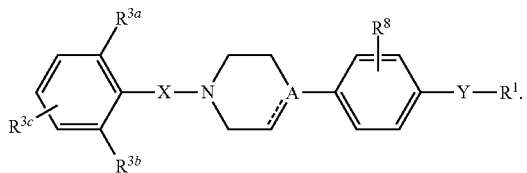

wherein $R^{3a}$ and $R^{3b}$ each independently represent hydrogen; hydroxyl; carboxyl; halo; $C_{1-6}$alkyl; polyhalo-$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono-or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl; and wherein $R^{3c}$ represents hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono-or di($C_{1-4}$alkyl)amino; —S(=O)$_p$—$C_{1-4}$alkyl; $R^5R^4N$—C(=O)—; $R^5R^4N$—$C_{1-6}$alkyl; $C_{3-6}$cycloalkyl; aryl; aryloxy; aryl$C_{1-4}$alkyl; aryl-C(=O)—$C_{1-4}$alkyl; aryl-C(=O)—; Het; Het$C_{1-4}$alkyl; Het-C(=O)—$C_{1-4}$alkyl; Het-C(=O)—; Het-O—;

or

D-10) compounds of class D or any subgroup thereof as mentioned hereinbefore as embodiment wherein the compound of class D is a compound of formula (I")

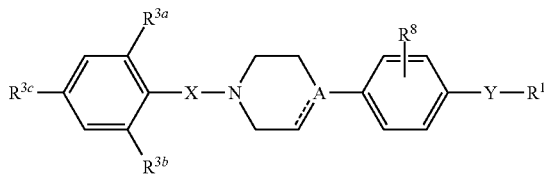

wherein $R^{3a}$ and $R^{3b}$ each independently represent hydrogen; hydroxyl; carboxyl; halo; $C_{1-6}$alkyl; polyhalo-$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono-or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl; and wherein $R^{3c}$ represents hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono- or di($C_{1-4}$alkyl)amino; —S(=O)$_p$—$C_{1-4}$alkyl; $R^5R^4N$—C(=O)—; $R^5R^4N$—$C_{1-6}$alkyl; $C_{3-6}$cycloalkyl; aryl; aryloxy; aryl-C(=O)—$C_{1-4}$alkyl; aryl$C_{1-4}$alkyl; aryl-C(=O)—; Het; Het$C_{1-4}$alkyl; Het-C(=O)—$C_{1-4}$alkyl; Het-C(=O)—; Het-O—;

or

D-11) compounds of class D or any subgroup thereof as mentioned hereinbefore as embodiment wherein the compound of class D is a compound of formula (I') or (I") and wherein $R^{3a}$ and $R^{3b}$ each independently represent halo, $C_{1-6}$alkyl or $C_{1-6}$alkyloxy; in particular halo or $C_{1-6}$alkyl; more in particular both $R^{3a}$ and $R^{3b}$ represent halo, more in particular both $R^{3a}$ and $R^{3b}$ represent chloro;

or

D-12) compounds of class D or any subgroup thereof as mentioned hereinbefore as embodiment wherein the compound of formula (I) is a compound of formula (I') or (I") and wherein $R^{3c}$ represents amino; mono-or di($C_{1-4}$alkyl)amino; $R^5R^4N$—C(=O)—; $R^5R^4N$—$C_{1-6}$alkyl; Het-C(=O)—; Het-C(=O)—$C_{1-4}$alkyl or Het$C_{1-4}$alkyl; or $R^{3c}$ represents hydrogen; more in particular wherein $R^{3c}$ represents amino; mono-or di($C_{1-4}$alkyl)amino; $R^5R^4N$—C(=O)—; $R^5R^4N$—$C_{1-6}$alkyl; Het-C(=O)— or Het$C_{1-4}$alkyl; or $R^{3c}$ represents hydrogen; even more in particular wherein $R^{3c}$ represents Het$C_{1-4}$alkyl, e.g. pyrrolidinylmethyl;

or

D-13) compounds of class D or any subgroup thereof as mentioned hereinbefore as embodiment wherein p represents 2;

or

D-14) compounds of class D or any subgroup thereof as mentioned hereinbefore as embodiment wherein Y represents —NR$^x$—C(=O)—Z$^2$—; —NR$^x$—C(=O)—Z$^2$—NR$^y$; —NR$^x$—C(=O)—Z$^2$—NR$^y$—C(=O)—O—; —NR$^x$—C(=O)—Z$^2$—O—C(=O)—; —NR$^x$—C(=O)—Z$^2$—C(=O)—O—; —NR$^x$—C(=O)—O—Z$^2$—C(=O)—O—; —NR$^x$—C(=O)—O—Z$^2$—O—C(=O)—; —NR$^x$—C(=O)—Z$^2$—C(=O)—NR$^y$—; —NR$^x$—C(=O)—Z$^2$—NR$^y$—C(=O)—NR$^y$—; —C(=O)—NR$^x$—Z$^2$—; —C(=O)—NR$^x$—Z$^2$—O—; —C(=O)—NR$^x$—Z$^2$—C(=O)—O—; —C(=O)—NR$^x$—Z$^2$—O—C(=O)—; —C(=O)—NR$^x$—O—Z$^2$—; —C(=O)—NR$^x$—Z$^2$—NR$^y$—; —C(=O)—NR$^x$—Z$^2$—NR$^y$—C(=O)—; —C(=O)—NR$^x$—Z$^2$—NR$^y$—C(=O)—O—; or wherein Y represents NR$^x$—C(=O)—Z$^2$—; —NR$^x$—C(=O)—Z$^2$—NR$^y$; —NR$^x$—C(=O)—Z$^2$—NR$^y$—C(=O)—; —NR$^x$—C(=O)—Z$^2$—NR$^y$—C(=O)—O—; —NR$^x$—C(=O)—Z$^2$—O—; —NR$^x$—C(=O)—Z$^2$—C(=O)—O—; —NR$^x$—C(=O)—Z$^2$—C(=O)—NR$^y$—; —NR$^x$—C(=O)—Z$^2$—NR$^y$—C(=O)—NR$^y$—; —C(=O)—Z$^2$—; or wherein Y represents NR$^x$—C(=O)—Z$^2$— or —NR$^x$—C(=O)—Z$^2$—NR$^y$; or wherein Y represents —NR$^x$—C(=O)—

$Z^2$—$NR^y$—C(=O)—O— or —$NR^x$—C(=O)—$Z^2$—C(=O)—O—. More in particular Y represents —$NR^x$—C(=O)—$Z^2$—;

or

D-15) compounds of class D or any subgroup thereof as mentioned hereinbefore as embodiment wherein Y represents $NR^x$—C(=O)—$Z^2$—; —$NR^x$—C(=O)—$Z^2$—$NR^y$—; —$NR^x$—C(=O)—$Z^2$—$NR^y$—C(=O)—; —$NR^x$—C(=O)—$Z^2$—$NR^y$—C(=O)—O—; —$NR^x$—C(=O)—$Z^2$—O—; —$NR^x$—C(=O)—$Z^2$—O—C(=O)—; —$NR^x$—C(=O)—$Z^2$—C(=O)—O—; —$NR^x$—C(=O)—$Z^2$—C(=O)—$NR^y$—; —$NR^x$—C(=O)—$Z^2$—$NR^y$—C(=O)—$NR^y$—; —C(=O)—$Z^2$—; —C(=O)—$NR^x$—$Z^2$—; —C(=O)—$NR^x$—$Z^2$—O—;

or

D-16) compounds of class D or any subgroup thereof as mentioned hereinbefore as embodiment wherein $Z^2$ represents $C_{1-6}$alkanediyl or $C_{2-6}$alkenediyl; in particular $C_{1-6}$alkanediyl; more in particular methylene;

or

D-17) compounds of class D or any subgroup thereof as mentioned hereinbefore as embodiment wherein $Z^1$ represents $C_{1-6}$alkanediyl, optionally substituted with hydroxyl or amino, or wherein two hydrogen atoms attached to the same carbon atom in $C_{1-6}$alkanediyl may optionally be replaced by $C_{1-6}$alkanediyl; in particular wherein $Z^1$ represents $C_{1-6}$alkanediyl;

or

D-18) compounds of class D or any subgroup thereof as mentioned hereinbefore as embodiment wherein $R^x$ represents hydrogen;

or

D-19) compounds of class D or any subgroup thereof as mentioned hereinbefore as embodiment wherein $R^y$ represents hydrogen or $C_{1-4}$alkyl or $C_{2-4}$alkenyl or —S(=O)$_p$-aryl;

or

D-20) compounds of class D or any subgroup thereof as mentioned hereinbefore as embodiment wherein $R^8$ represents hydrogen;

or

D-21) compounds of class D or any subgroup thereof as mentioned hereinbefore as embodiment wherein $R^8$ represents halo, $C_{1-4}$alkyl or $C_{1-4}$alkyl substituted with hydroxyl;

or

D-22) compounds of class D or any subgroup thereof as mentioned hereinbefore as embodiment wherein aryl represents phenyl or phenyl substituted with one or two substituents, preferably each substituent independently selected from halo, $C_{1-6}$alkyl, polyhalo$C_{1-6}$alkyl, $C_{1-6}$alkyloxy, $C_{1-6}$alkyloxycarbonyl or nitro;

or

D-23) compounds of class D or any subgroup thereof as mentioned hereinbefore as embodiment wherein Het$^1$ represents a monocyclic non-aromatic or aromatic heterocycle or a bicyclic non-aromatic heterocycle, each of said cycles may optionally be substituted. In particular Het$^1$ represents morpholinyl, pyrrolidinyl, piperazinyl, homopiperazinyl, piperidinyl, furanyl, imidazolyl, thienyl, pyridyl, 1,3-benzodioxolyl, tetrahydropyranyl, each of said heterocycles optionally being substituted with one or two substituents, preferably each substituent independently being selected from halo, $C_{1-6}$alkyl, $C_{1-6}$alkyloxycarbonyl, —S(=O)$_p$—$C_{1-4}$alkyl, aryl, aryl$C_{1-4}$alkyl, polyhalo$C_{1-6}$alkyl, $C_{1-6}$alkyloxy, nitro; more preferably each substituent independently being selected from halo, $C_{1-6}$alkyl, $C_{1-6}$alkyloxycarbonyl, —S(=O)$_p$—$C_{1-4}$alkyl, aryl, aryl$C_{1-4}$alkyl;

or

D-24) compounds of class D or any subgroup thereof as mentioned hereinbefore as embodiment wherein aryl$^1$ represents phenyl, naphthalenyl or phenyl substituted with one or two substituents, preferably each substituent independently being selected from hydroxyl, halo, $C_{1-6}$alkyl, $C_{1-6}$alkyloxy, $C_{1-6}$alkyloxycarbonyl or Het;

or

D-25) compounds of class D or any subgroup thereof as mentioned hereinbefore as embodiment wherein Het is a monocyclic non-aromatic or aromatic heterocycle, each of said heterocycles may optionally be substituted. In particular, Het is piperidinyl, pyrrolidinyl, piperazinyl, pyridyl, morpholinyl, each of said heterocycles optionally being substituted with one substituent, preferably the substituent is selected from $C_{1-6}$alkyl, $C_{1-6}$alkyl substituted with $C_{1-4}$alkyloxy, —S(=O)$_p$—$C_{1-4}$alkyl, $C_{1-6}$alkylcarbonyl;

or

D-26) compounds of class D or any subgroup thereof as mentioned hereinbefore as embodiment wherein one or more, preferably all, of the following restrictions apply:

a) X represents —$NR^x$—C(=O)—; —$Z^1$—C(=O)—; —$Z^1$—$NR^x$—C(=O)—; —C(=O)—$Z^1$—; —S(=O)p-; —$NR^x$—C(=S)—;

b) $R^2$ represents $C_{1-6}$alkyl or $R^3$, with $R^3$ representing phenyl, naphthalenyl or 1,3-benzodioxolyl, each of said cycles being optionally substituted with one to five substituents, said substituents being in particular halo, $C_{1-6}$alkyl optionally substituted with hydroxy, polyhalo$C_{1-6}$alkyl, polyhalo$C_{1-6}$alkyloxy, carboxyl, hydroxyl, $C_{1-6}$alkylcarbonyl, $C_{1-6}$alkyloxy, $C_{1-6}$alkylthio, $C_{1-6}$alkyloxycarbonyl, nitro, $R^5R^4N$—$C_{1-6}$alkyl, Het$C_{1-4}$alkyl.

c) A represents N;

d) A represents CH;

e) Y represents $NR^x$—C(=O)—$Z^2$—; —$NR^x$—C(=O)—$Z^2$—$NR^y$; —$NR^x$—C(=O)—$Z^2$—$NR^y$—C(=O)—; —$NR^x$—C(=O)—$Z^2$—$NR^y$—C(=O)—O—; —$NR^x$—C(=O)—$Z^2$—O—; —$NR^x$—C(=O)—$Z^2$—C(=O)—O—; —$NR^x$—C(=O)—$Z^2$—C(=O)—$NR^y$—; —$NR^x$—C(=O)—$Z^2$—$NR^y$—C(=O)—$NR^y$—; —C(=O)—$Z^2$—;

f) $Z^1$ represents $C_{1-6}$alkanediyl optionally substituted with hydroxy;

g) $R^y$ represents hydrogen; $C_{1-4}$alkyl optionally substituted with $C_{3-6}$cycloalkyl or aryl; $C_{2-4}$alkenyl; or —S(=O)$_p$-aryl;

h) aryl$^1$ represents phenyl, said phenyl optionally substituted with $C_{1-6}$alkyl, halo, polyhalo$C_{1-6}$alkyl, $C_{1-6}$alkyloxy, nitro, $C_{1-6}$alkyloxycarbonyl;

i) Het$^1$ represents a 5-or 6-membered non-aromatic or aromatic heterocycle, such as for example morpholinyl, piperidinyl, piperazinyl, pyrrolidinyl, furanyl, imidazolyl, thienyl, pyridyl, said 5-or 6-membered heterocycle optionally substituted with aryl, $C_{1-6}$alkyl, aryl$C_{1-6}$alkyl, halo, polyhalo$C_{1-6}$alkyl, $C_{1-6}$alkyloxycarbonyl, —S(=O)$_2$—$C_{1-4}$alkyl;

or

D-27) compounds of class D having the following formula

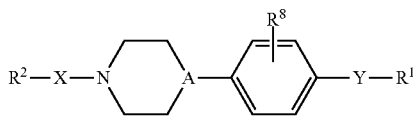

wherein one or more, preferably all, of the following restrictions apply:
a) A represents CH or N;
b) X represents —O—C(=O)—; —C(=O)—C(=O)—; —NR$^x$—C(=O)—; —Z$^1$—C(=O)—; —Z$^1$—NR$^x$—C(=O)—; —C(=O)—Z$^1$—; —S(=O)p-; —NR$^x$—C(=S)—;
c) Z$^1$ represents C$_{1-6}$alkanediyl; wherein said C$_{1-6}$alkanediyl may optionally be substituted with hydroxyl or amino; and wherein two hydrogen atoms attached to the same carbon atom in C$_{1-6}$alkanediyl may optionally be replaced by C$_{1-6}$alkanediyl;
d) Y represents NR$^x$—C(=O)—Z$^2$—; —NR$^x$—C(=O)—Z$^2$—NR$^y$—; —NR$^x$—C(=O)—Z$^2$—NR$^y$—C(=O)—; —NR$^x$—C(=O)—Z$^2$—NR$^y$—C(=O)—O—; —NR$^x$—C(=O)—Z$^2$—O—; —NR$^x$—C(=O)—Z$^2$—O—C(=O)—; —NR$^x$—C(=O)—Z$^2$—C(=O)—O—; —NR$^x$—C(=O)—Z$^2$—C(=O)—NR$^y$—; —NR$^x$—C(=O)—Z$^2$—NR$^y$—C(=O)—NR$^y$—; —C(=O)—Z$^2$—; —C(=O)—NR$^x$—Z$^2$—; —C(=O)—NR$^x$—Z$^2$—O—;
e) Z$^2$ represents a bivalent radical selected from C$_{1-6}$alkanediyl, C$_{2-6}$alkenediyl or C$_{2-6}$alkynediyl; wherein each of said C$_{1-6}$alkanediyl, C$_{2-6}$alkenediyl or C$_{2-6}$alkynediyl may optionally be substituted with C$_{1-4}$alkyloxy, C$_{1-4}$alkylthio, hydroxyl, cyano or aryl; and wherein two hydrogen atoms attached to the same carbon atom in the definition of Z$^2$ may optionally be replaced by C$_{1-6}$alkanediyl;
f) R$^x$ represents hydrogen or C$_{1-4}$alkyl;
g) R$^y$ represents hydrogen; C$_{1-4}$alkyl; C$_{2-4}$alkenyl; or —S(=O)$_p$-aryl;
h) R$^1$ represents C$_{1-12}$alkyl optionally substituted with cyano, C$_{1-4}$alkyloxy, C$_{1-4}$alkyl-oxyC$_{1-4}$alkyloxy, C$_{3-6}$cycloalkyl or aryl; C$_{2-6}$alkenyl; C$_{2-6}$alkynyl; C$_{3-6}$cycloalkyl; adamantanyl; aryl$^1$; Het$^1$; or Het$^1$C$_{1-6}$alkyl; provided that when Y represents —NR$^x$—C(=O)—Z$^2$—; —NR$^x$—C(=O)—Z$^2$—NR$^y$—; —NR$^x$—C(=O)—Z$^2$—C(=O)—NR$^y$—; —C(=O)—Z$^2$—; —NR$^x$—C(=O)—Z$^2$—NR$^y$—C(=O)—NR$^y$—; —C(=O)—NR$^x$—Z$^2$—; —C(=O)—NR$^x$—O—Z$^2$—; or —C(=O)—NR$^x$—Z$^2$—NR$^y$—; then R$^1$ may also represent hydrogen;

i) R$^2$ represents C$_{1-12}$alkyl or R$^3$;
j) R$^3$ represents phenyl, naphtalenyl, 2,3-dihydrobenzofuranyl or a 6-membered aromatic heterocycle containing 1 or 2 N atoms, wherein said phenyl, naphtalenyl, 2,3-dihydrobenzofuranyl or 6-membered aromatic heterocycle containing 1 or 2 N atoms may optionally be substituted with at least one substituent, in particular one, two, three, four or five substituents, each substituent independently selected from hydroxyl; carboxyl; halo; C$_{1-6}$alkyl optionally substituted with hydroxy; polyhaloC$_{1-6}$alkyl; C$_{1-6}$alkyloxy; C$_{1-6}$alkylthio; polyhalo-C$_{1-6}$alkyloxy; C$_{1-6}$alkyloxycarbonyl; C$_{1-6}$alkylcarbonyl; nitro; R$^5$R$^4$N—C(=O)—; R$^5$R$^4$N—C$_{1-6}$alkyl; HetC$_{1-4}$alkyl; Het-C(=O)—C$_{1-4}$alkyl; Het-C(=O)—;
k) R$^4$ represents hydrogen; C$_{1-4}$alkyl optionally substituted with hydroxyl or C$_{1-4}$alkyloxy; R$^7$R$^6$N—C$_{1-4}$alkyl; Het-C$_{1-4}$alkyl; R$^7$R$^6$N—C(=O)—C$_{1-4}$alkyl;
l) R$^5$ represents hydrogen or C$_{1-4}$alkyl;
m) R$^6$ represents C$_{1-4}$alkyl or C$_{1-4}$alkylcarbonyl;
n) R$^7$ represents hydrogen or C$_{1-4}$alkyl; or
o) R$^6$ and R$^7$ may be taken together with the nitrogen to which they are attached to form a saturated monocyclic 5, 6 or 7-membered heterocycle which may further contain one or more heteroatoms each independently selected from O or N;
p) R$^8$ represents hydrogen, halo, C$_{1-4}$alkyl substituted with hydroxyl;
q) aryl represents phenyl or phenyl substituted with at least one substituent, in particular one or two substituents, each substituent independently being selected from halo; C$_{1-6}$alkyl; polyhaloC$_{1-6}$alkyl; C$_{1-6}$alkyloxy; nitro;
r) aryl$^1$ represents phenyl or naphthalenyl; wherein phenyl may optionally be substituted with one or two substituents, each substituent independently being selected from hydroxyl; halo; C$_{1-6}$alkyl; C$_{1-6}$alkyloxy; C$_{1-6}$alkyloxycarbonyl or Het;
s) Het represents a monocyclic non-aromatic or aromatic heterocycle containing at least one heteroatom each independently selected from O, S, S(=O)$_p$ or N, in particular N; said monocyclic heterocycle optionally being substituted with one substituent, said substituent being selected from C$_{1-6}$alkyl optionally substituted with C$_{1-4}$alkyloxy; C$_{1-6}$alkylcarbonyl or —S(=O)$_p$—C$_{1-4}$alkyl;
t) Het$^1$ represents a monocyclic non-aromatic or aromatic heterocycle containing at least one heteroatom each independently selected from O, S, S(=O)$_p$ or N, in particular N, O or S; or a bicyclic non-aromatic heterocycle containing at least one heteroatom each independently selected from O, S, S(=O)$_p$ or N, in particular O; said monocyclic heterocycle or said bicyclic heterocycle optionally being substituted with one or two substituents, each substituent independently being selected from halo; C$_{1-6}$alkyl; C$_{1-6}$alkyloxy-carbonyl; —S(=O)$_p$—C$_{1-4}$alkyl; aryl; or arylC$_{1-4}$alkyl;
u) p represents 2;
or
D-28) compounds of class D selected from

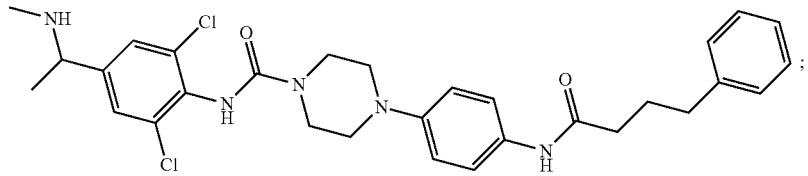

-continued
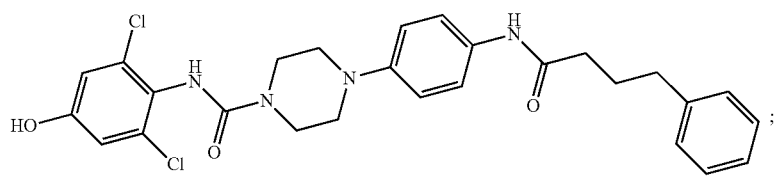;
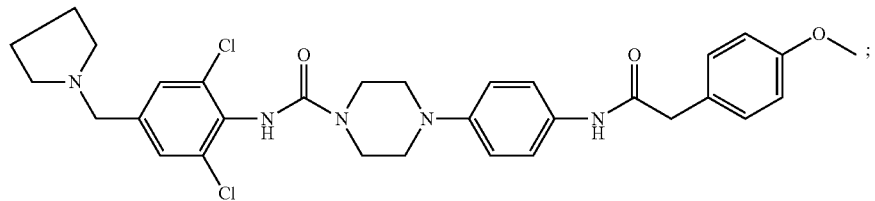;
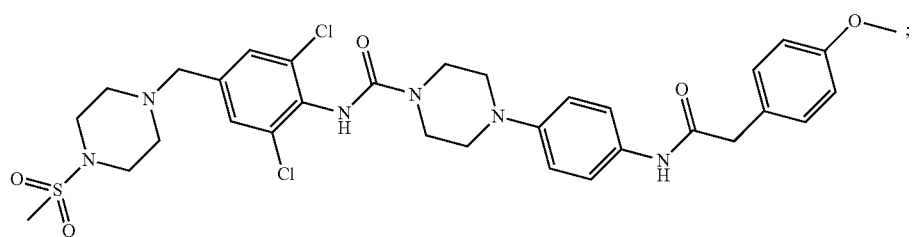;
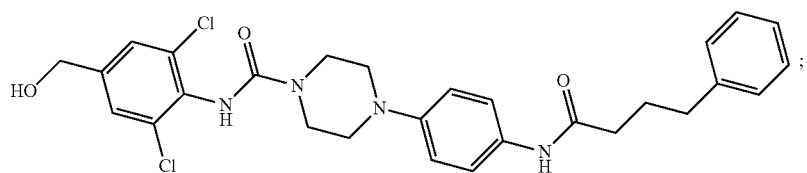;
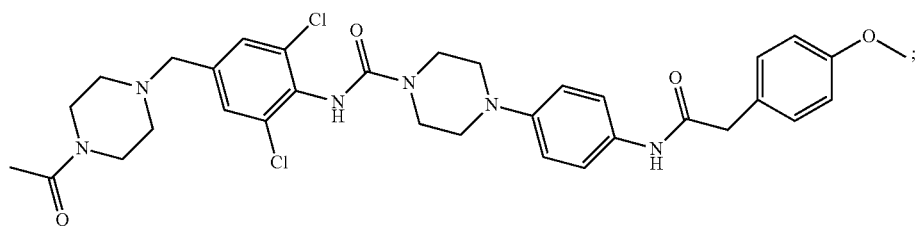;
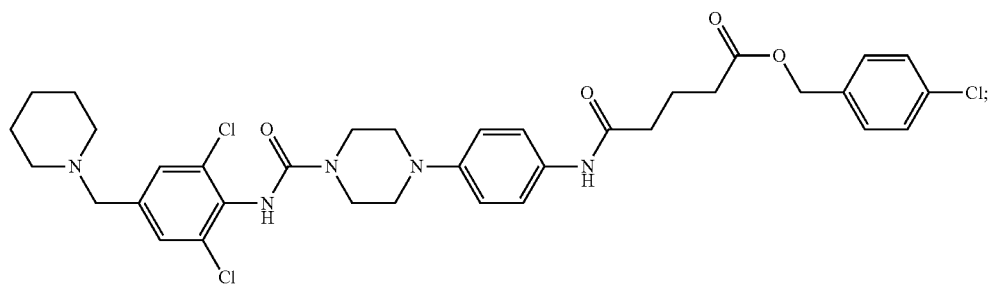;
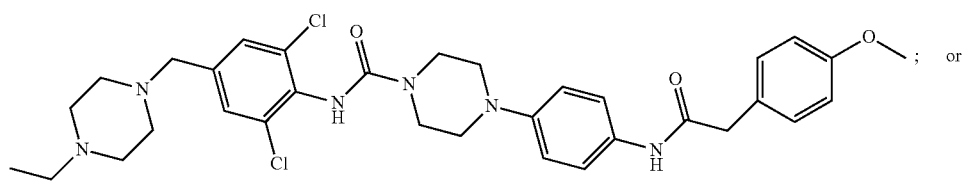; or

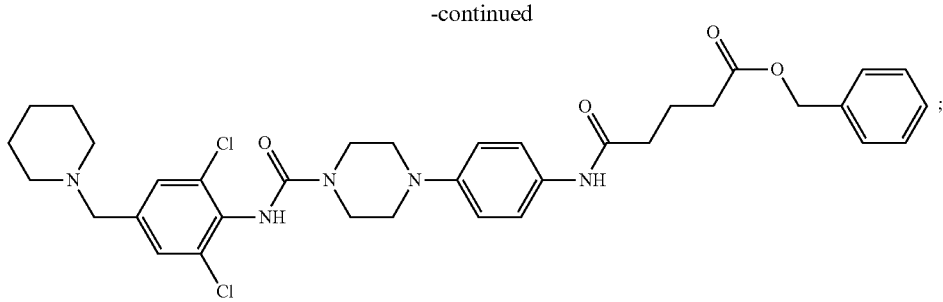
including any stereochemically isomeric form thereof;
a N-oxide thereof, a pharmaceutically acceptable salt thereof or a solvate thereof.
or
D-29) compounds of class D selected from
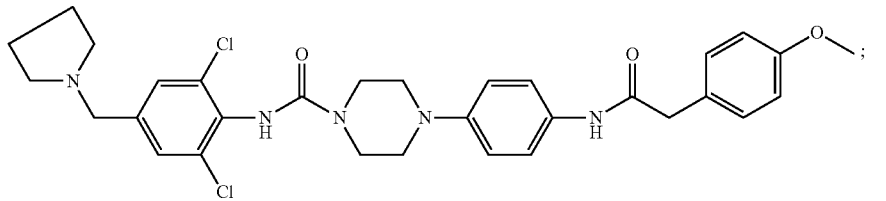
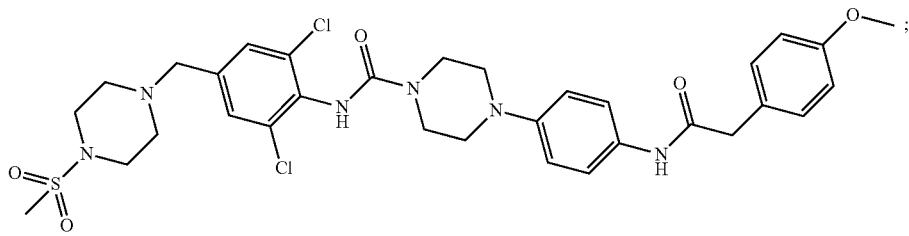
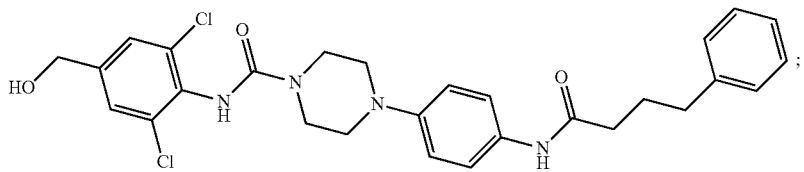
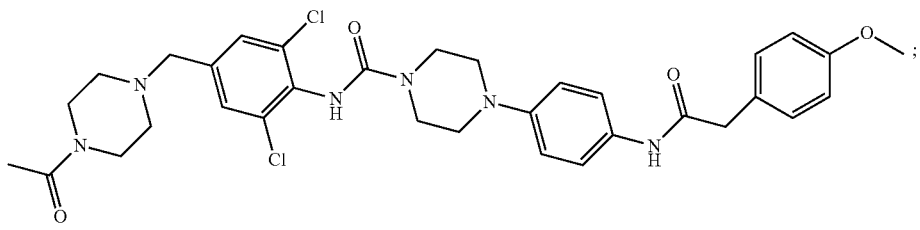
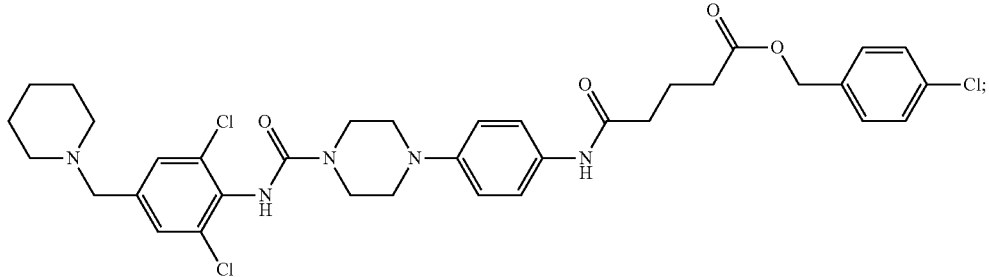

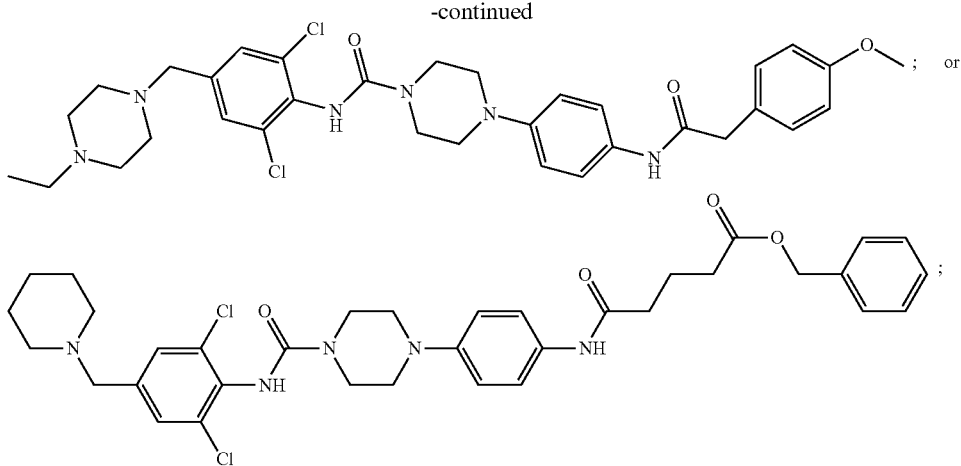

including any stereochemically isomeric form thereof;
a N-oxide thereof, a pharmaceutically acceptable salt thereof or a solvate thereof.
or
D-30) compounds of class D selected from:
N-[4-[4-[[2-chloro-4-(1-pyrrolidinylmethyl)phenyl]acetyl]-1-piperazinyl]phenyl]-4-methoxy-benzeneacetamide (compound 355 Class D);
4-[4-[[2-chloro-4-(1-pyrrolidinylmethyl)phenyl]acetyl]-1-piperazinyl]-N-[[3-(1-pyrrolidinyl)phenyl]methyl]-benzamide (compound 354 Class D);
4-[4-[[2-chloro-4-(1-pyrrolidinylmethyl)phenyl]hydroxyacetyl]-1-piperazinyl]-N-[[3-(1-pyrrolidinyl)phenyl]methyl]-benzamide (compound 356 Class D);
4-[4-[[2,6-dichloro-4-(1-pyrrolidinylmethyl)phenyl]acetyl]-1-piperazinyl]-N-[(3,5-dimethoxyphenyl)methyl]-benzamide (compound 358 Class D);
4-[4-[[2-chloro-4-(1-pyrrolidinylmethyl)phenyl]acetyl]-1-piperazinyl]-N-[(3,5-dimethoxyphenyl)methyl]-benzamide (compound 353 Class D);
4-[4-[[2-chloro-4-(1-pyrrolidinylmethyl)phenyl]hydroxyacetyl]-1-piperazinyl]-N-[(3,5-dimethoxyphenyl)methyl]-benzamide (compound 357 Class D);
4-[4-[[2,6-dichloro-4-[(4-ethyl-1-piperazinyl)methyl]phenyl]acetyl]-1-piperazinyl]-N-[(3,5-dimethoxyphenyl)methyl]-benzamide (compound 360 Class D);
4-[4-[[2,6-dichloro-4-[(4-ethyl-1-piperazinyl)methyl]phenyl]acetyl]-1-piperazinyl]-N-[[3-(1-pyrrolidinyl)phenyl]methyl]-benzamide (compound 359 Class D);
4-[4-[[2,6-dichloro-4-[(4-(methylsulfonyl)-1-piperazinyl]methyl]phenyl]acetyl]-1-piperazinyl]-N-[(3,5-dimethoxyphenyl)methyl]-benzamide (compound 364 Class D);
4-[4-[[4-[(4-acetyl-1-piperazinyl)methyl]-2,6-dichlorophenyl]acetyl]-1-piperazinyl]-N-[[3-(1-pyrrolidinyl)phenyl]methyl]-benzamide (compound 361 Class D);
4-[4-[[2,6-dichloro-4-[[4-(methylsulfonyl)-1-piperazinyl]methyl]phenyl]acetyl]-1-piperazinyl]-N-[[3-(1-pyrrolidinyl)phenyl]methyl]-benzamide (compound 363 Class D);
4-[4-[[4-[(4-acetyl-1-piperazinyl)methyl]-2,6-dichlorophenyl]acetyl]-1-piperazinyl]-N-[(3,5-dimethoxyphenyl)methyl]-benzamide (compound 362 Class D);
N-[4-[4-[[2-chloro-4-(1-pyrrolidinylmethyl)phenyl]hydroxyacetyl]-1-piperazinyl]phenyl]-4-methoxy-benzeneacetamide (compound 352 Class D);
N-[4-[4-[[2,6-dichloro-4-(1-pyrrolidinylmethyl)phenyl]acetyl]-1-piperazinyl]phenyl]-4-methoxy-benzeneacetamide (compound 351 Class D);
4-[4-[[2,6-dichloro-4-(1-pyrrolidinylmethyl)phenyl]acetyl]-1-piperazinyl]-N-[[3-(1-pyrrolidinyl)phenyl]methyl]-benzamide (compound 267 Class D);

including any stereochemically isomeric form thereof;
a N-oxide thereof, a pharmaceutically acceptable salt thereof or a solvate thereof.

In an embodiment, the present invention also relates to a combination of

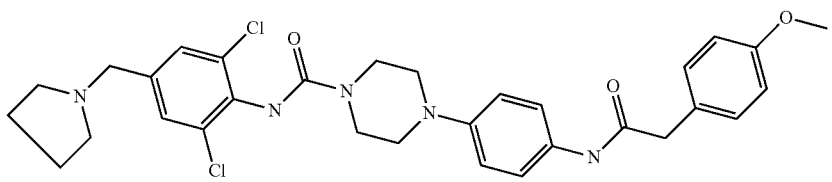 [SMILES: COc1ccc(CC(=O)Nc2ccc(N3CCN(C(=O)Nc4c(Cl)cc(CN5CCCC5)cc4Cl)CC3)cc2)cc1]

including any stereochemically isomeric form thereof;
a N-oxide thereof, a pharmaceutically acceptable salt thereof or a solvate thereof; and fenofibrate.

In an embodiment, the present invention also relates to a combination of 4-[4-[[2,6-dichloro-4-(1-pyrrolidinylmethyl)phenyl]acetyl]-1-piperazinyl]-N-[(3,5-dimethoxyphenyl)methyl]-benzamide (compound 358 Class D), including any stereochemically isomeric form thereof; a N-oxide thereof, a pharmaceutically acceptable salt thereof or a solvate thereof;

and fenofibrate.

General Preparation

I) Class A Compounds

The general preparation of the compounds of Class A is described in WO2008/148851, the content of which is enclosed by reference in the present application.

II) Class B Compounds

The general preparation of the compounds of Class B is described in WO2008/148840, the content of which is enclosed by reference in the present application.

III) Class C Compounds

The general preparation of the compounds of Class C is described in WO2008/148849, the content of which is enclosed by reference in the present application.

IV) Class D Compounds

The general preparation of the compounds of Class D is described in WO2008/148868, the content of which is enclosed by reference in the present application.

In addition to the general procedures described in WO2008/148868, intermediates of Class D of formula (XI) can also be prepared from an intermediate of formula (LXIV) in the presence of an acid such as, for example, an HCl solution. The reaction may be performed in the presence of a suitable solvent such as, for example, dioxane. Intermediates of formula (LXIV) wherein $R^2$ contains Het-$C_{1-4}$alkyl as substituent (Het is defined as a saturated N-containing heterocycle such as, for example, pyrrollidinyl) and wherein $X_1$ is a direct bond, said intermediates being represented by formula (LXIV-a) can be prepared by reacting an intermediate of formula (LXV) in het presence of a saturated N-containing heterocycle such as, for example, pyrrolidine, and water. Intermediates of formula (LXV) can be prepared by reacting an intermediate of formula (LXII) wherein $R^2$ contains Het-$C_{1-4}$alkyl as substituent, hereby named (LXII-a), in the presence of tetrabromomethane and a catalyst such as, for example, triphenylphosphine. This reaction can be performed in a suitable solvent such as, for example, DCM.

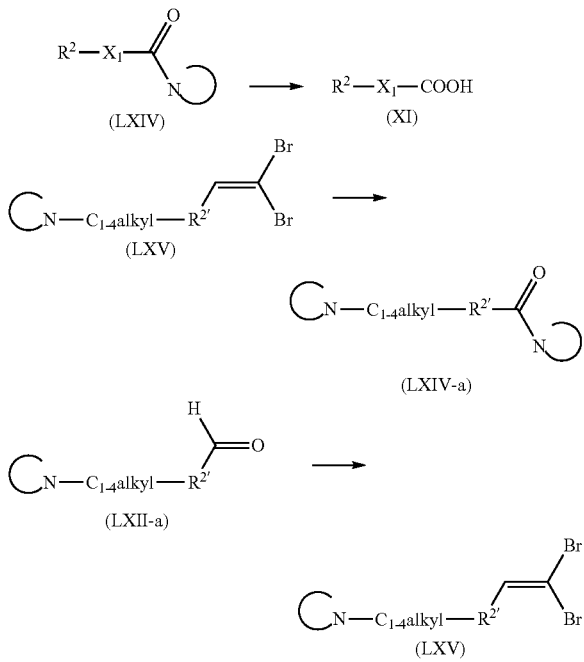

Pharmacological Part

As already indicated above, the present invention relates to the use of a drug combination comprising a DGAT inhibitor and a PPAR agonist or a prodrug thereof, as a medicament.

In particular, the present invention relates to the use of a drug combination comprising a DGAT inhibitor and a PPAR-α agonist or a prodrug thereof, as a medicament.

In particular, the present invention relates to the use of a drug combination comprising a DGAT1 inhibitor and a PPAR-α agonist or a prodrug thereof, as a medicament.

In particular, the combinations according to the present invention are suitable for reducing food intake, for reducing weight, for suppressing appetite, for inducing satiety; or for the treatment or prevention, in particular treatment, of metabolic disorders, such as obesity and/or obesity related disorders (including, but not limited to, peripheral vascular disease, cardiac failure, myocardial ischaemia, cerebral ischaemia, cardiac myopathies), diabetes, in particular type II diabetes mellitus, and/or complications arising therefrom (such as retinopathy, neuropathy, nephropathy), syndrome X, insulin resistance, impaired glucose tolerance, conditions of impaired fasting glucose, hypoglycemia, hyperglycemia, hyperuricemia, hyperinsulinemia, pancreatitis, hypercholesterolemia, hyperlipidemia, dyslipidemia, mixed dyslipidemia, hypertriglyceridemia, nonalcoholic fatty liver disease, fatty liver, increased mesenteric fat, non-alcoholic steatohepatitis, liver fibrosis, metabolic acidosis, ketosis, dysmetabolic syndrome; dermatological conditions such as acne, psoriasis; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis or vascular stenosis; alzheimer's disease; neoplastic diseases, such as solid tumors, skin cancer, melanoma, lymphoma or endothelial cancers, e.g., breast cancer, lung cancer, colorectal cancer, stomach cancer, other cancers of the gastrointestinal tract (e.g., esophageal cancer or pancreatic cancer), prostate cancer, kidney cancer, liver cancer, bladder cancer, cervical cancer, uterine cancer, testicular cancer or ovarian cancer.

In an embodiment, the combinations according to the present invention are suitable for reducing food intake, for reducing weight, for suppressing appetite, for inducing satiety; or for the treatment or prevention, in particular treatment, of metabolic disorders, such as obesity and/or obesity related disorders (including, but not limited to, peripheral vascular disease, cardiac failure, myocardial ischaemia, cerebral ischaemia, cardiac myopathies), diabetes, in particular type II diabetes mellitus, and/or complications arising therefrom (such as retinopathy, neuropathy, nephropathy), syndrome X, insulin resistance, impaired glucose tolerance, conditions of impaired fasting glucose, hypoglycemia, hyperglycemia, hyperuricemia, hyperinsulinemia, pancreatitis, hypercholesterolemia, hyperlipidemia, dyslipidemia, mixed dyslipidemia, hypertriglyceridemia, nonalcoholic fatty liver disease, fatty liver, increased mesenteric fat, non-alcoholic steatohepatitis, liver fibrosis, metabolic acidosis, ketosis, dysmetabolic syndrome; dermatological conditions such as acne, psoriasis; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis or vascular stenosis.

In an embodiment, the combinations according to the present invention are suitable for reducing food intake, for reducing weight, for suppressing appetite, for inducing satiety; or for the treatment or prevention, in particular treatment, of obesity and/or obesity related disorders, hypercholesterolemia, hyperlipidemia, dyslipidemia, mixed dyslipidemia, hypertriglyceridemia, fatty liver, nonalcoholic fatty liver disease, liver fibrosis, non-alcoholic steatohepatitis or diabetes.

In an embodiment, the combinations according to the present invention are suitable for reducing food intake, for reducing weight, for suppressing appetite, for inducing satiety; for the treatment or prevention of obesity and/or obesity related disorders, obesity or cardiovascular diseases.

In an embodiment, said obesity related disorder is selected from peripheral vascular disease, cardiac failure, myocardial ischaemia, cerebral ischaemia or cardiac myopathies.

In an embodiment, the combinations according to the present invention are suitable for reducing food intake and/or for reducing weight.

In an embodiment, the combinations according to the present invention are suitable for reducing food intake.

In an embodiment, the combinations according to the present invention are suitable for the treatment of said diseases or conditions.

In an embodiment, the combinations according to the present invention are suitable for use in the treatment or prevention, in particular treatment, of said diseases or conditions.

In an embodiment, the combinations according to the present invention are suitable for the manufacture of a medicament; in particular a medicament for the treatment or prevention, in particular the treatment, of the diseases or conditions mentioned hereinbefore.

The present invention also relates to a product containing a) a DGAT inhibitor, in particular a DGAT1 inhibitor, more in particular a compound of Class A, Class B, Class C or Class D, and (b) an agonist of peroxisome proliferators-activator receptor or a prodrug thereof such as for example fenofibrate, as a combined preparation for simultaneous, separate or sequential use in the treatment of a disease which can benefit from an elevated level of GLP-1 or DGAT inhibition, such as for example diabetes, in particular type II diabetes mellitus, obesity, for suppressing appetite, inducing satiety or for reducing food intake.

In view of the utility of the combinations of the present invention, there is provided a method of treating warm-blooded animals, including humans, suffering from or a method of preventing warm-blooded animals, including humans, to suffer from any one of the diseases or conditions mentioned hereinbefore.

Said methods comprise the administration, i.e. the systemic or topical administration, preferably oral administration, of an effective amount of an above mentioned combination to warm-blooded animals, including humans.

Those of skill in the treatment of such diseases could determine the effective therapeutic daily amount from the test results presented hereinafter. An effective therapeutic daily amount of a combination of PPAR agonist (or prodrug thereof)/DGAT inhibitor would be from about 0.01 mg/kg to 250 mg/kg body weight, preferably from 0.01 mg/kg to 50 mg/kg body weight, more preferably from about 0.01 mg/kg to about 10 mg/kg, even more preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

In an embodiment, the present invention also relates to pharmaceutical compositions comprising a pharmaceutically acceptable carrier, and as active ingredient a therapeutically effective amount of the combinations mentioned hereinbefore or hereinafter.

The combinations of the present invention may be formulated into various pharmaceutical forms for administration purposes. As appropriate compositions there may be cited all compositions usually employed for systemically administering drugs. To prepare the pharmaceutical compositions of this invention, an effective amount of the particular combination, as the active ingredient, is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations, which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The combinations of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

The combinations of the present invention may also be topically administered in the form of drops, in particular eye drops. Said eye drops may be in the form of a solution or a suspension. Any system developed for the delivery of solutions or suspensions as eye drops are suitable for the administration of the present compounds.

It is especially advantageous to formulate the aforementioned pharmaceutical compositions in unit dosage form for ease of administration and uniformity of dosage.

Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The exact dosage and frequency of administration depends on the particular combination of the present invention used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the combinations of the instant invention.

Depending on the mode of administration, the pharmaceutical composition will preferably comprise from 0.05 to 99% by weight, more preferably from 0.1 to 70% by weight, even more preferably from 0.1 to 50% by weight of the combination of PPAR agonist/DGAT inhibitor, and, from 1 to 99.95% by weight, more preferably from 30 to 99.9% by weight, even more preferably from 50 to 99.9% by weight of a pharmaceutically acceptable carrier, all percentages being based on the total weight of the composition.

In all previous embodiments, the different drugs of a combination or product may be combined in a single preparation together with pharmaceutically acceptable carriers or they may be present in a separate preparation together with pharmaceutically acceptable carriers.

As already indicated above, the present invention also relates to the use of the novel DGAT inhibitors of group Q, in particular DGAT1 inhibitors of group Q, to elevate levels of one or more satiety hormones, in particular GLP-1 levels. The present invention also relates to the use of a DGAT inhibitor of group Q, in particular a novel DGAT1 inhibitor of group Q, for the manufacture of a medicament for the prevention or the treatment, in particular for the treatment, of a disease which can benefit from an elevated level of one or more satiety hormones, in particular a disease which can benefit from an elevated GLP-1 level. In particular, GLP-1 levels are elevated in plasma or in portal blood, more in particular in plasma. By elevated GLP-1 levels, e.g. elevated GLP-1 plasma level or an elevated GLP-1 level in portal blood, it is meant that the GLP-1 level of a subject having taken a DGAT1 inhibitor is elevated or increased compared to the subject under the same conditions but not having taken the DGAT1 inhibitor. In particular GLP-1 levels are elevated in fasting conditions or postprandial, more in particular postprandial.

Therapeutic uses for a compound which elevates GLP-1 level include, but are not limited to, improving learning, enhancing neuro-protection, and/or alleviating a symptom of a disease or disorder of the central nervous system, e.g., through modulation of neurogenesis, and e.g., Parkinson's Disease, Alzheimer's Disease, Huntington's Disease, ALS, stroke, hemorrhage, cerebrovascular accident, ADD, and neuropsychiatric syndromes; converting liver stem/progenitor cells into functional pancreatic cells; preventing beta-cell deterioration and stimulation of beta-cell proliferation; treating pancreatitis; treating obesity; suppressing appetite and inducing satiety; treating irritable bowel syndrome or inflammatory bowel disease such as Crohn's disease and ulcerative colitis; reducing the morbidity and/or mortality associated with myocardial infarction and stroke; treating acute coronary syndrome characterized by an absence of Q-wave myocardial infarction; attenuating post-surgical catabolic changes; treating hibernating myocardium or diabetic cardiomyopathy; suppressing plasma blood levels of norepinepherine; increasing urinary sodium excretion, decreasing urinary potassium concentration; treating conditions or disorders associated with toxic hypervolemia, e.g., renal failure, congestive heart failure, nephrotic syndrome, cirrhosis, pulmonary edema, and hypertension; inducing an inotropic response and increasing cardiac contractility; treating polycystic ovary syndrome; treating respiratory distress; improving nutrition via a non-alimentary route, i.e., via intravenous, subcutaneous, intramuscular, peritoneal, or other injection or infusion; treating nephropathy; treating left ventricular systolic dysfunction, e.g., with abnormal left ventricular ejection fraction; inhibiting antro-duodenal motility, e.g., for the treatment or prevention of gastrointestinal disorders such as diarrhea, postoperative dumping syndrome and irritable bowel syndrome, and as premedication in endoscopic procedures; treating critical illness polyneuropathy (CIPN) and systemic inflammatory response syndrome (SIRS); modulating triglyceride levels and treating dyslipidemia; treating organ tissue injury (e.g. brain tissue injury) caused by reperfusion of blood flow following ischemia; improving the function of ischemic and reperfused brain tissue; treating coronary heart disease risk factor (CHDRF) syndrome. Further diseases which can benefit from an elevated GLP-1 level, include, but are not limited to, ischemic myocardial stunning; ishemic/reperfusion injury; acute myocardial infarction; left ventricular dysfunction; vascular disease; neuropathy, including periphere sensoric neuropathy associated with type II diabetes; bone-related disorders, including osteoporosis, obesity, diabetes. Because of the effect on GLP-1, the DGAT inhibitors of group Q can also be used to provide cardioprotection.

References supporting the above indications include Experimental Neurology, Vol. 203(2), pp 293-301 (2007); U.S. Pat. No. 7,186,683; J. Pharm. Exp. Ther. vol. 312, No. 1, pp 303-308 (2005); Diabetes, vol. 54, pp 146-151 (2005); US2007/0021339, which are incorporated herein by reference.

In view of the DGAT inhibitory activity, in particular the DGAT1 inhibitory activity, the present novel compounds of group Q can be used as a medicament. In particular, the present invention relates to a compound of group Q for use as a medicament, in particular for use as a medicament for the prevention or the treatment of a disease which can benefit from an elevated GLP-1 level. In particular, the present invention also relates to the use of a compound of group Q for the manufacture of a medicament for the prevention or the treatment of a disease which can benefit from an elevated GLP-1 level, such as the diseases and disorders mentioned above.

In view of the DGAT inhibitory activity of the compounds of group Q, there is provided a method of treating a warm-blooded mammal, including a human, suffering from or a method of preventing a warm-blooded mammal, including a human, to suffer from a disease which can benefit from an elevated level of GLP-1, in particular a method of treating a warm-blooded mammal, including a human, suffering from a disease which can benefit from an elevated level of GLP-1. Said methods comprise the administration of an effective amount of a compound of group Q to a warm-blooded mammal, including a human.

In view of the DGAT inhibitory activity, in particular the DGAT1 inhibitory activity, the present invention also relates to a compound of group Q for use as a medicament, in particular for use as a medicament for the prevention or the treatment of a diseases which can benefit from inhibition of DGAT, in particular DGAT1.

The invention also relates to a compound of group Q for the prevention or the treatment of a disease or disorder which can benefit from inhibition of DGAT, in particular DGAT1. Diseases or disorders which can benefit from inhibition of DGAT, in particular DGAT1 include, but are not limited to metabolic disorders, such as obesity and/or obesity related disorders (including peripheral vascular disease, cardiac failure, myocardial ischaemia, cerebral ischaemia, cardiac myopathies), diabetes, in particular type II diabetes mellitus, and/or complications arising therefrom (such as retinopathy, neuropathy, nephropathy), syndrome X, insulin resistance, impaired glucose tolerance, conditions of impaired fasting glucose, hypoglycemia, hyperglycemia, hyperuricemia, hyperinsulinemia, pancreatitis, hypercholesterolemia, hyperlipidemia, dyslipidemia, mixed dyslipidemia, hypertriglyceridemia, nonalcoholic fatty liver disease, fatty liver, increased mesenteric fat, non-alcoholic steatohepatitis, liver fibrosis, metabolic acidosis, ketosis, dysmetabolic syndrome; dermatological conditions such as acne, psoriasis; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis or vascular stenosis; neoplastic diseases, such as solid tumors, skin cancer, melanoma, lymphoma or endothelial cancers, e.g., breast cancer, lung cancer, colorectal cancer, stomach cancer, other cancers of the gastrointestinal tract (e.g., esophageal cancer and pancreatic cancer), prostate cancer, kidney cancer, liver cancer, bladder cancer, cervical cancer, uterine cancer, testicular cancer or ovarian cancer; or other diseases and conditions that are sensitive or responsive to modulation, in particular inhibition, of DGAT function, in particular DGAT1 function.

Particular diseases or disorders which can benefit from inhibition of DGAT, in particular DGAT1, are selected from obesity, hypercholesterolemia, hyperlipidemia, dyslipidemia, mixed dyslipidemia, hypertriglyceridemia, fatty liver, nonalcoholic fatty liver disease, liver fibrosis, non-alcoholic steatohepatitis or diabetes, in particular type II diabetes.

The invention also relates to a compound of group Q for use in the prevention or the treatment, in particular for use in the treatment, of a disease or disorder which can benefit from inhibition of DGAT, in particular DGAT1.

In an embodiment the invention also relates to the use of a compound of group Q for the manufacture of a medicament for treating or preventing the above mentioned diseases or conditions.

In view of the DGAT inhibitory activity of the compounds of group Q, there is provided a method of treating a warm-blooded mammal, including a human, suffering from or a method of preventing a warm-blooded mammal, including a human, to suffer from a disease which can benefit from inhibition of DGAT, in particular a method of treating a warm-blooded mammal, including a human, suffering from a disease which can benefit from inhibition of DGAT. Said methods comprise the administration of an effective amount of a compound of group Q to a warm-blooded mammal, including a human.

In an embodiment, the present invention also relates to pharmaceutical compositions comprising a pharmaceutically acceptable carrier, and as active ingredient a therapeutically effective amount of a compound of group Q.

The present invention also provides compositions for preventing or treating a disease which can benefit from an elevated GLP-1 level or which can benefit from inhibition of DGAT, in particular DGAT1, in particular for treating a disease which can benefit from elevated GLP-1 levels or which can benefit from inhibition of DGAT, in particular DGAT1. Said compositions comprise a therapeutically effective amount of a compound of group Q and a pharmaceutically acceptable carrier.

The novel compounds of group Q of the present invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations, which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The compounds of group Q of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

The compounds of the present invention may also be topically administered in the form of drops, in particular eye drops. Said eye drops may be in the form of a solution or a suspension. Any system developed for the delivery of solutions or suspensions as eye drops are suitable for the administration of the present compounds.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The exact dosage and frequency of administration depends on the particular compound of group Q used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will preferably comprise from 0.05 to 99% by weight, more preferably from 0.1 to 70% by weight, even more preferably from 0.1 to 50% by weight of the compound of group Q, and, from 1 to 99.95% by weight, more preferably from 30 to 99.9% by weight, even more preferably from 50 to 99.9% by weight of a pharmaceutically acceptable carrier, all percentages being based on the total weight of the composition.

The following examples are intended to illustrate the present invention.

EXPERIMENTAL PART

Hereinafter, the term 'THF' means tetrahydrofuran, 'Et$_2$O' means diethyl ether, 'CH$_3$OH' means methanol, 'EtOAc' means ethyl acetate, 'NaHCO$_3$' means carbonic acid monosodium salt, 'CH$_2$Cl$_2$' or 'DCM' means dichloromethane, 'CH$_3$CN' means acetonitrile, 'EtOH' means ethanol, 'HBTU' means 1-[bis(di-methylamino)methylene]-1H-benzo-triazoliumhexafluorophosphate(1-)3-oxide, 'DMF' means N,N-dimethyl-formamide, 'DIPEA' means N-ethyl-N-(1-methylethyl)-2-propanamine, 'HOBt' or 'HOBT' means 1-hydroxy-1H-benzotriazole, 'EDCI' means N-(ethylcarbonimidoyl)-NN-dimethyl-1,3-propanediamine monohydrochloride, 'DMSO' means dimethylsulfoxide, 'm.p.' means melting point, 'MeOH' means methanol, 'Et$_3$N' means triethylamine, 'eq.' means equivalent, 'r.m.' means reaction mixture, 'I.t.' means room temperature, 'h' means hour(s), 'min' means minute(s), and 'TFA' means trifluoroacetic acid.

Experimental Procedures for the Class A Compounds

The experimental procedures for the preparation of the compounds of Class A, are described in WO2008/148851, the content of which is enclosed by reference in the present application.

Experimental Procedures for the Class B Compounds

The experimental procedures for the preparation of the compounds of Class B, are described in WO2008/148840, the content of which is enclosed by reference in the present application.

Experimental Procedures for the Class C Compounds

The experimental procedures for the preparation of the compounds of Class C, are described in WO2008/148849, the content of which is enclosed by reference in the present application.

In addition, some typical examples of Class C compounds are described below.

Intermediates (Class C)

Preparation of 4-(1-piperazinyl)-N-[3-(1-pyrrolidinyl)phenyl]-benzamide and 4-(1-piperazinyl)-N-[3-(1-pyrrolidinyl)phenyl]-benzamide .HCl

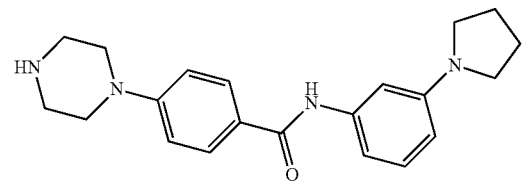 [SMILES: O=C(Nc1cccc(N2CCCC2)c1)c1ccc(N2CCNCC2)cc1]

Pd/C 10% (1 g) was suspended in MeOH (150 ml) under N$_2$ flow. 4-[4-(phenylmethyl)-1-piperazinyl]-N-[3-(1-pyrrolidinyl)phenyl]-benzamide (5.62 g, 0.0126 mol; prepared according to the teachings described in WO2008/148849) was added and the r.m. was stirred at 50° C. under H$_2$ atmosphere until 1 eq. of H$_2$ was absorbed. The catalyst was filtered off over diatomaceous earth (DICALITE® (diatomaceous earth)). The solvent was evaporated and co-evaporated with toluene. The residue was stirred in Et$_2$O and filtered off. The product was dried (50° C., 18 h, in vacuo). Yield: 4.23 g of 4-(1-piperazinyl)-N-[3-(1-pyrrolidinyl)phenyl]-benzamide (96%).

4-(1-piperazinyl)-N-[3-(1-pyrrolidinyl)phenyl]-benzamide .HCl was prepared in analogy to the free base form. For the preparation of the hydrochloric acid salt, 4-[4-[[[3-(1-pyrrolidinyl)phenyl]amino]carbonyl]phenyl]-1-piperazinecarboxylic acid, 1,1-dimethylethyl ester (the tert-butoxy variant of 4-[4-(phenylmethyl)-1-piperazinyl]-N-[3-(1-pyrrolidinyl)phenyl]-benzamide) was deprotected with a HCl solution in dioxane.

Preparation of 1-[(4-bromo-3-chlorophenyl)methyl]-pyrrolidine

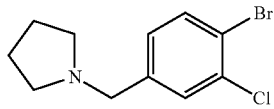 [SMILES: Clc1cc(CN2CCCC2)ccc1Br]

A solution of 1-bromo-2-chloro-4-(chloromethyl)-benzene (25.2 g, 105.03 mmol) and Et₃N (16.1 ml, 115.53 mmol) in THF (150 ml) was stirred at r.t. Pyrrolidine (8.2 g, 115.53 mmol) was added dropwise. The r.m. was stirred overnight at r.t. and was then concentrated in vacuo. The residue was taken up into water and extracted with CH₂Cl₂ (3×100 ml). The combined organic layer was washed with saturated NaHCO₃ and brine, and was then dried (MgSO₄), filtered and the solvent was evaporated in vacuo. Yield: 25.8 g of 1-[(4-bromo-3-chlorophenyl)methyl]-pyrrolidine (90% yield, crude product; used in next reaction step, without further purification).

Preparation of 2-chloro-4-(1-pyrrolidinylmethyl)-benzaldehyde

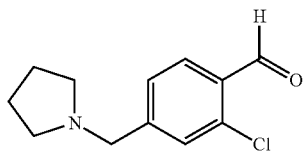 [SMILES: O=Cc1ccc(CN2CCCC2)cc1Cl]

Reaction under N₂ atmosphere. A solution of 1-[(4-bromo-3-chlorophenyl)methyl]-pyrrolidine (25.8 g, 93.96 mmol) in THF (200 ml) was stirred at −78° C. for 15 min A 2.5 M n-BuLi solution in hexane was added to the mixture over a period of 15 min After 30 min, a solution of DMF (7.3 ml, 93.96 mmol) in THF (50 ml) was added dropwise to the mixture. The reaction temperature was allowed to rise to r.t. slowly, and the mixture was stirred overnight. The reaction was quenched by the addition of water at 0° C. The mixture was extracted with EtOAc (3×150 ml). The combined organic layer was washed with brine, dried (MgSO₄), filtered and the solvent was evaporated in vacuo.

Yield: 20.3 g of 2-chloro-4-(1-pyrrolidinylmethyl)-benzaldehyde (97%, crude Yield:). The crude product was used for next step directly without further purification.

Preparation of 2-chloro-α-hydroxy-4-(1-pyrrolidinylmethyl)-benzeneacetonitrile

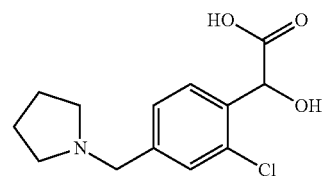 [SMILES: O=C(O)C(O)c1ccc(CN2CCCC2)cc1Cl]

Trimethylsilanecarbonitrile (10 ml, 76.6 mmol) and ZnBr₂ (0.5 g) were added to a solution of 2-chloro-4-(1-pyrrolidinylmethyl)-benzaldehyde (9.8 g, 43.8 mmol) in DCM (100 ml). The r.m. was stirred for 5 h at r.t. Then, the mixture was heated to 50° C. and stirred overnight. 2-chloro-α-hydroxy-4-(1-pyrrolidinylmethyl)-benzeneacetonitrile was used as a crude in the next reaction step.

Preparation of 2-chloro-α-hydroxy-4-(1-pyrrolidinylmethyl)-benzeneacetic acid (TFA-salt)

A mixture of 2-chloro-α-hydroxy-4-(1-pyrrolidinylmethyl)-benzeneacetonitrile (10.9 g, 43.8 mmol) in concentrated HCl (50 ml) was stirred and refluxed for 24 h. The mixture was cooled and the solvent was evaporated. The crude product was purified by preparative HPLC (Synergi: 250×20 mm; Mobile Phase: 0-30% CH₃CN in H₂O (0.1% TFA); Flow Rate: 80 ml/min; Finished Time: 30 min) The desired fraction was collected and the organic phase was evaporated to give a yellow oil. Yield: 6.2 g of 2-chloro-α-hydroxy-4-(1-pyrrolidinylmethyl)-benzeneacetic acid (TFA-salt), used as such in the next reaction step (52.5%; TFA-salt).

Final Compounds (Class C)

Preparation of Compound 152

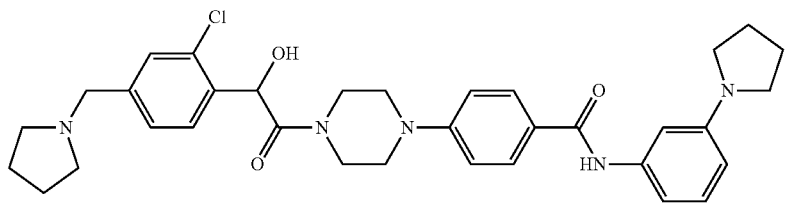 [SMILES: O=C(Nc1cccc(N2CCCC2)c1)c1ccc(N2CCN(C(=O)C(O)c3ccc(CN4CCCC4)cc3Cl)CC2)cc1]

A mixture of 2-chloro-α-hydroxy-4-(1-pyrrolidinylmethyl)-benzeneacetic acid (1.1 g, 2.87 mmol), 4-(1-piperazinyl)-N-[3-(1-pyrrolidinyl)phenyl]-benzamide .HCl (1.1 g, 2.87 mmol), EDCI (0.55 g, 2.87 mmol), HOBT (0.39 g, 2.87 mmol) and Et₃N (1.6 ml, 11.48 mmol) in DCM (50 ml) was stirred overnight at r.t. Water was added to the mixture, and the organic layer was separated. The aqueous layer was extracted with DCM (3×30 ml). The combined organic layer was washed with brine, dried (MgSO₄), filtered and the solvent was evaporated in vacuo. The residue was purified by flash column chromatography over silica gel (eluent: DCM/MeOH 30/1). The product fractions were collected and the solvent was evaporated. Yield: 0.8 g of crude compound 152 (purity 82% on LCMS). The crude compound 152 was purified by neutral high performance liquid chromatography (Column: Daisopak 250×20 mm; Mobile Phase: 80-100% CH₃CN in water; Flow Rate: 14 ml/min; Finished Time: 15 min). The desired fraction was collected and evaporated in vacuo. Yield: 0.4 g of compound 152 (23%).

Compound 151 was prepared by analogy to compound 152, but 2-chloro-4-(1-pyrrolidinylmethyl)-benzeneacetic acid (for which the synthesis protocol is described in detail in the experimental procedures for the Class D compounds) was used as starting material.

Compounds 147, 148, 149 and 150 were also prepared by analogy to compound 152, starting from the appropriate starting materials.

Experimental Procedures for the Class D Compounds

The experimental procedures for the preparation of the compounds of Class D, are described in WO2008/148868, the content of which is enclosed by reference in the present application.

In addition, some typical examples of Class D compounds are described below.

Intermediates (Class D)

Preparation of 1-[[3-chloro-4-(2,2-dibromoethenyl) phenyl]methyl]-pyrrolidine

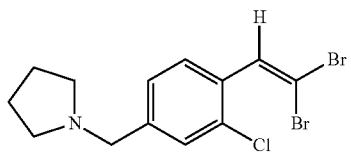 [SMILES: Clc1cc(CN2CCCC2)ccc1C=C(Br)Br]

A mixture of 2-chloro-4-(1-pyrrolidinylmethyl)-benzaldehyde (prepared according to the teachings in WO2008/148868) (10.0 g, 44.70 mmol) and tetrabromomethane (22.2 g, 67.05 mmol) in DCM (300 ml) was stirred at 0° C. A solution of triphenylphosphine (35.2 g, 134.10 mmol) in DCM (500 ml) was added. The mixture was stirred for 30 min at 0° C. The mixture was concentrated in vacuo. The residue was taken up into CHCl₃, and the precipitate was filtered off. The filtrate was concentrated in vacuo. The residue (crude 1-[[3-chloro-4-(2,2-dibromoethenyl)phenyl]methyl]-pyrrolidine) was used as such in the next reaction step.

Preparation of 1-[[2-chloro-4-(1-pyrrolidinylmethyl) phenyl]acetyl]-pyrrolidine

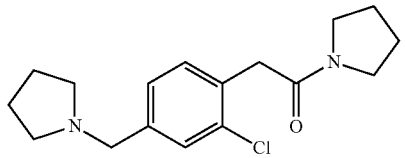 [SMILES: O=C(Cc1ccc(CN2CCCC2)cc1Cl)N1CCCC1]

A mixture of pyrrolidine (150 ml) and water (15 ml) was stirred at r.t. 1-[[3-chloro-4-(2,2-dibromoethenyl)phenyl]methyl]-pyrrolidine (crude, max. 44.70 mmol) was added to the mixture and subsequently, the mixture was stirred overnight at r.t. The solvent was evaporated, yielding 1-[[2-chloro-4-(1-pyrrolidinylmethyl)phenyl]acetyl]-pyrrolidine as a crude that was used as such in the next reaction step.

Preparation of 2-chloro-4-(1-pyrrolidinylmethyl)-benzeneacetic acid

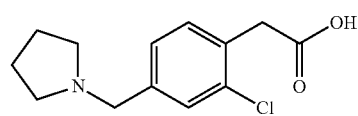 [SMILES: O=C(O)Cc1ccc(CN2CCCC2)cc1Cl]

A solution of 1-[[2-chloro-4-(1-pyrrolidinylmethyl)phenyl]acetyl]-pyrrolidine (crude, max. 44.70 mmol) in dioxane (100 ml) was stirred at r.t. A 6 M HCl solution was added. The mixture was stirred and refluxed for 3 days. The mixture was concentrated in vacuo. The residue was taken up in water and the mixture was brought to pH 10 with a 4 N NaOH solution. The solution was washed with diethyl ether (3×40 ml). The aqueous layer was acidified to pH 3 with a 6 N HCl solution. The mixture was concentrated in vacuo. The residue was purified by neutral high performance liquid chromatography (Column: Lana 300×50 mm, 10 μm; Mobile Phase: 0-20% CH₃CN in water; Flow Rate: 80 ml/min; Finished Time: 25 min). The desired fraction was collected and evaporated in vacuo. Yield: 2.8 g of 2-chloro-4-(1-pyrrolidinylmethyl)-benzeneacetic acid (25% yield over last 3 steps).

2,6-Dichloro-4-(1-pyrrolidinylmethyl)-benzeneacetyl chloride .HCl was prepared by analogy to 2-chloro-4-(1-pyrrolidinylmethyl)-benzeneacetic acid by using the appropriate reaction conditions well known to those skilled in the art.

2,6-Dichloro-4-(1-pyrrolidinylmethyl)-benzeneacetic acid .HCl was prepared by analogy to 2-chloro-4-(1-pyrrolidinylmethyl)-benzeneacetic acid by using the appropriate reaction conditions well known to those skilled in the art.

Preparation of 4-[4-[[[(3,5-dimethoxyphenyl) methyl]amino]carbonyl]phenyl]-1-piperazinecarboxylic acid, 1,1-dimethylethyl ester

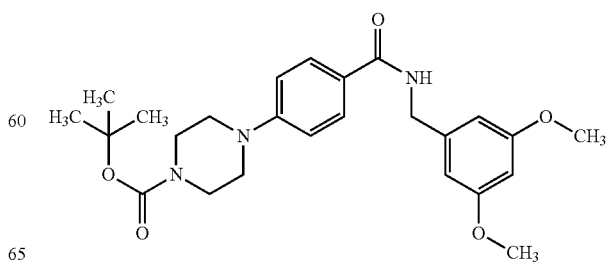

A mixture of 3,5-dimethoxybenzenemethanamine (3.34 g, 20 mmol), 4-(4-carboxyphenyl)-1-piperazinecarboxylic acid, 1-(1,1-dimethylethyl) ester (6.13 g, 20 mmol), EDCI (4.2 g, 22 mmol), HOBT (2.97 g, 22 mmol), N(CH₂CH₃)₃ (12 ml) and DCM (80 ml) was stirred overnight at r.t. The solvent was evaporated. The residue was purified by column chromatography (eluent: petroleum ether/EtOAc 2/1). The desired fractions were collected and the solvent was evaporated. Yield: 5.3 g of 4-[4-[[[(3,5-dimethoxyphenyl)methyl]amino]carbonyl]phenyl]-1-piperazinecarboxylic acid, 1,1-dimethylethyl ester (58.24% yield).

Preparation of N-[(3,5-dimethoxyphenyl)methyl]-4-(1-piperazinyl)-benzamide (HCl-salt)

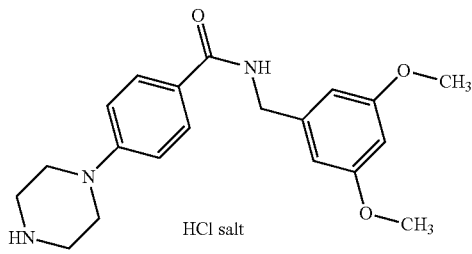 [SMILES: COc1cc(CNC(=O)c2ccc(N3CCNCC3)cc2)cc(OC)c1]

4-[4-[[[(3,5-dimethoxyphenyl)methyl]amino]carbonyl]phenyl]-1-piperazinecarboxylic acid, 1,1-dimethylethyl ester (5.2 g, 11.4 mmol) was dissolved in HCl/dioxane (100 ml) and the reaction solution was stirred overnight. The solvent was evaporated. The solid residue was washed with petroleum ether and dried. Yield: 4.2 g of N-[(3,5-dimethoxyphenyl)methyl]-4-(1-piperazinyl)-benzamide (HCl-salt) as a crude (97.7%). 1 g of the crude product was purified by preparative HPLC (YMC: 250×80 mm; Mobile Phase: 10-35% CH₃CN % in H₂O (0.1% TFA); Finished Time: 25 min) The desired fractions were collected and solvent was evaporated. The residue was neutralized with an aqueous NaHCO₃ solution and extracted with EtOAc. The separated organic layer was washed with brine, dried (Na₂SO₄), filtered and the solvent was evaporated to yield a white solid. Yield: 0.4 g of N-[(3,5-dimethoxyphenyl)methyl]-4-(1-piperazinyl)-benzamide (HCl-salt).

Final Compounds (Class D)

Preparation of Compound 353

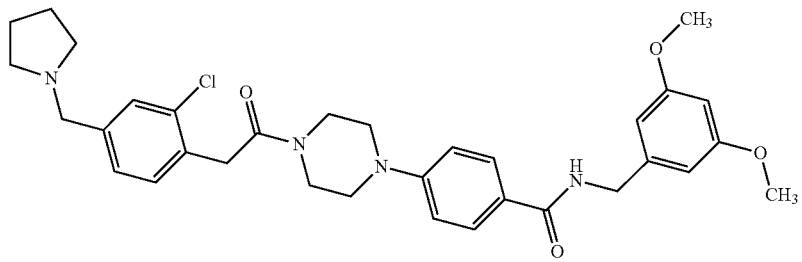 [SMILES: COc1cc(CNC(=O)c2ccc(N3CCN(C(=O)Cc4ccc(CN5CCCC5)cc4Cl)CC3)cc2)cc(OC)c1]

A mixture of 2-chloro-4-(1-pyrrolidinylmethyl)-benzeneacetic acid (0.94 g, 3.70 mmol) and N-[(3,5-dimethoxyphenyl)methyl]-4-(1-piperazinyl)-benzamide (HCl-salt) (1.5 g, 3.83 mmol) in DCM (20 ml) was stirred at r.t. Et₃N (1.3 ml, 9.58 mmol) was added to the mixture. Then EDCI (0.73 g, 3.83 mmol) and HOBT (0.52 g, 3.83 mmol) were added to the mixture. The mixture was stirred overnight at r.t. The mixture was washed with water, dried (MgSO₄), filtered and the solvent was evaporated in vacuo. The residue was purified by flash column chromatography over silica gel (eluent: CH₂Cl₂/CH₃OH 20/1). The product fractions were collected and the solvent was evaporated. Yield: 0.78 g of compound 353 (36%).

Preparation of Compound 358

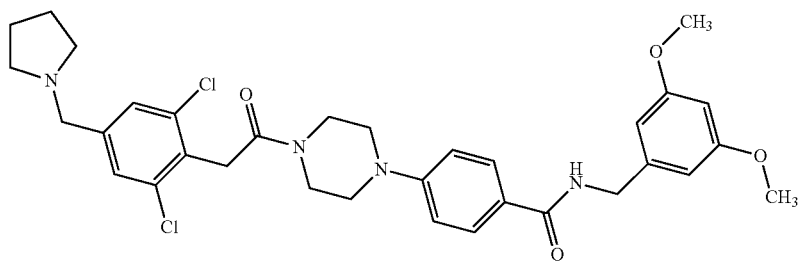 [SMILES: COc1cc(CNC(=O)c2ccc(N3CCN(C(=O)Cc4c(Cl)cc(CN5CCCC5)cc4Cl)CC3)cc2)cc(OC)c1]

A mixture of 2,6-dichloro-4-(1-pyrrolidinylmethyl)-benzeneacetyl chloride .HCl and 2,6-dichloro-4-(1-pyrrolidinylmethyl)-benzeneacetic acid .HCl (1.29 g of the mixture) was added portionwise to a stirring mixture of N-[(3,5-dimethoxyphenyl)methyl]-4-(1-piperazinyl)-benzamide .HCl (1.406 g, 0.00358 mol) and NaHCO$_3$ (0.993 g, 0.0118 mol) in CH$_3$CN (60 ml; dried on molecular sieves). The r.m. was stirred under N$_2$ atmosphere for 4 h. Subsequently, Et$_3$N (1 ml) and HBTU (1.358 g, 0.00358 mol) were added and the r.m. was stirred at r.t. for 65 h. Then, the mixture was poured into stirring H$_2$O (300 ml) and this aqueous mixture was stirred for 20 min. The product was filtered off and washed with H$_2$O (3×). The product was stirred in boiling 2-propanol (70 ml), filtered off hot, and the filtrate was left standing for 3 h (crystallization started after 5 min) The product was filtered off, washed with 2-propanol (3×), and dried (50° C., in vacuo) to yield 1.12 g of compound 358 (50%). An additional amount of compound 358 (0.481 g) was obtained by evaporation of the filtrate and purification of the residue by HPLC. The desired fractions were evaporated and crystallized from boiling 2-propanol again.

Compounds 354, 355, 359, 360, 361, 362, 363 and 364 from Class D were prepared by analogy to compound 353, starting from the appropriate starting materials.

Compounds 356 and 357 from Class D were prepared by analogy to compounds 152 from Class C, starting from the appropriate starting materials.

The tables below list compounds of class A, class B, class C or class D. The novel compounds of group Q (compounds 147 till 152 from Class C and compounds 353 till 364 from Class D) are enclosed in class C and class D.

Table for the Class A Compounds

TABLE A1

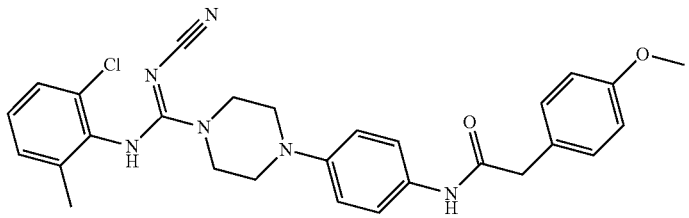 [SMILES: COc1ccc(CC(=O)Nc2ccc(N3CCN(/C(=N\C#N)Nc4c(C)cccc4Cl)CC3)cc2)cc1]
Compound 8

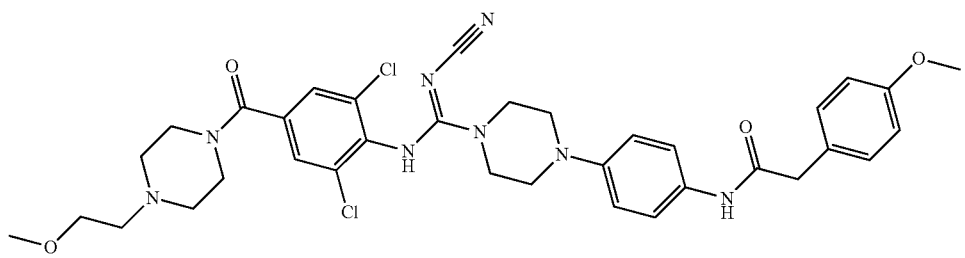
Compound 10

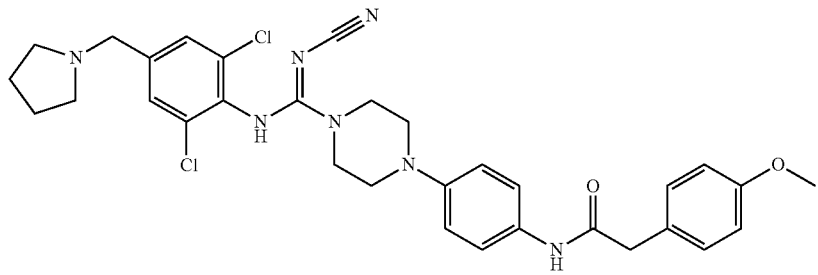 [SMILES: COc1ccc(CC(=O)Nc2ccc(N3CCN(/C(=N\C#N)Nc4c(Cl)cc(CN5CCCC5)cc4Cl)CC3)cc2)cc1]
Compound 11

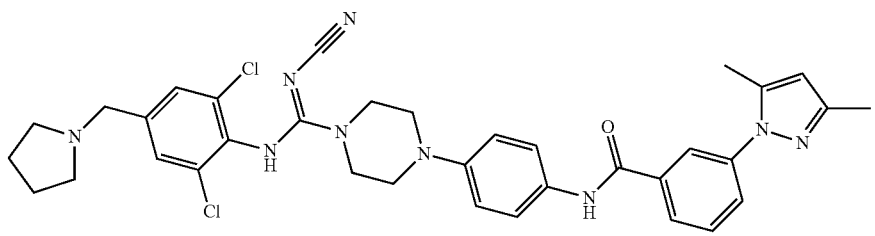 [SMILES: Cc1cc(C)n(-c2cccc(C(=O)Nc3ccc(N4CCN(/C(=N\C#N)Nc5c(Cl)cc(CN6CCCC6)cc5Cl)CC4)cc3)c2)n1]
Compound 12

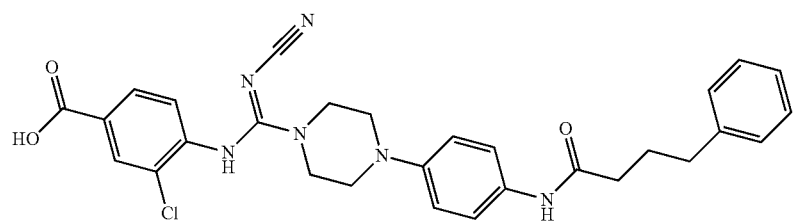 [SMILES: N#C/N=C(/Nc1ccc(C(=O)O)cc1Cl)N1CCN(c2ccc(NC(=O)CCCc3ccccc3)cc2)CC1]
Compound 13

TABLE A1-continued
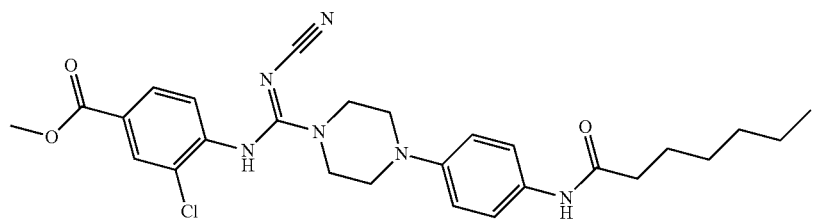 [SMILES: CCCCCCC(=O)Nc1ccc(N2CCN(/C(=N\C#N)Nc3ccc(C(=O)OC)cc3Cl)CC2)cc1]
Compound 14
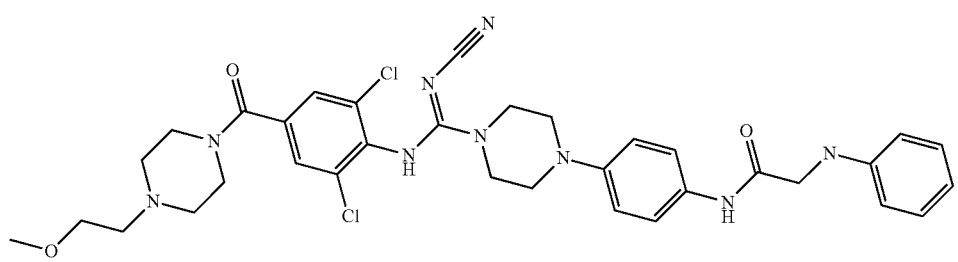 [SMILES: COCCN1CCN(C(=O)c2cc(Cl)c(N/C(=N/C#N)N3CCN(c4ccc(NC(=O)CNc5ccccc5)cc4)CC3)c(Cl)c2)CC1]
Compound 15
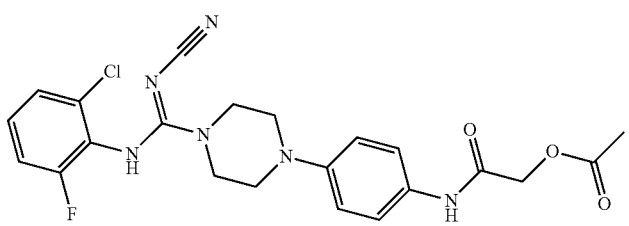 [SMILES: CC(=O)OCC(=O)Nc1ccc(N2CCN(/C(=N\C#N)Nc3c(F)cccc3Cl)CC2)cc1]
Compound 16
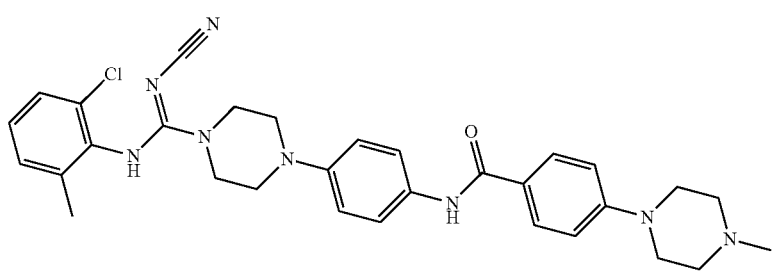 [SMILES: Cc1cccc(Cl)c1N/C(=N/C#N)N1CCN(c2ccc(NC(=O)c3ccc(N4CCN(C)CC4)cc3)cc2)CC1]
Compound 17
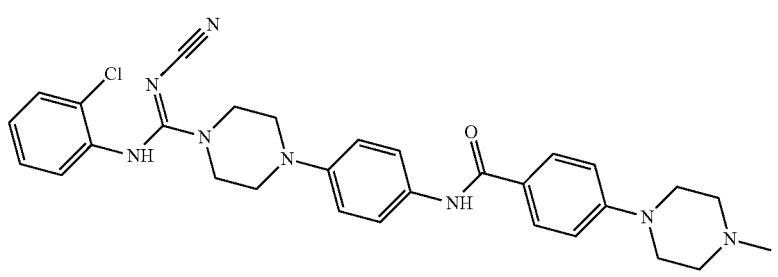 [SMILES: CN1CCN(c2ccc(C(=O)Nc3ccc(N4CCN(/C(=N\C#N)Nc5ccccc5Cl)CC4)cc3)cc2)CC1]
Compound 18
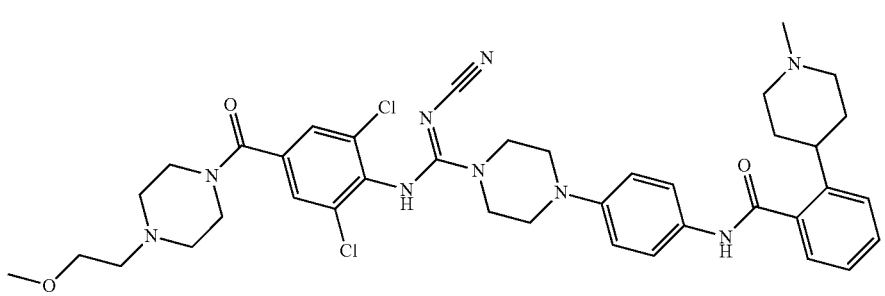 [SMILES: COCCN1CCN(C(=O)c2cc(Cl)c(N/C(=N/C#N)N3CCN(c4ccc(NC(=O)c5ccccc5C5CCN(C)CC5)cc4)CC3)c(Cl)c2)CC1]
Compound 19

Tables for the Class B Compounds
TABLE B1
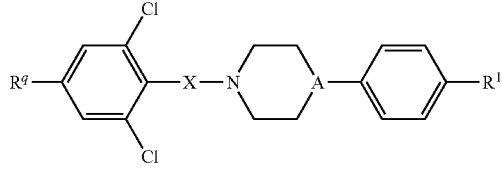
| Co. No. | A | X | R[1] | R[q] |
|---|---|---|---|---|
| 1 | N | 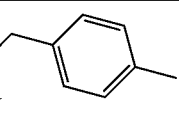 | 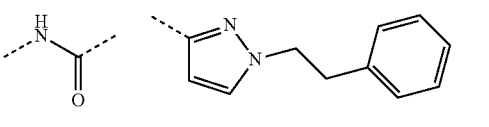 | H— |
| 2 | N | 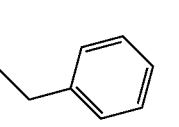 | 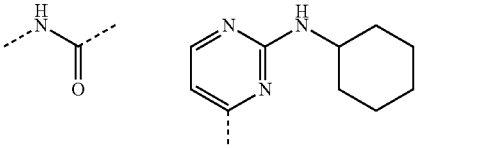 | H— |
| 3 | N |  | 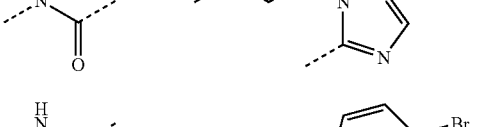 | H— |
| 4 | N |  | 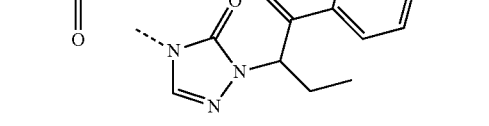 | H— |
| 5 | N |  | 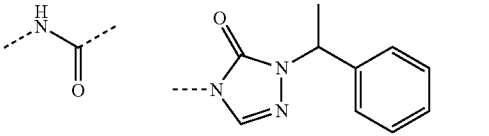 | H— |
| 6 | N | 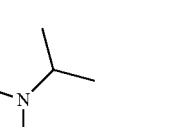 | 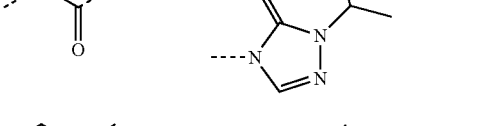 | H— |
| 7 | CH | 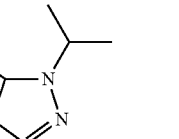 | 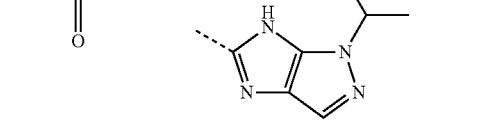 | H— |
| 8 | N | 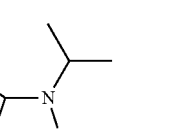 | 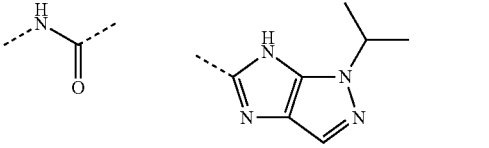 | H— |
| 9 | N |  | | H— |

TABLE B1-continued

[Structure: Rq-substituted 2,6-dichlorophenyl-X-N(piperidine with A)-phenyl-R1]

| Co. No. | A | X | R1 | Rq |
|---|---|---|---|---|
| 10 | N | -NH-C(=O)- | 1-benzyl-pyrazol-3-yl | H— |
| 11 | N | -NH-C(=O)- | 2-(2,6-dichlorobenzyl)pyrimidin-4-yl | H— |
| 12 | N | -NH-C(=O)- | 2-pentylpyrimidin-4-yl | H— |
| 13 | N | -NH-C(=O)- | 1-(2-phenylethyl)-5-pyrazolyl | H— |
| 14 | N | -NH-C(=O)- | 2-phenylpyrimidin-4-yl | H— |
| 15 | N | -NH-C(=O)- | 1-butyl-5-pyrazolyl | H— |
| 16 | N | -NH-C(=O)- | 2-tert-butylpyrimidin-4-yl | H— |
| 17 | N | -NH-C(=O)- | 2-[(1-ethoxycarbonylpiperidin-4-yl)amino]pyrimidin-4-yl | H— |
| 18 | N | -NH-C(=O)- | 1-(4-methoxyphenyl)-5-pyrazolyl | H— |

TABLE B1-continued

| Co. No. | A | X | R¹ | R^q |
|---|---|---|---|---|
| 19 | N | -NH-C(=O)- | 2-(3-methylbutylamino)pyrimidin-4-yl | H— |
| 20 | N | -NH-C(=O)- | 2-(benzylamino)pyrimidin-4-yl | H— |
| 21 | N | -NH-C(=O)- | 2-(piperidin-1-yl)pyrimidin-4-yl | H— |
| 22 | N | -NH-C(=O)- | 1-benzyl-1H-1,2,4-triazol-5-yl | H— |
| 23 | N | -NH-C(=O)- | 1-(2-phenylethyl)-1H-1,2,4-triazol-5-yl | H— |
| 24 | N | -NH-C(=O)- | 2-[1-(4-chlorophenyl)-1-hydroxybutan-2-yl]-3-oxo-2,3-dihydro-1H-1,2,4-triazol-4-yl (mixture of RR and SS) | H— |
| 25 | N | -NH-C(=O)- | 2-(butan-2-yl)-3-oxo-2,3-dihydro-1H-1,2,4-triazol-4-yl | H— |
| 26 | N | -NH-C(=O)- | 2-isopropyl-3-oxo-2,3-dihydro-1H-1,2,4-triazol-4-yl | H— |
| 27 | N | -CH₂-C(=O)- | 1-(4-methylbenzyl)-1H-imidazo[4,5-c]pyrazol-5-yl | H— |

TABLE B1-continued
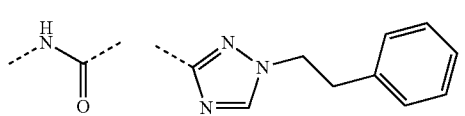
| Co. No. | A | X | R¹ | Rq |
|---|---|---|---|---|
| 28 | N | -NH-C(O)- | triazole-N-CH₂CH₂-phenyl | H— |
| 29 | N | -NH-C(O)- | triazole-N-CH₂-(4-methoxyphenyl) | H— |
| 30 | N | -NH-C(O)- | triazole-N-CH₂CH₂CH₂-phenyl | H— |
| 31 | N | -NH-C(O)- | 1,3,4-oxadiazole-CH₂CH₂-phenyl | H— |
| 32 | N | -NH-C(O)- | triazole-N-butyl | H— |
| 33 | N | -NH-C(O)- | 1,2,4-oxadiazole-CH₂CH₂CH₂-phenyl | H— |
| 34 | N | -NH-C(O)- | 1,2,4-oxadiazole-CH₂-phenyl | H— |
| 35 | N | -NH-C(O)- | 1,3,4-oxadiazole-CH₂-phenyl | H— |
| 36 | N | -NH-C(O)- | 1,3,4-oxadiazole-butyl | H— |
| 37 | N | -NH-C(O)- | 1,2,4-oxadiazole-phenyl | H— |

TABLE B1-continued

| Co. No. | A | X | R¹ | R^q |
|---|---|---|---|---|
| 38 | N | -NH-C(=O)- | 2-tert-butyl-1,3,4-oxadiazol-5-yl | H— |
| 39 | N | -NH-C(=O)- | 3-tert-butyl-1,2,4-oxadiazol-5-yl | H— |
| 40 | N | -NH-C(=O)- | 1-tert-butyl-1,2,4-triazol-3-yl | H— |
| 41 | N | -NH-C(=O)- | 1-(3-phenylpropyl)-1H-pyrazol-3-yl | H— |
| 42 | N | -NH-C(=O)- | 1H-1,2,4-triazol-5-yl | H— |
| 43 | N | -NH-C(=O)- | imidazo[2,1-b]thiazol-6-yl | H— |
| 44 | CH | -NH-C(=O)- | 1-(3-phenylpropyl)-5-oxo-4H-1,2,4-triazol-4-yl | H— |
| 45 | N | -NH-C(=O)- | 1-(4-methoxybenzyl)-1H-1,2,4-triazol-5-yl | H— |
| 46 | CH | -NH-C(=O)- | 1-(4-methoxybenzyl)-5-oxo-4H-1,2,4-triazol-4-yl | H— |
| 47 | N | -NH-C(=O)- | 1-isopropyl-1H-1,2,4-triazol-5-yl | H— |

TABLE B1-continued

| Co. No. | A | X | R¹ | Rq |
|---|---|---|---|---|
| 48 | CH | —NH—C(=O)— | 4-(2-phenylethyl)-5-oxo-4,5-dihydro-1,2,4-triazol-1-yl | H— |
| 49 | N | —NH—C(=O)— | 5-methyl-1,3,4-oxadiazol-2-yl | H— |
| 50 | CH | —NH—C(=O)— | 1-benzyl-5-oxo-4,5-dihydro-1H-1,2,4-triazol-4-yl | H— |
| 51 | N | —NH—C(=O)— | 3-(3-diethylaminopropyl)-1,2,4-oxadiazol-5-yl | H— |
| 52 | N | —C(=O)— | 2-phenyl-imidazo[2,1-b]thiazol-6-yl | H— |
| 53 | N | —NH—C(=O)— | 1-cyclopentyl-pyrazolo-imidazolyl | pyrrolidin-1-ylmethyl |
| 54 | N | —NH—C(=O)— | 1-phenyl-pyrazolo-imidazolyl | pyrrolidin-1-ylmethyl |
| 55 | N | —NH—C(=O)— | 1-(1-phenylethyl)-pyrazolo-imidazolyl | pyrrolidin-1-ylmethyl |
| 56 | N | —NH—C(=O)— | 1-benzyl-pyrazolo-imidazolyl | pyrrolidin-1-ylmethyl |
| 57 | N | —NH—C(=O)— | 1-(2-phenylethyl)-1H-pyrazol-3-yl | HOCH₂— |

TABLE B1-continued

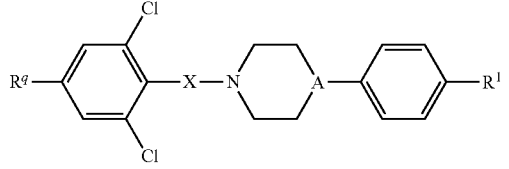

| Co. No. | A | X | R¹ | Rq |
|---|---|---|---|---|
| 58 | N | -NH-C(O)- | 2-(1H-imidazo-fused)-N-isopropyl purine | pyrrolidin-1-ylmethyl |
| 59 | N | -NH-C(O)- | 1-(3-phenylpropyl)-1H-pyrazol-3-yl | HOCH₂— |
| 60 | N | -NH-C(O)- | 1-(2-phenylethyl)-1H-1,2,4-triazol-3-yl | pyrrolidin-1-ylmethyl |
| 61 | N | -NH-C(O)- | 1-(2-phenylethyl)-1H-pyrazol-3-yl | HO— |
| 62 | N | -NH-C(O)- | 1-(3-phenylpropyl)-1H-pyrazol-3-yl | HO— |
| 63 | N | -NH-C(O)- | 1-(2-phenylethyl)-1H-pyrazol-3-yl | methoxycarbonyl |
| 64 | N | -NH-C(O)- | imidazo[2,1-b]thiazol-6-yl | pyrrolidin-1-ylmethyl |
| 65 | N | -NH-C(O)- | 1-(3-phenylpropyl)-1H-pyrazol-3-yl | methoxycarbonyl |

TABLE B2

| Co. No. | X | R¹ | R² | Salt |
|---|---|---|---|---|
| 66 | -NH-C(=O)- | 1-isopropyl-1H-imidazo[4,5-c]pyrazol-5-yl | 2-(trifluoromethyl)phenyl | |
| 67 | -NH-C(=O)- | 1-isopropyl-1H-imidazo[4,5-c]pyrazol-5-yl | 2-chlorophenyl | |
| 68 | -NH-C(=O)- | 1-(4-methylbenzyl)-1H-imidazo[4,5-c]pyrazol-5-yl | 2-(trifluoromethyl)phenyl | |
| 69 | -NH-C(=O)- | 1-isopropyl-1H-pyrazolo[3,4-d]imidazol-5-yl | 2,4-dichlorophenyl | |
| 70 | -NH-C(=O)- | 1-(4-methylbenzyl)-1H-pyrazolo[3,4-d]imidazol-5-yl | 2-chlorophenyl | |
| 71 | -NH-C(=O)- | 5-(4-methylphenyl)-1,2,4-oxadiazol-3-yl | 2-chlorophenyl | |
| 72 | -NH-C(=O)- | 1-isopropyl-1H-imidazo[4,5-c]pyrazol-5-yl | naphthalen-1-yl | |
| 73 | -NH-C(=O)- | 5-cyclohexyl-1,2,4-oxadiazol-3-yl | 2-(trifluoromethyl)phenyl | |

TABLE B2-continued

R²—X—N⌒N—phenyl—R¹

| Co. No. | X | R¹ | R² | Salt |
|---|---|---|---|---|
| 74 | -NH-C(=O)- | 5-cyclopropyl-1,2,4-oxadiazol-3-yl | 2-chloro-4-methylphenyl | |
| 75 | -NH-C(=O)- | 1-(4-methylbenzyl)-1H-pyrazolo[3,4-d]imidazol-5-yl | 2,4-dichlorophenyl | |
| 76 | -NH-C(=O)- | 5-cyclohexyl-1,2,4-oxadiazol-3-yl | 2-chlorophenyl | |
| 77 | -NH-C(=O)- | 1-(4-methylbenzyl)-1H-pyrazolo[3,4-d]imidazol-5-yl | naphthalen-1-yl | |
| 78 | -NH-C(=O)- | 1-isopropyl-1H-pyrazolo[3,4-d]imidazol-5-yl | 4-(dimethylamino)phenyl | |
| 79 | -NH-C(=O)- | 1-(4-methylbenzyl)-1H-pyrazolo[3,4-d]imidazol-5-yl | 4-(dimethylamino)phenyl | |
| 80 | -NH-C(=O)- | 5-cyclobutyl-1,2,4-oxadiazol-3-yl | 2-bromophenyl | |
| 81 | -NH-C(=O)- | 1-isopropyl-1H-pyrazolo[3,4-d]imidazol-5-yl | 4-methylphenyl | |
| 82 | -NH-C(=O)- | 1-isopropyl-1H-pyrazolo[3,4-d]imidazol-5-yl | 4-methoxyphenyl | |

TABLE B2-continued

| Co. No. | X | R¹ | R² | Salt |
|---|---|---|---|---|
| 83 | -NH-C(=O)- | imidazo-pyrazole with N-(4-methylbenzyl) | 2-methoxyphenyl | |
| 84 | -NH-C(=O)- | imidazo-pyrazole with N-isopropyl | 2-methoxyphenyl | |
| 85 | -NH-C(=O)- | imidazo-pyrazole with N-isopropyl | 3-methylphenyl | |
| 86 | -NH-C(=O)- | imidazo-pyrazole with N-isopropyl | 4-(methylthio)phenyl | |
| 87 | -CH₂-C(=O)- | 5-methyl-1,2,4-oxadiazol-3-yl | 2-chloro-6-fluorophenyl | |
| 88 | -NH-C(=O)- | imidazo-pyrazole with N-isopropyl | naphthalen-2-yl | |
| 89 | -CH₂-NH-C(=O)- | imidazo-pyrazole with N-isopropyl | phenyl | |
| 90 | -NH-C(=O)- | imidazo-pyrazole with N-isopropyl | 3-methoxyphenyl | |

TABLE B2-continued

R²—X—N(piperazine)N—C₆H₄—R¹

| Co. No. | X | R¹ | R² | Salt |
|---|---|---|---|---|
| 91 | -NH-C(=O)- | 1-isopropyl-1H-pyrazolo[3,4-d]imidazol-5-yl | 3-(morpholin-4-yl)phenyl | |
| 92 | -NH-C(=O)- | 1-isopropyl-1H-pyrazolo[3,4-d]imidazol-5-yl | 1,3-benzodioxol-5-yl | |
| 93 | -C(=O)- | 5-ethyl-1,2,4-oxadiazol-3-yl | 2-chloro-6-fluorophenyl | |
| 94 | -NH-C(=O)- | 1-(4-methylbenzyl)-1H-pyrrolo[3,2-d]imidazol-5-yl | 4-methoxyphenyl | |
| 95 | -NH-C(=O)- | 1-(4-methylbenzyl)-1H-pyrrolo[3,2-d]imidazol-5-yl | phenyl | |
| 96 | -NH-C(=O)- | 1-(4-methylbenzyl)-1H-pyrrolo[3,2-d]imidazol-5-yl | cyclopropyl | |
| 97 | -NH-C(=O)- | 1-(4-methylbenzyl)-1H-pyrrolo[3,2-d]imidazol-5-yl | 4-(acetylamino)phenyl | |
| 98 | -NH-C(=O)- | 5-methyl-1,2,4-oxadiazol-3-yl | 2-bromophenyl | |
| 99 | -NH-C(=O)- | 1-(4-methylbenzyl)-1H-pyrrolo[3,2-d]imidazol-5-yl | 1,3-benzodioxol-5-yl | |

TABLE B2-continued

| Co. No. | X | R¹ | R² | Salt |
|---|---|---|---|---|
| 100 | -NH-C(=O)- | 5-(1-isopropyl-1H-pyrazolo-imidazole) | 3-fluorophenyl | |
| 101 | -NH-C(=O)- | 1-isopropyl-pyrazolo-imidazole | phenyl | |
| 102 | -CH2-NH-C(=O)- | 1-(4-methylbenzyl)-pyrazolo-imidazole | phenyl | |
| 103 | -NH-C(=O)- | 1-(4-methylbenzyl)-pyrazolo-imidazole | 3-morpholinophenyl | |
| 104 | -C(=O)- | 1-isopropyl-pyrazolo-imidazole | phenyl | |
| 105 | -NH-C(=O)- | 1-(4-methylbenzyl)-pyrazolo-imidazole | 4-methylphenyl | |
| 106 | -NH-C(=O)- | 1-isopropyl-pyrazolo-imidazole | 3-(dimethylamino)phenyl | |
| 107 | -C(=O)- | 5-cyclopropyl-1,2,4-oxadiazole | 2-chloro-6-fluorophenyl | |
| 108 | -C(=O)- | 1-(4-methylbenzyl)-pyrazolo-imidazole | phenyl | |

TABLE B2-continued

R²—X—N⌒N—⟨phenyl⟩—R¹

| Co. No. | X | R¹ | R² | Salt |
|---|---|---|---|---|
| 109 | —NH—C(=O)— | 5-cyclohexyl-1,2,4-oxadiazol-3-yl | 2,4-dimethoxyphenyl | |
| 110 | —CH₂—C(=O)— | 5-(4-methylbenzyl)-5H-pyrrolo[3,2-d]pyrazol-2-yl (imidazo-pyrazole) | phenyl | |
| 111 | —C(=O)— | 5-methyl-1,2,4-oxadiazol-3-yl | 2-bromophenyl | |
| 112 | —NH—C(=O)— | 1-isopropyl-1H-imidazo[4,5-c]pyrazol-5-yl | 4-chlorophenyl | |
| 113 | —C(=O)— | 5-cyclobutyl-1,2,4-oxadiazol-3-yl | 2-bromophenyl | |
| 114 | —NH—C(=O)— | 1-isopropyl-1H-imidazo[4,5-c]pyrazol-5-yl | pyridin-4-yl | |
| 115 | —NH—C(=O)— | 1-isopropyl-1H-imidazo[4,5-c]pyrazol-2-yl | 4-carboxyphenyl | trifluoroacetate salt |
| 116 | —NH—C(=O)— | 1-(4-methylbenzyl)-1H-imidazo[4,5-c]pyrazol-5-yl | 4-chlorophenyl | |
| 117 | —C(=O)— | 5-cyclopropyl-1,2,4-oxadiazol-3-yl | 2-bromophenyl | |

Tables for the Class C Compounds
TABLE C1
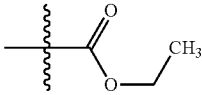 [SMILES: *C(=O)OCC]
| Comp. no. | R$^{1a}$ | R$^{1b}$ | R$^{1c}$ |
|---|---|---|---|
| 125 | H | 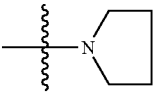 | H |
| 12 | H | 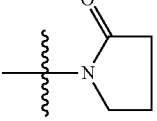 | H |
| 13 | H | 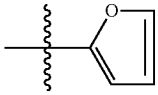 | H |
| 4 | 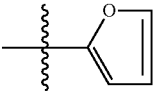 | H | H |
| 14 | H | 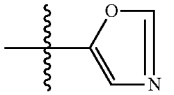 [SMILES: *c1cnco1] | H |
| 15 | H | H | 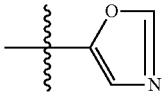 |
| 16 | H | 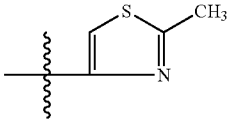 | H |
| 17 | H | 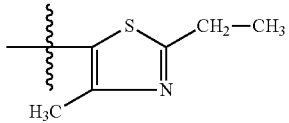 | H |
| 18 | 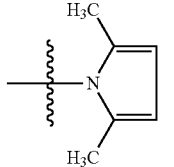 [SMILES: *n1c(C)ccc1C] | H | H |
| 19 | H | H |  |

TABLE C1-continued
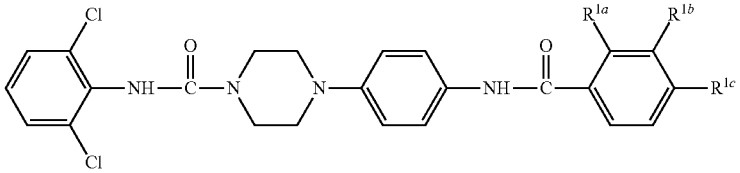
| Comp. no. | R$^{1a}$ | R$^{1b}$ | R$^{1c}$ |
|---|---|---|---|
| 20 | H | 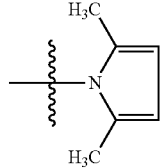 | H |
| 21 | H | H | 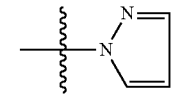 |
| 22 | 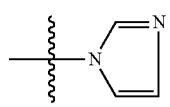 | H | H |
| 23 | H | 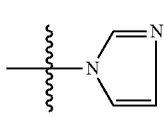 [SMILES: *n1ccnc1] | H |
| 24 | H | H | 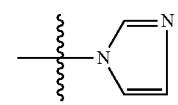 |
| 25 | H | H | 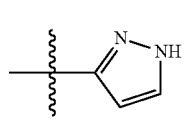 |
| 26 | 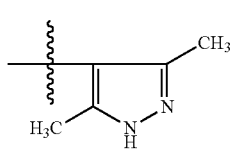 | H | H |
| 27 | H | H | 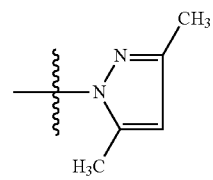 [SMILES: *n1nc(C)cc1C] |
| 28 | H | 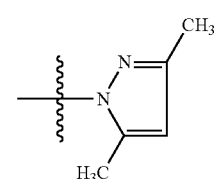 | H |
| 29 | H | H | 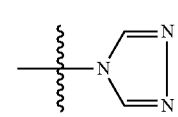 [SMILES: *n1cnnc1] |

TABLE C1-continued

| Comp. no. | R¹ᵃ | R¹ᵇ | R¹ᶜ |
|---|---|---|---|
| 30 | H | H | 3-methyl-1,2,4-oxadiazol-5-yl (5-methyl-1,2,4-oxadiazol-3-yl) |
| 31 | H | 5-methyl-tetrazol-1-yl | H |
| 32 | 1H-tetrazol-5-yl | H | H |
| 33 | H | H | 1H-tetrazol-5-yl |
| 34 | phenyl | H | H |
| 35 | 4-tert-butylphenyl | H | H |
| 36 | H | 2-methylphenyl | H |
| 127 | H | 4-(isopropoxycarbonyl)phenyl | H |
| 37 | H | piperidin-1-yl | H |
| 38 | H | H | morpholin-4-yl |
| 39 | morpholin-4-yl | H | H |

TABLE C1-continued
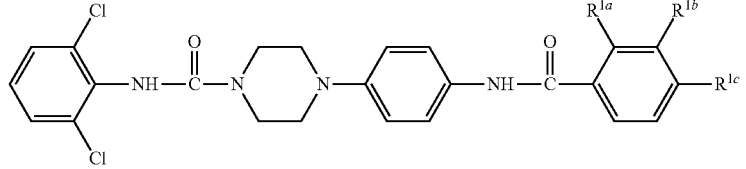
| Comp. no. | R$^{1a}$ | R$^{1b}$ | R$^{1c}$ |
|---|---|---|---|
| 40 | H | 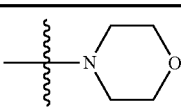 | H |
| 41 | H | 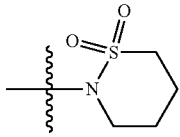 [SMILES: *N1CCCCS1(=O)=O] | H |
| 42 | 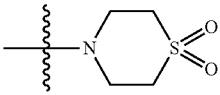 | H | H |
| 43 | H | 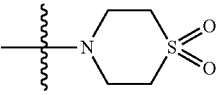 | H |
| 44 | H | H | 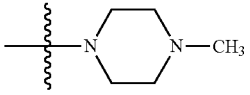 |
| 45 | 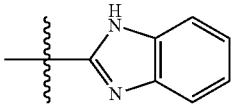 [SMILES: *c1nc2ccccc2[nH]1] | H | H |
| 126 | H | H | 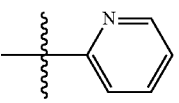 [SMILES: *c1ccccn1] |
TABLE C2
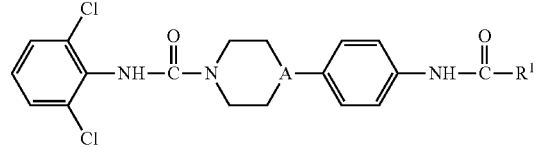
| Comp. no. | A | R$^{1}$ | Salt |
|---|---|---|---|
| 46 | CH | 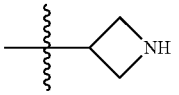 | trifluoro-acetate |
| 47 | CH | 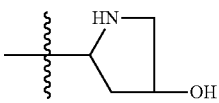 | trifluoro-acetate |
TABLE C2-continued
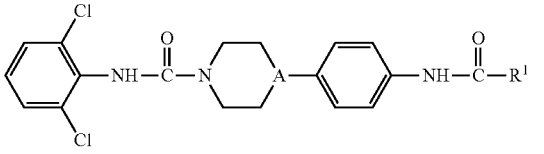
| Comp. no. | A | R$^{1}$ | Salt |
|---|---|---|---|
| 48 | CH | 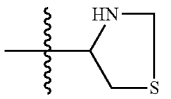 | trifluoro-acetate |
| 10 | CH | 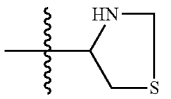 | trifluoro-acetate |

TABLE C2-continued
| Comp. no. | A | R¹ | Salt |
|---|---|---|---|
| 49 | CH | 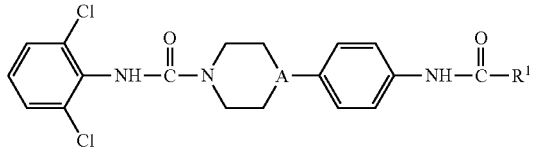 | trifluoroacetate |
| 1 | CH | 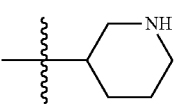 | |
| 50 | CH | 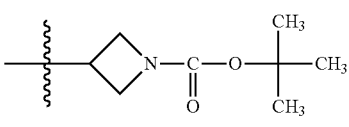 | |
| 51 | CH | 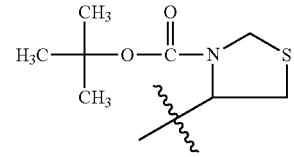 | |
| 52 | CH | 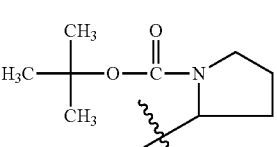 | |
| 3 | CH | 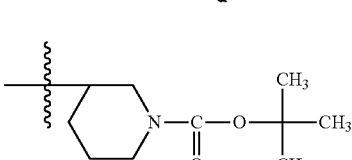 | |
| 53 | CH | 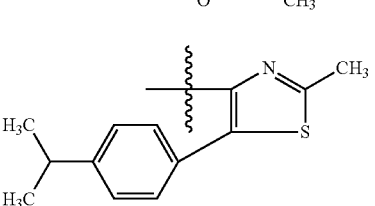 | |
| 54 | CH | 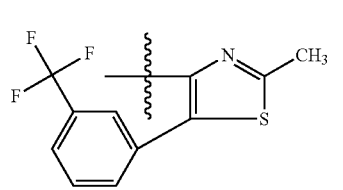 [SMILES: *c1nc(C)sc1-c1cccc(C(F)(F)F)c1] | |
TABLE C2-continued
| Comp. no. | A | R¹ | Salt |
|---|---|---|---|
| 55 | CH | 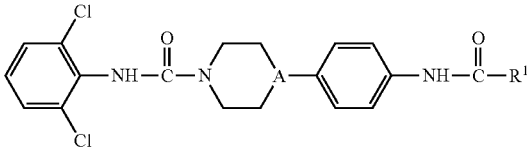 | |
| 56 | CH | 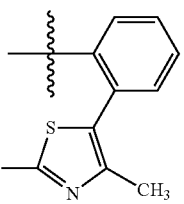 | |
| 57 | CH | 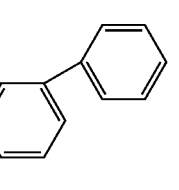 | |
| 58 | CH | 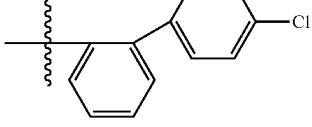 | |
| 59 | CH | 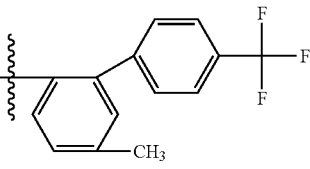 | |
| 60 | CH | 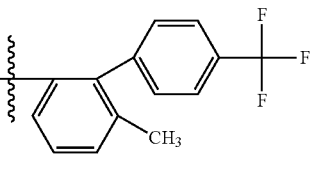 | |
| 61 | CH | 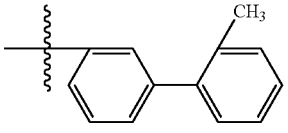 [SMILES: *c1cccc(-c2ccccc2C)c1] | |
| 62 | CH | 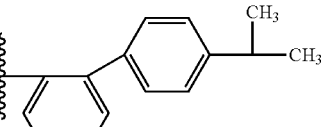 | |

TABLE C2-continued
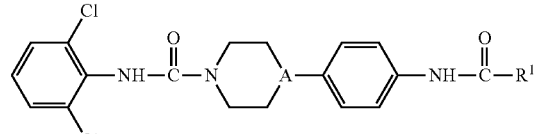
| Comp. no. | A | R¹ | Salt |
|---|---|---|---|
| 63 | CH | 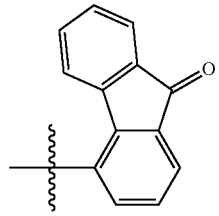 [SMILES: *c1cccc2c1-c1ccccc1C2=O] | |
| 64 | CH | 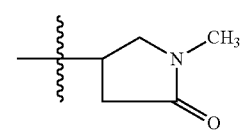 [SMILES: *C1CC(=O)N(C)C1] | |
| 11 | N | 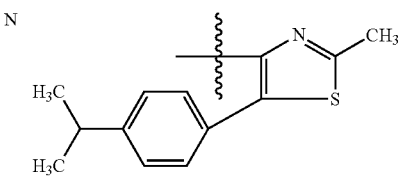 | |
| 2 | N | 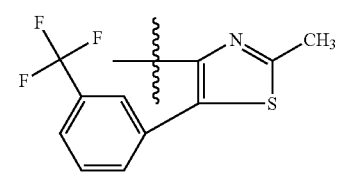 | |
| 65 | N | 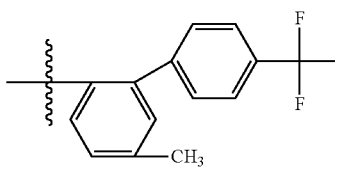 | |
| 66 | N | 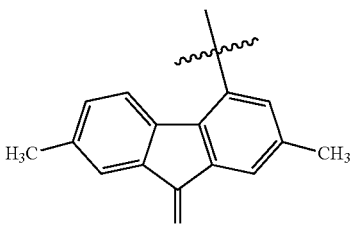 | |
| 67 | N | 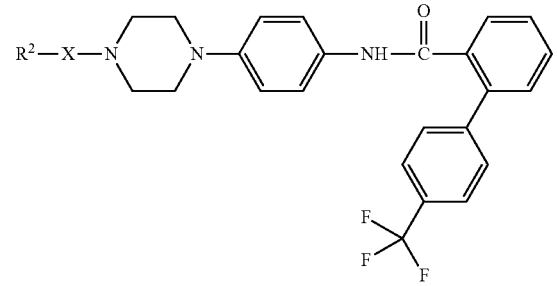 | |
TABLE C3
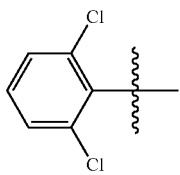 [SMILES: *c1c(Cl)cccc1Cl]
| Co. no. | X | R² |
|---|---|---|
| 6 | —C=O | 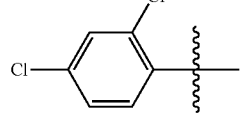 |
| 68 | —NH—C=S | 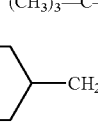 |
| 8 | —NH—C=S | 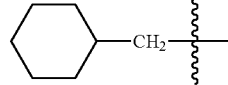 |
| 69 | —NH—C=O | (CH₃)₃—C— |
| 5 | —NH—C=O | 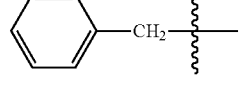 |
| 70 | —NH—C=O | 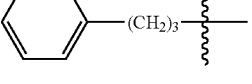 |
| 71 | —NH—C=O | 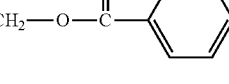 |
| 72 | —NH—C=O | 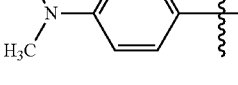 |
| 73 | —NH—C=O | 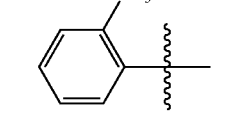 |
| 74 | —NH—C=O | |

TABLE C3-continued

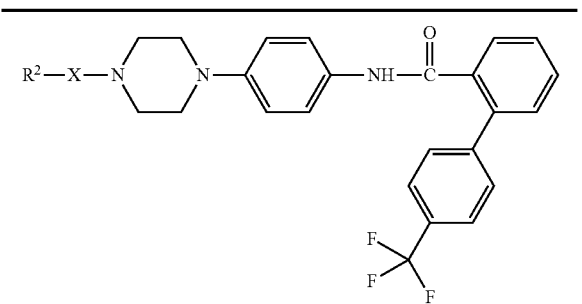

| Co. no. | X | R² |
|---|---|---|
| 75 | —NH—C═O | CH₂—CH₃ on phenyl |
| 76 | —NH—C═O | (CH₂)₂—CH₃ on phenyl |
| 77 | —NH—C═O | CH(CH₃)₂ on phenyl |
| 78 | —NH—C═O | C(CH₃)₃ on phenyl |
| 79 | —NH—C═O | H₃C—CH—CH₂—CH₃ on phenyl |
| 80 | —NH—C═O | OCH₃ on phenyl |
| 81 | —NH—C═O | O—CH₂—CH₃ on phenyl |
| 82 | —NH—C═O | 2,3-dimethylphenyl |

TABLE C3-continued

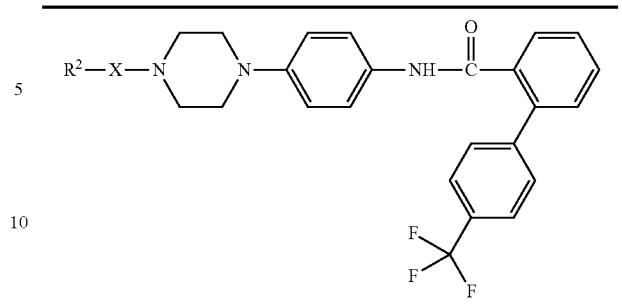

| Co. no. | X | R² |
|---|---|---|
| 83 | —NH—C═O | 2,3-dimethylphenyl (CH₂—CH₃ and CH₃) |
| 84 | —NH—C═O | 2,3-dimethoxyphenyl |
| 85 | —NH—C═O | 2,4,6-trimethylphenyl |
| 86 | —NH—C═O | 2-(C(O)—O—CH₃)phenyl |
| 87 | —NH—C═O | 2-(C(O)—O—CH₂—CH₃)phenyl |
| 88 | —NH—C═O | 2-bromophenyl |
| 89 | —NH—C═O | 2-chlorophenyl |
| 90 | —NH—C═O | 2-fluorophenyl |

TABLE C3-continued
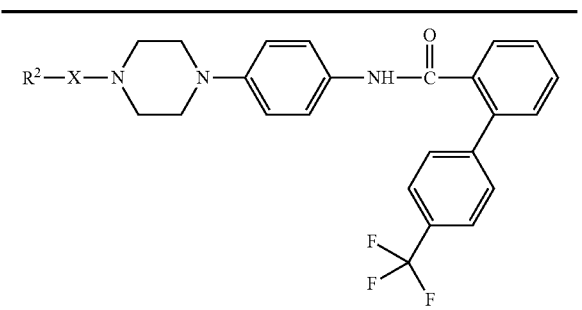
| Co. no. | X | R² |
|---|---|---|
| 91 | —NH—C=O | 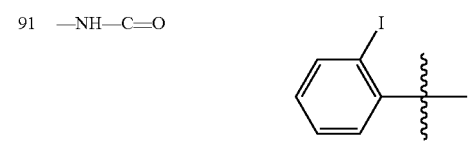 |
| 92 | —NH—C=O | 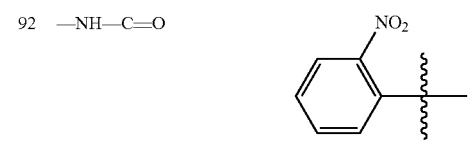 |
| 93 | —NH—C=O | 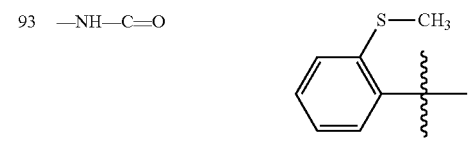 |
| 94 | —NH—C=O | 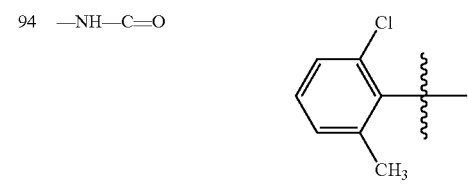 |
| 9 | —NH—C=O | 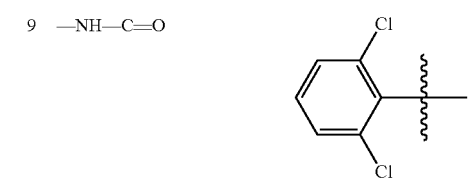 |
| 95 | —NH—C=O | 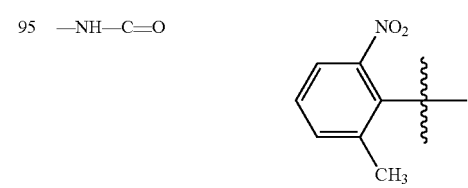 |
| 96 | —NH—C=O | 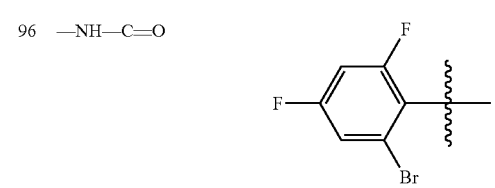 |
TABLE C3-continued
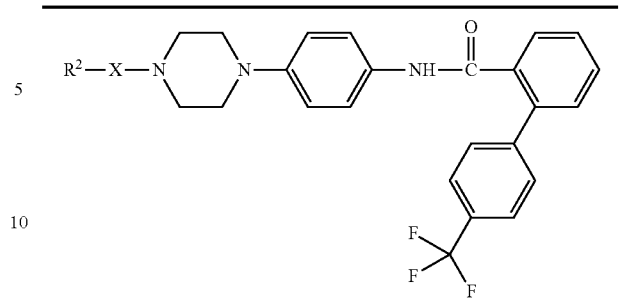
| Co. no. | X | R² |
|---|---|---|
| 97 | —NH—C=O | 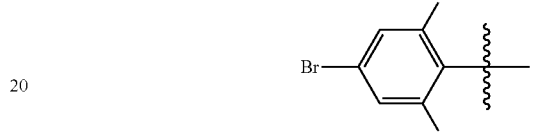 |
| 98 | —NH—C=O | 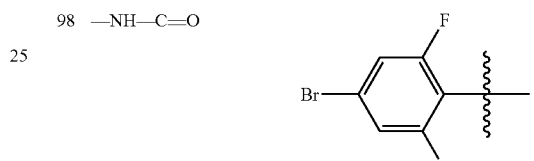 |
| 99 | —NH—C=O | 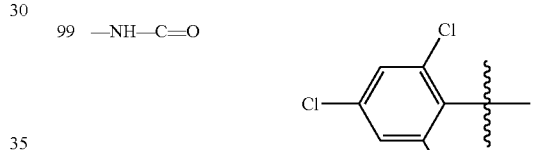 |
| 100 | —NH—C=O | 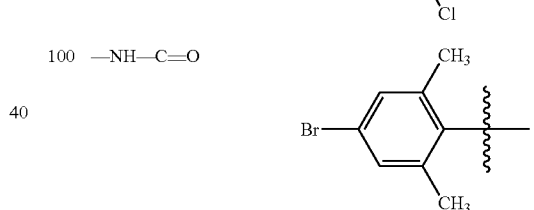 |
| 101 | —NH—C=O | 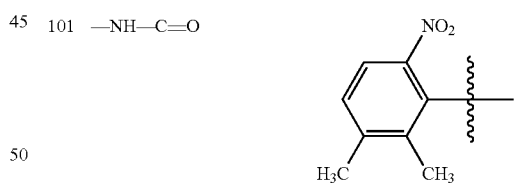 |
| 102 | —NH—C=O | 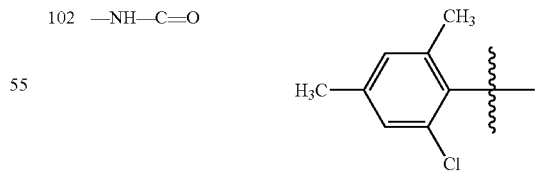 |
| 103 | —NH—C=O | 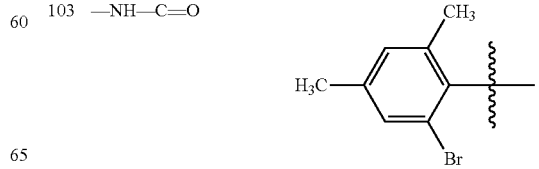 |

TABLE C3-continued
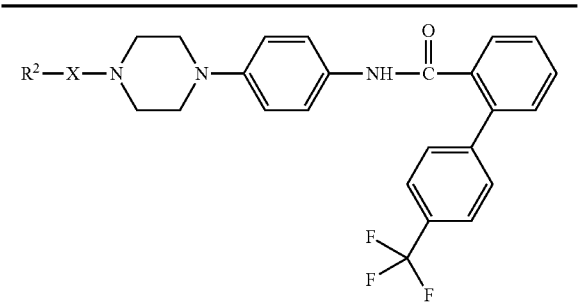
| Co. no. | X | R² |
|---|---|---|
| 104 | —NH—C=O | 3-bromo-2,4,6-trimethylphenyl |
| 105 | —NH—C=O | 2-phenoxyphenyl |
| 106 | —NH—C=O | 2,3-dihydro-1,4-benzodioxin-6-yl |
TABLE C4
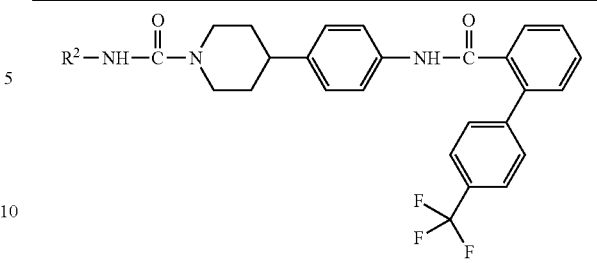
| Co. no. | R² |
|---|---|
| 107 | CH₂=CH—CH₂— |
| 7 | 2-methylphenyl |
| 108 | 2-ethylphenyl |
| 109 | 2-isopropylphenyl |
| 110 | 2-ethyl-3-methylphenyl |
| 111 | 2,6-dimethoxyphenyl |
| 128 | 2,6-dimethylphenyl |
| 112 | 2,4,6-trimethylphenyl |
| 113 | 2-chloro-6-methylphenyl |
| 114 | 3-bromo-2,4-difluorophenyl |

TABLE C4-continued
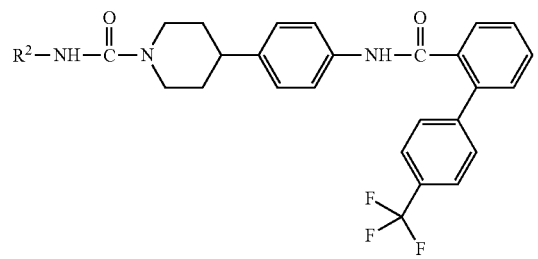
| Co. no. | R² |
|---|---|
| 115 | 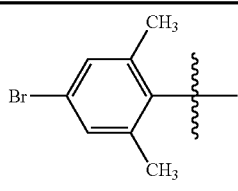 |
| 116 | 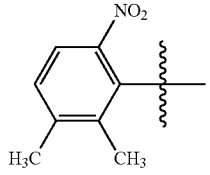 |
| 117 | 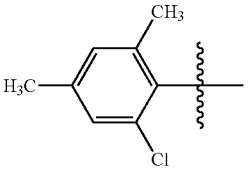 |
| 118 | 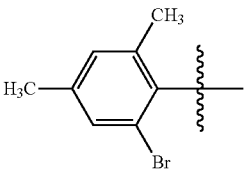 [SMILES: *c1c(C)cc(C)cc1Br] |
TABLE C5
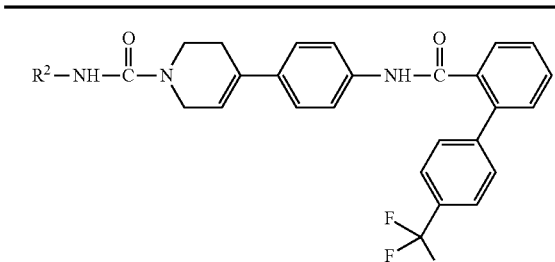
| Co. no. | R² |
|---|---|
| 119 | CH₃—CH₂—CH₂— |
| 120 | 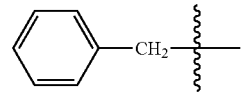 |
TABLE C5-continued
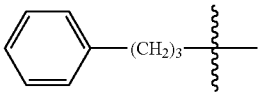
| Co. no. | R² |
|---|---|
| 121 | 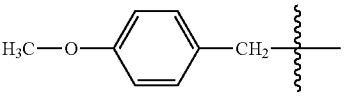 |
| 122 | 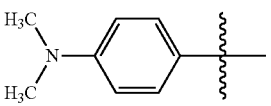 |
| 123 | 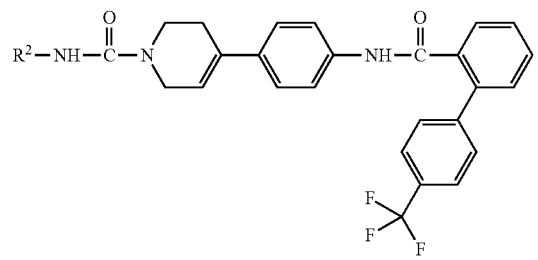 |
| 124 | 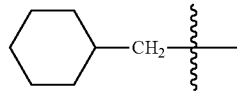 |

TABLE C6
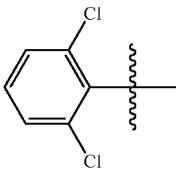 [SMILES: *c1c(Cl)cccc1Cl]
| Comp. no. | X | R² | R¹ᵃ | R¹ᵃ' | R¹ᵇ | R¹ᶜ | R⁷ |
|---|---|---|---|---|---|---|---|
| 131 | —CH₂—C=O | 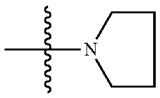 [SMILES: *N1CCCC1] | H | H | 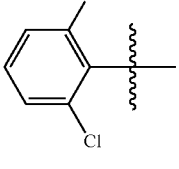 | H | H |
| 134 | —CH₂—C=O | 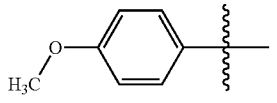 | Cl | Cl | H | H | H |
| 135 | —CH₂—NH—C=O | 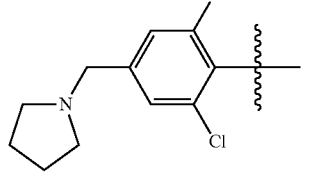 | Cl | Cl | H | H | H |
| 133 | —NH—C=O | 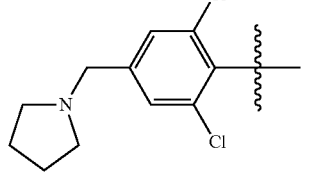 | H | H | H | —OCH₃ | F |
| 130 | —NH—C=O | 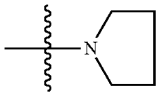 | H | H | 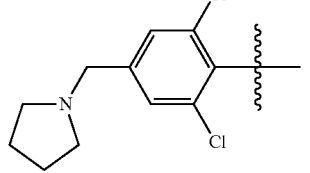 | H | H |
| 147 | —CH₂—C=O | 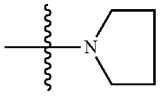 | H | H | 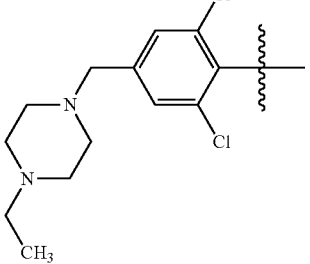 | H | H |
| 148 | —CH₂—C=O | 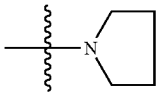 | H | H | 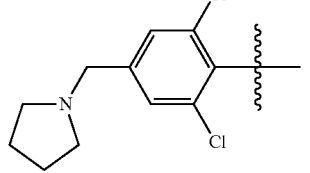 | H | H |

TABLE C6-continued
| Comp. no. | X | R² | R¹ᵃ | R¹ᵃ' | R¹ᵇ | R¹ᶜ | R⁷ |
|---|---|---|---|---|---|---|---|
| 149 | —CH₂—C=O | 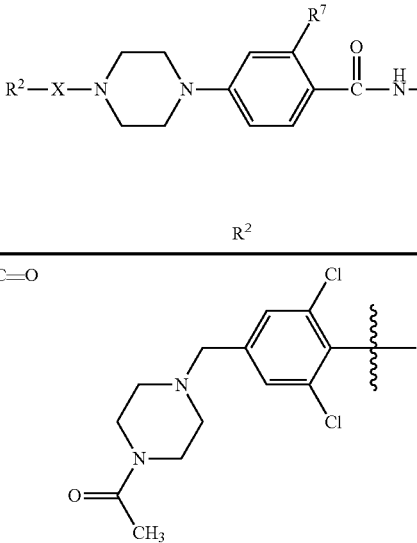 | H | H | 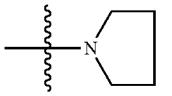 | H | H |
| 150 | —CH₂—C=O | 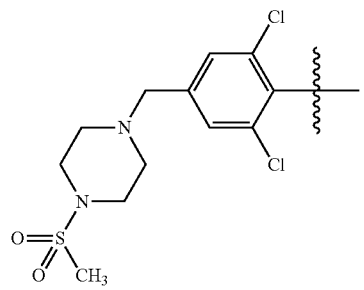 [SMILES: *c1c(Cl)cc(CN2CCN(S(C)(=O)=O)CC2)cc1Cl] | H | H | 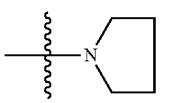 | H | H |
| 151 | —CH₂—C=O | 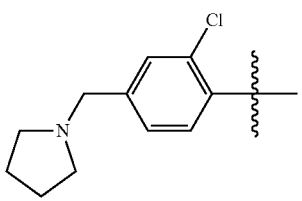 [SMILES: *c1ccc(CN2CCCC2)cc1Cl] | H | H | 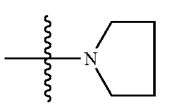 | H | H |
| 152 | —CH(OH)—C=O | 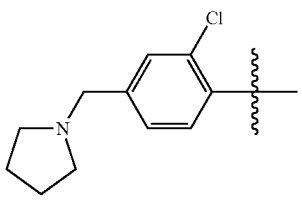 | H | H | 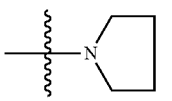 | H | H |
| 129 | —NH—C=O | 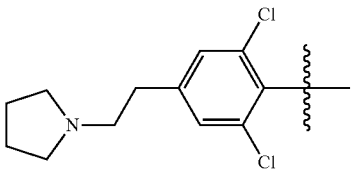 [SMILES: *c1c(Cl)cc(CCN2CCCC2)cc1Cl] | H | H | 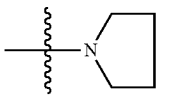 | H | H |
| 132 | —CH₂—C=O | 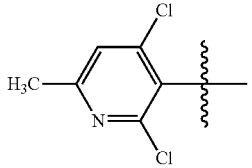 [SMILES: *c1c(Cl)cc(C)nc1Cl] | H | H | 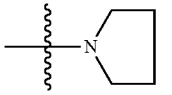 | H | H |

TABLE C7

| Comp. no. | X | R² | R¹ᵃ | R¹ᵇ | R¹ᶜ |
|---|---|---|---|---|---|
| 144 | —NH—C=O | cyclohexyl | 4-(trifluoromethyl)phenyl | H | H |
| 142 | —CH₂—C=O | 2-methylphenyl | H | Br | H |
| 141 | —CH₂—C=O | 2-methylphenyl | H | H | —(CH₂)₃CH₃ |
| 139 | —O—C=O | 2,6-dichlorophenyl | H | pyrrolidin-1-yl | H |
| 137 | —NH—C=O | 3,5-dichloro-4-(diisopropylaminomethyl)phenyl | H | pyrrolidin-1-yl | H |
| 146 | —CH₂—C=O | 3,5-dichloro-4-(pyrrolidin-1-ylmethyl)phenyl | H | —C(CH₃)₂COOH | H |
| 145 | —CH₂—C=O | 3,5-dichloro-4-(pyrrolidin-1-ylmethyl)phenyl | H | —C(CH₃)₂COOCH₃ | H |
| 140 | —NH—C=O | 3,5-dichloro-4-(pyrrolidin-1-ylmethyl)phenyl | H | —C(CH₃)₂COOCH₃ | H |

TABLE C7-continued
| Comp. no. | X | R² | R¹ᵃ | R¹ᵇ | R¹ᶜ |
|---|---|---|---|---|---|
| 143 | —NH—C=O | 2,6-dichloro-4-(piperidin-1-ylmethyl)phenyl | H | —CH₂C(=O)OH | H |
| 138 | —NH—C=O | 2,6-dichloro-4-(piperidin-1-ylmethyl)phenyl | H | —CH₂C(=O)OCH₂CH₃ | H |
| 136 | —NH—C=O | 2,6-dichloro-4-[2-(4-methylpiperazin-1-yl)-2-oxoethyl]phenyl | H | pyrrolidin-1-ylmethyl | H |
Tables for the Class D Compounds
TABLE D1
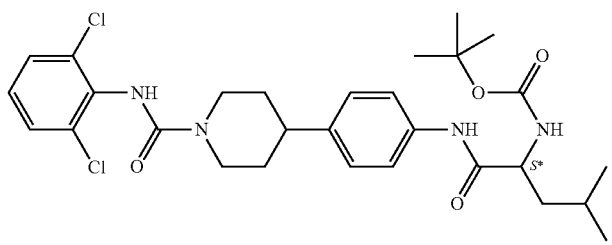
Co. No. 33
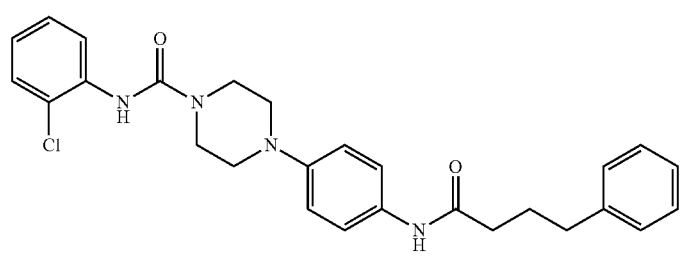
Co. No. 34

TABLE D1-continued
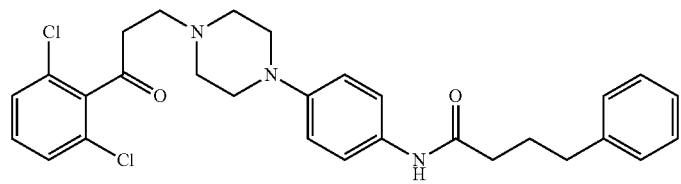
Co. No.18
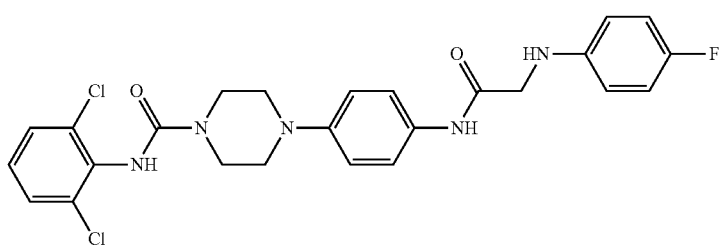
Co. No.36
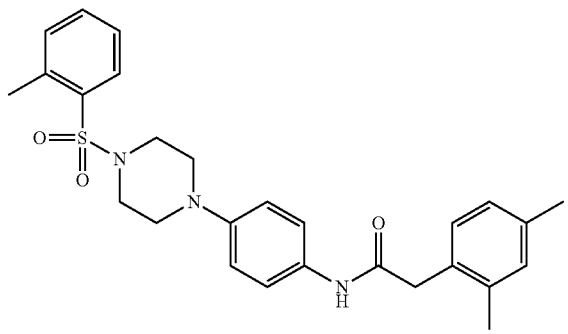
Co. No.17
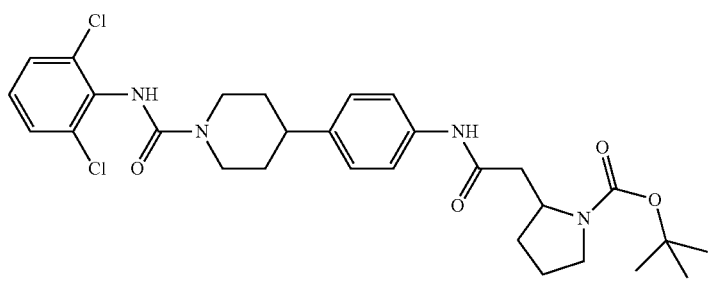
Co. No.39
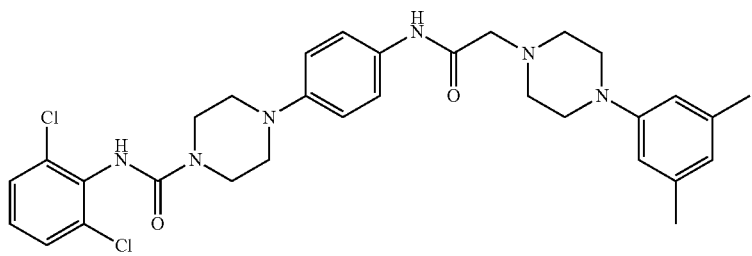
Co. No.41

TABLE D1-continued
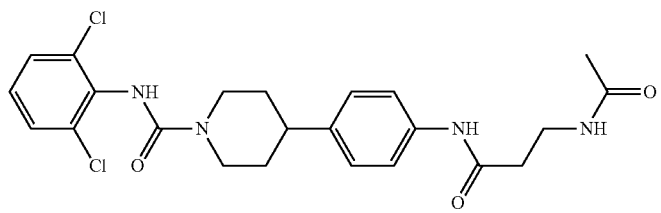
Co. No.43
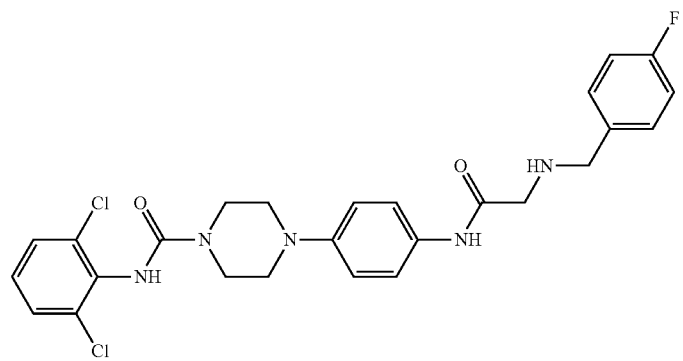
Co. No.35
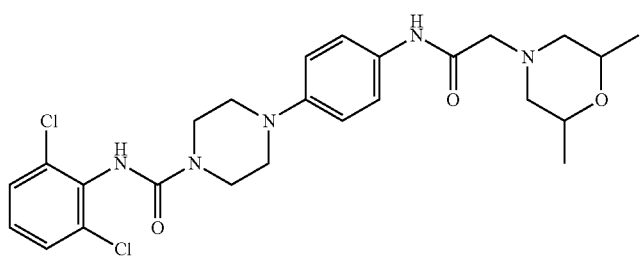
Co. No.37
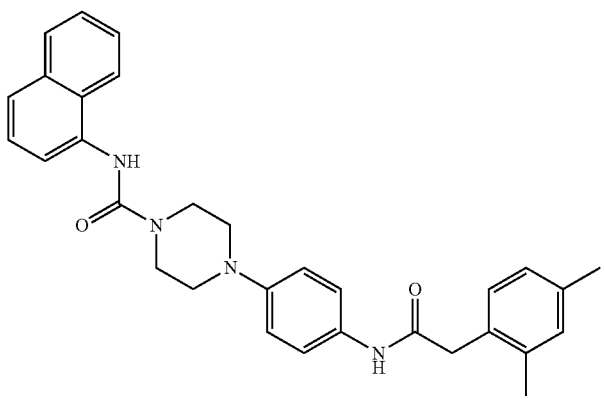
Co. No.38
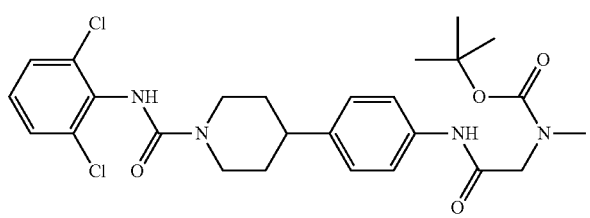
Co. No.40

TABLE D1-continued
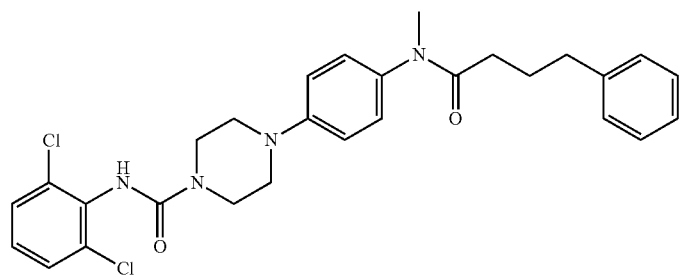
Co. No.42
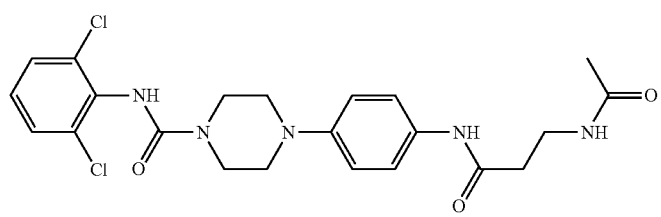
Co. No.44
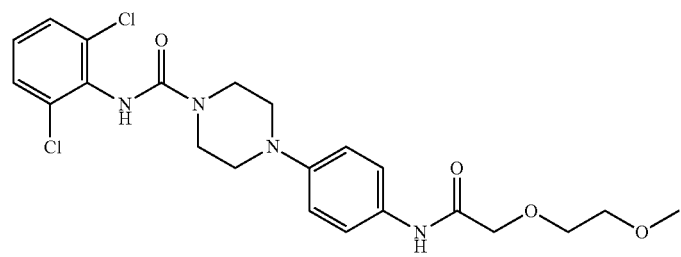
Co. No.45
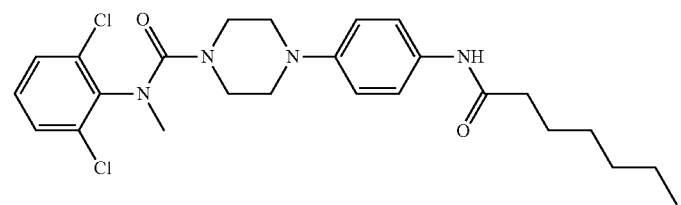
Co. No.10
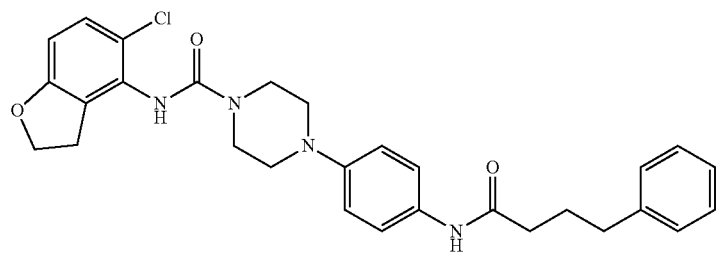
Co. No. 12

TABLE D1-continued
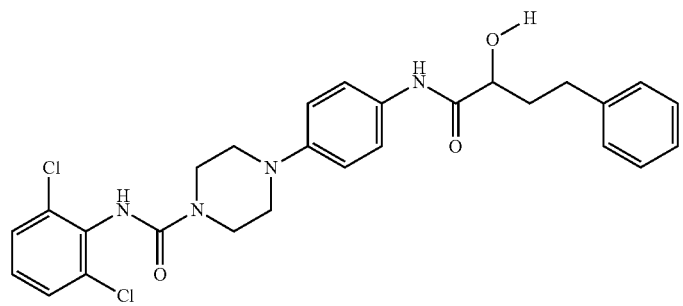
Co. No.48
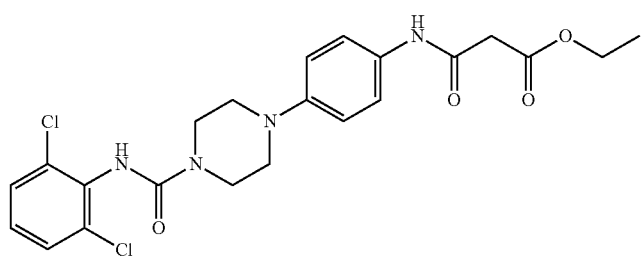
Co. No.50
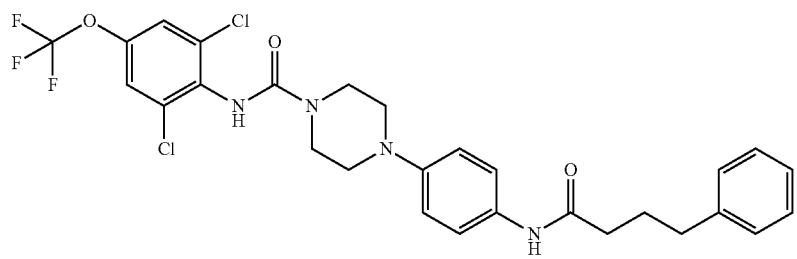
Co. No. 13
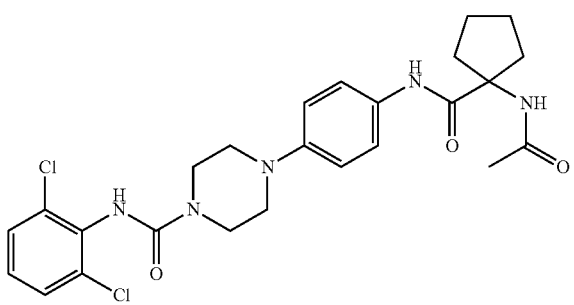
Co. No. 2
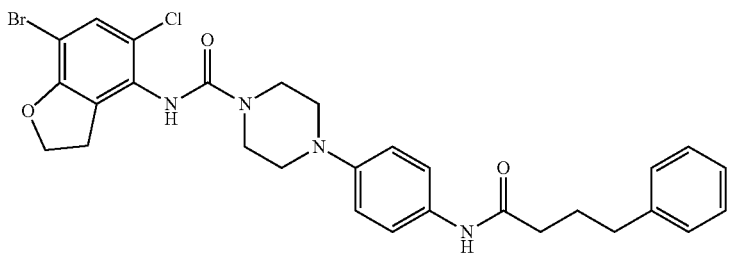
Co. No.46

TABLE D1-continued
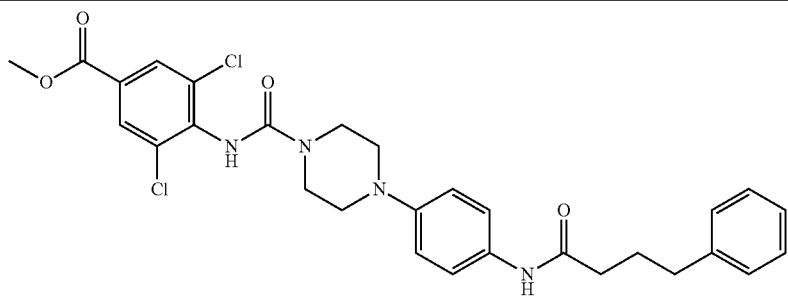
Co. No. 47
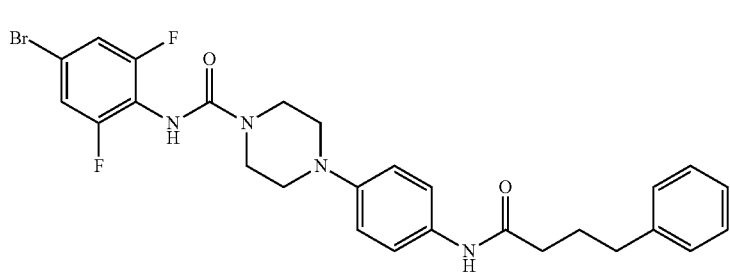
Co. No. 49
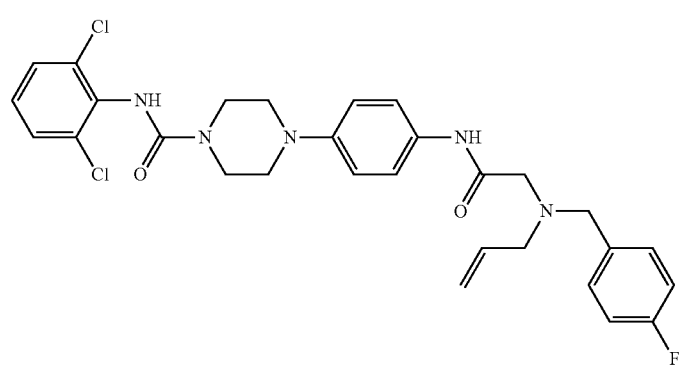
Co. No. 51
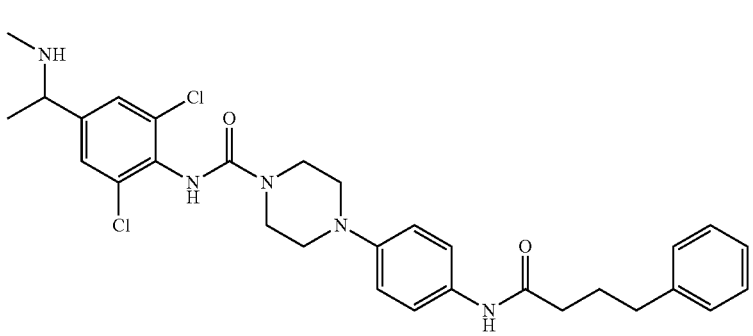
Co. No. 24
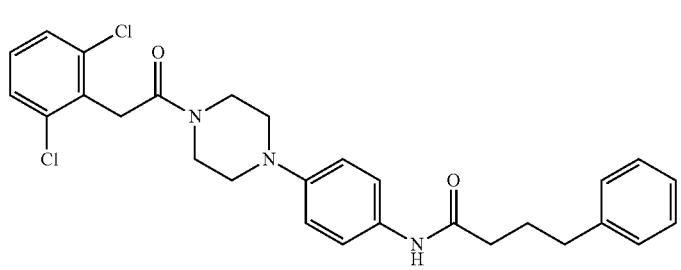
Co. No. 52

TABLE D1-continued
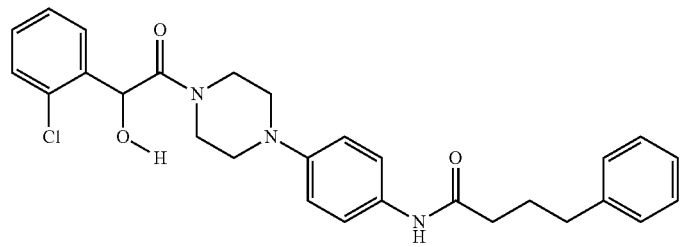
Co. No.19; RS mixture
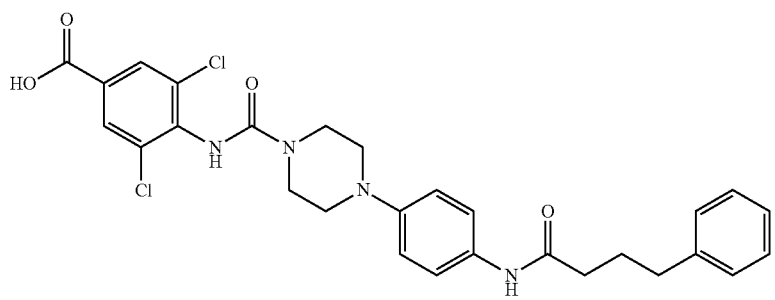
Co. No. 27
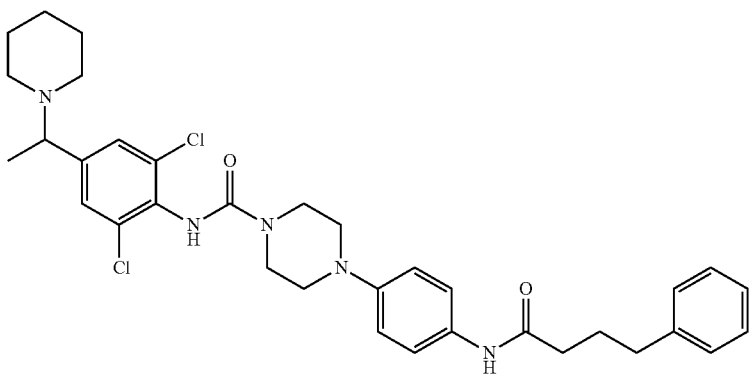
Co. No.56
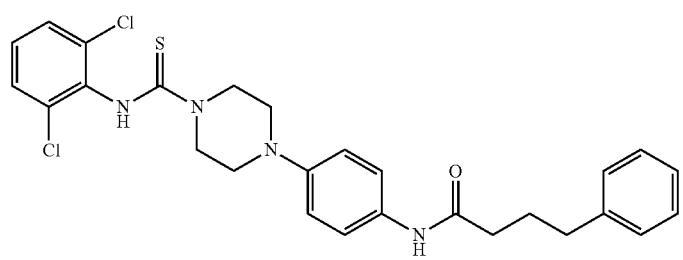
Co. No.189

TABLE D1-continued
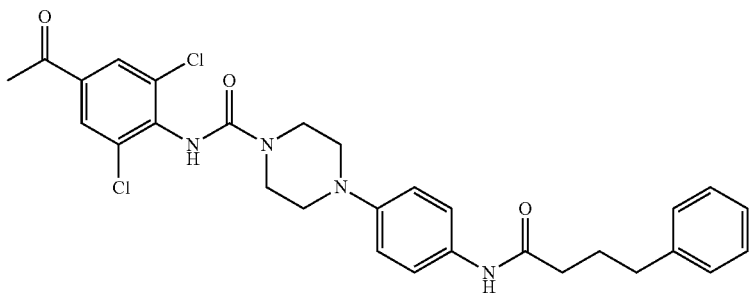
Co. No. 53
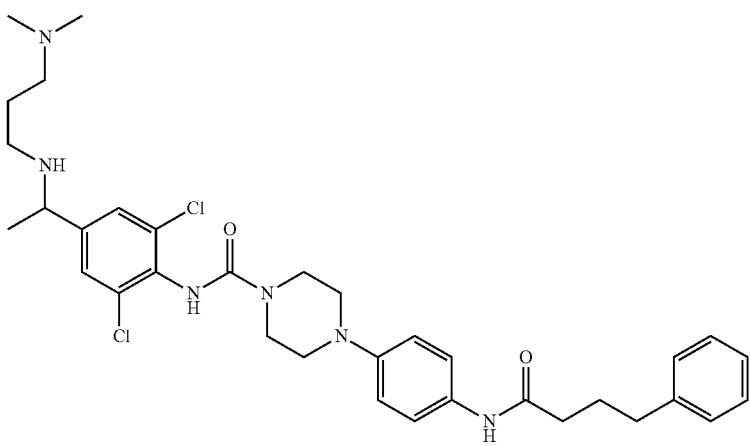
Co. No. 54
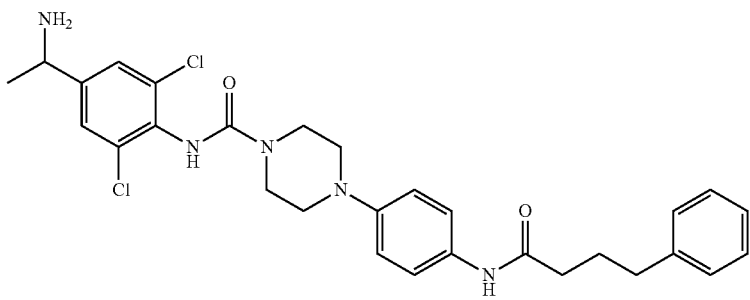
Co. No. 55
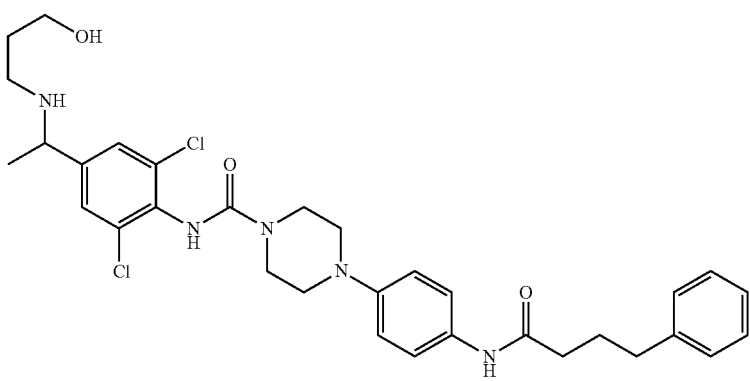
Co. No. 57

TABLE D1-continued
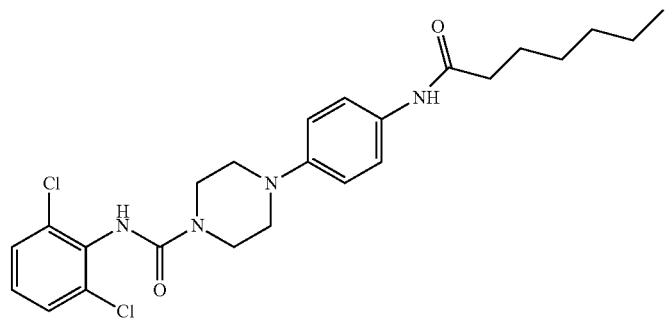
Co. No. 8
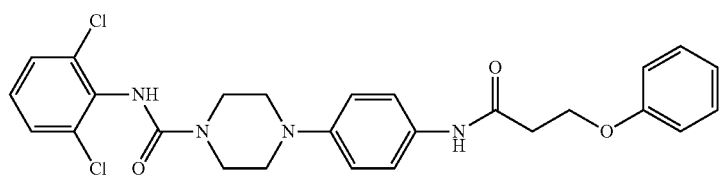
Co. No. 3
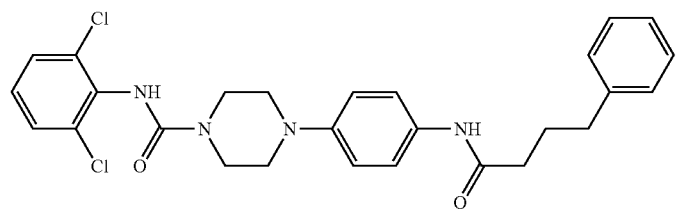
Co. No.58
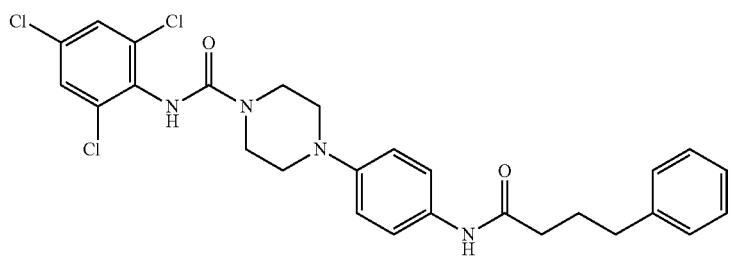
Co. No.59
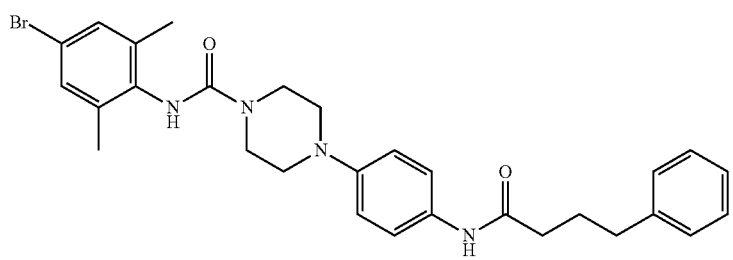
Co. No.61; Ex. [B6.a]

TABLE D1-continued
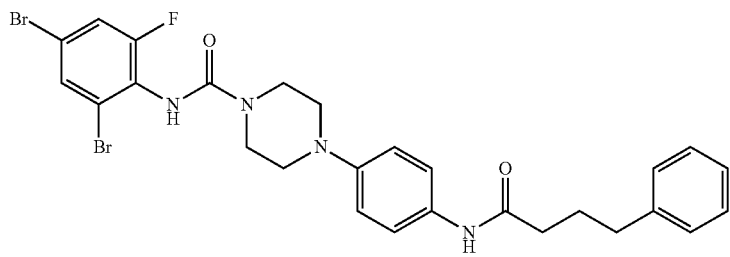
Co. No.63
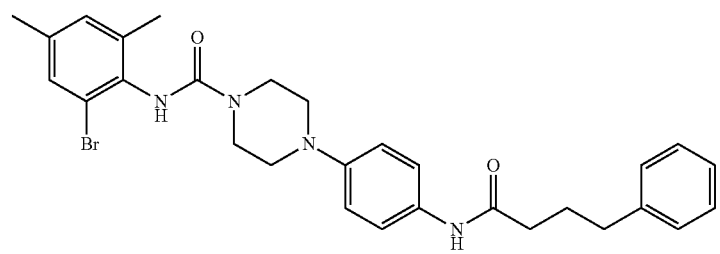
Co. No. 11
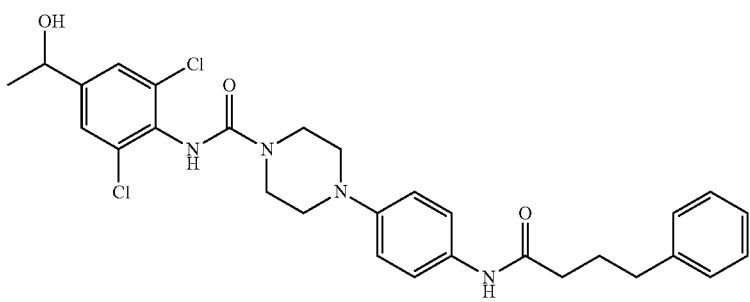
Co. No.29
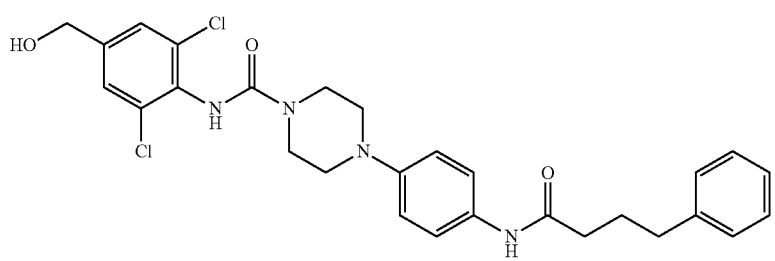
Co. No.28
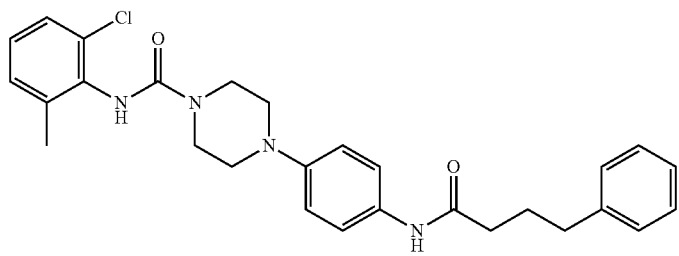
Co. No.60

TABLE D1-continued
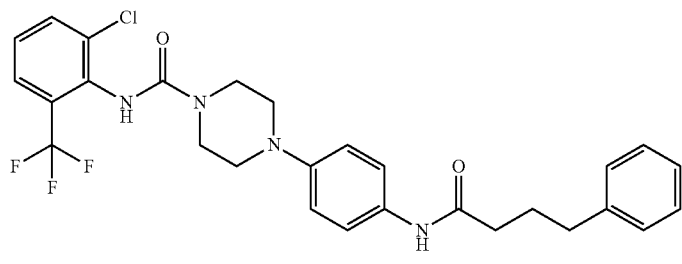
Co. No.62
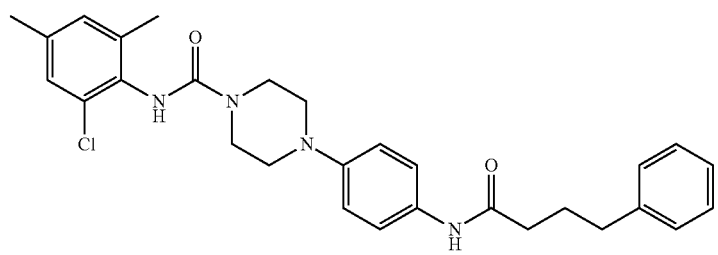
Co. No.64
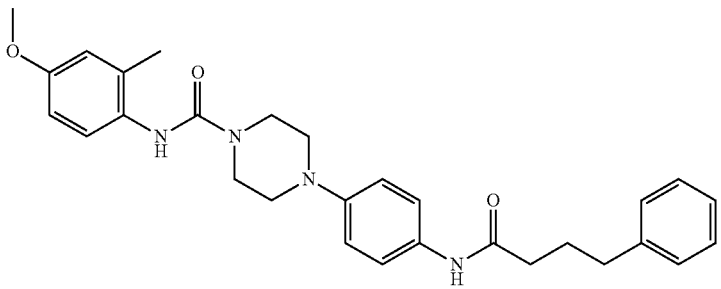
Co. No.65
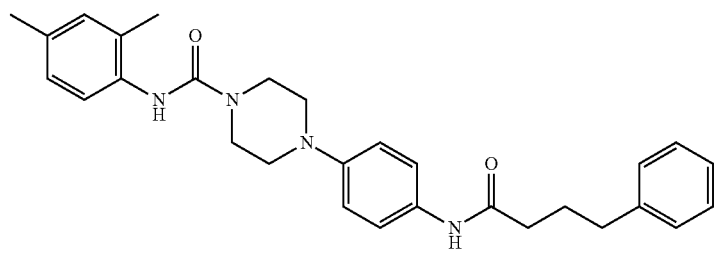
Co. No.66
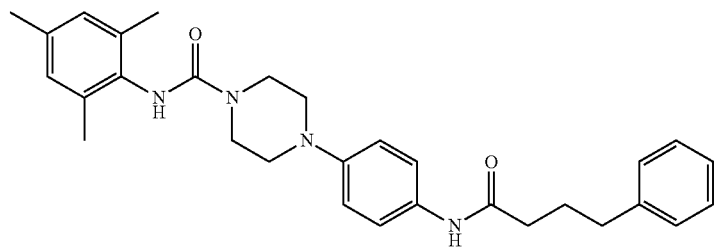
Co. No.68

TABLE D1-continued
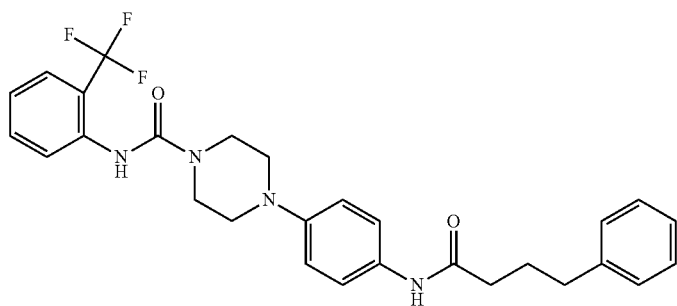
Co. No. 70
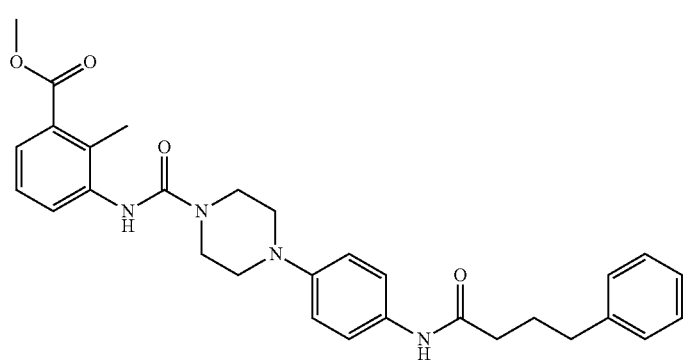
Co. No. 72
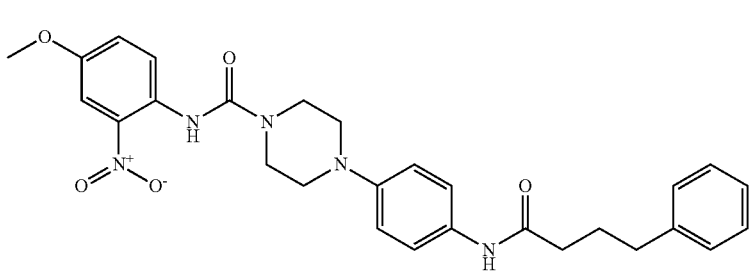
Co. No. 74
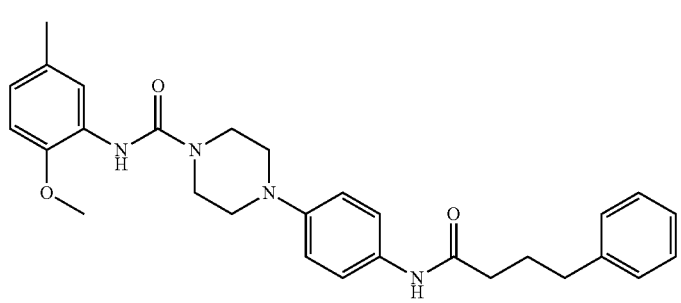
Co. No. 76
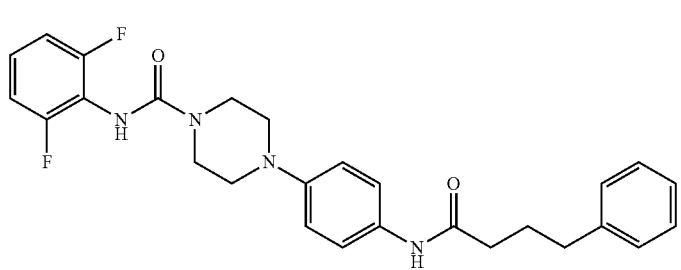
Co. No. 67

TABLE D1-continued
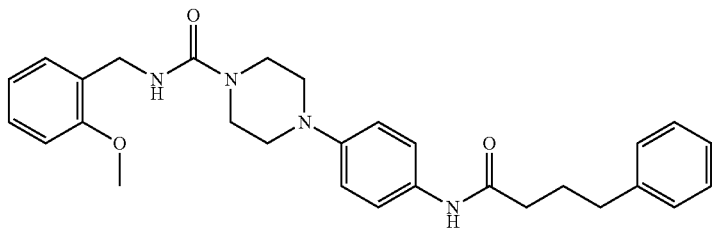
Co. No. 71
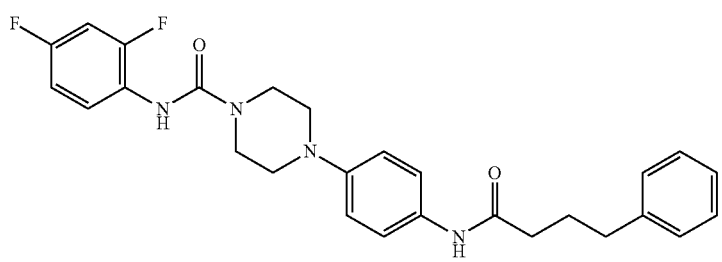
Co. No. 73
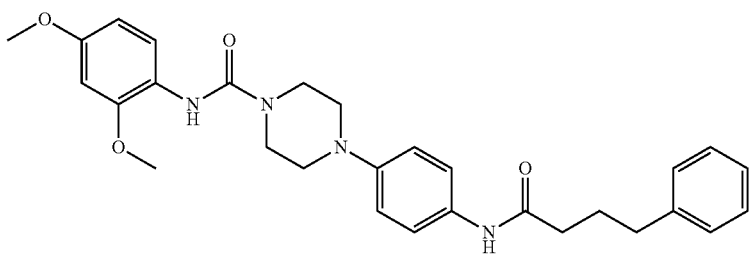
Co. No. 75
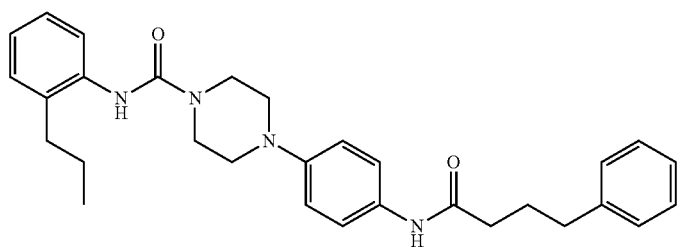
Co. No. 77
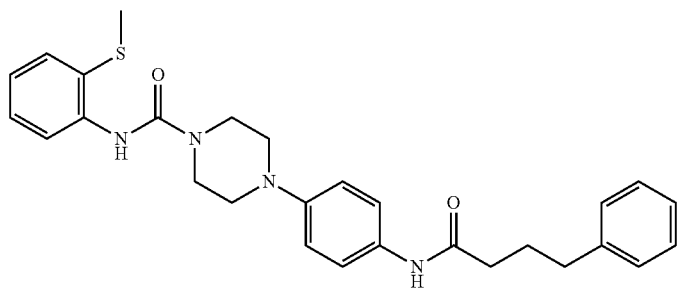
Co. No. 79

TABLE D1-continued
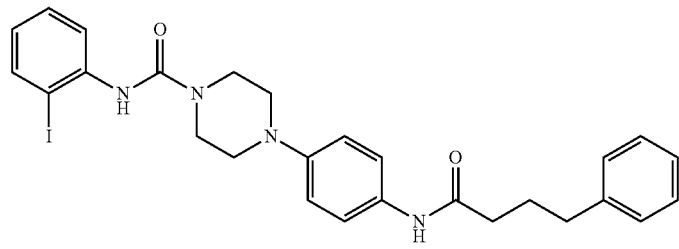
Co. No.78
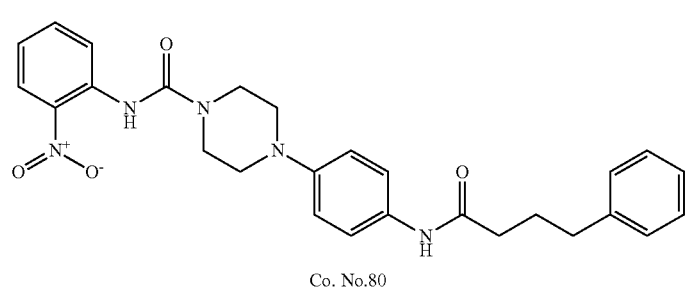 [SMILES: O=C(CCCc1ccccc1)Nc1ccc(N2CCN(C(=O)Nc3ccccc3[N+](=O)[O-])CC2)cc1]
Co. No.80
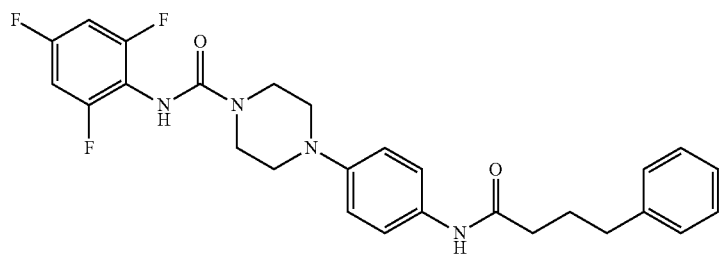
Co. No.82; Ex. [B6.a]
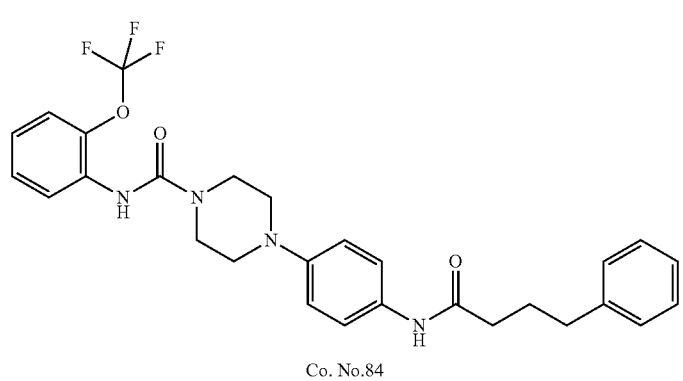 [SMILES: O=C(CCCc1ccccc1)Nc1ccc(N2CCN(C(=O)Nc3ccccc3OC(F)(F)F)CC2)cc1]
Co. No.84
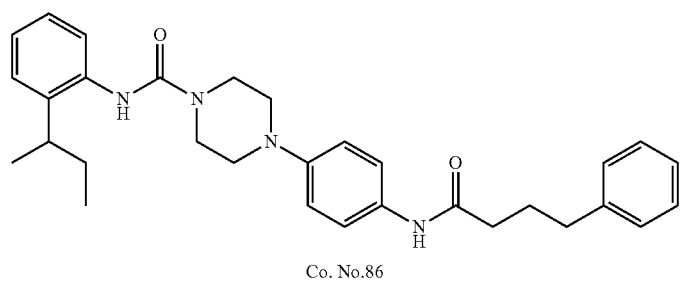 [SMILES: CCC(C)c1ccccc1NC(=O)N1CCN(c2ccc(NC(=O)CCCc3ccccc3)cc2)CC1]
Co. No.86

TABLE D1-continued
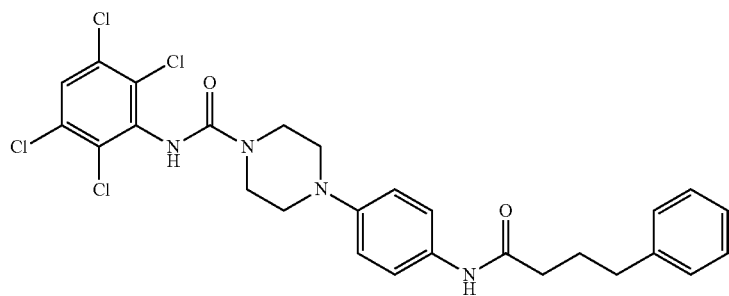
Co. No. 88
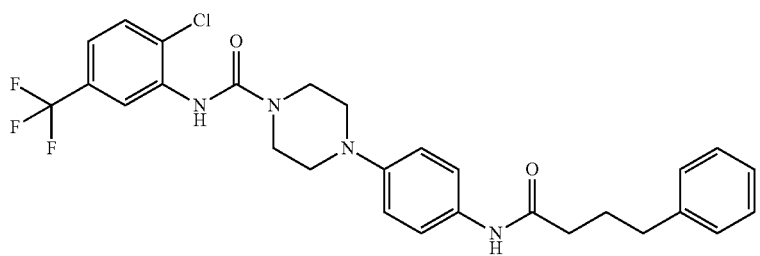
Co. No. 81
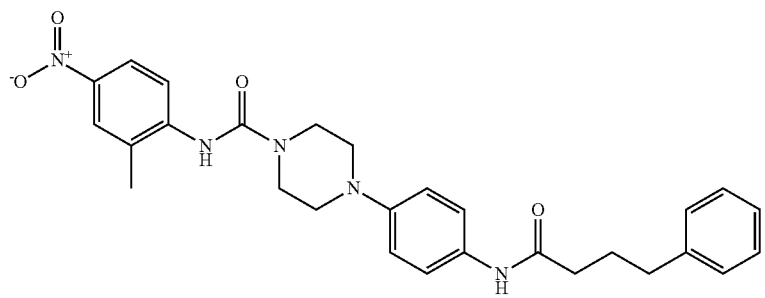
Co. No. 83
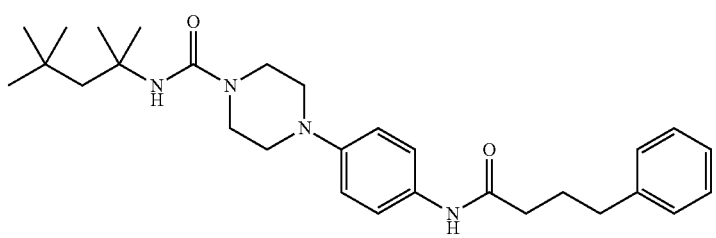
Co. No. 85; Ex. [B6.a]
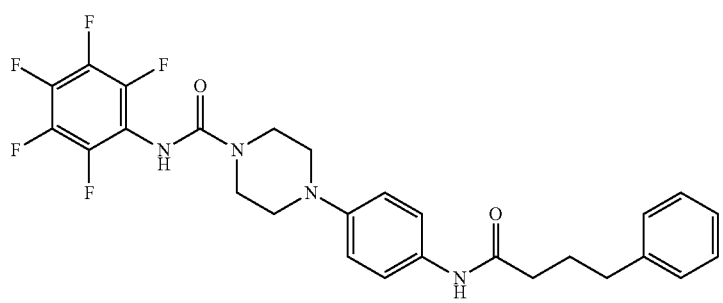
Co. No. 87

TABLE D1-continued
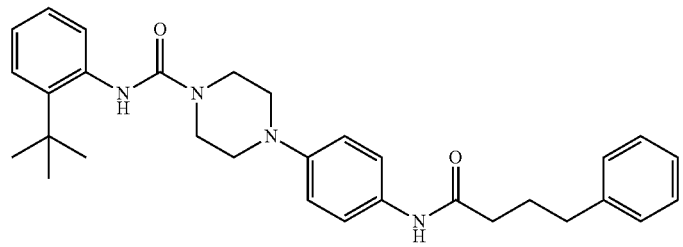
Co. No.89
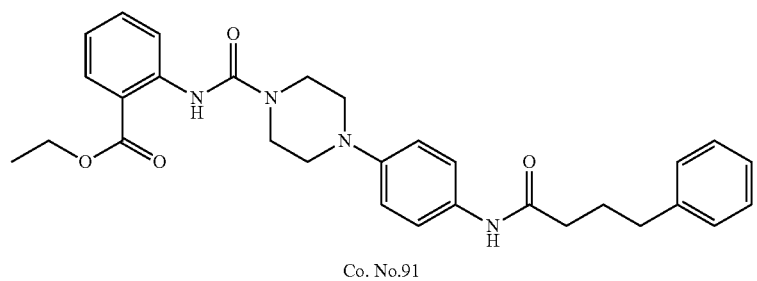 [SMILES: CCOC(=O)c1ccccc1NC(=O)N1CCN(c2ccc(NC(=O)CCCc3ccccc3)cc2)CC1]
Co. No.91
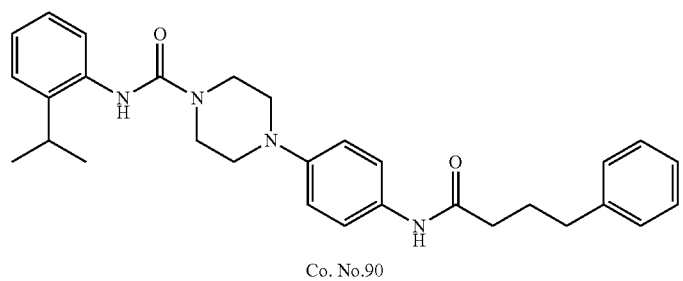 [SMILES: CC(C)c1ccccc1NC(=O)N1CCN(c2ccc(NC(=O)CCCc3ccccc3)cc2)CC1]
Co. No.90
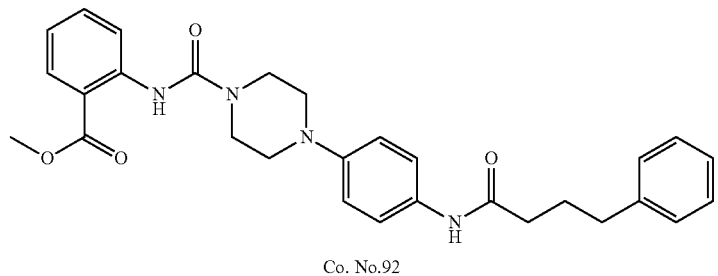 [SMILES: COC(=O)c1ccccc1NC(=O)N1CCN(c2ccc(NC(=O)CCCc3ccccc3)cc2)CC1]
Co. No.92
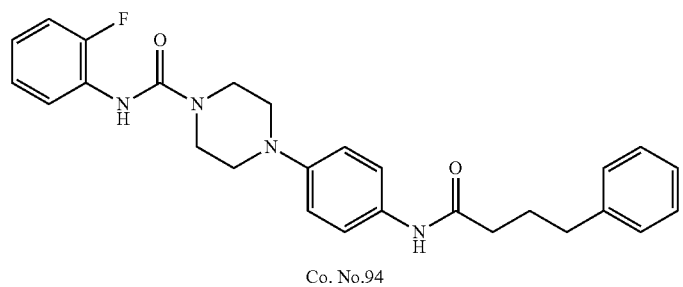 [SMILES: O=C(CCCc1ccccc1)Nc1ccc(N2CCN(C(=O)Nc3ccccc3F)CC2)cc1]
Co. No.94

TABLE D1-continued
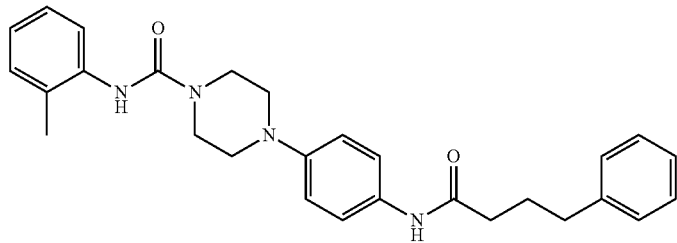
Co. No.96
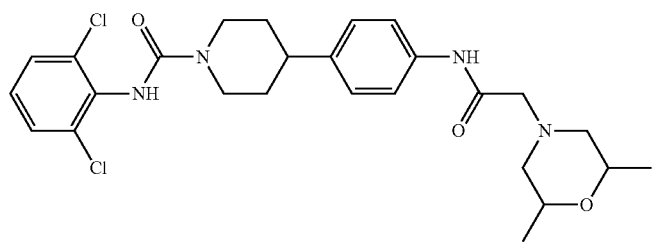
Co. No.98
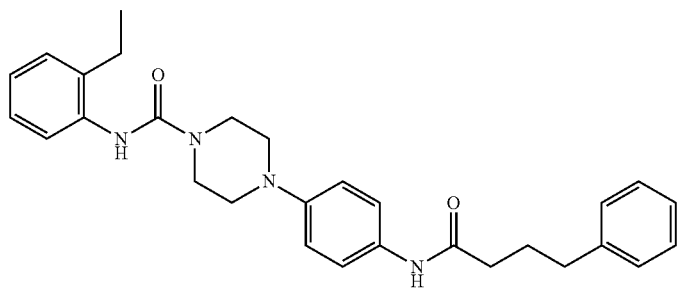
Co. No.93
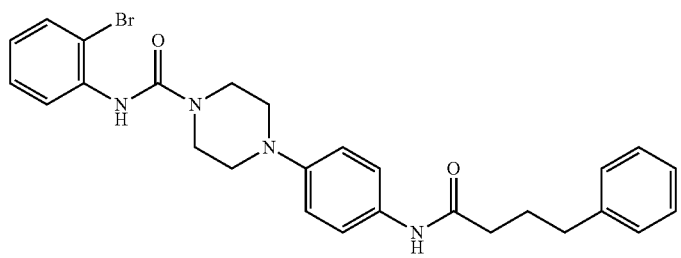
Co. No.95
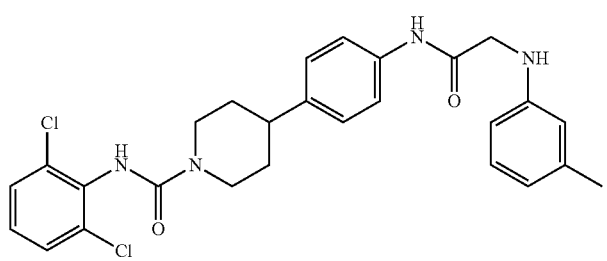
Co. No.97

TABLE D1-continued
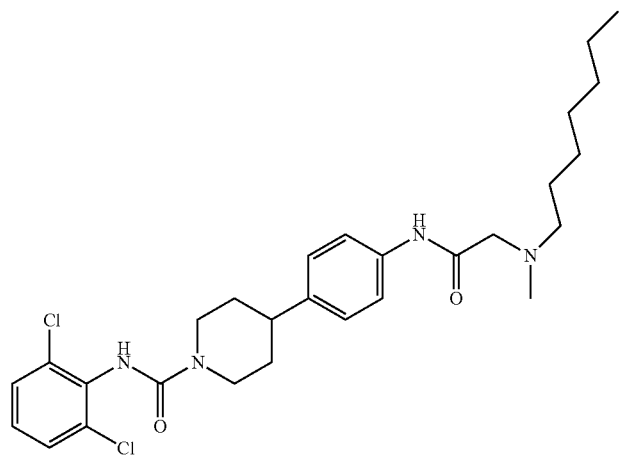
Co. No.99
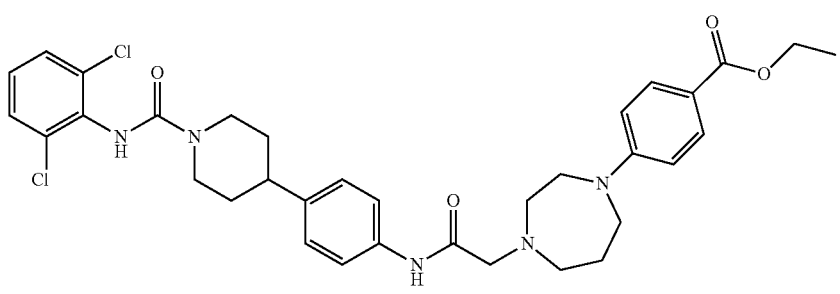
Co. No.101
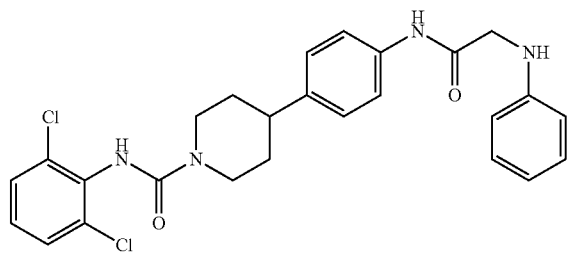
Co. No.100
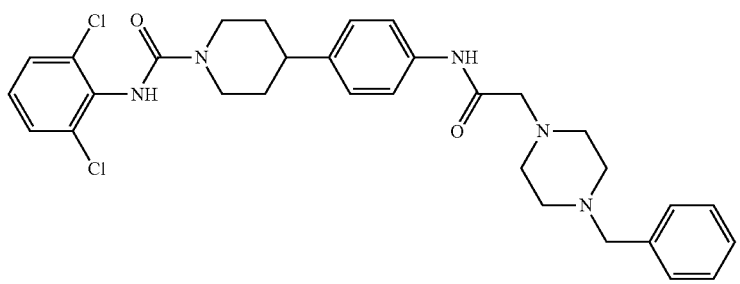
Co. No.102

TABLE D1-continued
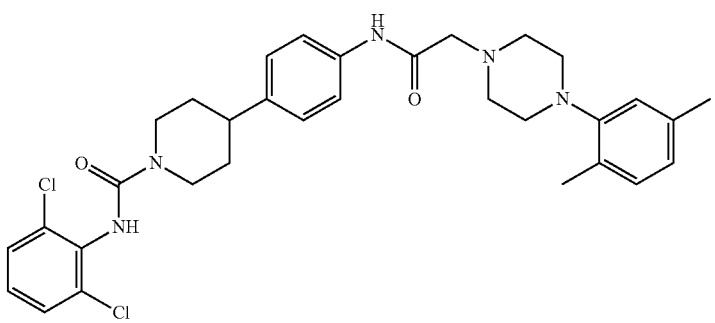
Co. No.104
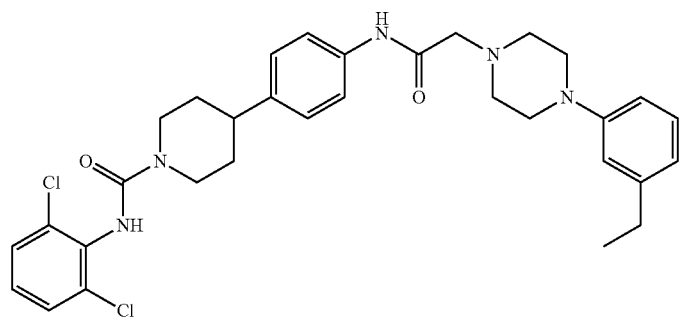
Co. No.106
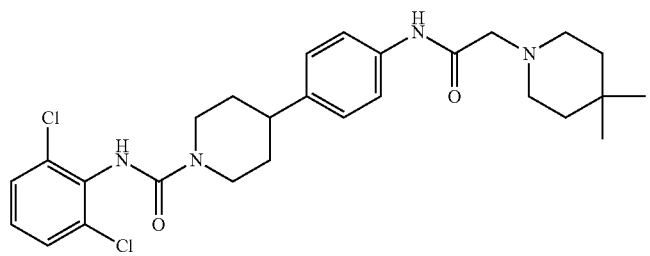
Co. No.108
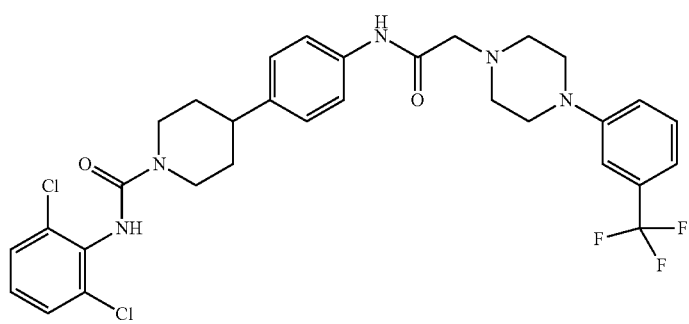
Co. No.103

TABLE D1-continued
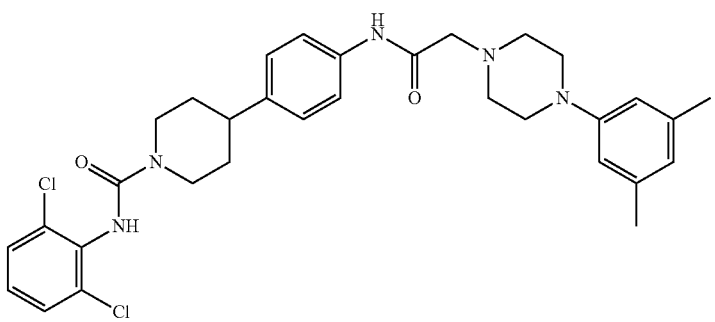
Co. No.105
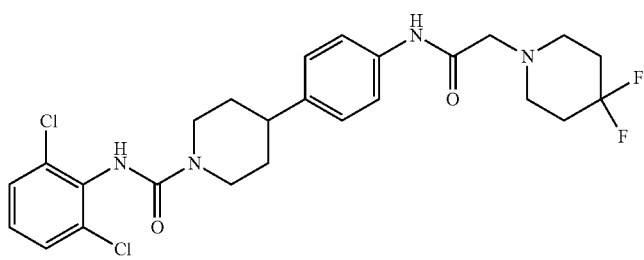
Co. No.107
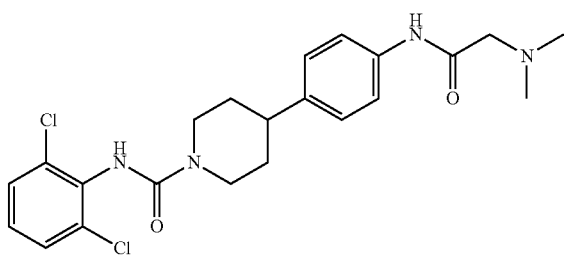
Co. No.109
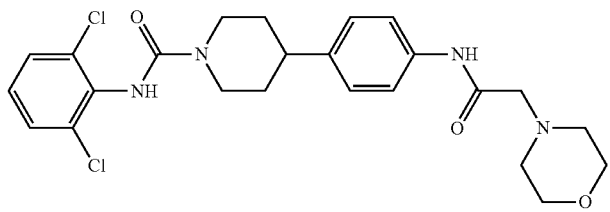
Co. No.111
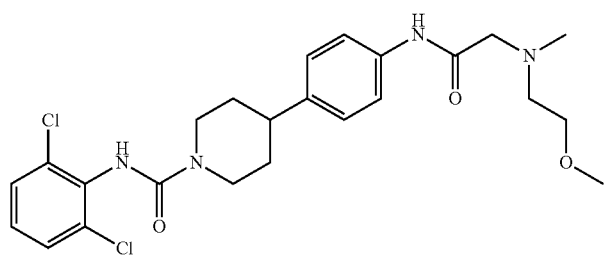
Co. No.110

TABLE D1-continued
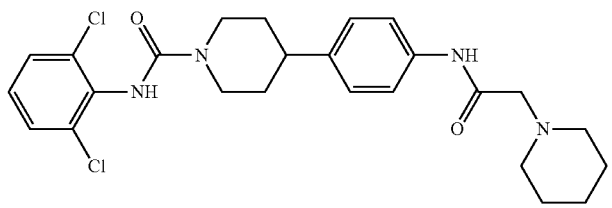
Co. No.112
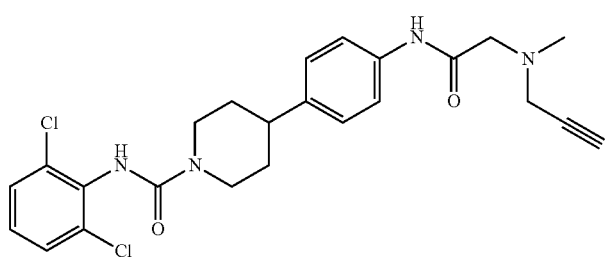
Co. No.114
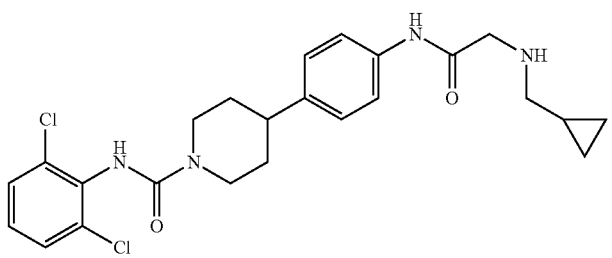
Co. No.116
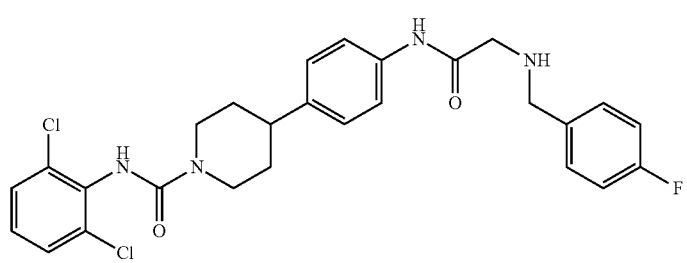
Co. No.118
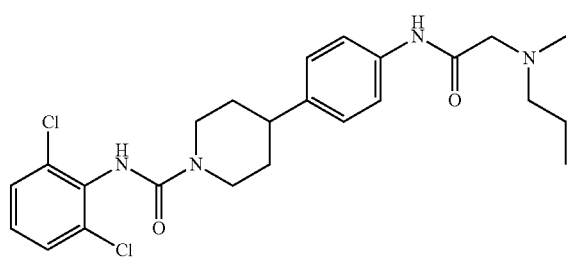
Co. No 113

TABLE D1-continued
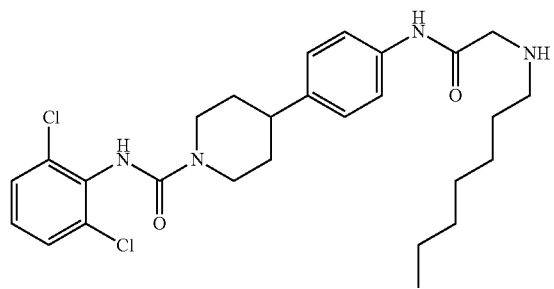
Co. No.115
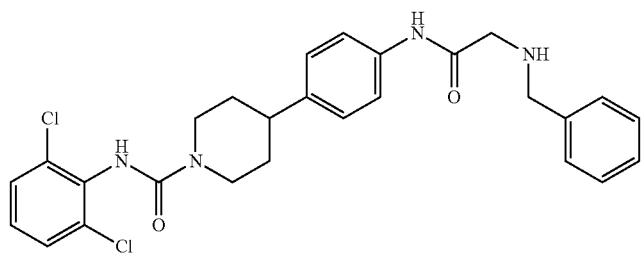
Co. No.117
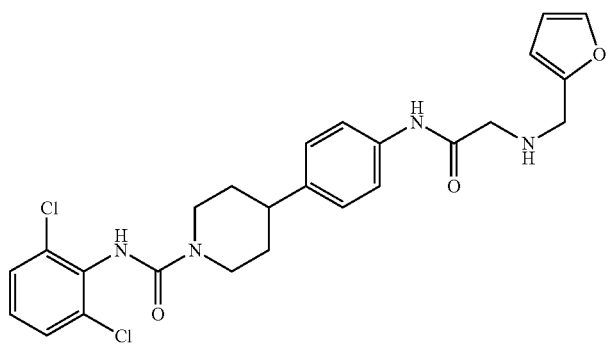
Co. No.119
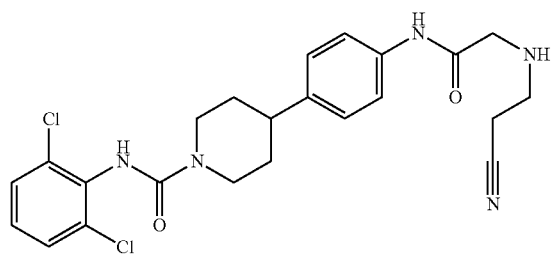
Co. No.121
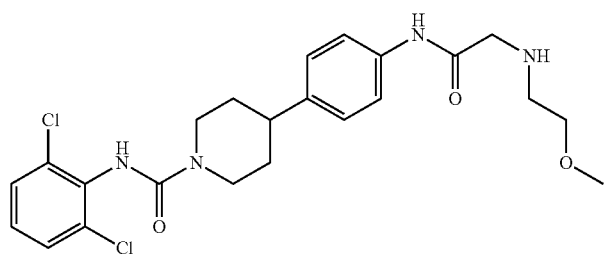
Co. No.120

TABLE D1-continued
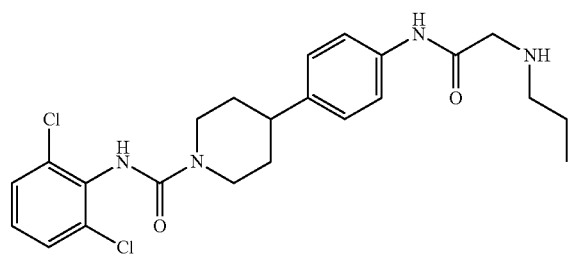
Co. No.122
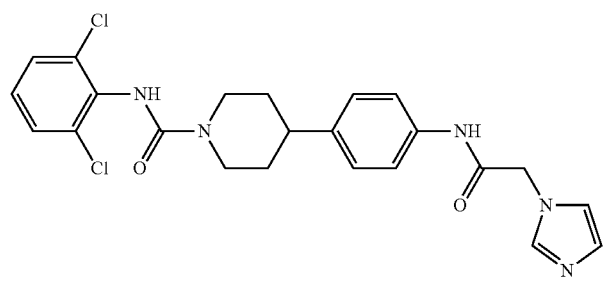
Co. No.123
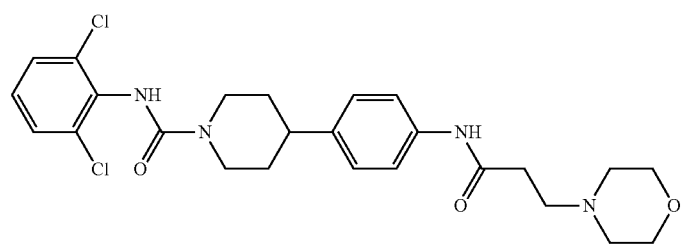
Co. No.125
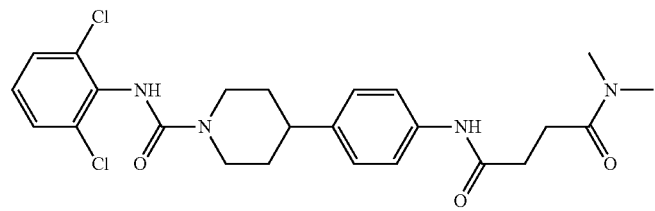
Co. No.127
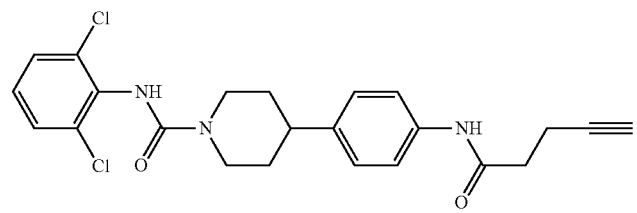
Co. No.129

TABLE D1-continued
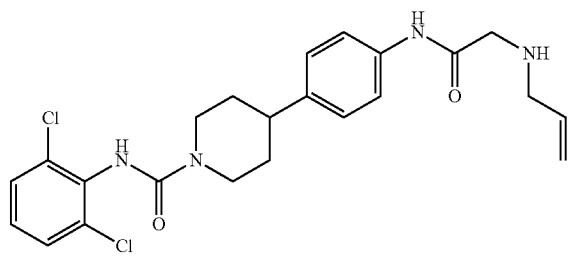
Co. No.20
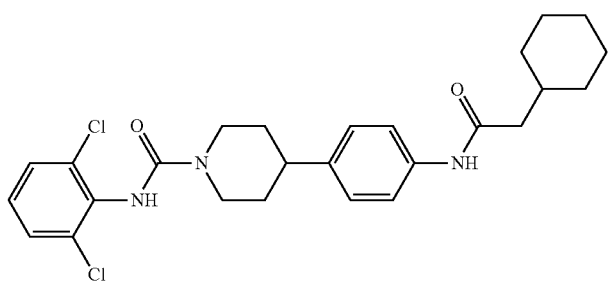
Co. No.124
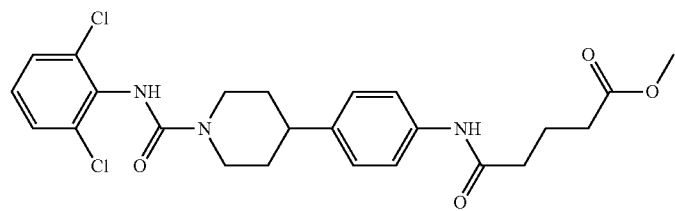
Co. No.126
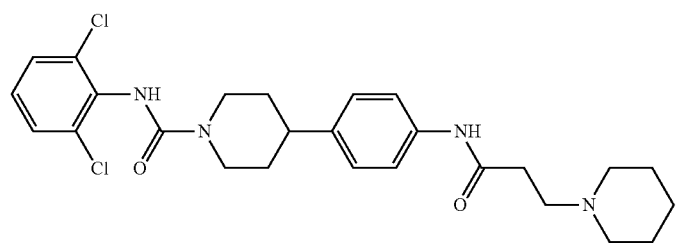
Co. No.128
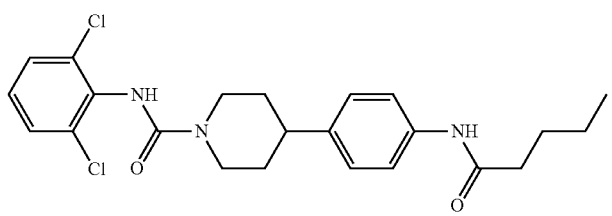
Co. No.130

TABLE D1-continued
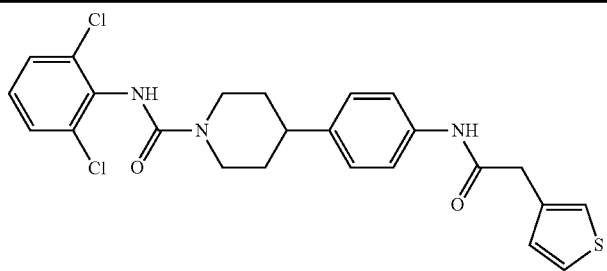
Co. No.132
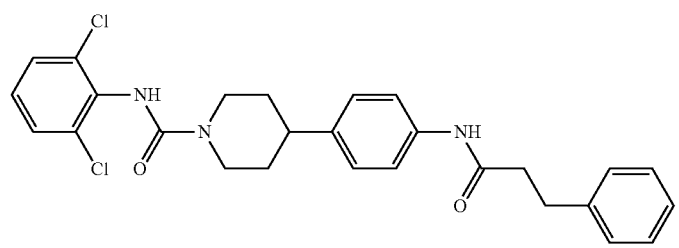
Co. No.131
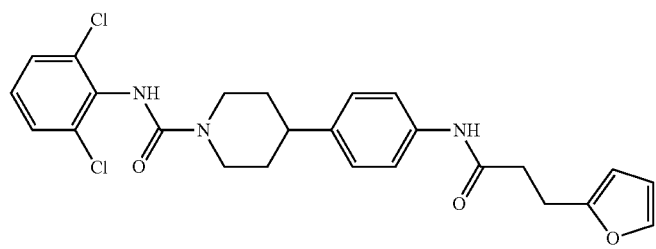
Co. No.133
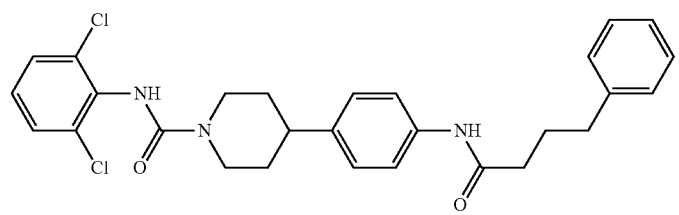
Co. No.135
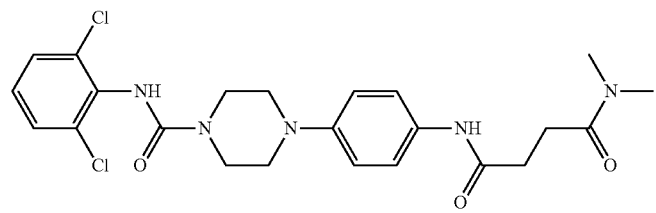
Co. No.137
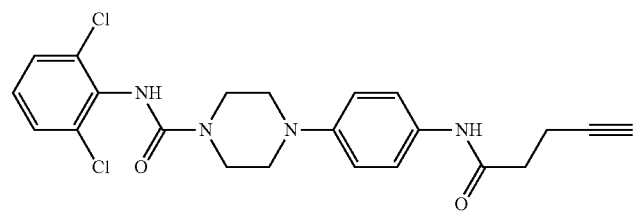
Co. No.139

TABLE D1-continued
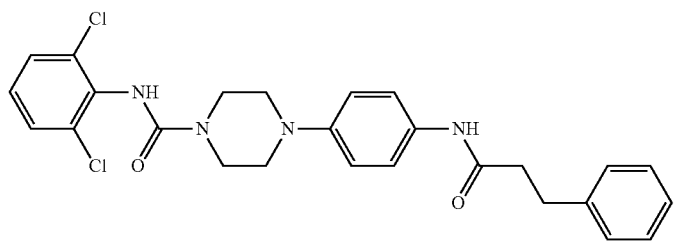
Co. No.141
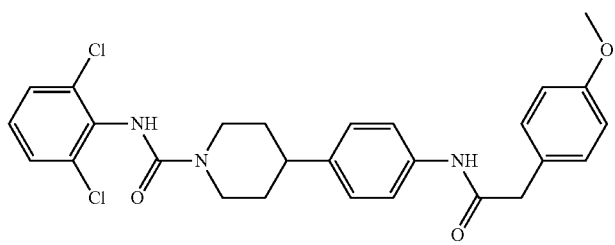
Co. No.134
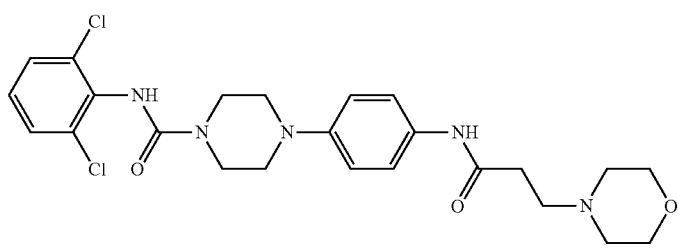
Co. No.136
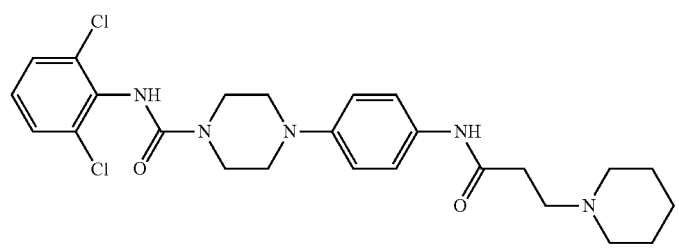
Co. No.138
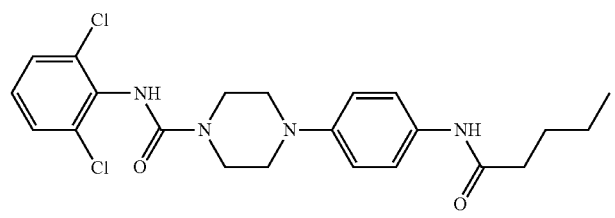
Co. No.140

TABLE D1-continued
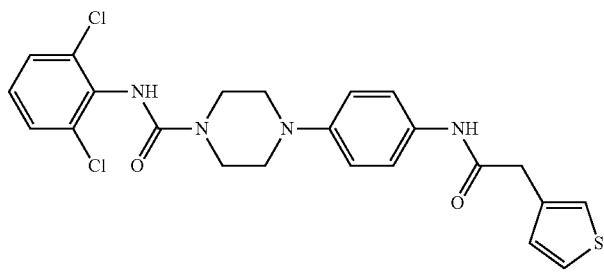
Co. No.142
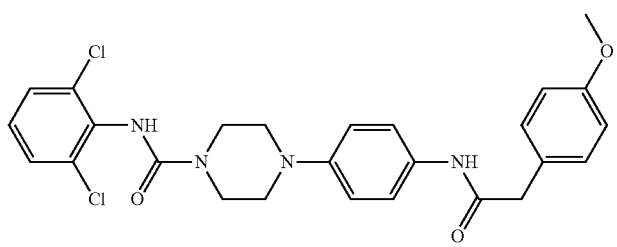
Co. No.144
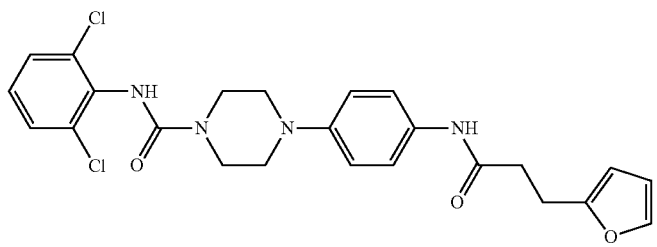
Co. No.143
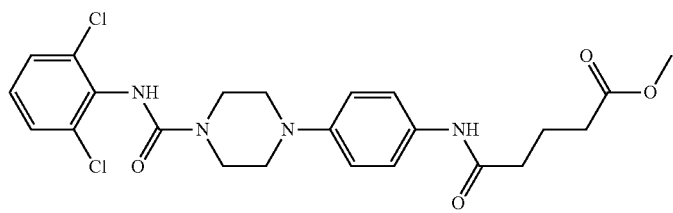
Co. No.145
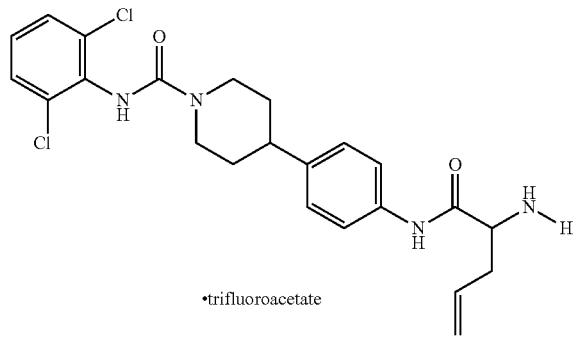
•trifluoroacetate
Co. No.146

TABLE D1-continued
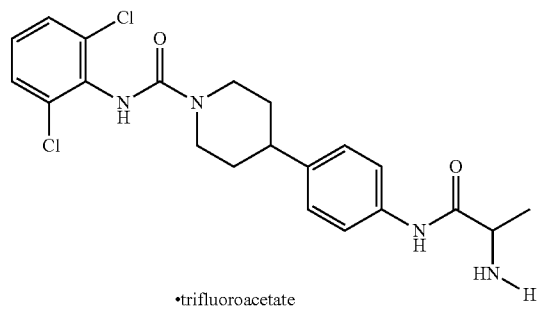
•trifluoroacetate
Co. No.148
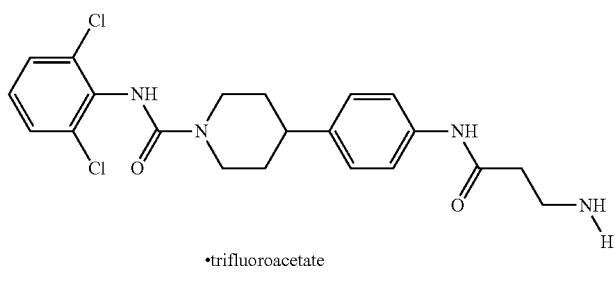
•trifluoroacetate
Co. No.150
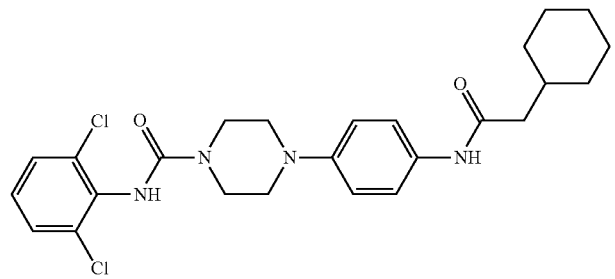
Co. No. 1
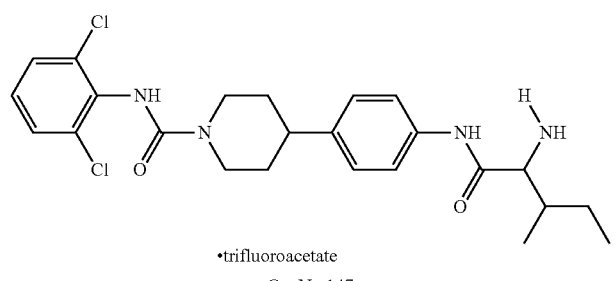
•trifluoroacetate
Co. No.147
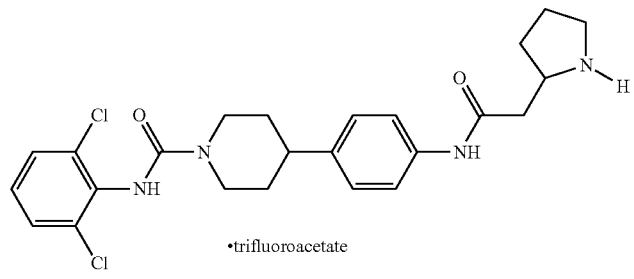
•trifluoroacetate
Co. No.149

TABLE D1-continued
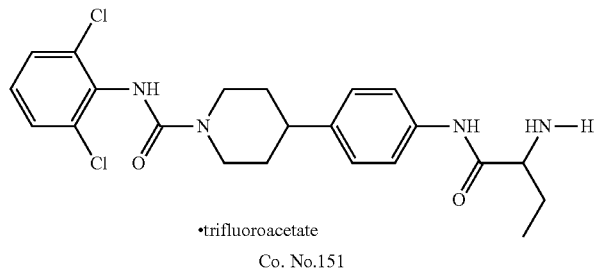 [SMILES: CCC(N)C(=O)Nc1ccc(C2CCN(C(=O)Nc3c(Cl)cccc3Cl)CC2)cc1]
•trifluoroacetate
Co. No.151
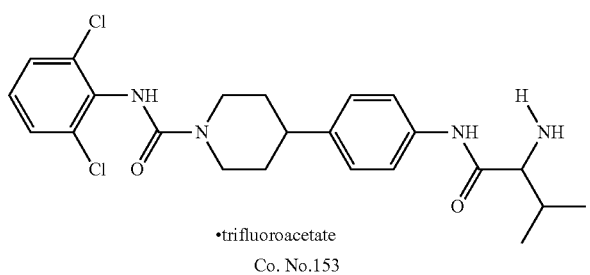 [SMILES: CC(C)C(N)C(=O)Nc1ccc(C2CCN(C(=O)Nc3c(Cl)cccc3Cl)CC2)cc1]
•trifluoroacetate
Co. No.153
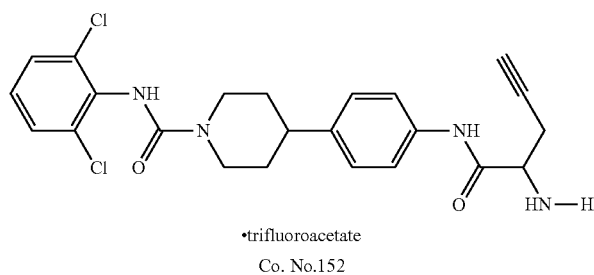 [SMILES: C#CCC(N)C(=O)Nc1ccc(C2CCN(C(=O)Nc3c(Cl)cccc3Cl)CC2)cc1]
•trifluoroacetate
Co. No.152
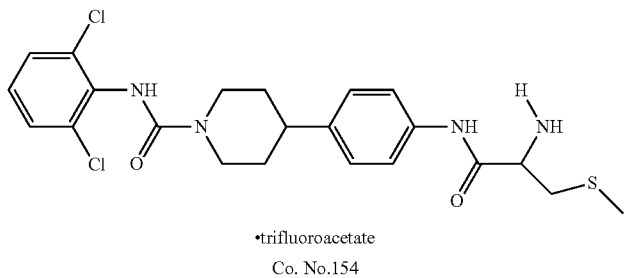 [SMILES: CSCC(N)C(=O)Nc1ccc(C2CCN(C(=O)Nc3c(Cl)cccc3Cl)CC2)cc1]
•trifluoroacetate
Co. No.154
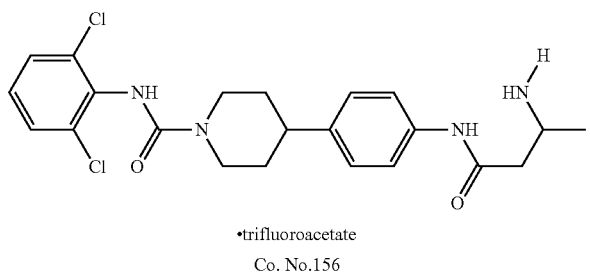 [SMILES: CC(N)CC(=O)Nc1ccc(C2CCN(C(=O)Nc3c(Cl)cccc3Cl)CC2)cc1]
•trifluoroacetate
Co. No.156

TABLE D1-continued
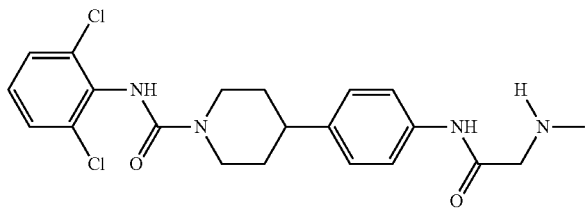
•trifluoroacetate
Co. No.158
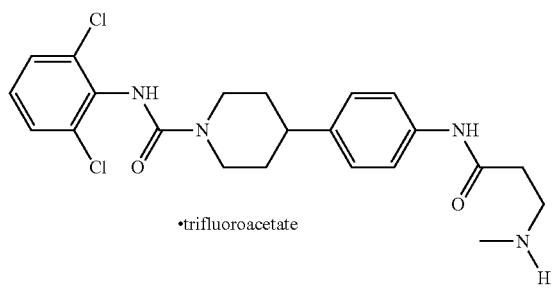
•trifluoroacetate
Co. No.160
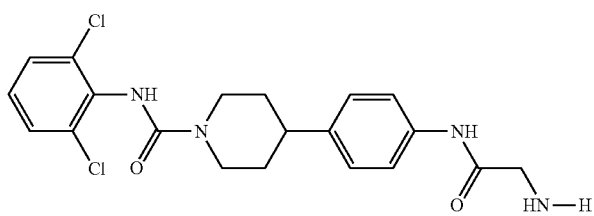
•trifluoroacetate
Co. No.155
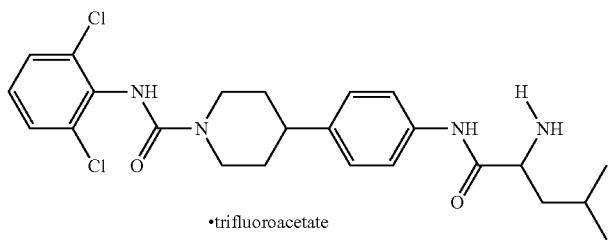
•trifluoroacetate
Co. No.157
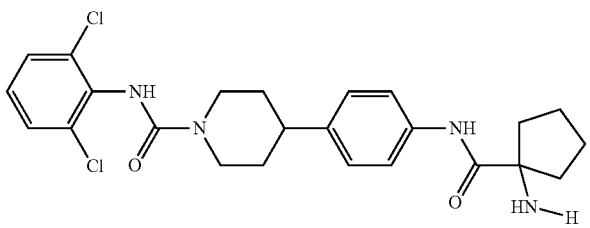
•trifluoroacetate
Co. No.159

TABLE D1-continued
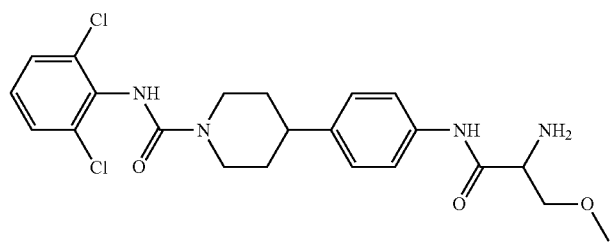
•trifluoroacetate
Co. No.161
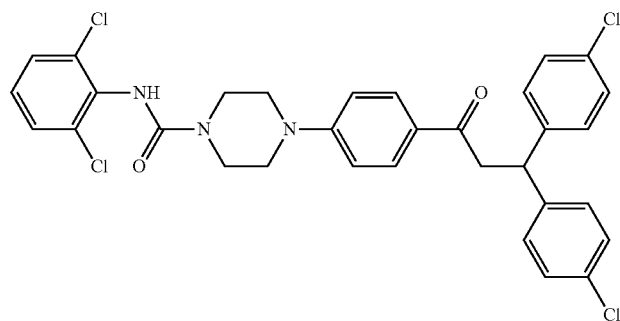
Co. No.162
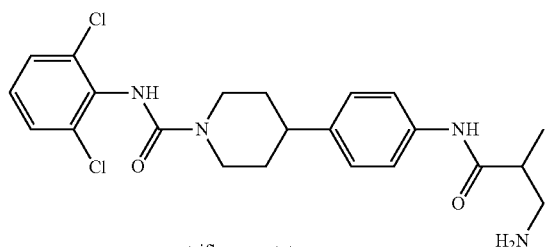
•trifluoroacetate
Co. No. 23
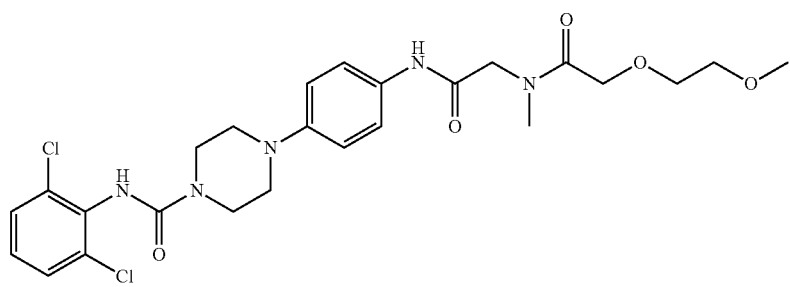
Co. No.163
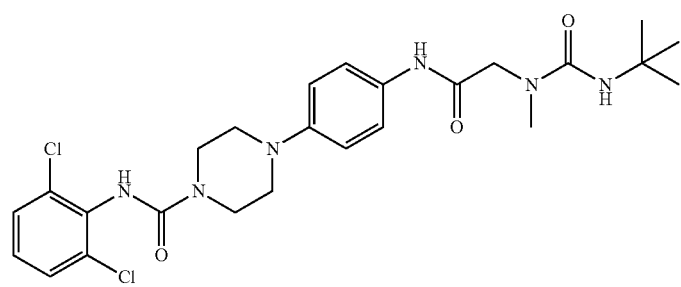
Co. No.165

TABLE D1-continued
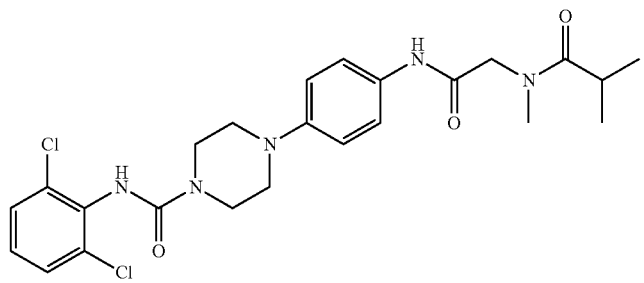
Co. No.166
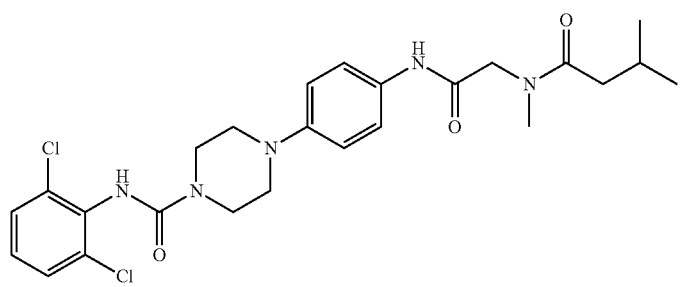
Co. No.168
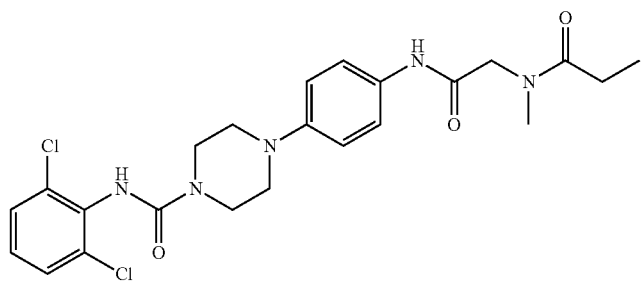
Co. No.170
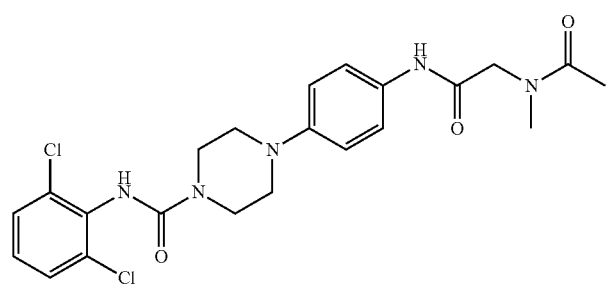
Co. No.164
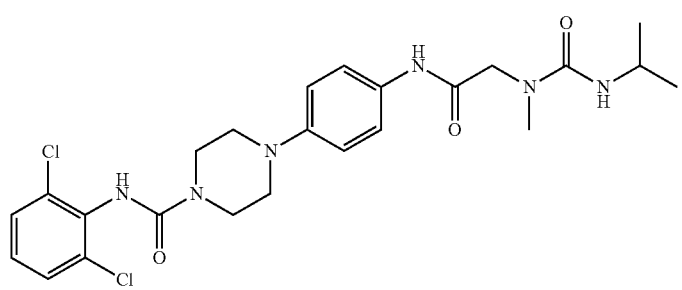
Co. No.14

TABLE D1-continued
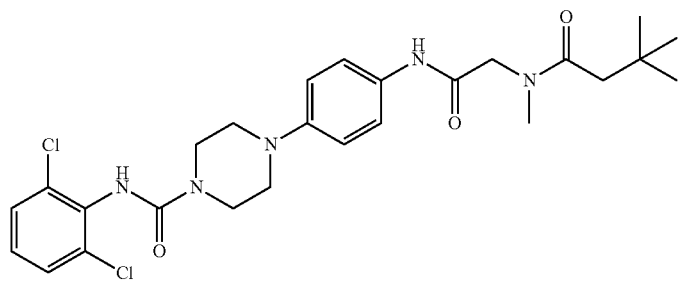
Co. No.167
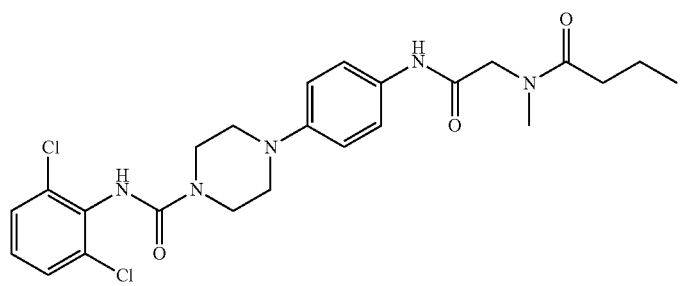
Co. No.169
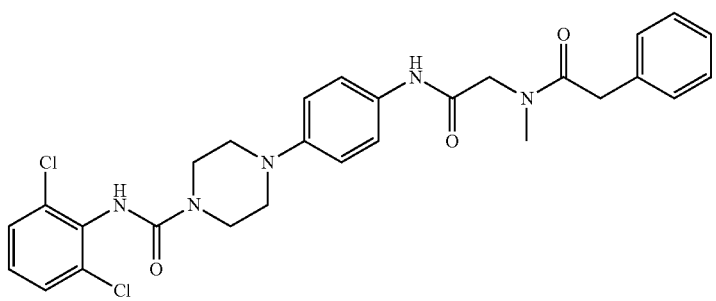
Co. No.171
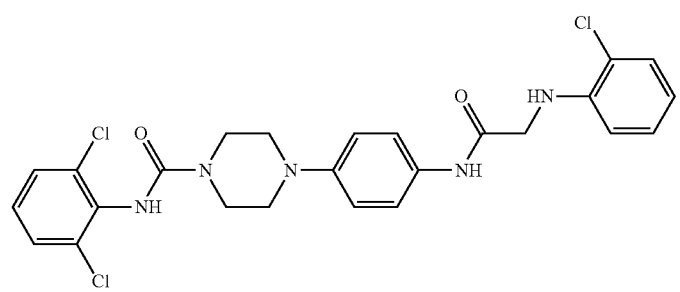
Co. No. 4
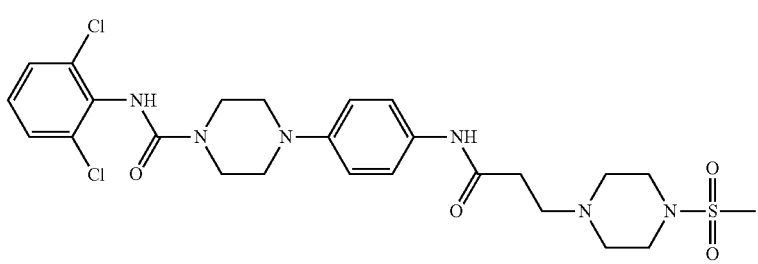
Co. No.172

TABLE D1-continued
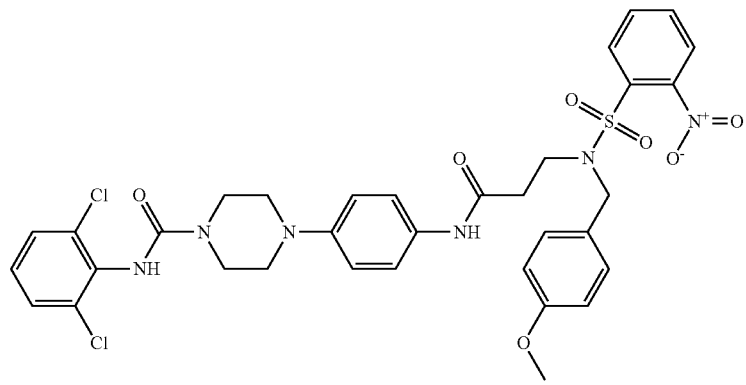 [SMILES: O=C(CCN(Cc1ccc(F)cc1)S(=O)(=O)c1ccccc1[N+](=O)[O-])Nc1ccc(N2CCN(C(=O)Nc3c(Cl)cccc3Cl)CC2)cc1]
Co. No.173
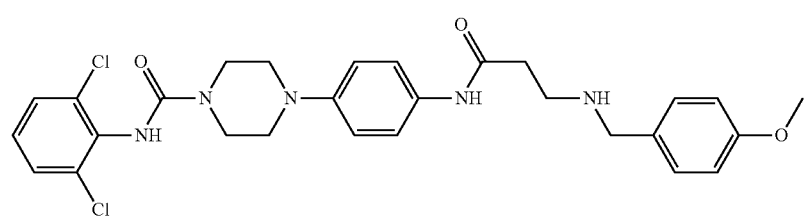
Co. No.32
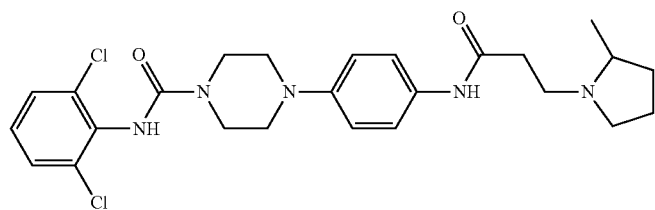
Co. No.176
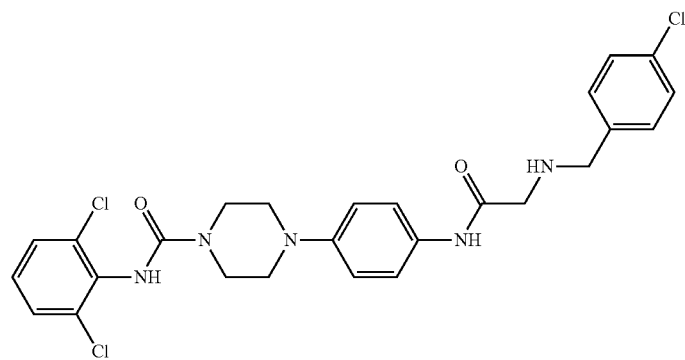
Co. No.178
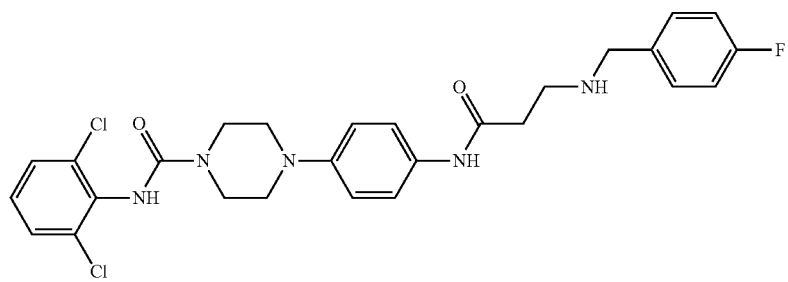
Co. No.174

TABLE D1-continued
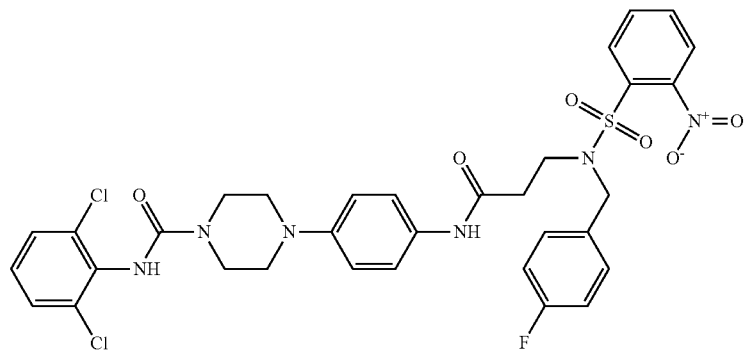
Co. No.175
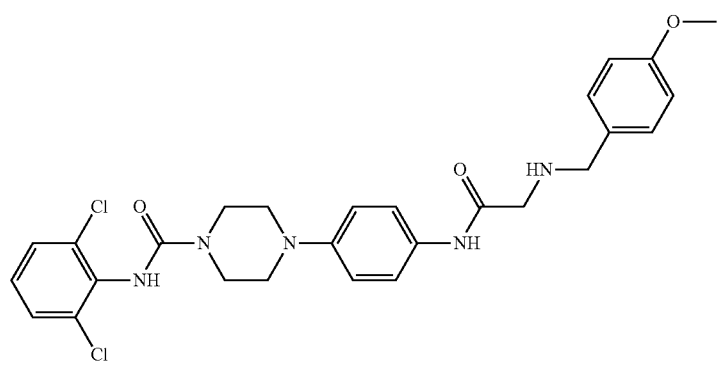
Co. No.177
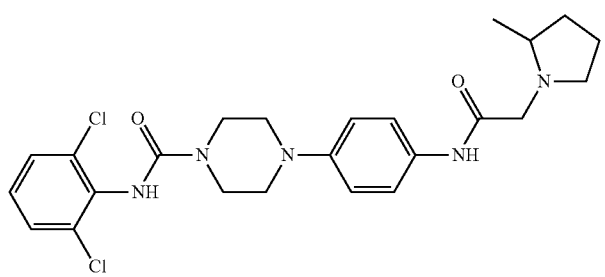
Co. No.179
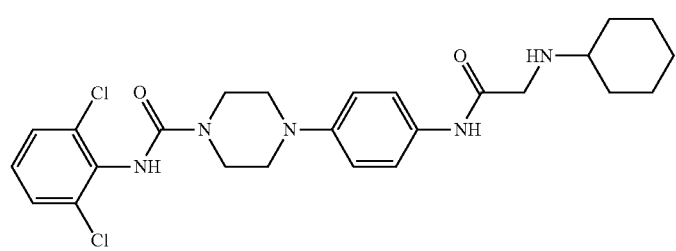
Co. No.180

TABLE D1-continued
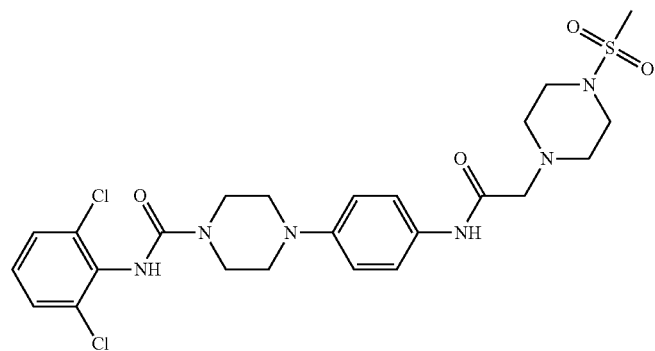
Co. No. 26
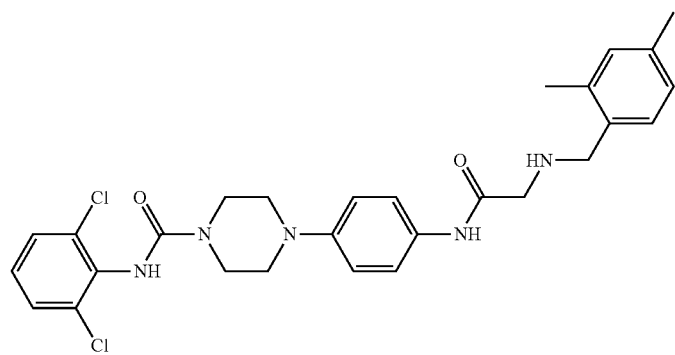
Co. No. 181
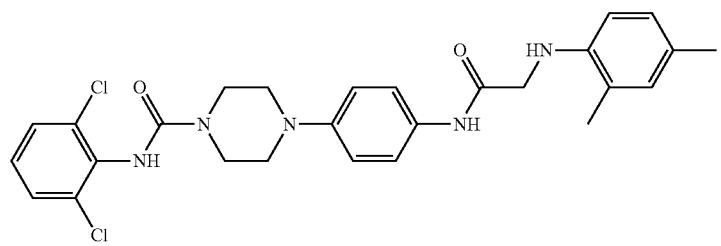
Co. No. 22
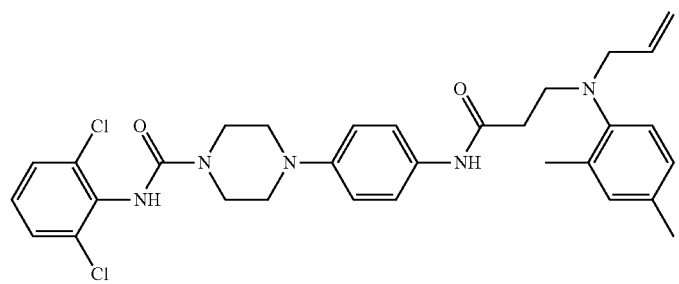
Co. No. 183

TABLE D1-continued
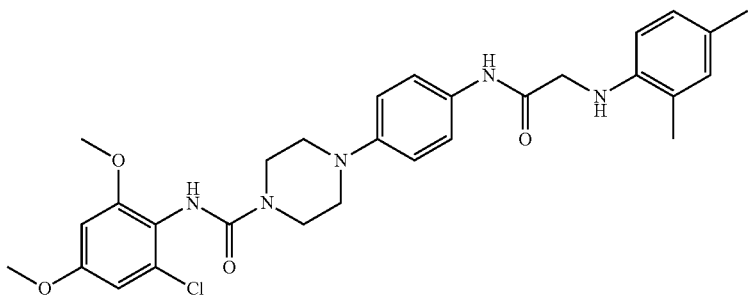
Co. No.184
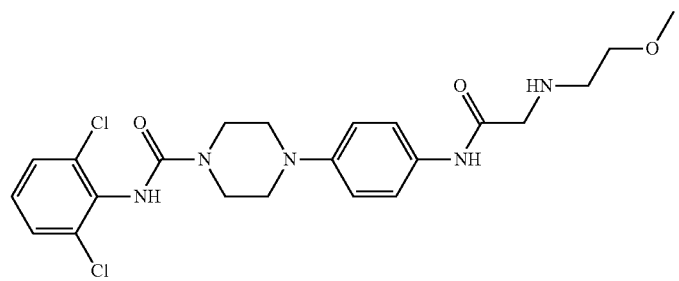
Co. No.182
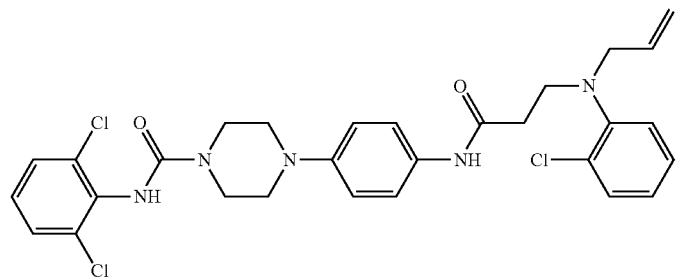
Co. No. 7
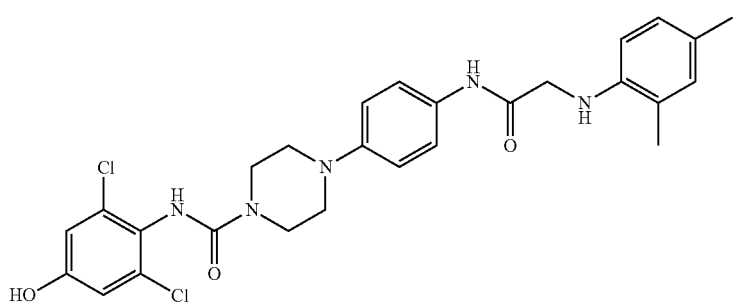
Co. No.185
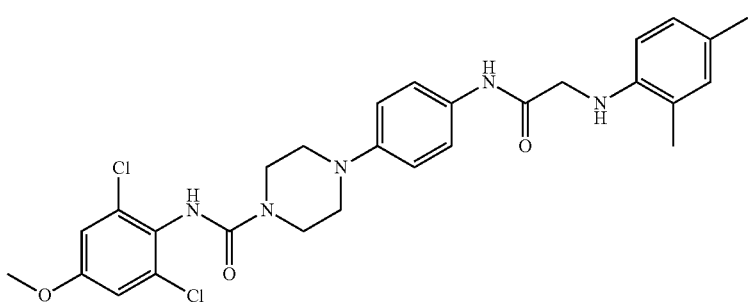
Co. No.31

TABLE D1-continued
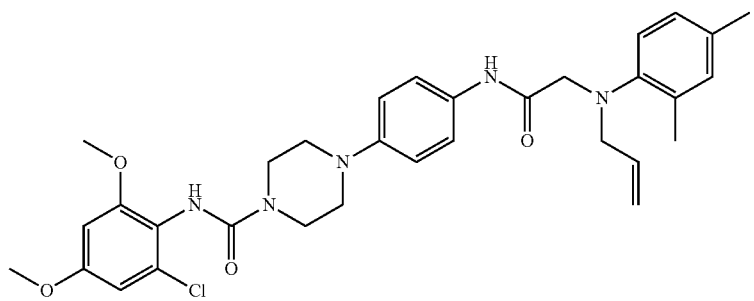
Co. No.186
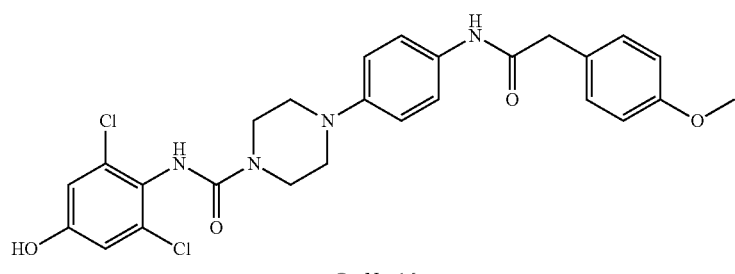
Co. No. 16
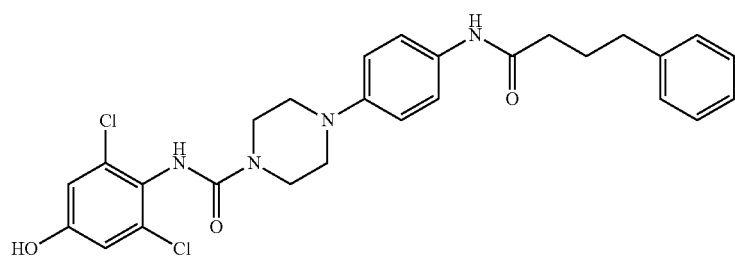
Co. No.30
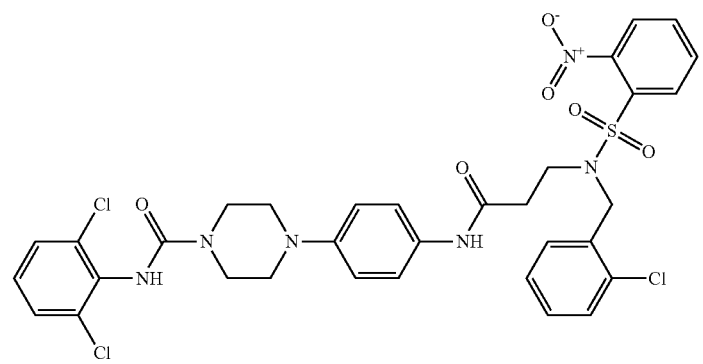
Co. No. 6

TABLE D1-continued
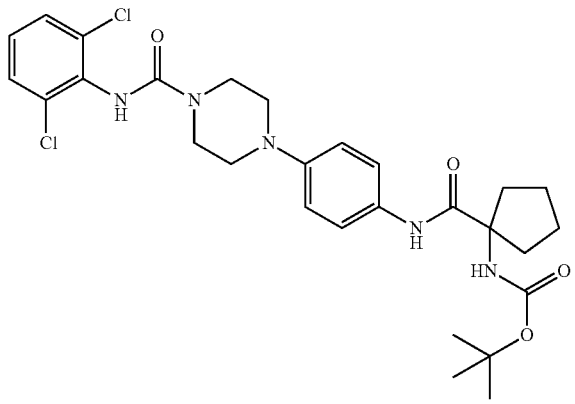
Co. No. 5
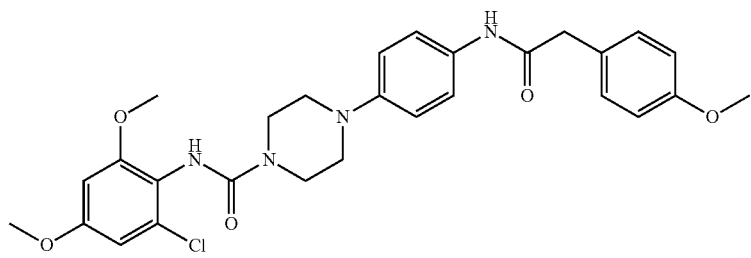
Co. No.191
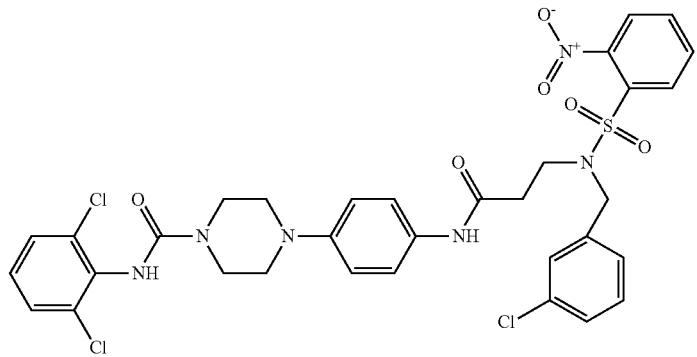
Co. No.187
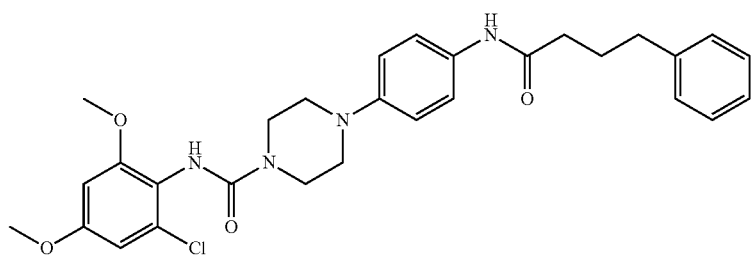
Co. No.188

TABLE D1-continued
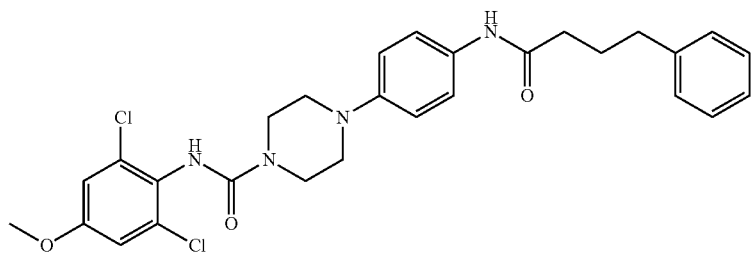
Co. No.190
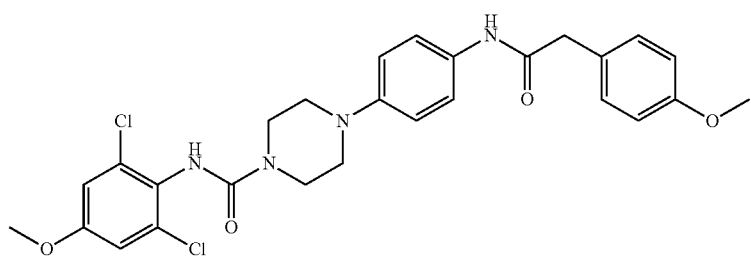
Co. No. 15
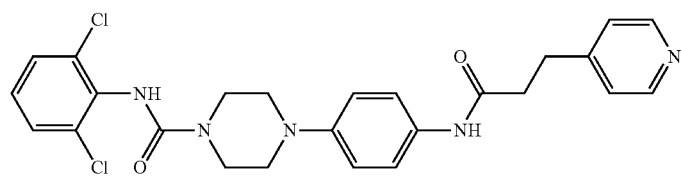
Co. No.193
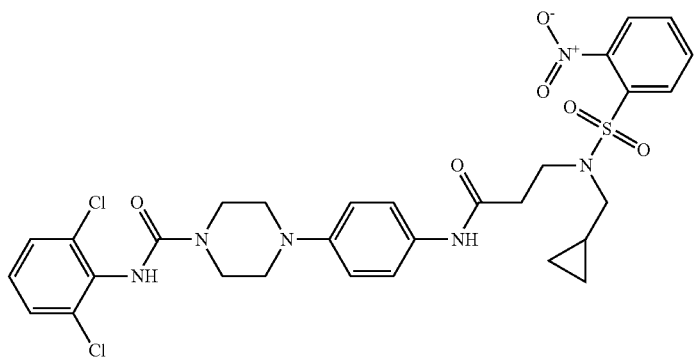
Co. No.192
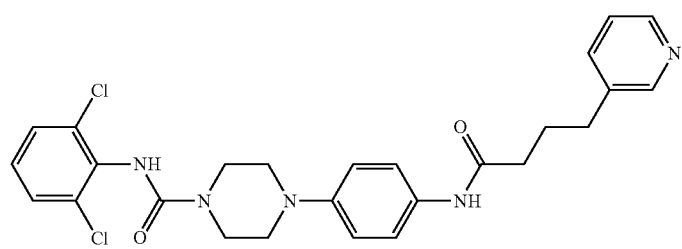
Co. No.194

TABLE D1-continued
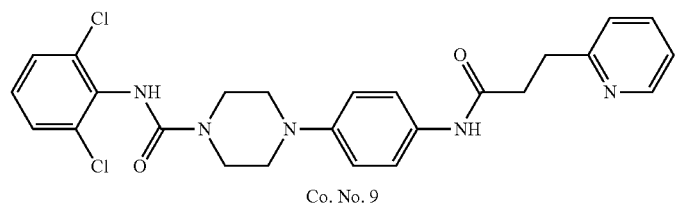 [SMILES: O=C(CCc1ccccn1)Nc1ccc(N2CCN(C(=O)Nc3c(Cl)cccc3Cl)CC2)cc1]
Co. No. 9
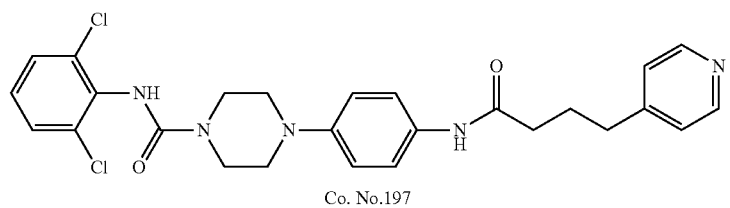 [SMILES: O=C(CCCc1ccncc1)Nc1ccc(N2CCN(C(=O)Nc3c(Cl)cccc3Cl)CC2)cc1]
Co. No.197
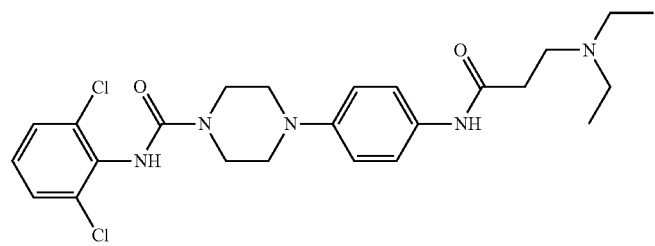
Co. No.199
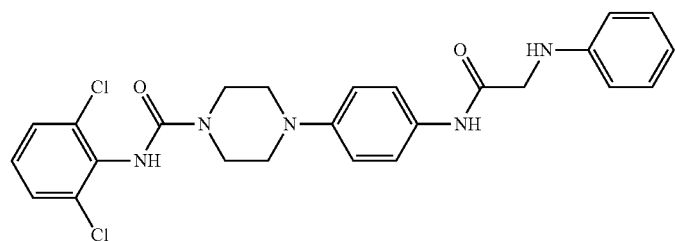
Co. No.21
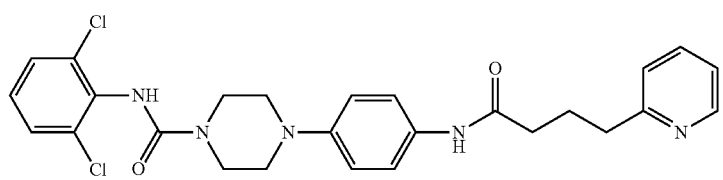
Co. No.195
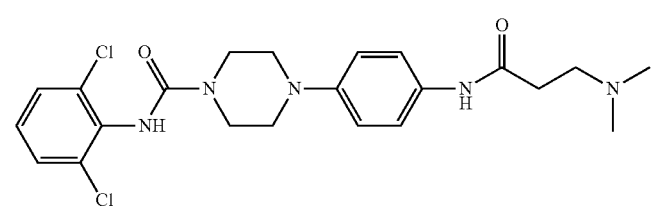
Co. No.196

TABLE D1-continued
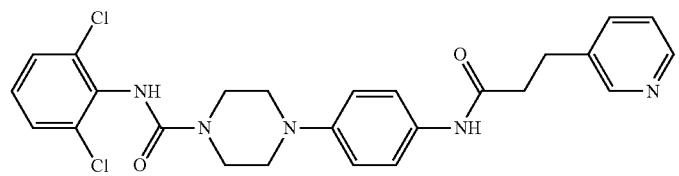
Co. No.198
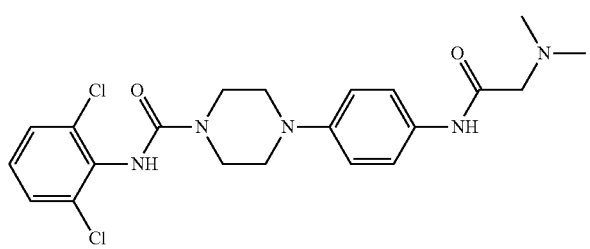
Co. No.200
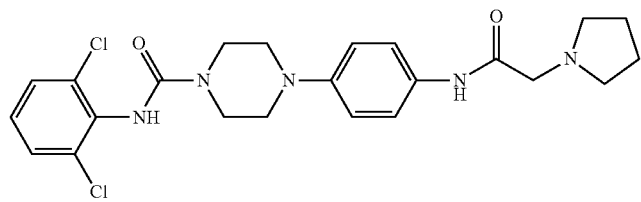
Co. No.201
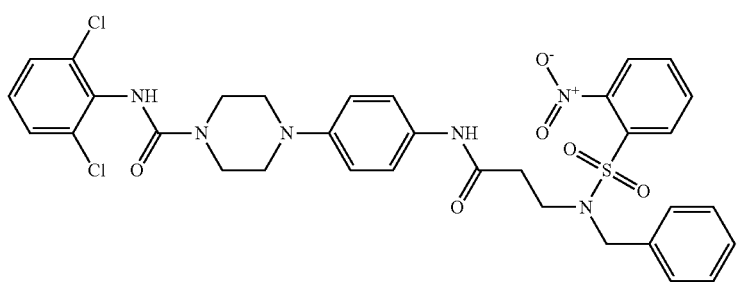
Co. No.203
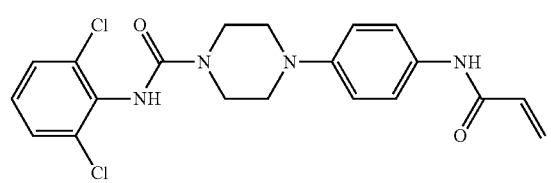
Co. No. 202

TABLE D1-continued
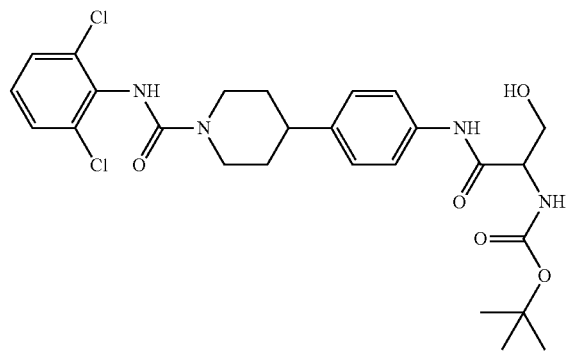
Co. No. 204
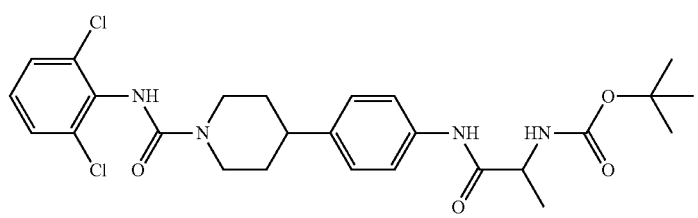
Co. No. 206
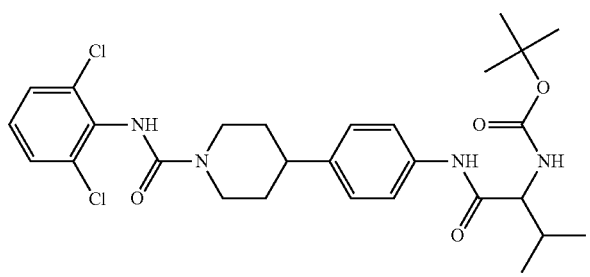
Co. No. 208
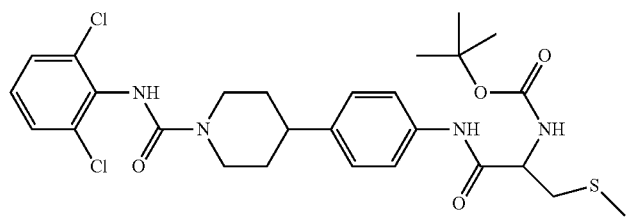
Co. No. 210
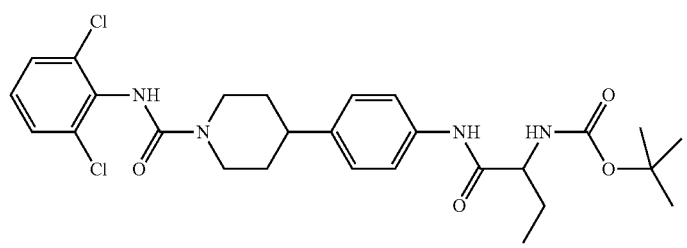
Co. No. 205

TABLE D1-continued
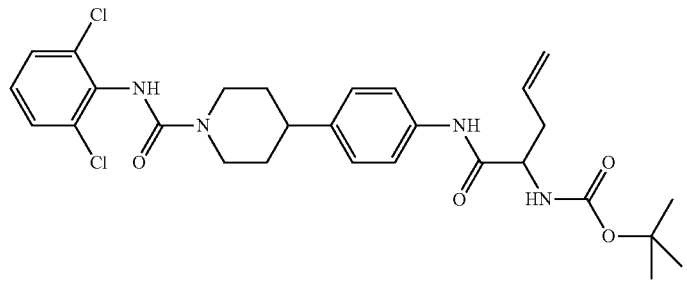
Co. No. 207
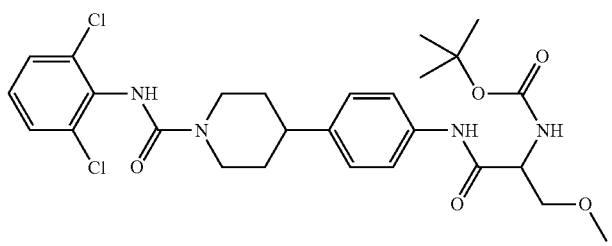
Co. No. 209
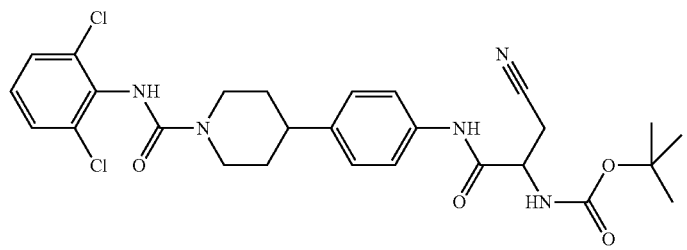
Co. No. 211
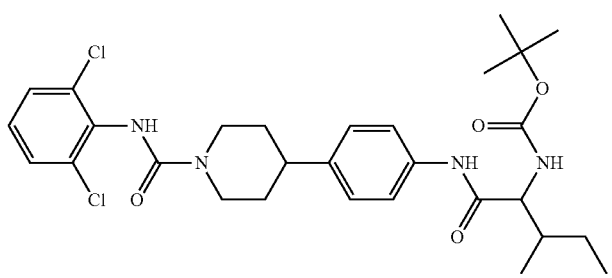
Co. No.213
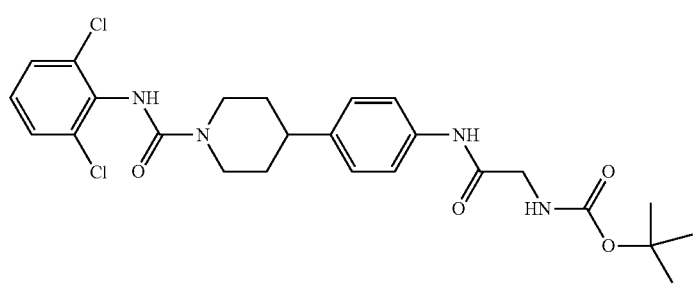
Co. No.212

TABLE D1-continued
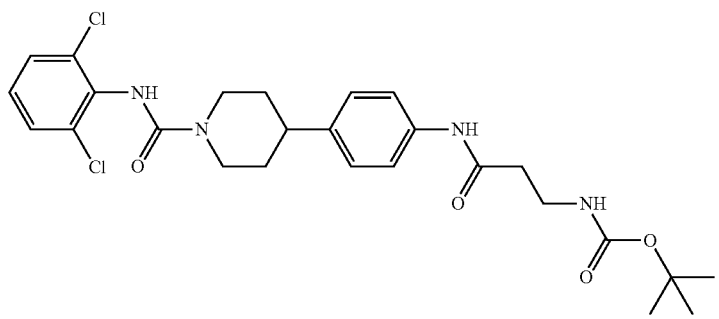
Co. No.214
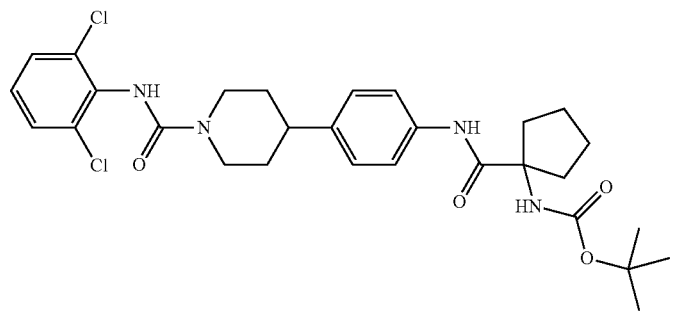
Co. No.216
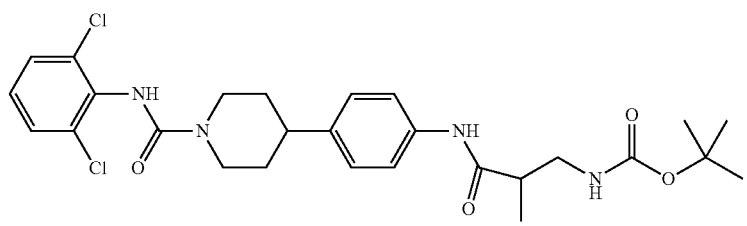
Co. No.218
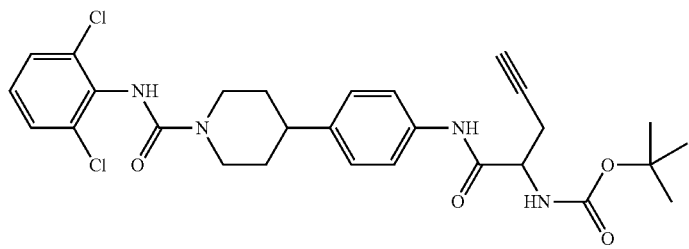
Co. No.220
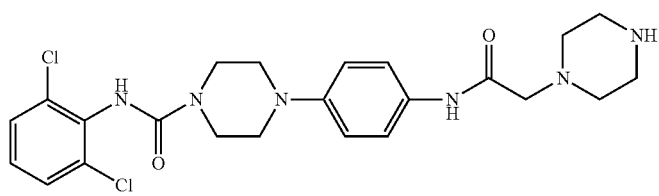
Co. No. 25

TABLE D1-continued
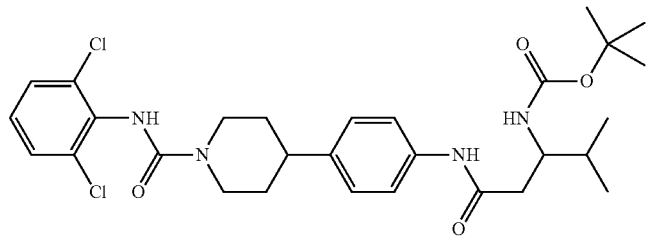
Co. No.215
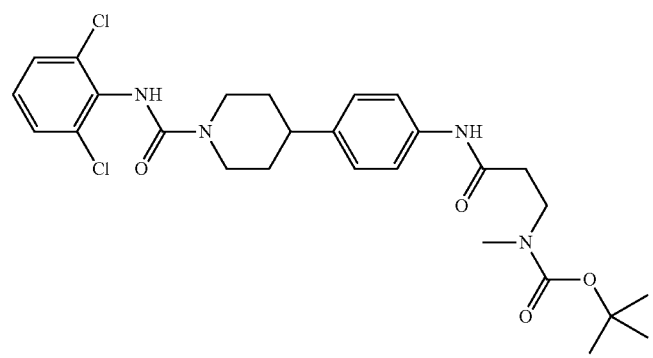
Co. No.217
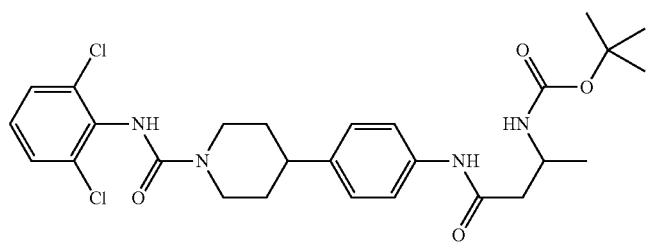
Co. No.219
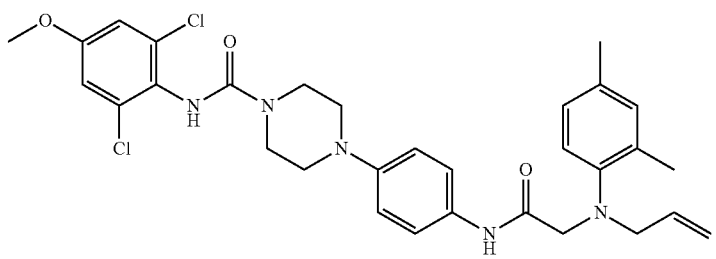
Co. No.221
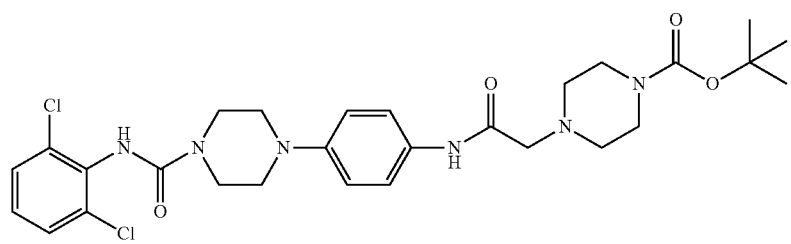
Co. No. 222

TABLE D1-continued
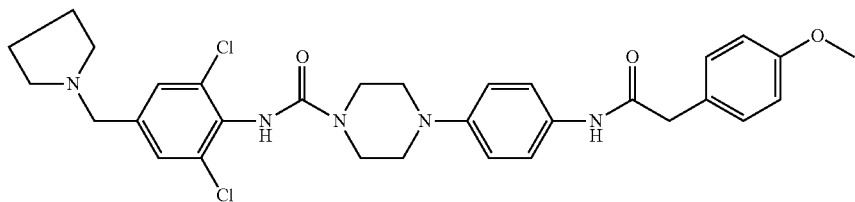
Co. No. 223
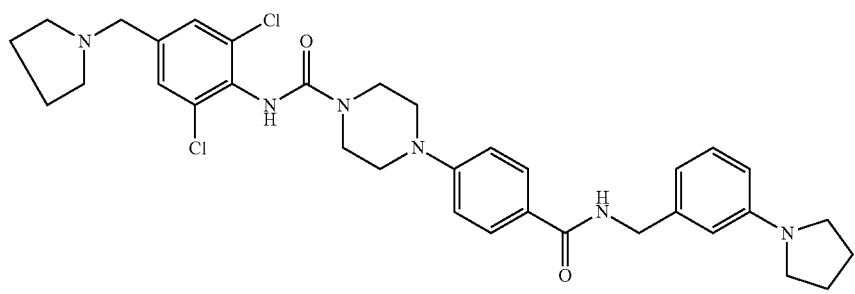
Co. No. 224
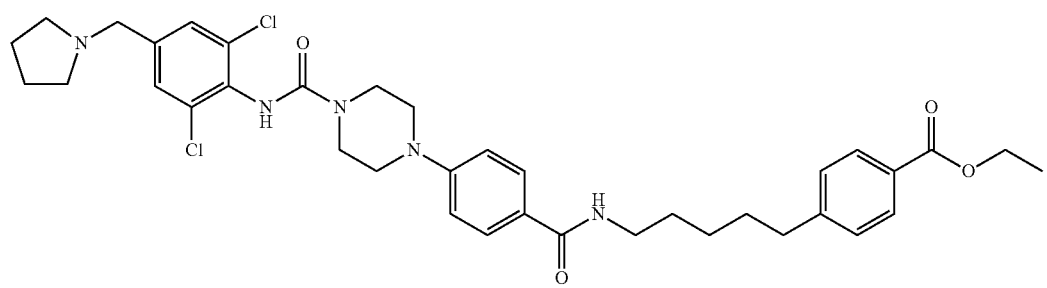
Co. No. 226
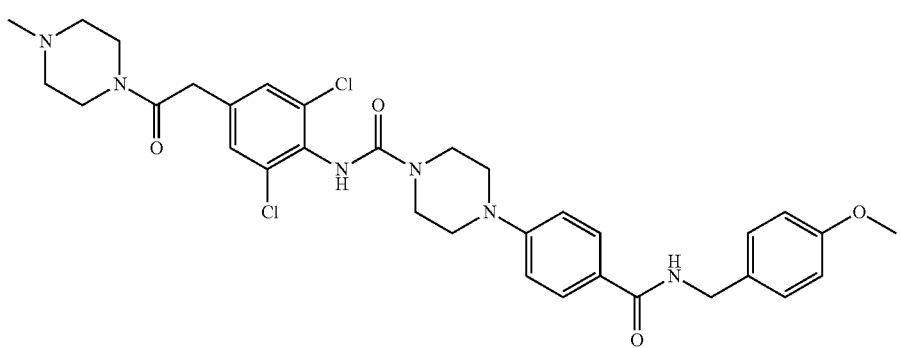
Co. No. 228
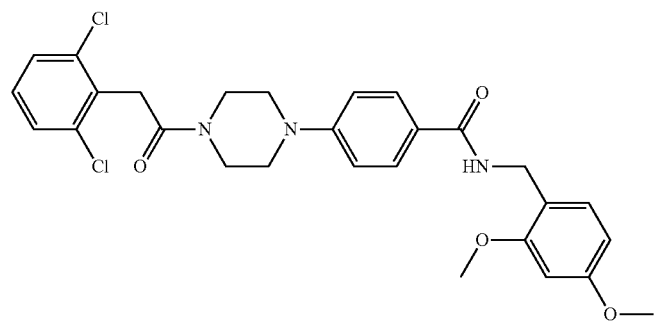
Co. No. 230

TABLE D1-continued
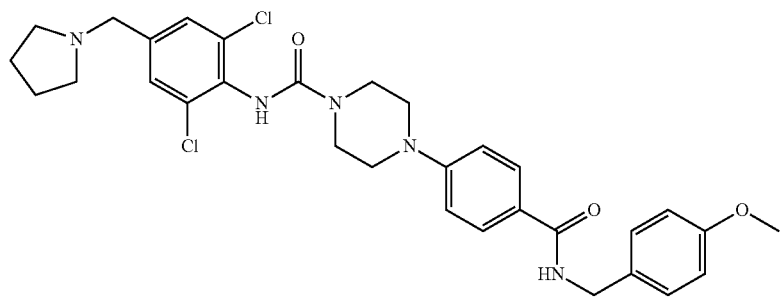
Co. No. 232
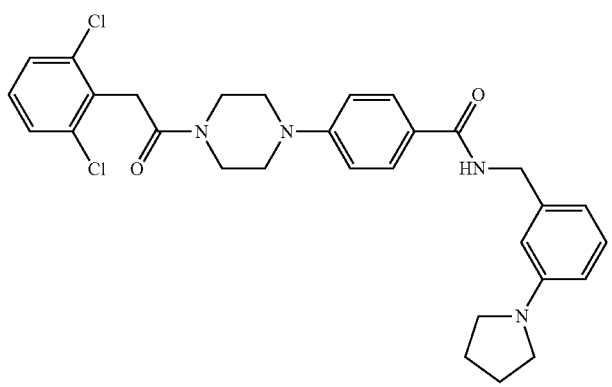
Co. No. 234
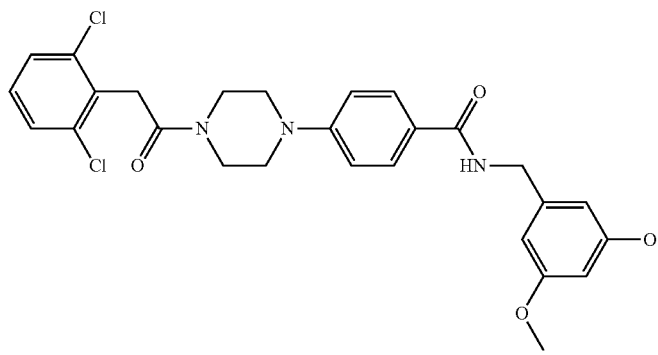
Co. No. 225
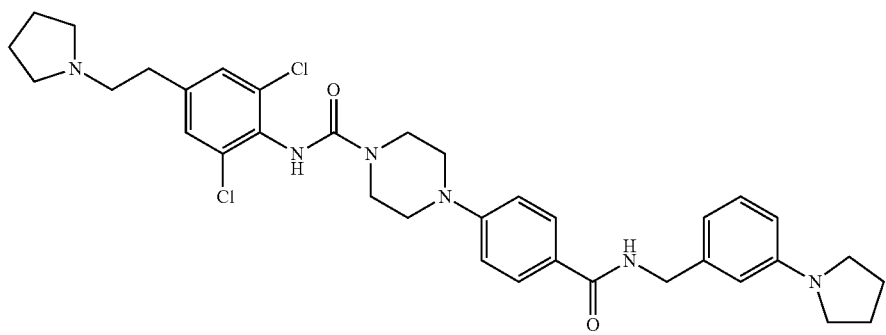
Co. No. 227

TABLE D1-continued
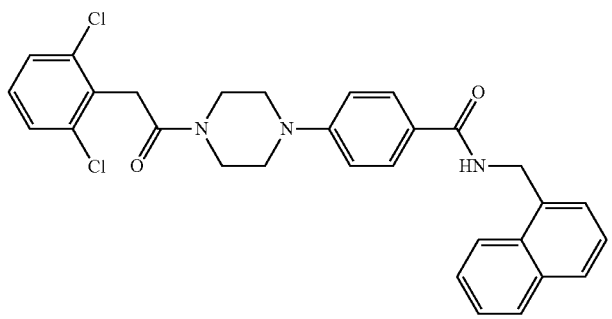
Co. No. 229
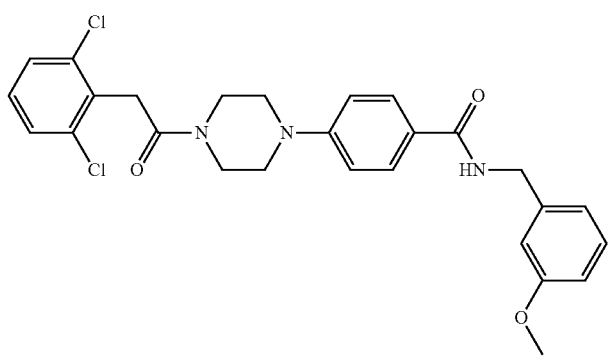
Co. No. 231
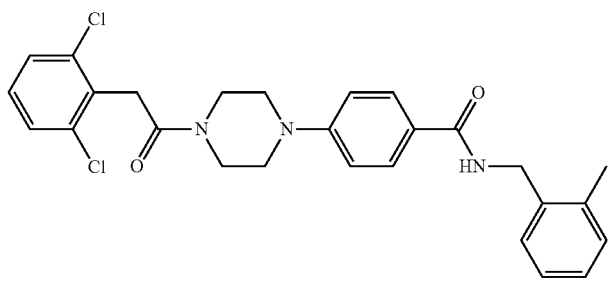
Co. No. 233
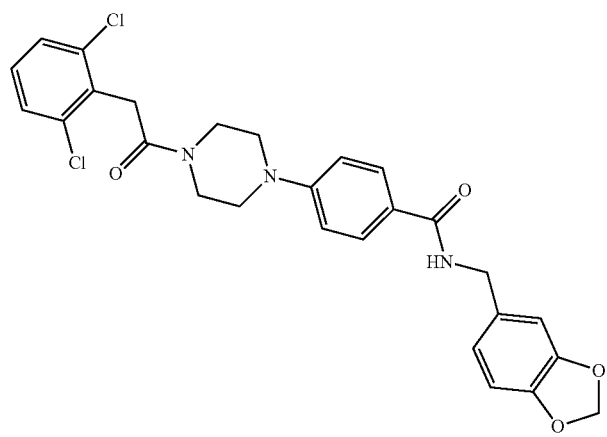
Co. No. 235

TABLE D1-continued
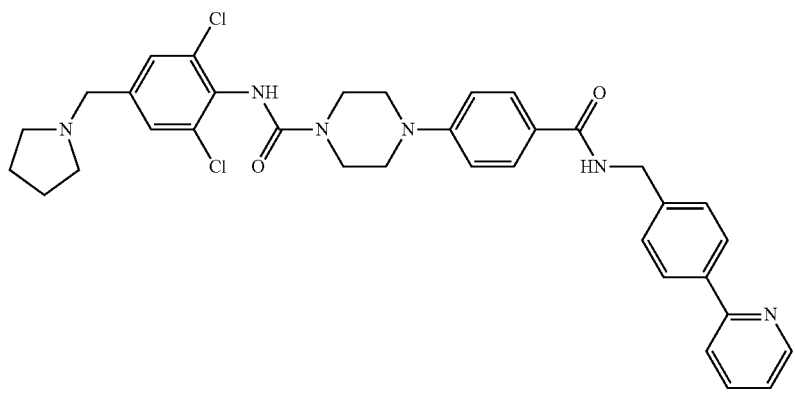
Co. No. 236
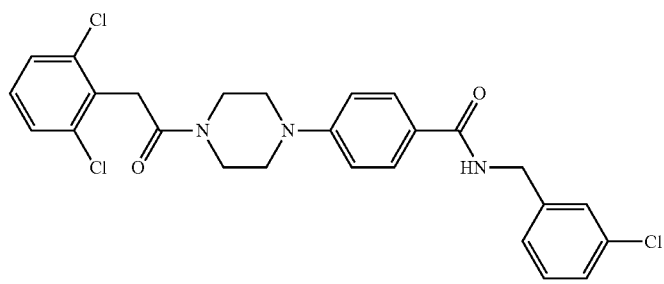
Co. No. 238
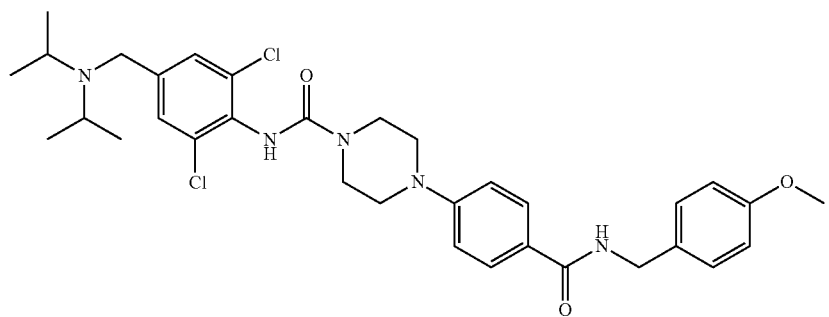
Co. No. 240
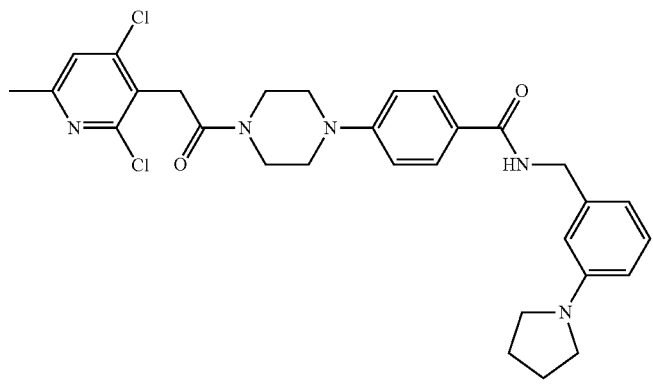
Co. No. 242

TABLE D1-continued
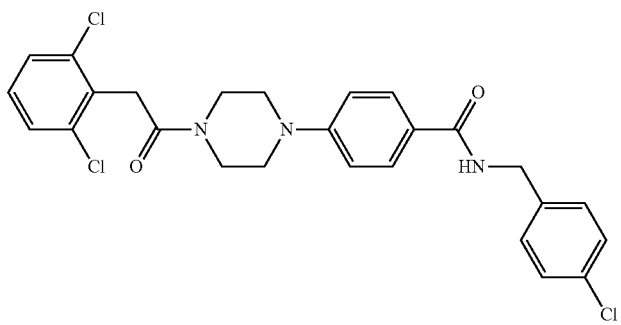
Co. No. 244
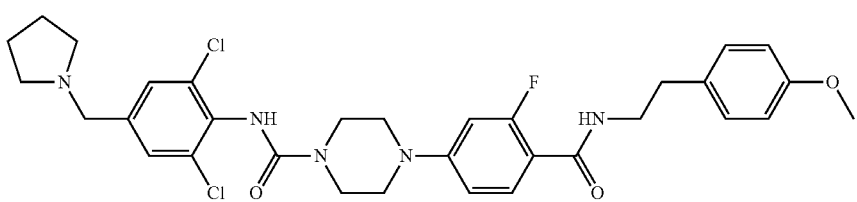
Co. No. 246
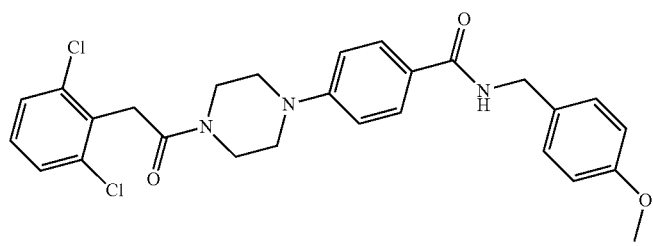
Co. No. 237
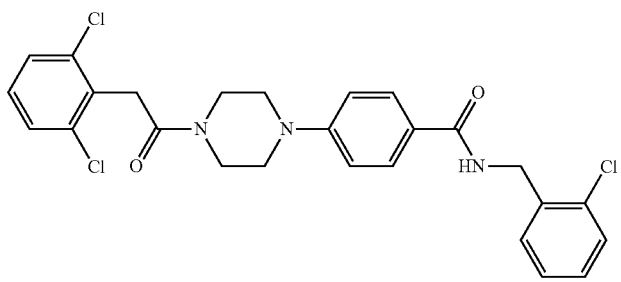
Co. No. 239
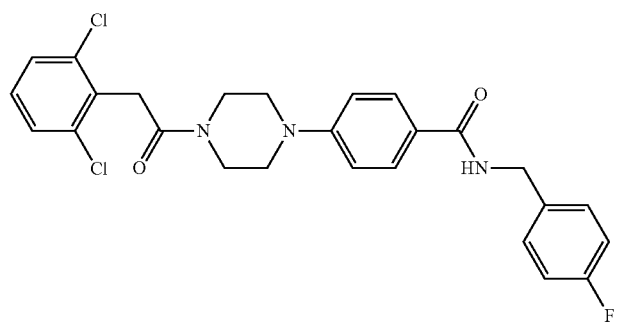
Co. No. 241

TABLE D1-continued
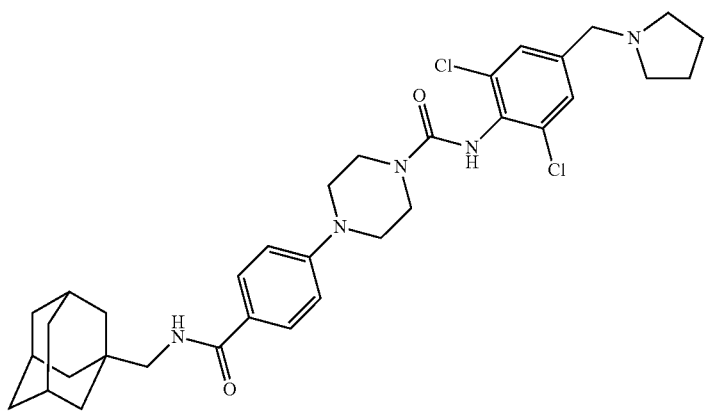
Co. No. 243
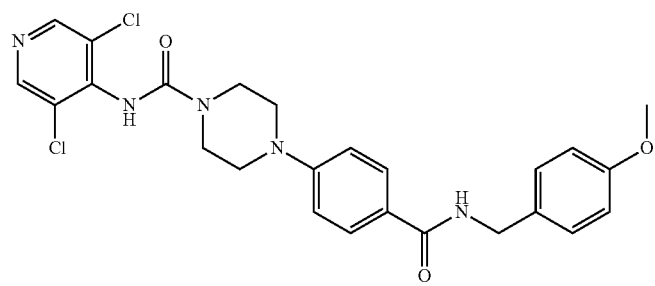
Co. No. 245
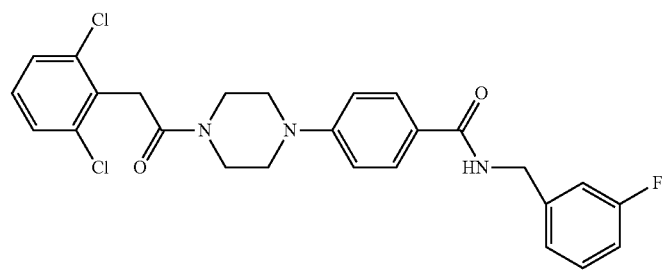
Co. No. 247
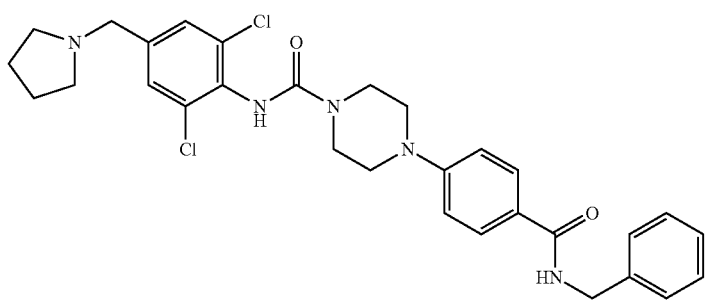
Co. No. 248

TABLE D1-continued
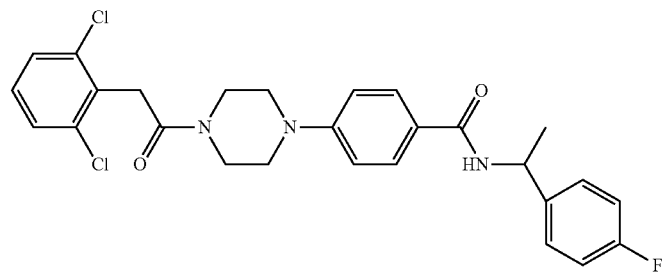
Co. No. 250
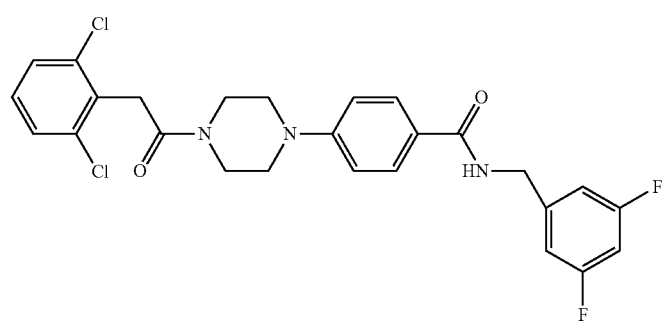
Co. No. 252
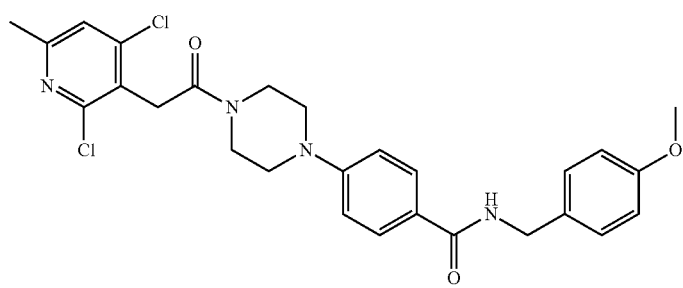
Co. No. 254
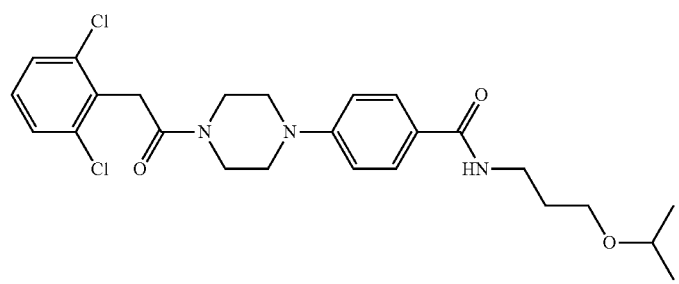
Co. No. 256
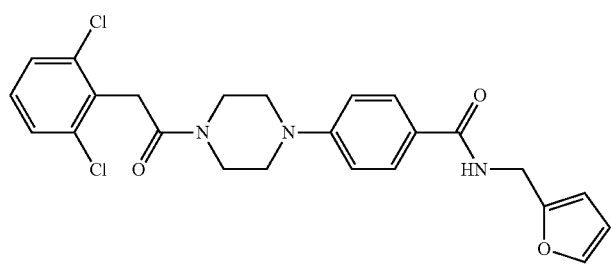
Co. No. 258

TABLE D1-continued
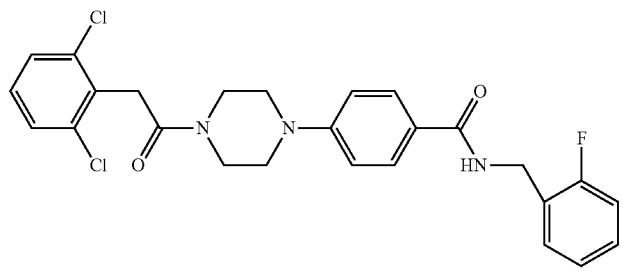
Co. No. 249
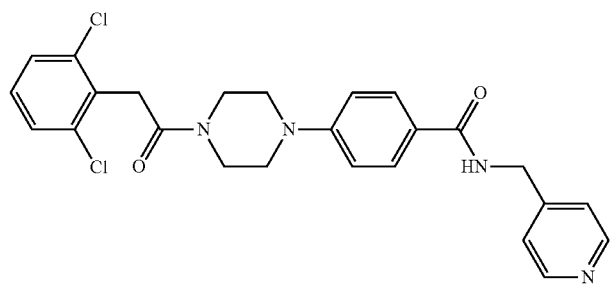
Co. No. 251
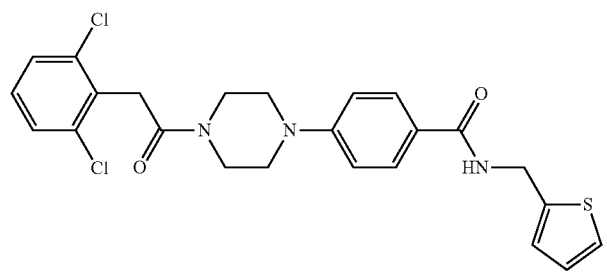
Co. No. 253
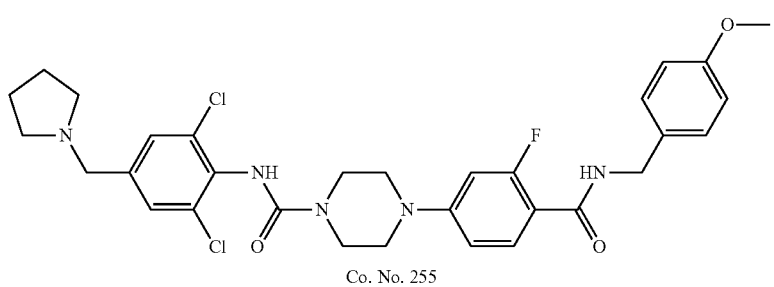 [SMILES: COc1ccc(CNC(=O)c2ccc(N3CCN(C(=O)Nc4c(Cl)cc(CN5CCCC5)cc4Cl)CC3)cc2F)cc1]
Co. No. 255
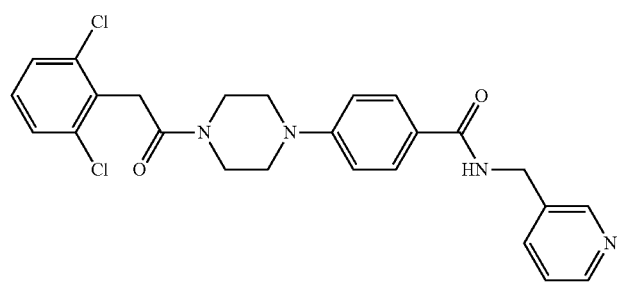
Co. No. 257

TABLE D1-continued
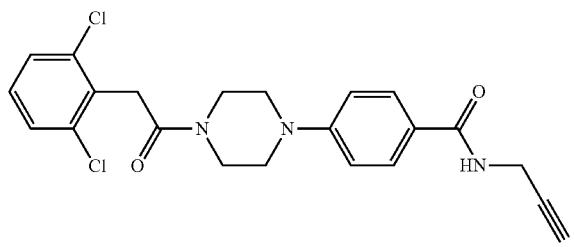
Co. No. 259
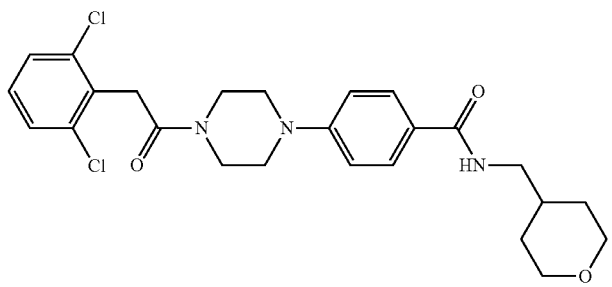
Co. No. 260
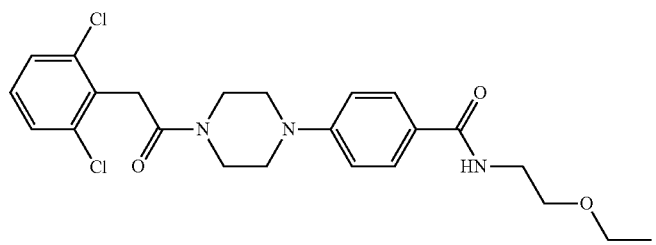
Co. No. 262
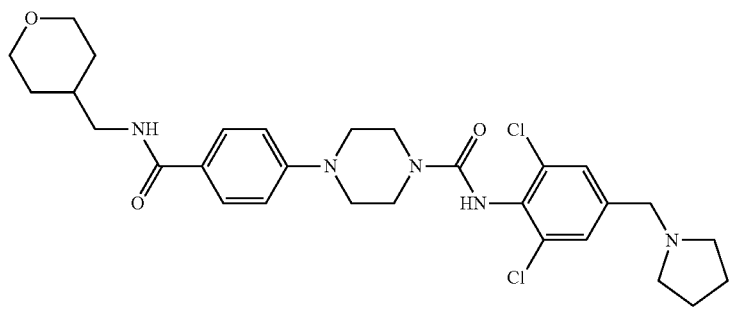
Co. No. 264
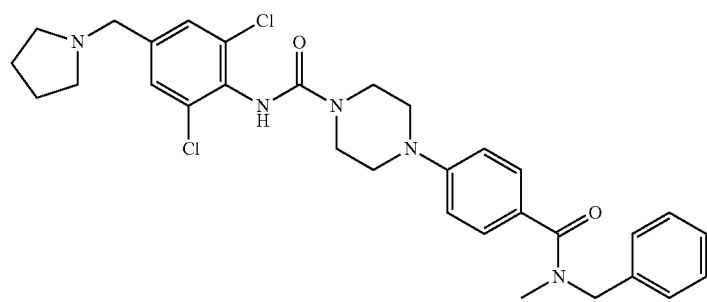
Co. No. 266

TABLE D1-continued
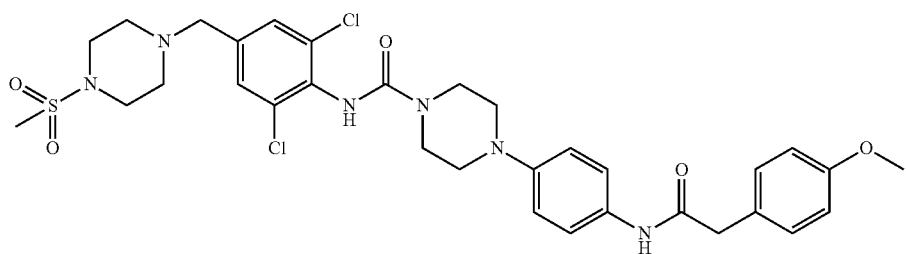
Co. No. 268
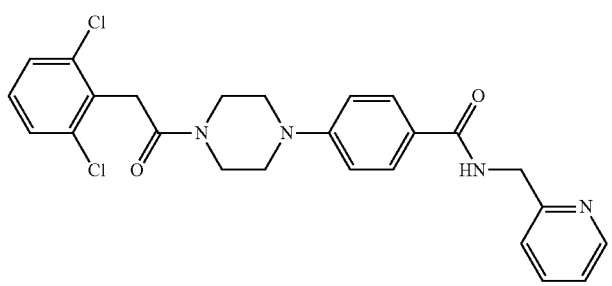
Co. No. 261
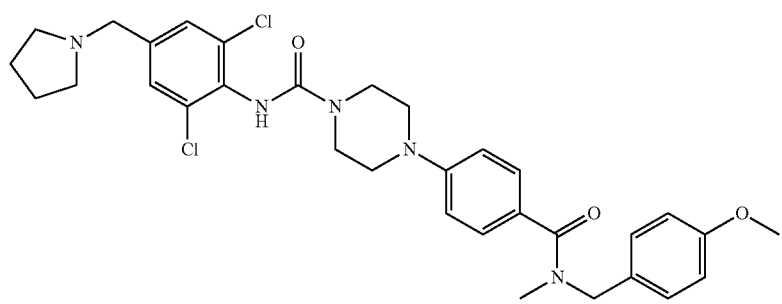
Co. No. 263
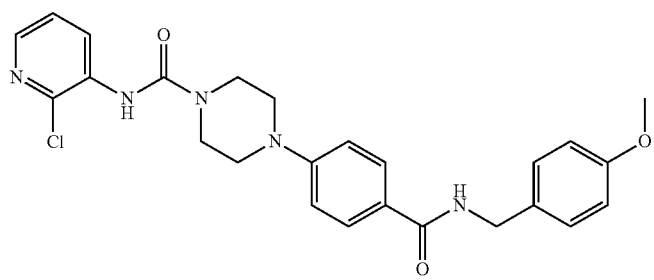
Co. No. 265
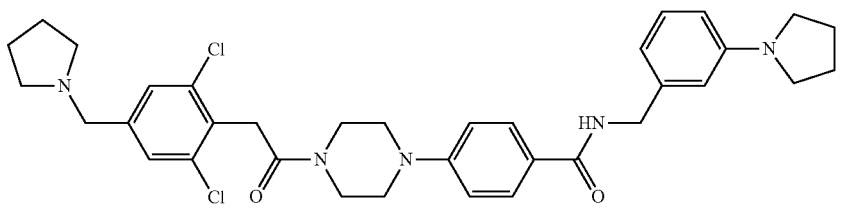
Co. No. 267

TABLE D1-continued
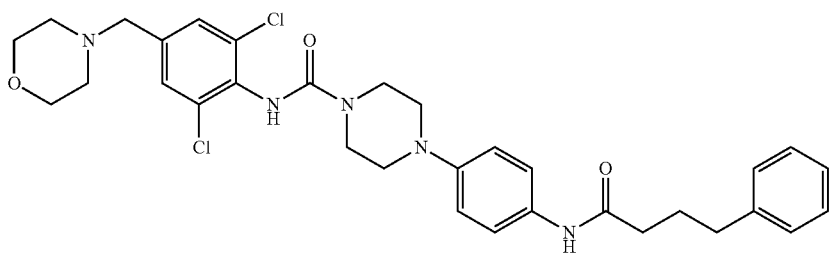
Co. No. 269
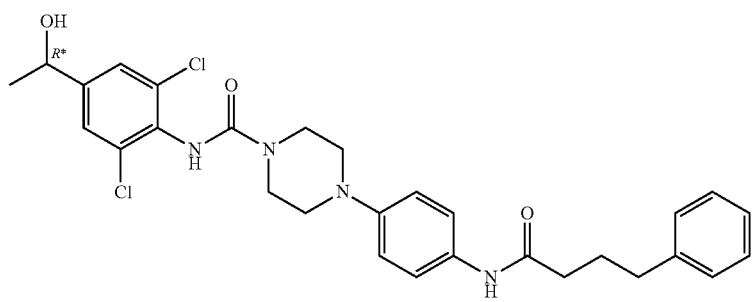
Co. No. 270
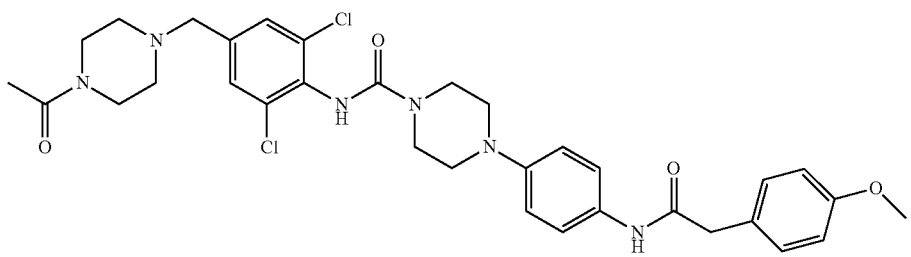
Co. No. 272
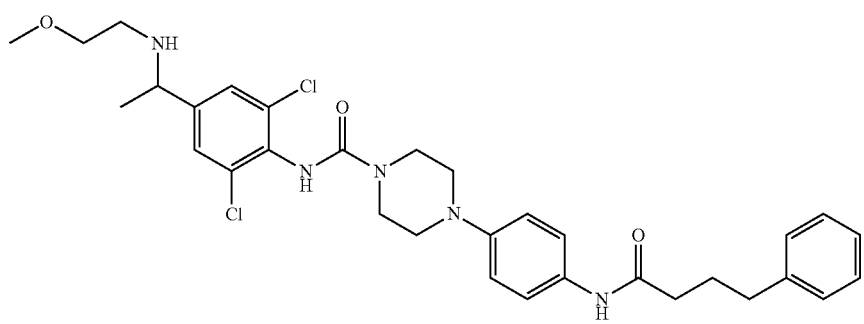
Co. No. 274
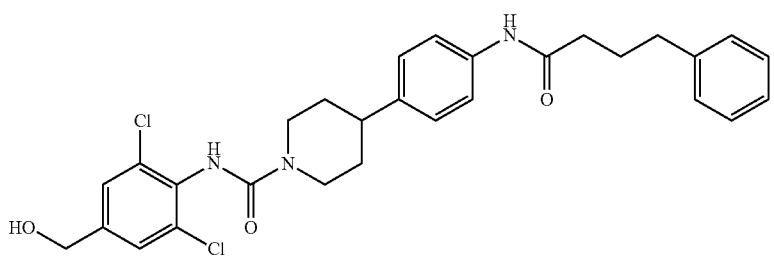
Co. No. 276

TABLE D1-continued
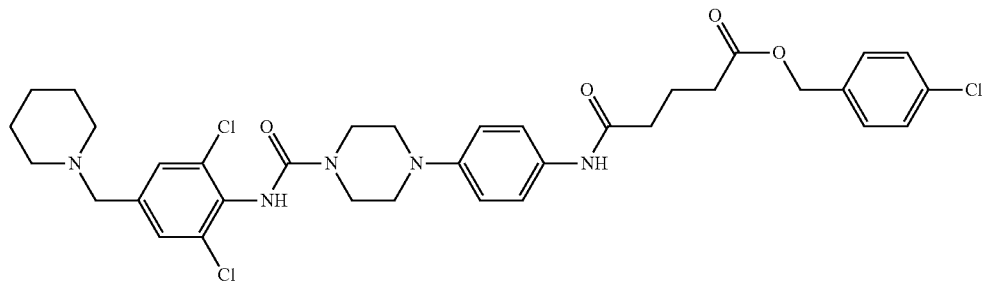
Co. No. 278
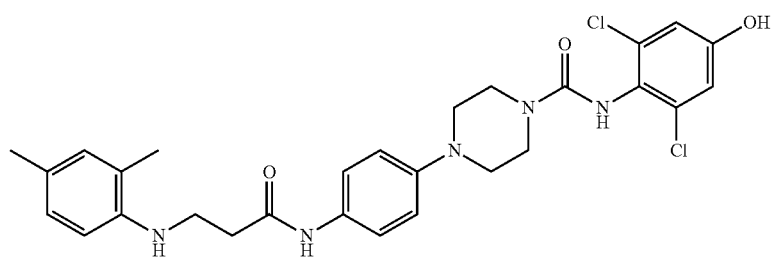
Co. No. 280
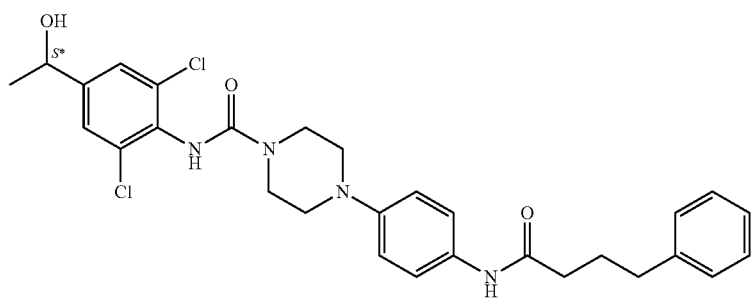
Co. No. 271
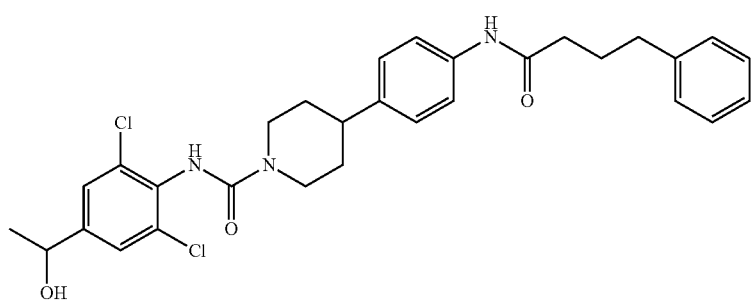
Co. No. 273

TABLE D1-continued
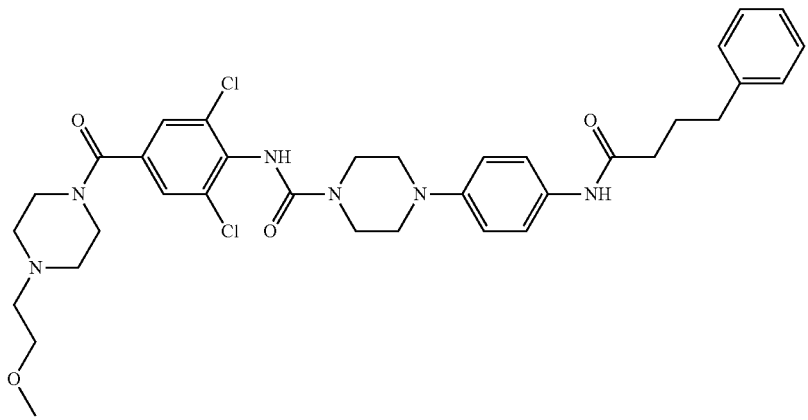
Co. No. 275
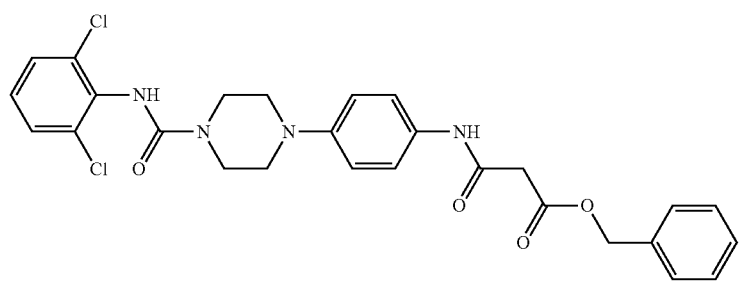
Co. No. 277
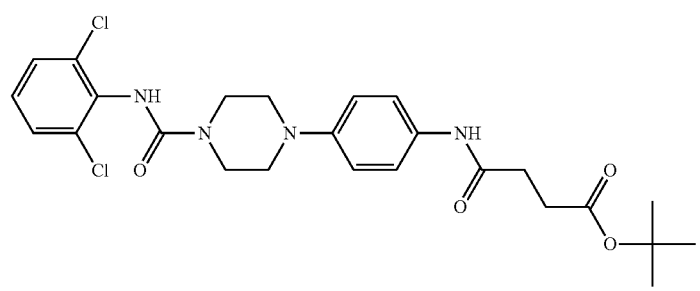
Co. No. 279
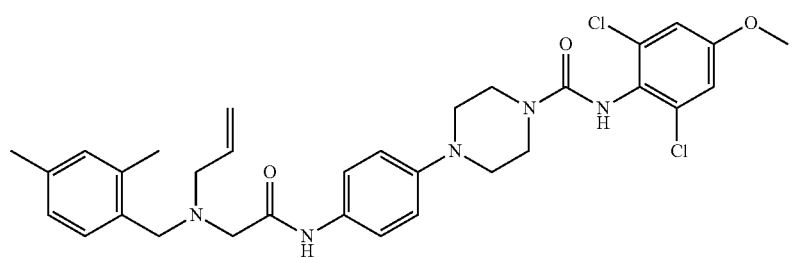
Co. No. 281

TABLE D1-continued
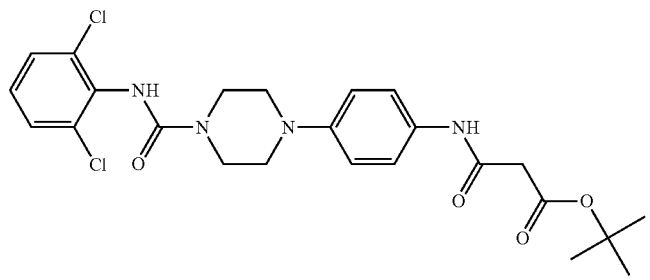
Co. No. 282
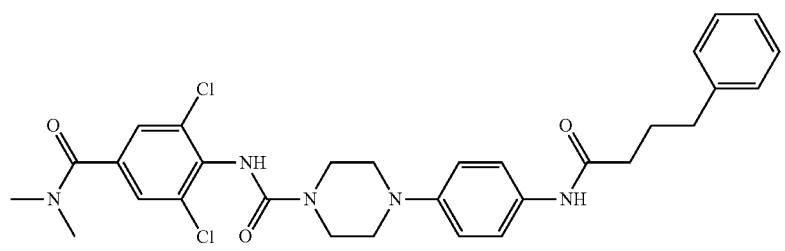
Co. No. 284
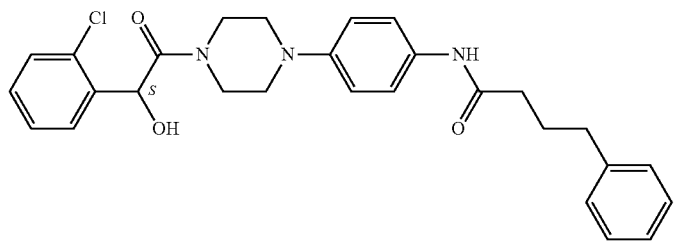
Co. No. 286
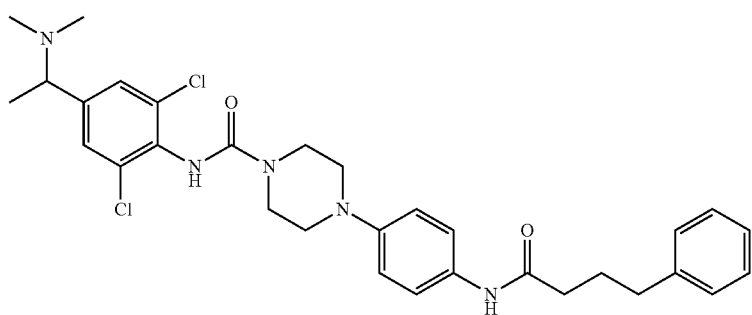
Co. No. 288
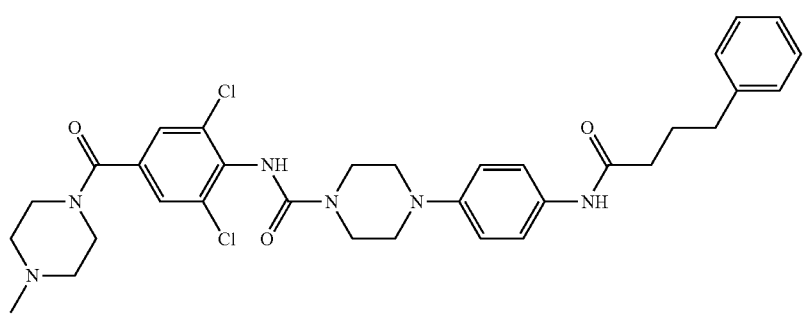 [SMILES: O=C(CCCc1ccccc1)Nc1ccc(N2CCN(C(=O)Nc3c(Cl)cc(C(=O)N4CCOCC4)cc3Cl)CC2)cc1]
Co. No. 290

TABLE D1-continued
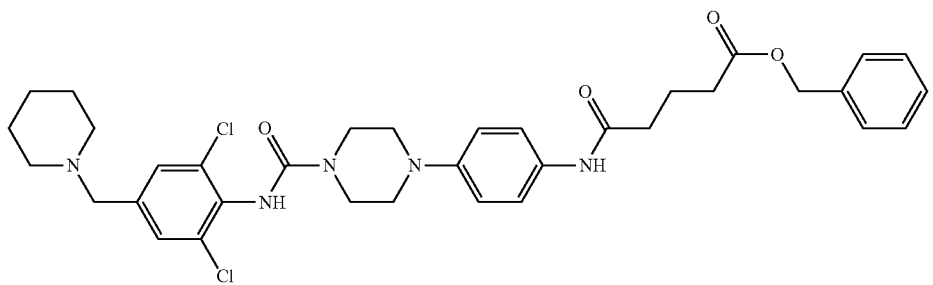
Co. No. 292
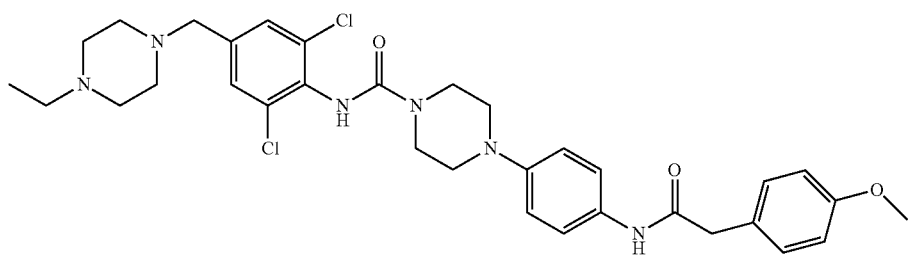
Co. No. 283
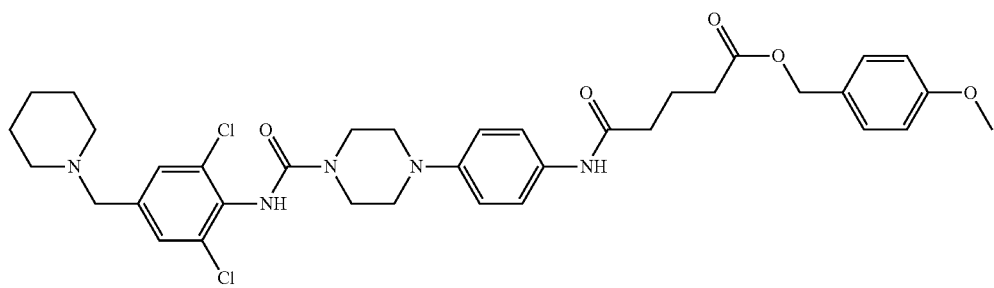
Co. No. 285
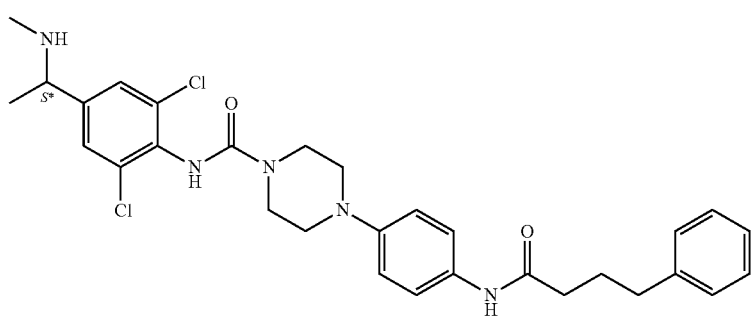
Co. No. 287
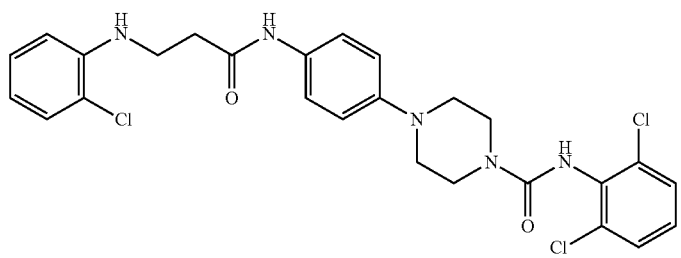
Co. No. 289

TABLE D1-continued
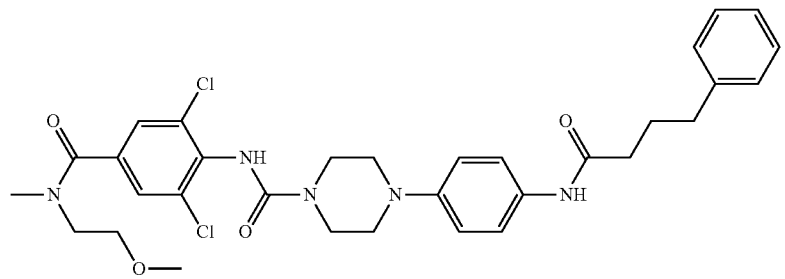
Co. No. 291
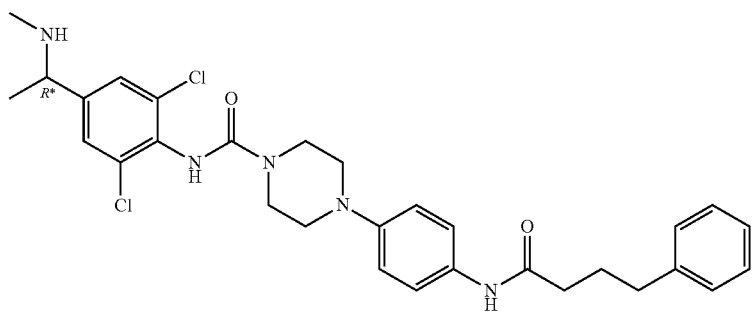
Co. No. 293
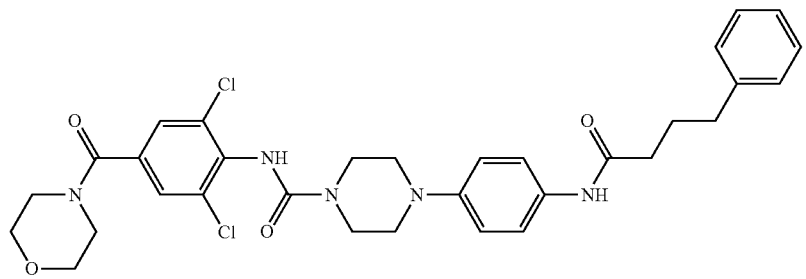
Co. No. 294
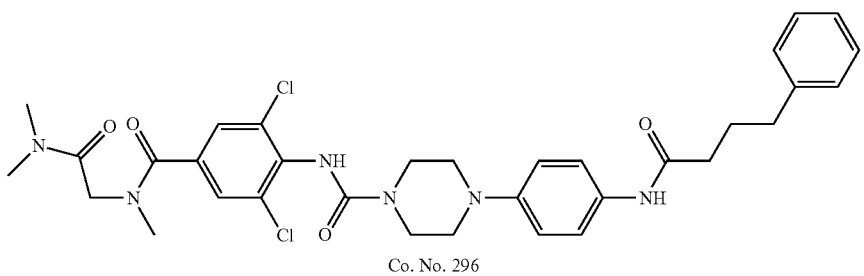 [SMILES: CN(C)C(=O)CN(C)C(=O)c1cc(Cl)c(NC(=O)N2CCN(c3ccc(NC(=O)CCCc4ccccc4)cc3)CC2)c(Cl)c1]
Co. No. 296
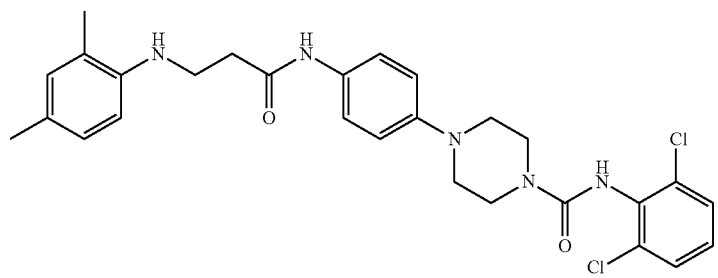
Co. No. 298

TABLE D1-continued
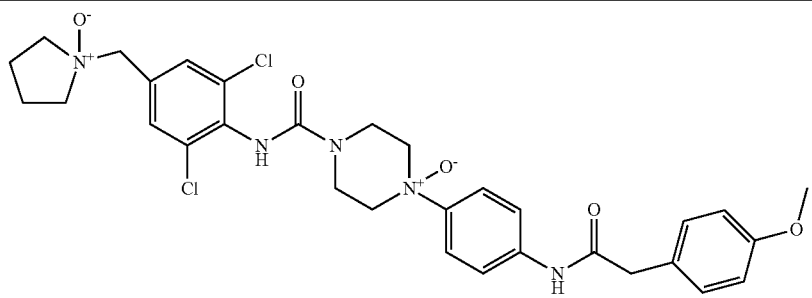
Co. No. 300
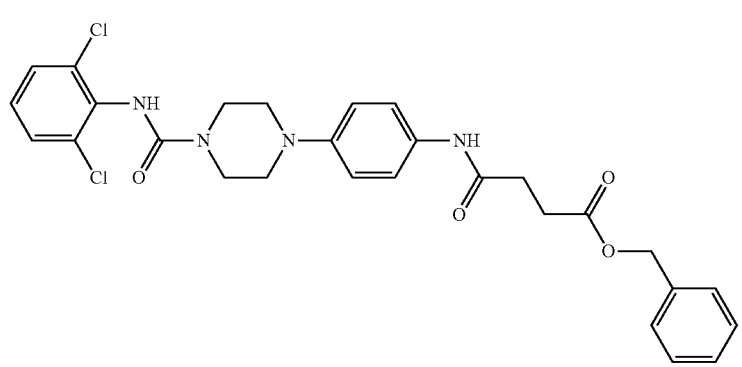
Co. No. 302
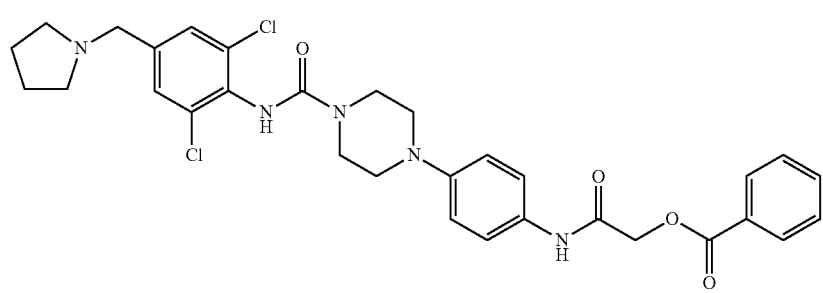
Co. No. 304
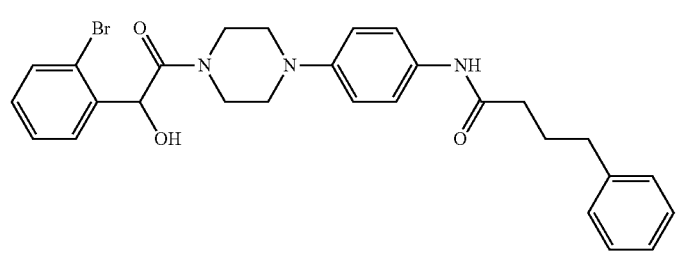
Co. No. 295
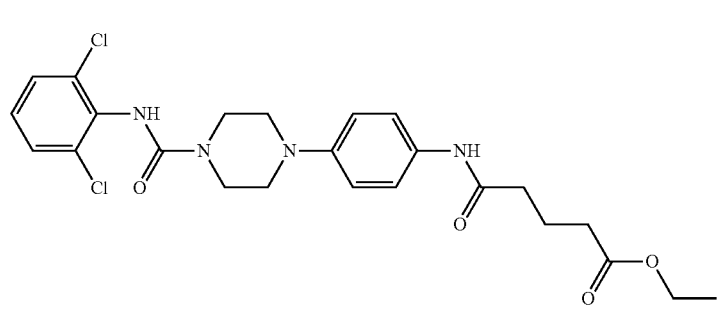
Co. No. 297

TABLE D1-continued
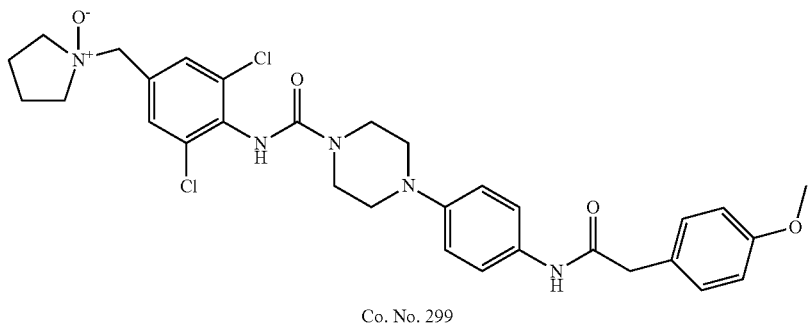 [SMILES: COc1ccc(CC(=O)Nc2ccc(N3CCN(C(=O)Nc4c(Cl)cc(C[N+]5([O-])CCCC5)cc4Cl)CC3)cc2)cc1]
Co. No. 299
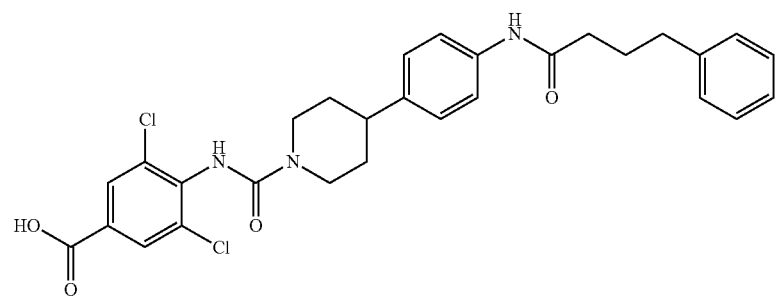
Co. No. 301
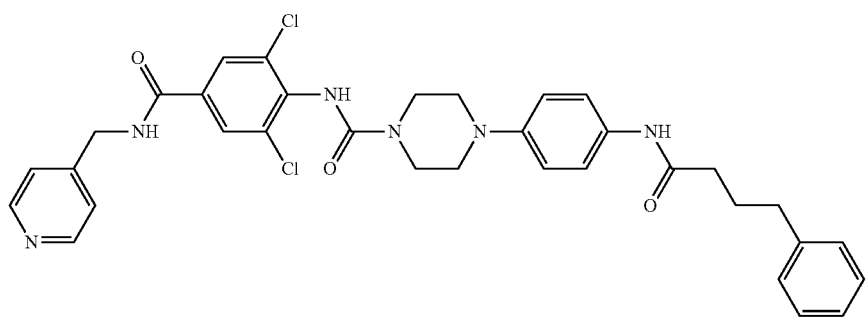
Co. No. 303
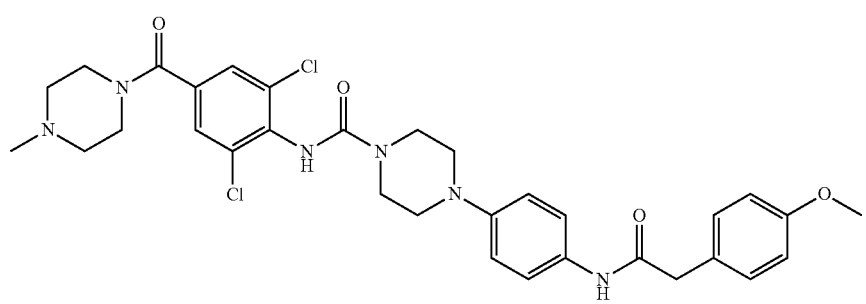
Co. No. 305

TABLE D1-continued
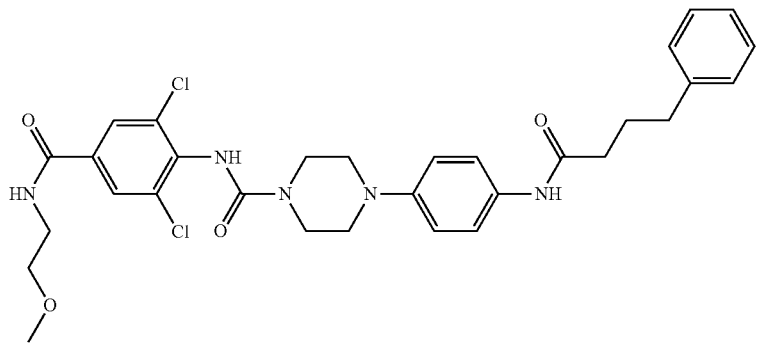
Co. No. 306
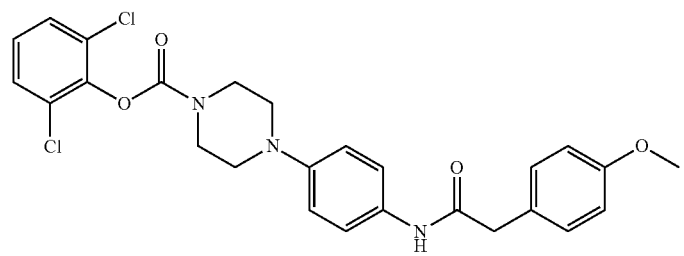
Co. No. 308
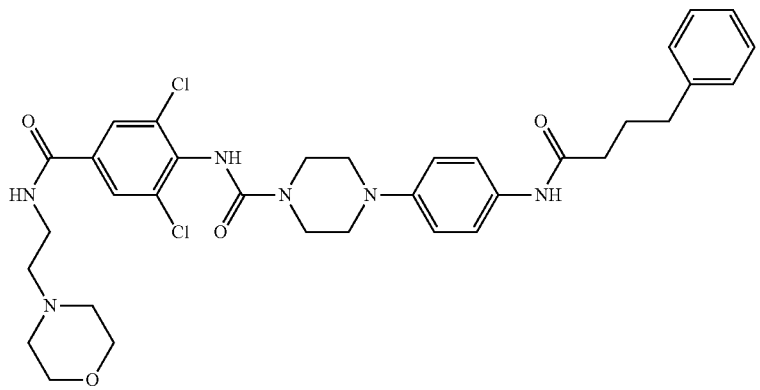
Co. No. 310
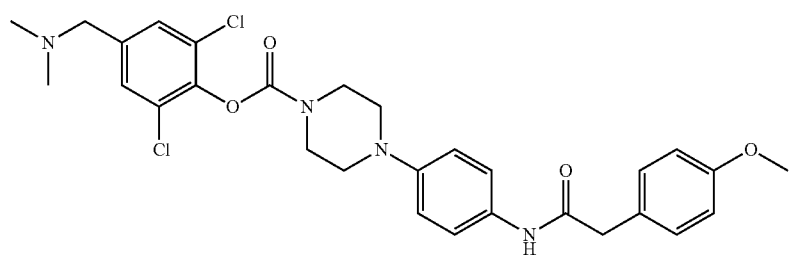
Co. No. 312

TABLE D1-continued
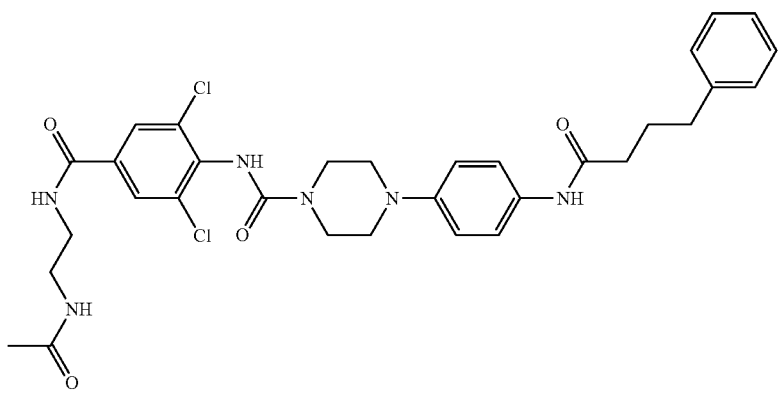
Co. No. 314
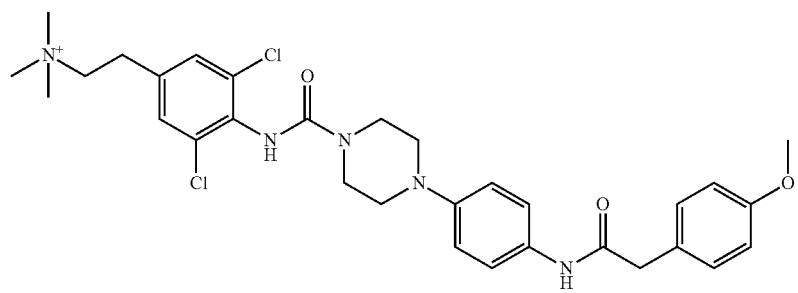
Co. No. 317
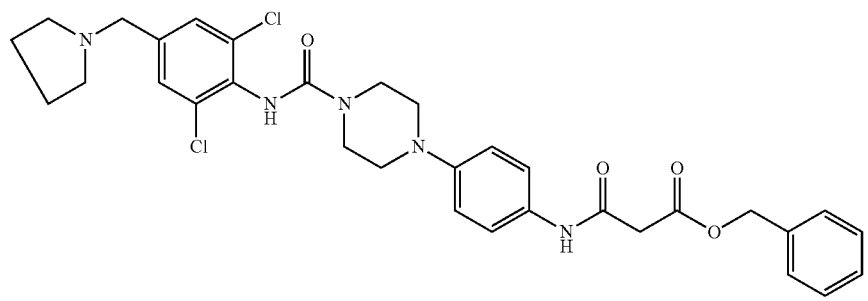
Co. No. 307
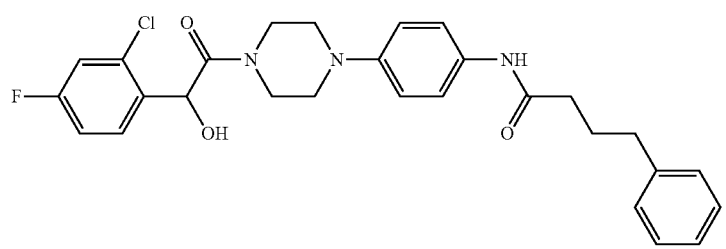
Co. No. 309

TABLE D1-continued
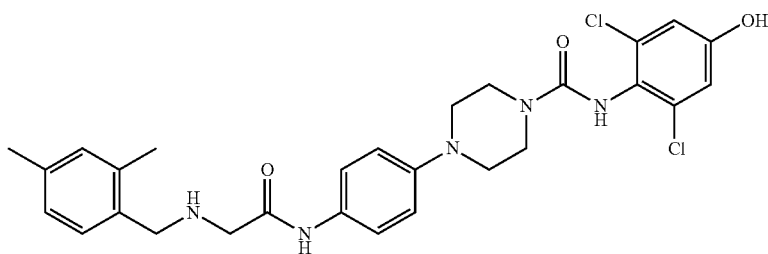
Co. No. 311
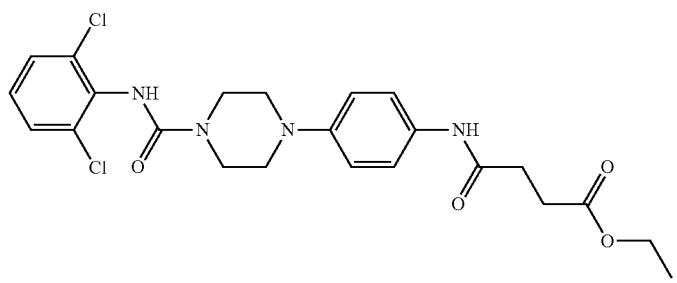
Co. No. 313
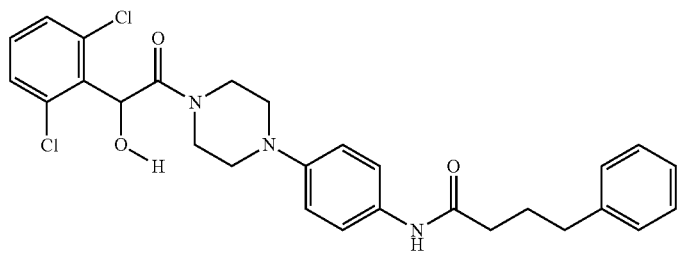
Co. No. 315
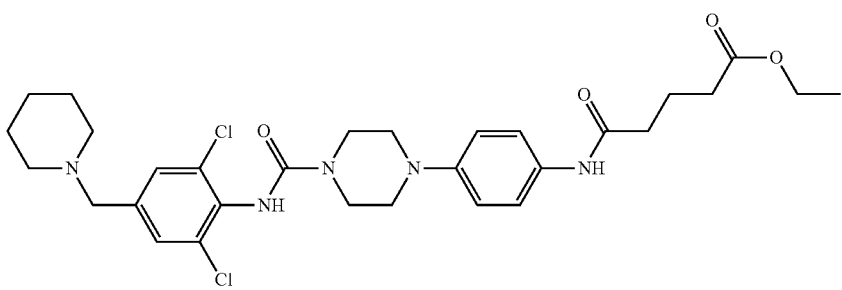
Co. No. 318
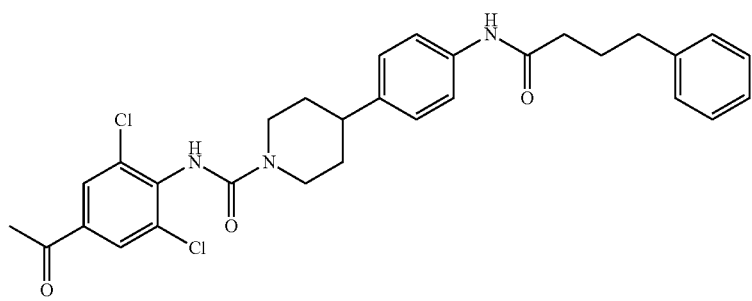
Co. No. 319

TABLE D1-continued
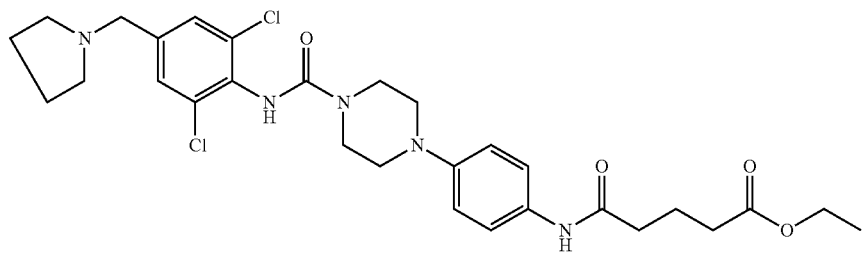
Co. No. 322
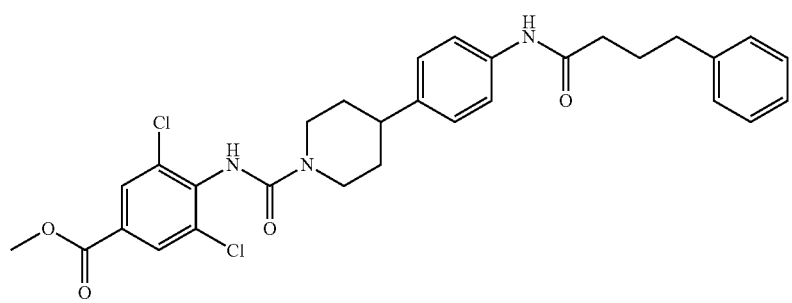
Co. No. 324
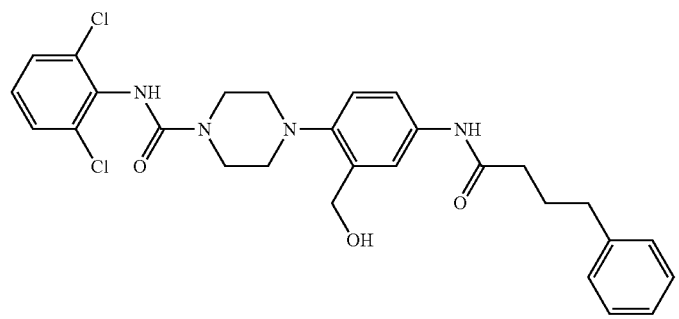
Co. No. 326
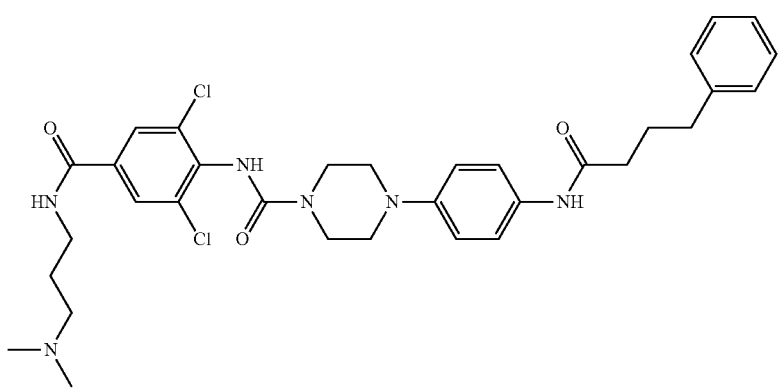
Co. No. 328

TABLE D1-continued
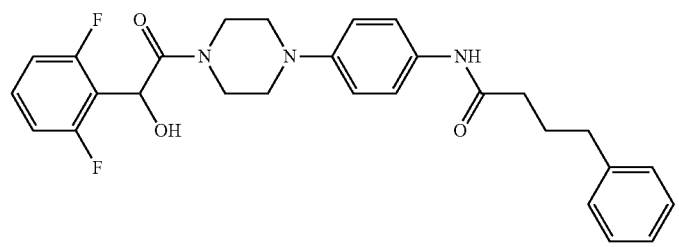
Co. No. 330
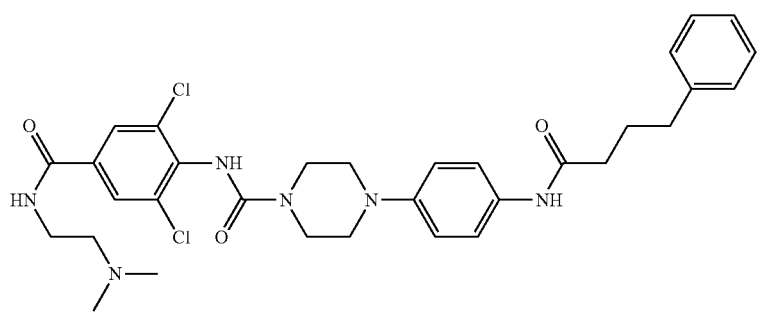
Co. No. 321
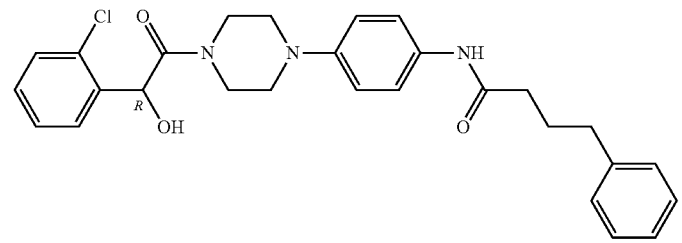
Co. No. 323
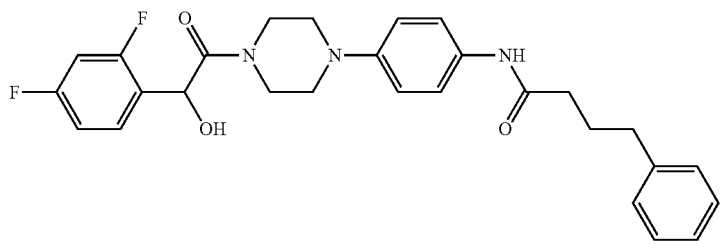
Co. No. 325
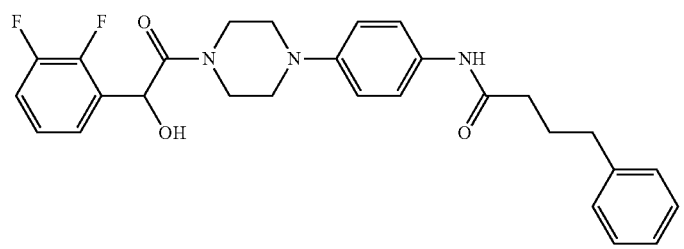
Co. No. 327

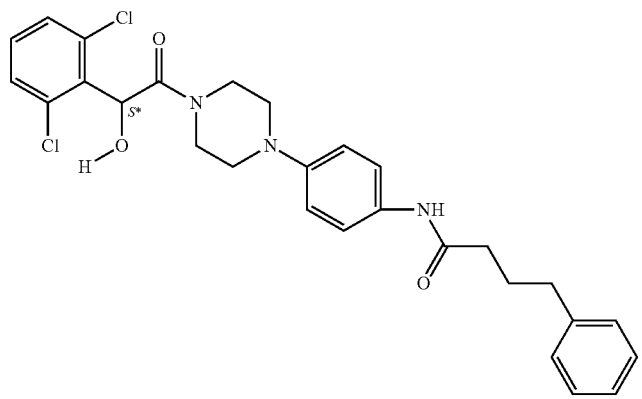
Co. No. 329
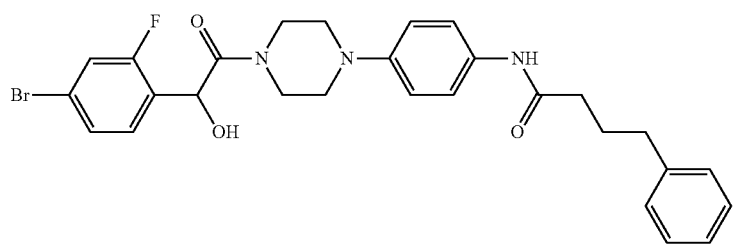
Co. No. 331
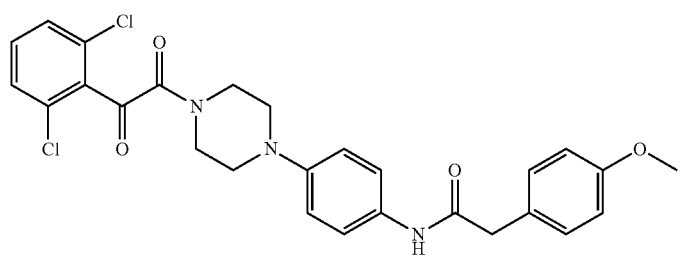
Co. No. 332
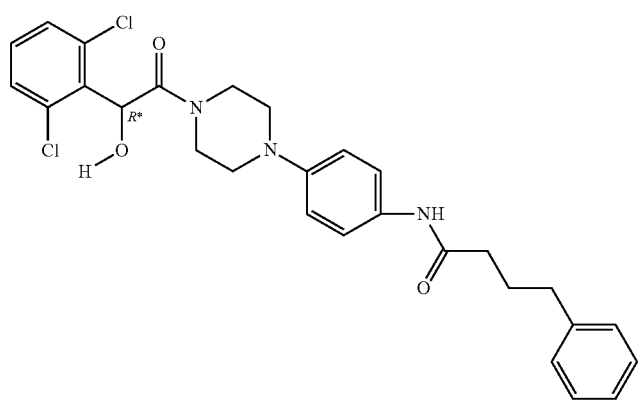
Co. No. 334

TABLE D1-continued
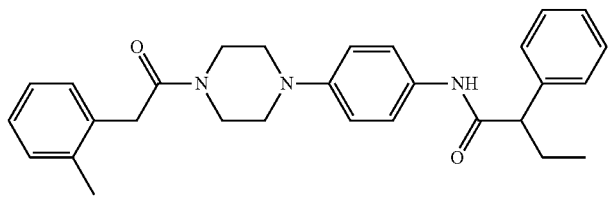
Co. No. 336
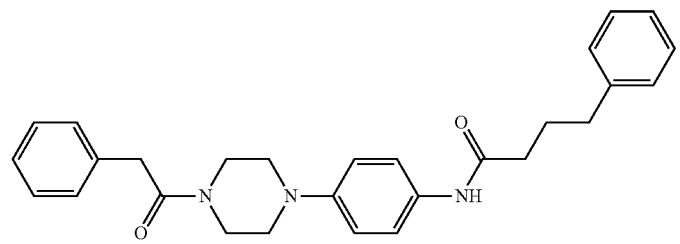
Co. No. 338
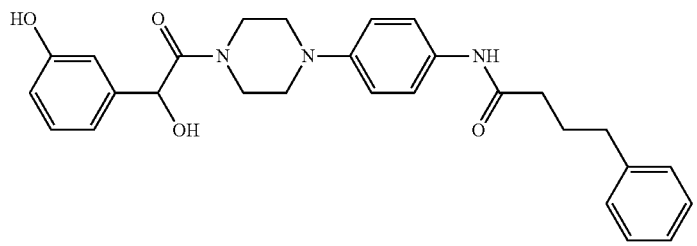
Co. No. 340
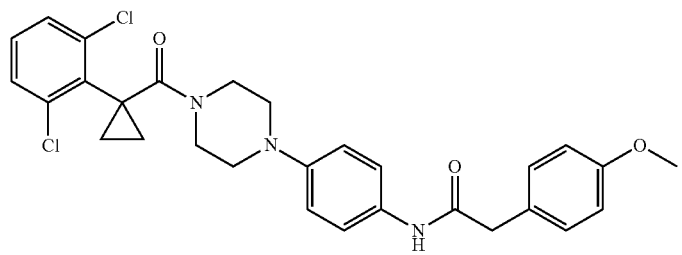
Co. No. 342
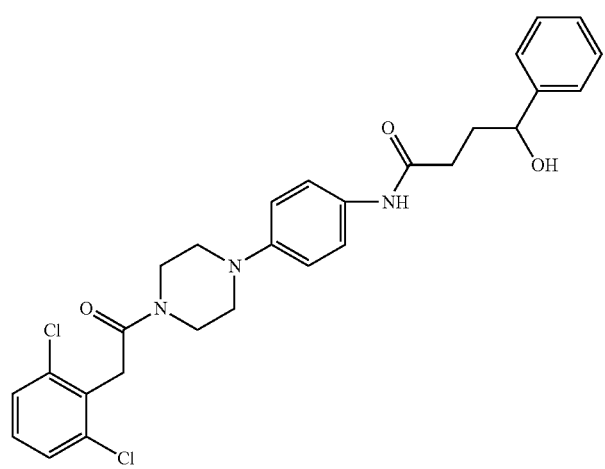
Co. No. 333

TABLE D1-continued
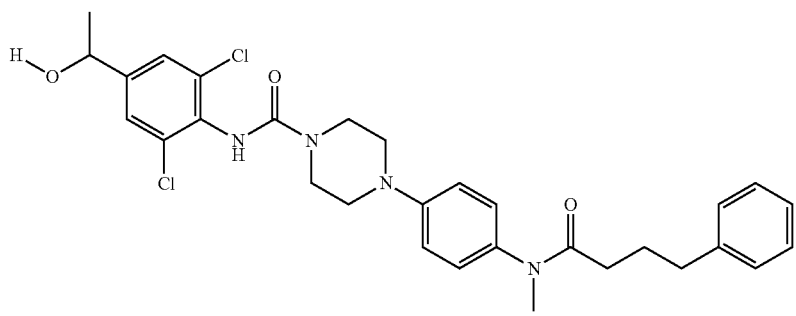
Co. No. 335
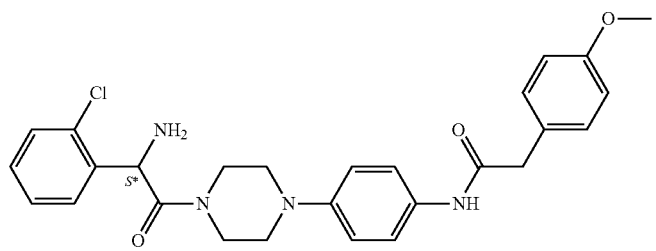
Co. No. 337
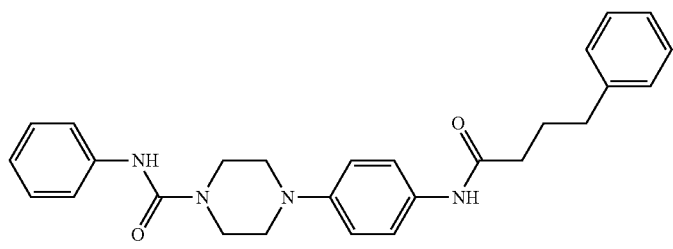
Co. No. 339
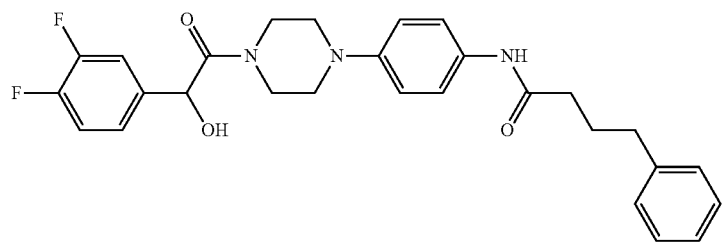
Co. No. 341
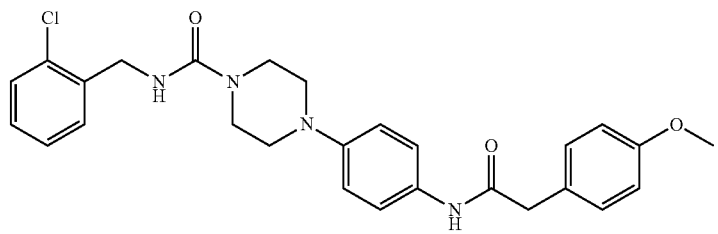
Co. No. 343

TABLE D1-continued
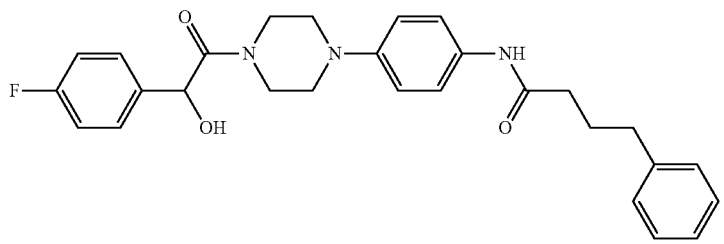
Co. No. 344
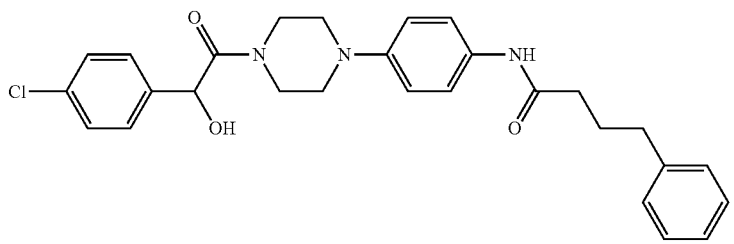
Co. No. 346
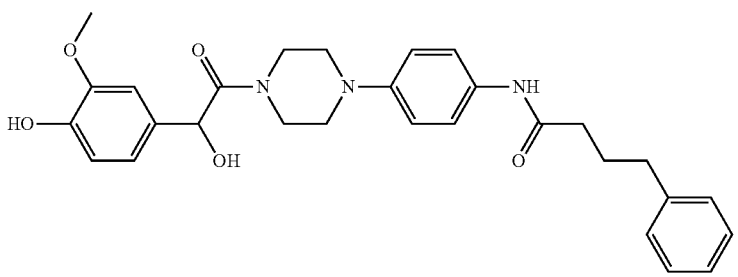
Co. No. 348
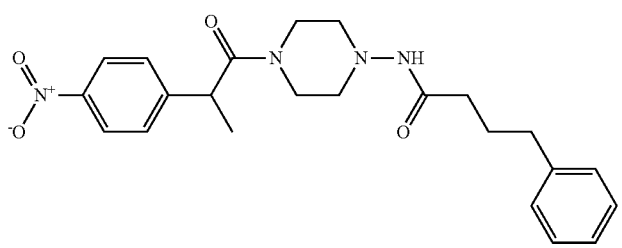
Co. No. 350
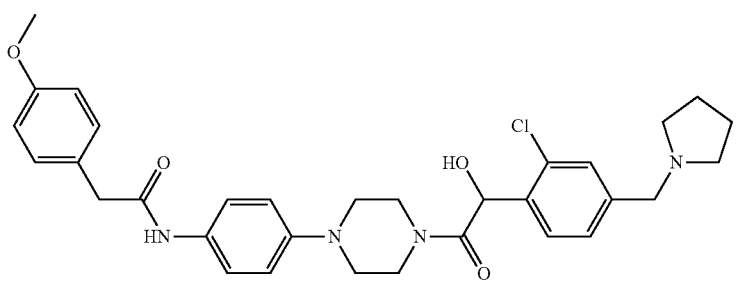
Co. No. 352

TABLE D1-continued
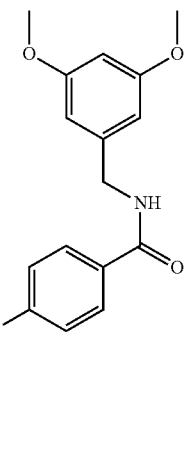
Co. No. 353
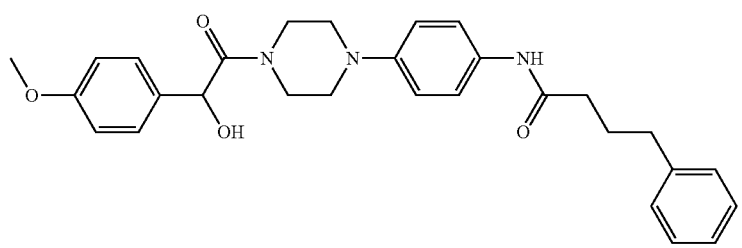
Co. No. 345
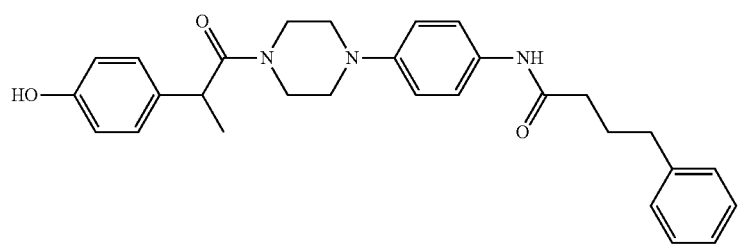
Co. No. 347
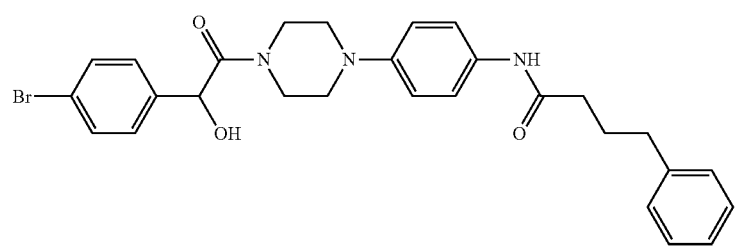
Co. No. 349
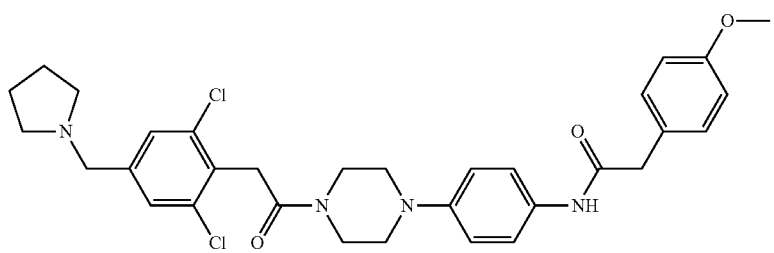
Co. No. 351

TABLE D1-continued
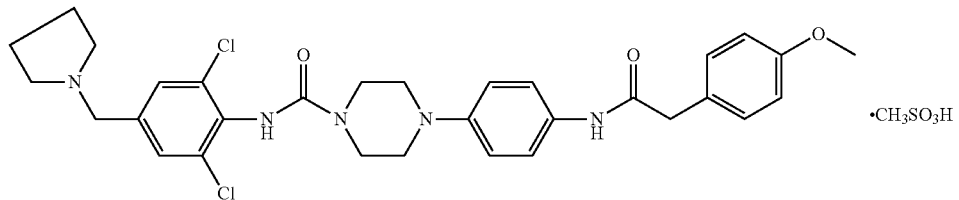
Co. No. 223a
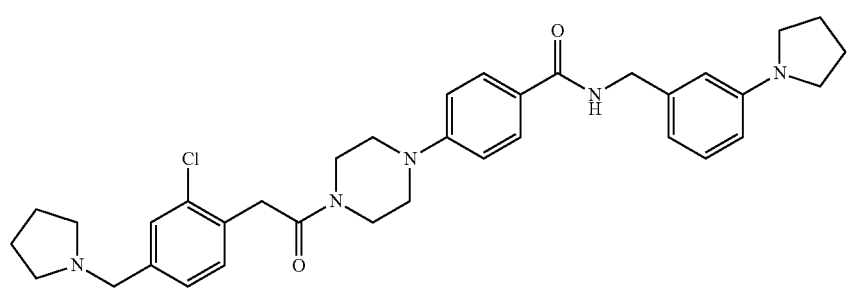
Co. No. 354
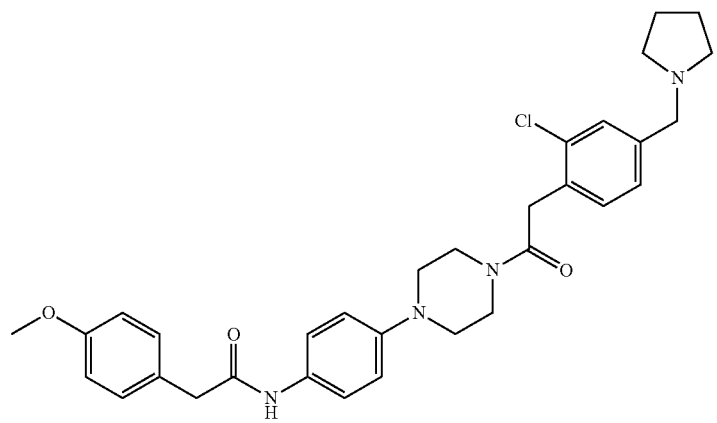
Co. No. 355
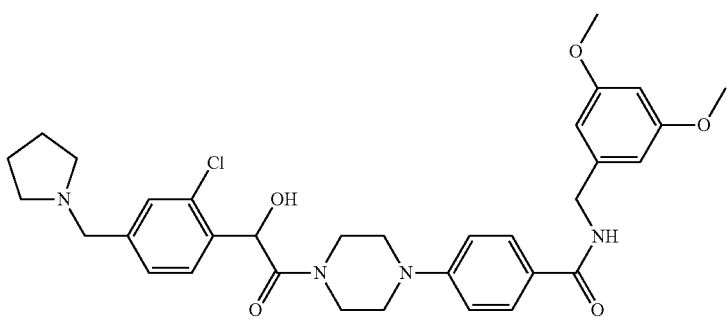
Co. No. 357

TABLE D1-continued
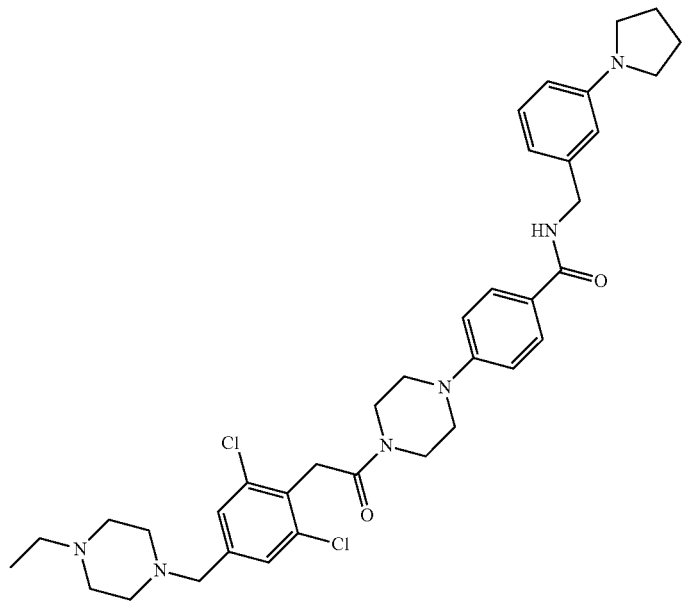
Co. No. 359
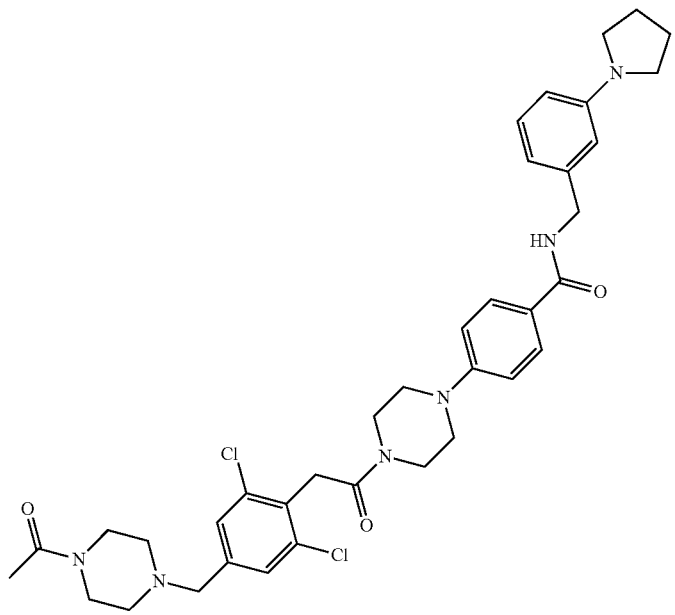
Co. No. 361
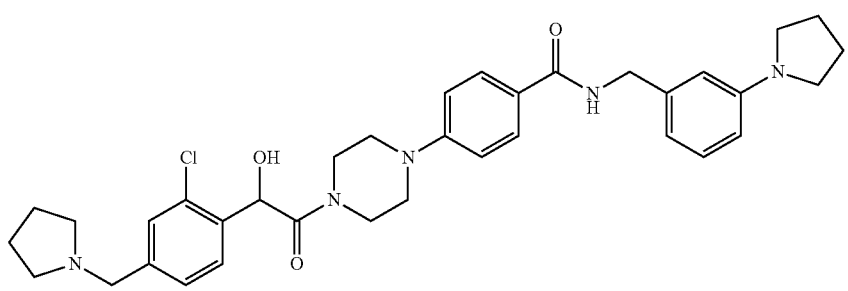
Co. No. 356

TABLE D1-continued
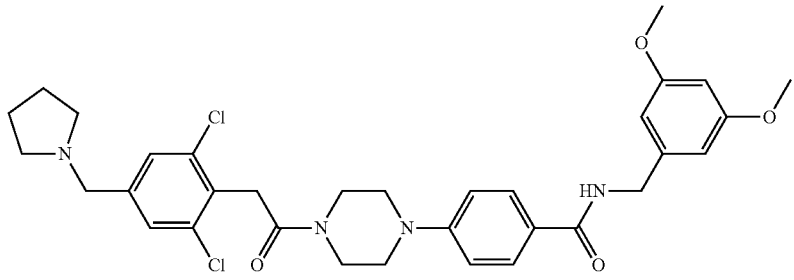
Co. No. 358
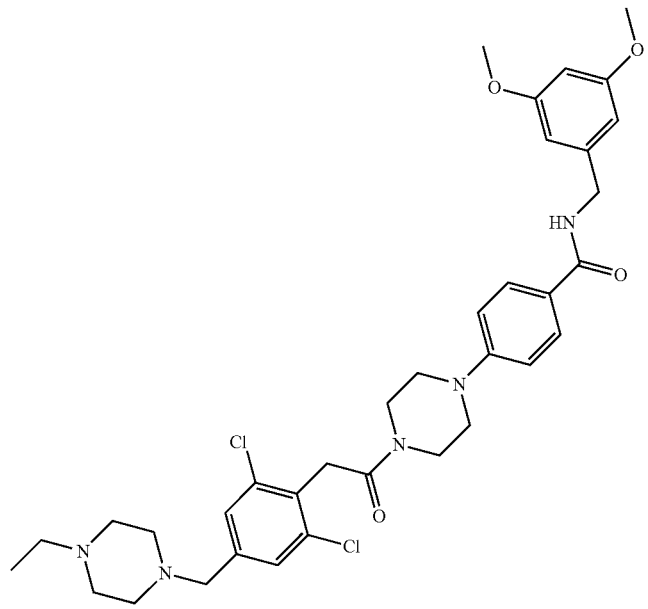
Co. No. 360
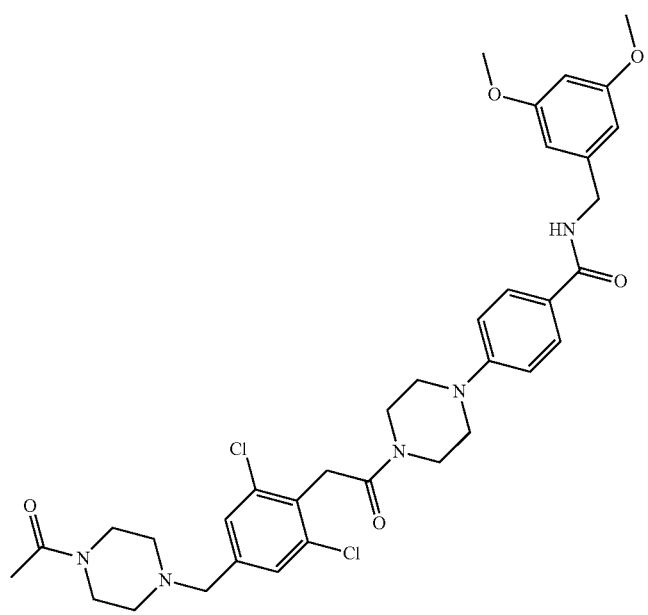
Co. No. 362

TABLE D1-continued

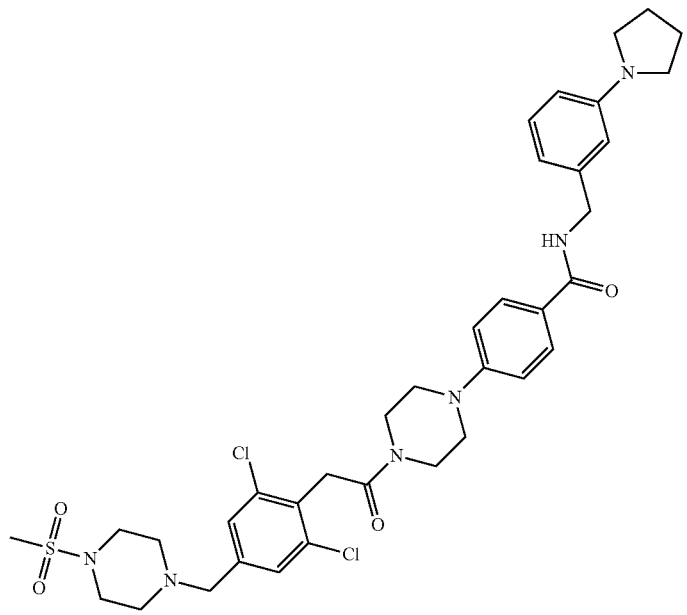

Co. No. 363

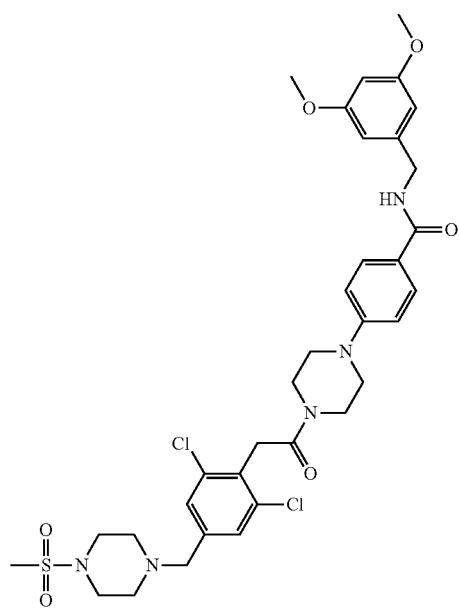

Co. No. 364

R*, S* = relative stereochemistry

Analytical Part

Analytical Data for the Compounds of Group Q (Compounds 147-152 from Class C and Compounds 353-364 from Class D):

LCMS

For (LC)MS-characterization of the compounds of the present invention, the following methods were used.

General Procedure A

The LCMS analyses for a number of compounds were done at the Surveyor MSQ™ (Thermo Finnigan, USA) comprising a photo diode array detector (PDA; 190-800 nm) and a column as specified in the respective methods below. Flow from the column was split to a MS spectrometer. The MS detector was configured with APCI (atmospheric pressure chemical ionization, + or − ions). Mass spectra were acquired by scanning from 45 to 1000 (of atomic mass unit) in 0.3 seconds. Typical APCI conditions use a corona discharge current of 10 μA and a cone voltage of 30 V. The APCI probe temperature was 640° C. Nitrogen was used as the nebulizer gas. Data acquisition was performed with an Xcalibur™ data system.

General Procedure B

The HPLC measurement was performed using an Agilent 1100 module comprising a pump, a diode-array detector (DAD) (wavelength used 220 nm), a column heater and a column as specified in the respective methods below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min.

Method 1

In addition to general procedure A: Reversed phase HPLC was carried out on a Waters XTerra MS C18 column (3.5 μm, 2.1×30 mm) with a flow rate of 1.0 ml/min Two mobile phases (mobile phase A: 0.1% aqueous solution of formic acid; mobile phase B: $CH_3CN$) were used. First, 100% A was hold for 0.1 minutes (min) Then a gradient was applied to 5% A and 95% B in 3 min and hold for 0.8 min. The injection volume was 1 μl. The column was at room temperature.

Method 2

In addition to general procedure B: Reversed phase HPLC was carried out on a YMC-Pack ODS-AQ, 50×2.0 mm 5 μm column with a flow rate of 0.8 ml/min. Two mobile phases (mobile phase A: water with 0.1% TFA; mobile phase B: $CH_3CN$ with 0.05% TFA) were used. First, 90% A and 10% B was hold for 0.8 min. Then a gradient was applied to 20% A and 80% B in 3.7 min and hold for 3 min Typical injection volumes of 2 μl were used. Oven temperature was 50° C. (MS polarity: positive)

Method 3

In addition to general procedure B: Reversed phase HPLC was carried out on an Ultimate XB-C18, 50×2.1 mm 5 μm column with a flow rate of 0.8 ml/min Two mobile phases (mobile phase C: 10 mmol/L $NH_4HCO_3$; mobile phase D: $CH_3CN$) were used. First, 90% C and 10% D was hold for 0.8 min. Then a gradient was applied to 20% C and 80% D in 3.7 min and hold for 3 min. Typical injection volumes of 2 μl were used. Oven temperature was 50° C. (MS polarity: positive)

Method 4

In addition to general procedure B: Reversed phase HPLC was carried out on an Ultimate XB-C18, 50×2.1 mm 5 μm column with a flow rate of 0.8 ml/min Two mobile phases (mobile phase C: 10 mmol/L $NH_4HCO_3$; mobile phase D: $CH_3CN$) were used. First, 100% C was hold for 1 min. Then a gradient was applied to 40% C and 60% D in 4 min and hold for 2.5 min. Typical injection volumes of 2 μl were used. Oven temperature was 50° C. (MS polarity: positive)

Melting Points

For a number of compounds (147-150 of Class C; 358-364 of Class D), m.p. were determined by using a Gallenkamp apparatus from Sanyo Gallenkamp.

For a number of compounds (151-152 of Class C; 353-357 of Class D), m.p. were determined with a WRS-2A melting point apparatus that was purchased from Shanghai Precision and Scientific Instrument Co. Ltd. Melting points were measured with a linear heating up rate of 0.2-5.0° C./min. The reported values are melt ranges. The maximum temperature was 300° C.

TABLE Y (LC)MS analytical data and m.p. - $R_t$ means retention time (in minutes); $[MH]^+$ means the protonated mass of the compound (free base); Method refers to the method used for (LC)MS; 'dec.' means decomposition.

| Comp. Nr. | $R_t$ | $[MH]^+$ | Method | m.p. (° C.) |
|---|---|---|---|---|
| 147 - Class C | 1.62 | 620 | 1 | 262-263 |
| 148 - Class C | 1.60 | 663 | 1 | 180-182 |
| 149 - Class C | 1.63 | 677 | 1 | 250-252 |
| 150 - Class C | 1.68 | 713 | 1 | 240-242 |
| 151 - Class C | 3.41 | 586 | 2 | 224.1-225.4 |
| 152 - Class C | 4.84 | 602 | 3 | 138.7-140.9 |
| 353 - Class D | 3.49 | 591 | 2 | 126.6-128.1 |
| 354 - Class D | 3.23 | 600 | 2 | 206.3-209.4 |
| 355 - Class D | 3.42 | 561 | 2 | 153.3-155.2 |
| 356 - Class D | 3.10 | 616 | 2 | 134.4-137.0 |
| 357 - Class D | 5.65 | 607 | 4 | dec. at 124.8 |
| 358 - Class D | 1.57 | 625 | 1 | 199-200 |
| 359 - Class D | 1.61 | 677 | 1 | 240-241 |
| 360 - Class D | 1.52 | 668 | 1 | 159-160 |
| 361 - Class D | 1.53 | 691 | 1 | 164-166 |
| 362 - Class D | 1.51 | 682 | 1 | 123-126 |
| 363 - Class D | 1.61 | 727 | 1 | 241-243 |
| 364 - Class D | 1.56 | 718 | 1 | 152-154 |

Analytical data for the other Class A, Class B, Class C and Class D compounds are listed in WO2008/148851, WO2008/148840, WO2008/148849 and WO2008/148868, the contents of which are enclosed by reference in the present application.

Pharmacological Example

All mpk (mg/kg/day) values mentioned in the measurements described below, were estimated based on average food intake and average body weight.

A) Measurement of Inhibition of DGAT1 Activity by the Compounds of Class A, Class B, Class C and Class D The inhibiting activity of compounds of Class A, Class B, Class C and Class D on DGAT1 activity was screened in a single well procedure assay using DGAT1 comprising membrane preparations and DGAT1 substrate comprising micelles and determining formed radio-active triacylglycerol coming in close proximity of a flashplate surface by radioluminescence.

Said assay is described in full detail in WO2006/067071, the content of which is incorporated herein by reference.

By DGAT1 activity is meant the transfer of coenzyme A activated fatty acids to the 3-position of 1,2-diacylglycerols, thus forming a triglyceride molecule, by enzyme DGAT1.

Step 1 of the Assay: Expression of DGAT1 human DGAT1 (NM012079.2) was cloned into the pFast-Bac vector, containing translation start, a FLAG-tag at the N-terminus as described in literature and a viral Kozak sequence (AAX) preceding the ATG to improve expression in insect cells. Expression was done as described in literature (Cases, S., Smith, S. J., Zheng, Y., Myers H. M., Lear, S. R., Sande, E., Novak, S., Collins, C., Welch, C. B., Lusis, A. J., Erickson, S. K. and Farese, R. V. (1998) *Proc. Natl. Acad. Sci. USA* 95, 13018-13023.) using SF9 cells.

Step 2 of the Assay: Preparation of DGAT1 Membranes 72 h transfected SF9 cells were collected by centrifugation (13000 rpm-15 min-4° C.) and lysed in 2×500 ml lysisbuffer (0.1M Sucrose, 50 mM KCl, 40 mM $KH_2PO_4$, 30 mM EDTA pH 7.2. Cells were homogenized by cell disruptor. After centrifugation 1380 rpm-15 min-4° C. (SN discarded), pellet was resuspended in 500 ml lysisbuffer and total cell membranes collected by ultracentrifugation at 34000 rpm (100 000 g) for 60 min (4° C.). The collected membranes were resuspended in lysis buffer, divided in aliquots and stored with 10% glycerol at −80° C. until use.
Step 3 of the Assay: Preparation of DGAT Substrate Comprising Micelles
Materials
a) 1,2-dioleoyl-sn-glycerol, 10 mg/ml (1,2-diacylglycerol (DAG))
   Dissolve in acetonitrile; evaporate the acetonitrile solution under nitrogen and reconstitute in chloroform at a final concentration of 10 mg/ml.
b) L-α-phosphatidylcholine, 1 mg/ml (phosphatidylcholine (PC))
   Dissolve in chloroform at a final concentration of 1 mg/ml and store at 4° C.
c) L-α-phosphatidyl-L-serine, 1 mg/ml (phophatidylserine (PS))
   Dissolve in chloroform at a final concentration of 1 mg/ml and store at 4° C.
Method
   Add 1 ml dioleoyl-sn-glycerol (10 mg/ml) to 10 ml of L-α-phosphatidylcholine (1 mg/ml) and 10 ml of L-α-phosphatidyl-L-serine (1 mg/ml) in a thick glass recipient. Evaporate under nitrogen and put on ice for 15 min Reconstitute in 10 ml Tris/HCl (10 mM, pH 7.4) by sonication on ice. The sonification process includes sonification cycles of 10 seconds in the sonification bath followed by 10 seconds cool down on ice and repeating this sonification cycle till a homogeneous solution is obtained (takes about 15 min). The thus obtained micelles are stored at −20° C. till later use and contain DAG at a final concentration of 1.61 mM.
Step 4 of the Assay: DGAT FlashPlate™ Assay
Materials
a) Assaybuffer
   50 mM Tris-HCl (pH 7.4), 150 mM MgCl$_2$, 1 mM EDTA, 0.2% BSA.
b) N-ethylmaleimide, 5M
   Dissolve 5 g into a final volume of 8 ml DMSO 100% and store at −20° C. in aliquots till later use.
c) Substrate mix (for 1 384 well plate=3840 μl)
   612 μl micelles stock (51 μM final)
   16.6 μl oleoylCoA 9.7 mM
   23 μl [$^3$H]-oleoylCoA (49 Ci/mmol, 500 μCi/ml)
   3188.4 μl Tris pH 7.4, 10 mM
d) Enzyme mix (for 1 384 well plate=3520 μl) (5 μg/ml)
   Add 11.73 μl of DGAT membrane stock (1500 μg/ml stock) to 3508 μl assay buffer.
e) Stop mix (for 1 384 well plate=7.68 ml) (250 mM)
   Add 384 μl of N-ethylmaleimide (5M) to 3.456 ml DMSO 100%, and further dilute 3.84 ml of said solution with 3.84 ml DMSO 10%.
Method
   DGAT activity in membrane preparations was assayed in 50 mM Tris-HCl (pH 7.4), 150 mM MgCl$_2$, 1 mM EDTA and 0.2% BSA, containing 50 μM DAG, 32 μg/ml PC/PS and 8.4 μM [$^3$H]-oleoylCoA (at a specific activity of 30 nCi/well) in a final volume of 50 μl in 384-well format using the red shifted Basic Image FlashPlate™ (Perkin Elmer Cat. No. SMP400).
   In detail, 10 μl enzyme mix and 10 μl substrate mix were added to 30 μl of assay buffer, optionally in the presence of 1 μl DMSO (blank and controls) or 1 μl of the compound to be tested. This r.m. was incubated for 120 min at 37° C. and the enzymatic reaction stopped by adding 20 μl of the stop mix. The plates were sealed and the vesicles allowed to settle overnight at room temperature. Plates were centrifuged for 5 min at 1500 rpm and measured in Leadseeker.

Experiments with different concentrations of the test compound were performed and curves were calculated and drawn based on % CTRL$_{min}$ (% of normalized control).
   % CTRL$_{min}$, was calculated according to equation 1, $$\% \text{ CTRL}_{min} = (\text{sample} - \text{LC})/(\text{HC} - \text{LC}) \qquad \text{Equation 1}$$

where HC (high control) refers to the median of radioluminescence value measured in the wells with enzyme and substrate but without test compound, LC (low control) refers to median background radioluminescence value measured in the wells with substrate without enzyme and without test compound, and sample refers to the radioluminescence value measured in the wells with substrate, enzyme and test compound at a particular concentration.
   The calculated % CTRL$_{min}$ values form a sigmoidal dose response descending curve and from this curve pIC$_{50}$ values were calculated (−logIC$_{50}$ where IC$_{50}$ represents the concentration at which the test compound gives 50% inhibition of DGAT1 activity). All the tested compounds of Class A, C and D showed pIC$_{50}$ values between 5 and 9. All the tested compounds of Class B showed pIC$_{50}$ values between 5 and 8.5.
   In order to determine selectivity of the present compounds for DGAT1 compared to DGAT2, the inhibiting activity of the compounds on DGAT2 was also determined in the above assay, slightly modified to obtain optimal assay conditions for DGAT2. The tested compounds did not show inhibiting activity for DGAT2 (Human DGAT2 (NM032564) was cloned and expressed as described in J. Biolog. Chem. 276(42), pp 38870-38876 (2001)).
   For a selected number of compounds, the pIC50 values are shown in Table E.

TABLE E

| Co. Nr. | pIC$_{50}$ values |
| --- | --- |
| | pIC$_{50}$ |
| 151 - Class C | 6.50 |
| 152 - Class C | 7.45 |
| 147 - Class C | 7.41 |
| 148 - Class C | 8.04 |
| 149 - Class C | 8.21 |
| 150 - Class C | 8.22 |
| 353 - Class D | 6.59 |
| 354 - Class D | 6.19 |
| 355 - Class D | 6.04 |
| 356 - Class D | 7.13 |
| 357 - Class D | 7.26 |
| 358 - Class D | 7.59 |
| 359 - Class D | 7.55 |
| 360 - Class D | 8.12 |
| 361 - Class D | 7.87 |
| 362 - Class D | 8.04 |
| 363 - Class D | 7.94 |

TABLE E-continued pIC$_{50}$ values

| Co. Nr. | pIC$_{50}$ |
|---|---|
| 364 - Class D | 8.24 |
| 352 - Class D | 6.45 |
| 351 - Class D | 6.62 |
| 267 - Class D | 6.97 |

Pharmacological data for the other Class A, Class B, Class C and Class D compounds are listed in WO2008/148851, WO2008/148840, WO2008/148849 and WO2008/148868, the contents of which are enclosed by reference in the present application.

B) In vivo Study for Effect of Test Compound on GLP-1 Plasma Levels

Elevation of GLP-1 plasma levels by a DGAT inhibitor can be studied as follows:

Dogs are deprived from food for a period of 22 h. At time 0, animals are given a liquid meal, containing 18% fat (w/w), by gavage with a stomach tube. The test compound is given orally together with the meal. Afterwards, a post-prandial plasma profile is determined for GLP-1. Therefore, blood is collected at predetermined time intervals in ice-cooled Vacutainers EDTA-plasma tubes and GLP-1 levels are measured in the samples taken at 0 h (just before the meal) and at 0.5, 1, 2, 4, 6, 8 and 24 h after dosing. Six dogs (3 males and 3 females) are included per dosage group and the plasma GLP-1 profile is compared with their own GLP-1 profile previously determined in the same conditions but without administration of the test compound. GLP-1 determinations in plasma are performed with a Glucagon-like peptide-1 (active) ELISA kit 96-well plate of LINCO Research.

C) Food Intake/Body Weight Effect of DGAT/Fenofibrate Combination

General Procedure

Male C57BL/6 mice were housed in individually ventilated cages under controlled temperature (21° C.), humidity (45-65%) and light (12 h-12 h reverse light/dark cycle; Lights on—6 PM-6 AM). Mice were set on 60 kcal % fat energy diet until their average body weight was over 45 grams, at which time they were switched to a 45 kcal % fat diet.

For the purpose of Tests A, B and C, the mice were moved into modified type-2 cages with: doublewide food cup, wire grids and a tissue for bedding for several months before experiment to adapt to new housing/feeding conditions. Food (Research diets 45 kcal % diet D12451—see Scheme A) was provided in powdered form in a food hopper located off the front of the cage. Mice had been used to test several compounds for effects on food intake before being used in the current experiment, but had a wash-out period of at least one month before starting the current experiments.

Scheme A:
Composition of control diet (high-fat) and premix (used for adding drug)

| Ingredient | Control Diet D12451 g/kg diet | Premix D04071407px | Added during diet preparation g/kg diet |
|---|---|---|---|
| Casein, 80 Mesh | 233.1 | 233.1 | |
| L-Cystine | 3.5 | 3.5 | |
| Corn Starch | 84.8 | 84.8 | |
| Maltodextrin 10 | 3.5 | 3.5 | |
| Sucrose | 201.4 | 201.4 | |
| Cellulose | 58.3 | 58.3 | |
| Soybean Oil | 29.1 | | 29.1 |
| Lard | 206.8 | 104.9 | 102 |
| Mineral Mix S10026 | 11.7 | 11.7 | |
| DiCalcium Phosphate | 15.1 | 15.1 | |
| Calcium Carbonate | 6.4 | 6.4 | |
| Potassium Citrate, 1 H20 | 19.2 | 19.2 | |
| Vitamin Mix | 11.7 | 11.7 | |
| Choline Bitartrate | 2.3 | 2.3 | |
| FD&C Red Dye #40 | 0.1 | | |

Compound 223 of Class D (Tests A and B) or compound 358 (Test C) of Class D, and/or fenofibrate (also called 'F' in the continuation of the pharmacological examples) were brought to a fine emulsion by stirring in the appropriate amount of soybean oil for 1 day. This was then mixed with the diet premix (Scheme A). The diet premix was formulated to contain none of the necessary soybean oil, and only half the final amount of lard. The soybean oil, and the rest of the lard was added in-house during diet preparation. After the soybean oil/drug was mixed with the premix for 15 min, the remainder of the lard was added to complete the diet. Diet was provided in powder form.

The mice were weighted the day before trial onset. For treatment allocation, mice were ranked according to body weight and randomly assigned to treatments within repetitions/blocks (40 mice, 4 treatments, 10 repetitions/block, unless otherwise mentioned). The food intake the day before trial onset was also measured.

At trial onset, mice's food (diet D12451) was replaced with the 'inhouse' diet made from premix D04071407px and added oil/lard, fenofibrate and/or the DGAT inhibitor. In tests A and B compound 223 of Class D (also called 'D' in the continuation of the pharmacological examples) was used:

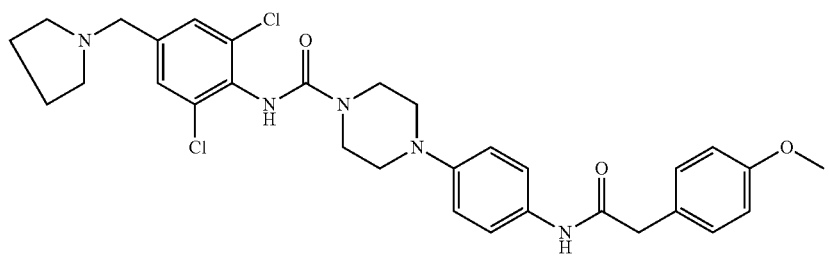 [SMILES: COc1ccc(CC(=O)Nc2ccc(N3CCN(C(=O)Nc4c(Cl)cc(CN5CCCC5)cc4Cl)CC3)cc2)cc1]

Food cups were filled and weighted daily during the experiment. Body weight was recorded every $2^{nd}$ or $3^{rd}$ day.

Food Intake and Body Weight data were analyzed using General Linear Models procedures appropriate for a 2×2 factorial design with blocking and repeated measures. Means comparisons were done using Duncan's Multiple Range test (SAS For Windows, Version 8.02; SAS®, Cary, N.C.). Results were expressed as means±SEM (standard error of the mean).

Test A

In test A, the efficacy of the treatment in DIO C57BL/6 mice with only fenofibrate and only a DGAT inhibitor (compound 223 from Class D) was compared with the combined treatment with both D and fenofibrate.

For the purpose of test A, the mice were assigned to one of the following treatments:
  45 kcal % fat diet (Control)
  45 kcal % fat diet+0.05% fenofibrate (F)
  45 kcal % fat diet+0.04% compound 223 from Class D (D)
  45 kcal % fat diet+0.04% compound 223 from Class D+0.05% fenofibrate (D+F)

The results of test A are shown in FIGS. A1 and A2.

In FIG. A1 it can be seen that except for 1 or 2 days out of the 12 day trial, food intake of mice fed with the compound 223 of Class D (D) or fenofibrate-containing (F) diet was not significantly less than control mice. In contrast, food intake of mice fed with the compound 223 of Class D and fenofibrate-containing (D+F) diet was significantly less (P<0.05) on 9 out of 12 days. The cumulative food intake of the compound 223 of Class D group (D) and the fenofibrate group (F) was not significantly less than the control group when compared by Duncans Multiple Range test (3.2% and 7.5% respectively); whereas food intake of the group with the compound 223 of Class D and fenofibrate-containing (D+F) diet was significantly less (23%) than all other groups (P<0.05). When cumulative intake was analysed as a 2×2 factorial design, there was a significant DGAT effect and fenofibrate effect (P<0.005), but there was also a significant DGAT (compound 223 from Class D) x fenofibrate interaction, indicating that the combined effect was larger than the main effect of either alone (P<0.05) (synergistic effect).

The average daily drug intake of mice fed with the compound 223 of Class D or fenofibrate-containing diet was 23.5 and 29 mpk/d respectively. The average daily drug intake of mice fed the compound 223 of Class D and fenofibrate-combination diet was 43.2 mg/kg/day.

In FIG. A2 it can be seen that by day 2, body weight loss of mice fed with the compound 223 of Class D and fenofibrate-containing diet was significantly greater than control mice (P<0.05). By day 4, body weight change of all drug treated mice was significantly different than controls. Mice fed with the compound 223 of Class D or fenofibrate-containing diet lost from 1-2 grams during the trial, whereas controls gained 0.6 grams. In contrast, mice fed with the compound 223 of Class D and fenofibrate-combination diet (D+F) significantly lost more weight than mice fed with either drug alone, indicating a synergistic effect of the 2 compounds on weight loss. When day 12 weight loss was analysed by a 2×2 factorial design, the main effect of DGAT and fenofibrate were both significant (P<0.001), but DGAT x fenofibrate interaction was also significant (type 3 SS, P<0.05). This test supports the increased effect on weight loss of the combination diet when compared with single treatment.

At the end of test A, blood was collected under isoflurane anesthesia for serum biochemistry determinations. There was no indication of enhanced liver enzymes with the combination diet. Blood glucose and serum triglyceride levels were consistently lower in the (D+F) diet group than the control group.

Test B

In test B, the efficacy of the treatment in DIO C57BL/6 mice with the fenofibrate/compound 223 from Class D combination was compared at different doses. In test A, fenofibrate and compound 223 of Class D were included at 0.05 and 0.04% of the diet (w/w) respectively. In test B, fenofibrate (F)/compound 223 of Class D (D) was included at 3 lower doses 0.05F/0.02D, 0.025F/0.02D and 0.0125F/0.01D.

For the purpose of test B, the mice were assigned to one of the following treatments:
  45 kcal % fat diet (Control)
  45 kcal % fat diet+0.02% D+0.05% F (0.05F/0.02D)
  45 kcal % fat diet+0.02% D+0.025% F (0.025F/0.02D)
  45 kcal % fat diet+0.01% D+0.0125% F (0.0125F/0.01D)

The results of test B are shown in FIGS. B1, B2 and B3.

The average daily drug intake of F/D was 26.0/10.4, 13.2/10.6 and 6.6/5.3 mpk/d respectively for mice fed with the high, medium and low concentration diets. In FIG. B1, it can be seen that the baseline food intake (i.e. day 0) of mice fed the 0.0125/0.01 was significantly lower than for other groups. During the first day of exposure to the drug-containing diets, all treatment groups ate significantly less than controls. (2.6 vs. 3.7 g for treated vs. controls respectively). Treated mice ate significantly (P<0.05 or less) less than controls on all trial days except days 9, 14 and 15.

In FIG. B2, it can be seen that body weight change of mice fed with F/D-containing diets was significantly different from control mice by the $2^{nd}$ day of the trial (all P<0.001). Body weight changed significantly over time (time effect, P<0.001), and was significantly influenced by treatment (time x treatment interaction (P<0.05).

In FIG. B3, food intake of all treatment groups on day 1 is shown. All groups ate about 30% less than controls regardless of dietary D/F combination.

It can be concluded that compound 223 of Class D in combination with fenofibrate, reduced food intake in diet-induced obese mice for almost 2 weeks. This reduction in food intake was accompanied with a significant weight change when compared to controls. Control mice gained almost 2 grams during the first 5 days of the experiment. It appeared that mice had lost some weight during adaptation to the feeding cages. Although they regained most of this weight prior to the trial, some control mice clearly still regained weight during the first week of the experiment. This was not the case for mice treated with the combination of compound 223 of Class D and fenofibrate, even when the 2 were combined in the diet at 0.01 and 0.0125% w/w respectively. These results suggest that fenofibrates may reduce the efficacious dose of a DGAT inhibitor and prolong the time a DGAT inhibitor will reduce food intake.

Test C

In test C, the efficacies of the treatments in DIO C57BL/6 mice with only fenofibrate and only a DGAT inhibitor (compound 358 from Class D) were compared with the combined treatment with both compound 358 of Class D and fenofibrate.

For the purpose of test C, the 32 DIO mice (n=8/group, average starting weight 46.5 g) were assigned to one of the following treatments:
  45 kcal % fat diet (Control)
  45 kcal % fat diet+0.05% fenofibrate (F)
  45 kcal % fat diet+0.04% compound 358 from Class D 45 kcal % fat diet+0.04% compound 358 from Class D+0.05% fenofibrate (F)

The results of test C are shown in FIGS. C1 and C2.

In FIG. C1 it can be seen that food intake of mice fed with a diet containing only compound 358 of Class D or a diet only containing fenofibrate, was not significantly less than control mice. Food intake of mice fed with the compound 358 of Class D+fenofibrate-containing diet was only significantly less (P<0.05) from controls on days 1 to 3, due to an increase in food intake above baseline levels in control mice rather than a decrease in intake of compound 358+fenofibrate-treated mice. The 21-day cumulative food intake of all drug-treated mice turned out not to be significantly less than the control group, although there was a tendency for mice fed compound 358 of Class D and fenofibrate-containing diet to eat less.

The average daily drug intake of mice fed with the compound 358 of Class D or fenofibrate-containing diet was 27 and 34 mpk/d respectively. The average daily drug intake of mice fed the compound 358 of Class D and fenofibrate-combination diet was 58 mg/kg/day.

When analysed as a 2×2 factorial experiment (FIG. C2), both DGAT and fenofibrate treated mice gained less weight than controls (21 days body weight change, both main effects P<0.05). The combination of the 2 treatments resulted in a weight loss corresponding to the additive effect of both (interaction P>0.05, no synergistic effect).

D) Short-term Food Intake Effect of DGAT/Fenofibrate Combination in Lean C57BL/6 Mice.

In Test A and Test B, it was demonstrated that DGAT inhibition (compound 223 of Class D, also called 'D') in combination with fenofibrate (F) significantly reduced food intake and body weight of diet-induced obese mice fed a high-fat diet to a greater degree than when either compound was administered alone. To further evaluate the mechanism of action of this food intake reduction, it was evaluated whether combined treatment with a DGAT inhibitor (compound 223 of Class D) and fenofibrate reduce food intake in mice fed with a low-fat diet.

For the experiment, animals were moved into modified type-2 cages as described before. Once in the feeding cages, mice were adapted to a 10 kcal % fat diet for 1 week before trial 1 was started.

For the purpose of this test, the mice were assigned to one of the following treatments:

Low Fat Diets (Trial 1; FIG. D1):
10 kcal % fat diet (Control)
10 kcal % fat diet+0.01% D+0.0125% F (0.01% D/0.0125% F)
10 kcal % fat diet+0.04% D+0.05% F (0.04% D/0.05% F)
High Fat Diet (Trial 2; FIG. D2)
45 kcal % fat diet (Control)
45 kcal % fat diet+0.01% D+0.0125% F (0.01% D/0.0125% F)
45 kcal % fat diet+0.02% D+0.05% F (0.02% D/0.05% F)

Compound 223 of Class D (D) and fenofibrate (F) were brought to a fine emulsion by stirring in the appropriate amount of soybean oil for 1 day. This was then mixed with the diet premix. After the soybean oil/drug was mixed with the premix for 15 min, the necessary amount of the lard was added to complete the diet. Diet was provided in powder form.

Mice's 'baseline' (BL) food intake was measured for 1 day before both Trial 1 (low-fat diet) and 2 (high-fat diet). For treatment allocation, mice were ranked according to their pretrial food intake and randomly assigned to treatments within repetitions/block (30 mice, 3 treatments, 8-9 repetitions/block). Several mice had low or high food intakes and were not included in the experiment.

Food intake data were analysed using General Linear Models procedures appropriate for a randomized complete block design. Means comparisons were done using Duncan's Multiple Range test (SAS For Windows, Version 8.02; SAS®, Cary, N.C.). Results are expressed as means±SEM.

Trial 1: Food Intake of Lean Mice Fed a Low-fat Diet

Mice were given 1 week to adapt to the food intake cages and a low-fat powdered diet (Research Diets D12450B—10 kcal % fat). After 1 day of baseline food intake measurement, mice's food was replaced by the same 10 kcal % fat diet containing 0/0, 0.01/0.0125 or 0.04/0.05% w/w D/F. The food cups were filled and weight daily during the 3-day experiment.

In FIG. D1 (Trial 1), it can be seen that food intake of mice fed the diet containing a 0.01/0.0125 D/F was not reduced at any time during the 3-day trial, whereas mice fed the diet containing 0.04/0.05 D/F reduced their food intake by 9% on day 1, but ate similar amounts as controls thereafter.

The average daily drug intake of F/D was 71/57 or 17/14 mpk/d respectively for mice fed the high, and low concentration diets.

Trial 2: Food Intake of Lean Mice Fed a High-fat Diet

At the termination of trial 1, mice were switched to a high-fat diet (D12451—45 kcal % fat) and allowed to adapt for 3 days. Once adapted, food intake was recorded for 1 day to establish a baseline food intake (for treatment allotment). The following day, mice were switched to the same 45 kcal % fat diet containing 0/0, 0.01/0.0125 or 0.02/0.05% w/w D/F (FIG. D2).

In FIG. D2, it is shown that food intake of mice fed the diets containing a 0.01/0.0125% and 0.02/0.05% D/F was significantly reduced compared to controls, especially on day 1. Thereafter lean mice adapted more quickly than was generally been observed with obese mice. By day 2, mice were eating 90% of control values.

The average daily drug intake of F/D was 44/18 or 10.8/8.6 mpk/d respectively for mice fed the high, and low concentration diets.

It can be seen from FIG. D3 that food intake during the first 24 h of exposure to the drug-supplemented diet (0.01% D/0.0125% F) was significantly reduced in mice fed a high-fat diet (24% below control levels), but not in mice fed a low-fat diet (4% below control levels). These results clearly indicate that a certain amount of dietary fat is necessary for the feeding suppressive effects of D/F.

E) Composition Examples

"Active ingredient" (a.i.) as used throughout these examples relates to, unless otherwise is indicated,
a) a combination of a DGAT inhibitor and a PPAR agonist or a prodrug thereof; in particular to any one of the exemplified DGAT inhibitors combined with a fibrate; or
b) a compound of group Q.

Typical examples of recipes for the formulation of the invention are as follows:

1. Tablets

| | |
|---|---|
| Active ingredient | 5 to 100 mg |
| Di-calcium phosphate | 20 mg |
| Lactose | 30 mg |
| Talcum | 10 mg |
| Magnesium stearate | 5 mg |
| Potato starch | ad 200 mg |

In addition to tablets wherein both the DGAT inhibitor and the PPAR agonist are comprised together in 1 tablet, the DGAT inhibitor and the PPAR agonist may also be present in separate tablets. In that case, the active ingredient will be the DGAT inhibitor for one tablet and the PPAR agonist for the second tablet.

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution.

4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

The invention claimed is:

1. A compound including any stereochemically isomeric form thereof, wherein the compound is selected from N-[4-[4-[[2-chloro-4-(1-pyrrolidinylmethyl)phenyl]acetyl]-1-piperazinyl]phenyl]-4-methoxy-benzeneacetamide;

4-[4-[[2-chloro-4-(1-pyrrolidinylmethyl)phenyl]acetyl]-1-piperazinyl]-N-[3-(1-pyrrolidinyl)phenyl]-benzamide;

4-[4-[[2-chloro-4-(1-pyrrolidinylmethyl)phenyl]acetyl]-1-piperazinyl]-N-[[3-(1-pyrrolidinyl)phenyl]methyl]-benzamide;

4-[4-[[2-chloro-4-(1-pyrrolidinylmethyl)phenyl]hydroxyacetyl]-1-piperazinyl]-N-[[3-(1-pyrrolidinyl)phenyl]methyl]-benzamide;

4-[4-[[2-chloro-4-(1-pyrrolidinylmethyl)phenyl]hydroxyacetyl]-1-piperazinyl]-N-[3-(1-pyrrolidinyl)phenyl]-benzamide;

4-[4-[[2,6-dichloro-4-(1-pyrrolidinylmethyl)phenyl]acetyl]-1-piperazinyl]-N-[(3,5-dimethoxyphenyl)methyl]-benzamide;

4-[4-[[2-chloro-4-(1-pyrrolidinylmethyl)phenyl]acetyl]-1-piperazinyl]-N-[(3,5-dimethoxyphenyl)methyl]-benzamide;

4-[4-[[2-chloro-4-(1-pyrrolidinylmethyl)phenyl]hydroxyacetyl]-1-piperazinyl]-N-[(3,5-dimethoxyphenyl)methyl]-benzamide;

4-[4-[[2,6-dichloro-4-(1-pyrrolidinylmethyl)phenyl]acetyl]-1-piperazinyl]-N-[3-(1-pyrrolidinyl)phenyl]-benzamide;

4-[4-[[2,6-dichloro-4-[(4-ethyl-1-piperazinyl)methyl]phenyl]acetyl]-1-piperazinyl]-N-[(3,5-dimethoxyphenyl)methyl]-benzamide;

4-[4-[[2,6-dichloro-4-[(4-ethyl-1-piperazinyl)methyl]phenyl]acetyl]-1-piperazinyl]-N-[[3-(1-pyrrolidinyl)phenyl]methyl]-benzamide;

4-[4-[[2,6-dichloro-4-[[4-(methylsulfonyl)-1-piperazinyl]methyl]phenyl]acetyl]-1-piperazinyl]-N-[(3,5-dimethoxyphenyl)methyl]-benzamide;

4-[4-[[4-[(4-acetyl-1-piperazinyl)methyl]-2,6-dichlorophenyl]acetyl]-1-piperazinyl]-N-[[3-(1-pyrrolidinyl)phenyl]methyl]-benzamide;

4-[4-[[2,6-dichloro-4-[[4-(methylsulfonyl)-1-piperazinyl]methyl]phenyl]acetyl]-1-piperazinyl]-N-[[3-(1-pyrrolidinyl)phenyl]methyl]-benzamide;

4-[4-[[4-[(4-acetyl-1-piperazinyl)methyl]-2,6-dichlorophenyl]acetyl]-1-piperazinyl]-N-[(3,5-dimethoxyphenyl)methyl]-benzamide;

4-[4-[[2,6-dichloro-4-[[4-(methylsulfonyl)-1-piperazinyl]methyl]phenyl]acetyl]-1-piperazinyl]-N-[3-(1-pyrrolidinyl)phenyl]-benzamide;

4-[4-[[4-(4-acetyl-1-piperazinyl)methyl]-2,6-dichlorophenyl]acetyl]-1-piperazinyl]-N-[3-(1-pyrrolidinyl)phenyl]-benzamide;

4-[4-[[2,6-dichloro-4-[(4-ethyl-1-piperazinyl)methyl]phenyl]acetyl]-1-piperazinyl]-N-[3-(1-pyrrolidinyl)phenyl]-benzamide;

a N-oxide thereof, a pharmaceutically acceptable salt thereof or a solvate thereof.

2. A pharmaceutical composition comprising a pharmaceutically acceptable carrier and a therapeutically effective amount of a compound according to claim 1.

* * * * *